US010418564B2

(12) United States Patent
Parham et al.

(10) Patent No.: US 10,418,564 B2
(45) Date of Patent: Sep. 17, 2019

(54) MATERIALS FOR ORGANIC ELECTROLUMINESCENT DEVICES

(71) Applicant: Merck Patent GmbH, Darmstadt (DE)

(72) Inventors: Amir Hossain Parham, Frankfurt am Main (DE); Christof Pflumm, Darmstadt (DE); Thomas Eberle, Landau (DE); Anja Jatsch, Frankfurt am Main (DE); Jonas Valentin Kroeber, Frankfurt am Main (DE); Tobias Grossmann, Darmstadt (DE)

(73) Assignee: Merck Patent GmbH (DE)

( * ) Notice: Subject to any disclaimer, the term of this patent is extended or adjusted under 35 U.S.C. 154(b) by 4 days.

(21) Appl. No.: 15/303,368

(22) PCT Filed: Mar. 12, 2015

(86) PCT No.: PCT/EP2015/000546
§ 371 (c)(1),
(2) Date: Oct. 11, 2016

(87) PCT Pub. No.: WO2015/154843
PCT Pub. Date: Oct. 15, 2015

(65) Prior Publication Data
US 2017/0033296 A1  Feb. 2, 2017

(30) Foreign Application Priority Data

Apr. 11, 2014  (EP) .................................. 14001336

(51) Int. Cl.
| | | |
|---|---|---|
| *H01L 51/50* | (2006.01) |
| *H01L 51/00* | (2006.01) |
| *C07D 403/04* | (2006.01) |
| *C07D 403/10* | (2006.01) |
| *C07D 405/04* | (2006.01) |
| *C07D 405/10* | (2006.01) |
| *C07D 209/86* | (2006.01) |
| *C09B 19/00* | (2006.01) |
| *C09B 21/00* | (2006.01) |
| *C09B 57/00* | (2006.01) |
| *C09B 57/10* | (2006.01) |
| *C07D 401/14* | (2006.01) |
| *C07D 403/14* | (2006.01) |
| *C07D 491/048* | (2006.01) |
| *C07D 495/04* | (2006.01) |
| *C07D 498/06* | (2006.01) |
| *C09K 11/02* | (2006.01) |
| *C09K 11/06* | (2006.01) |

(52) U.S. Cl.
CPC ........ *H01L 51/0072* (2013.01); *C07D 209/86* (2013.01); *C07D 401/14* (2013.01); *C07D 403/04* (2013.01); *C07D 403/10* (2013.01); *C07D 403/14* (2013.01); *C07D 405/04* (2013.01); *C07D 405/10* (2013.01); *C07D 491/048* (2013.01); *C07D 495/04* (2013.01); *C07D 498/06* (2013.01); *C09B 19/00* (2013.01); *C09B 21/00* (2013.01); *C09B 57/00* (2013.01); *C09B 57/001* (2013.01); *C09B 57/008* (2013.01); *C09B 57/10* (2013.01); *C09K 11/025* (2013.01); *C09K 11/06* (2013.01); *H01L 51/0054* (2013.01); *H01L 51/0056* (2013.01); *H01L 51/0058* (2013.01); *H01L 51/0061* (2013.01); *H01L 51/0071* (2013.01); *H01L 51/0085* (2013.01); *C09K 2211/1007* (2013.01); *C09K 2211/1029* (2013.01); *C09K 2211/185* (2013.01); *H01L 51/0067* (2013.01); *H01L 51/0073* (2013.01); *H01L 51/5012* (2013.01); *H01L 51/5016* (2013.01); *H01L 51/5056* (2013.01); *H01L 51/5096* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 7,252,781 B2 | 8/2007 | Spreitzer et al. | |
| 9,040,975 B2 | 5/2015 | Tani et al. | |
| 9,818,948 B2 | 11/2017 | Jatsch et al. | |
| 2004/0206939 A1 | 10/2004 | Spreitzer et al. | |
| 2012/0205636 A1* | 8/2012 | Kim | C09K 11/06 257/40 |
| 2013/0248845 A1 | 9/2013 | Ogawa et al. | |
| 2013/0306962 A1 | 11/2013 | Yamamoto et al. | |
| 2014/0070204 A1 | 3/2014 | Nagao et al. | |
| 2017/0301868 A1* | 10/2017 | Lee | C07D 209/82 |

FOREIGN PATENT DOCUMENTS

| | | |
|---|---|---|
| EP | 2479234 A1 | 7/2012 |
| JP | 200878362 A | 4/2008 |
| JP | 2008195841 A | 8/2008 |

(Continued)

OTHER PUBLICATIONS

International Search Report for PCT/EP2015/000546 dated Jun. 9, 2015.
Yamashita, M., et al., "Syntheis of Condensed Heteroaromatic Compounds by Palladium-Catalyzed Oxidative Coupling of Heteroarene Carboxylic Acids with Alkynes", Organic Letters, 2009, vol. 11, No. 11, pp. 2337-2340.

*Primary Examiner* — Gregory D Clark

(74) *Attorney, Agent, or Firm* — Drinker Biddle & Reath LLP

(57) ABSTRACT

The invention relates to compounds of the formula (1) which are suitable for use in electronic devices, in particular organic electroluminescent devices.

11 Claims, No Drawings

(56) References Cited

FOREIGN PATENT DOCUMENTS

| | | | | |
|---|---|---|---|---|
| JP | 2010251675 A | | 11/2010 | |
| JP | 2012-169325 | * | 9/2012 | ............ H01L 51/50 |
| JP | 2014125109 A | | 7/2014 | |
| KR | 20040049304 A | | 6/2004 | |
| KR | 20130127992 A | | 11/2013 | |
| KR | 20140017428 A | | 2/2014 | |
| KR | 20140040133 A | | 4/2014 | |
| WO | WO-03019694 A2 | | 3/2003 | |
| WO | WO-2009069442 A1 | | 6/2009 | |
| WO | WO-20120108879 A1 | | 8/2012 | |
| WO | WO-2012173079 A1 | | 12/2012 | |
| WO | WO-2013041176 A1 | | 3/2013 | |
| WO | WO-2014021572 A1 | | 2/2014 | |

* cited by examiner

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2015/000546, filed Mar. 12, 2015, which claims benefit of European Application No. 14001336.8, filed Apr. 11, 2014, both of which are incorporated herein by reference in their entirety.

The present invention relates to carbazole derivatives, especially for use as triplet matrix materials in organic electroluminescent devices. The invention further relates to a process for preparing the compounds of the invention and to electronic devices comprising these compounds.

The structure of organic electroluminescent devices (OLEDs) in which organic semiconductors are used as functional materials is described, for example, in U.S. Pat. Nos. 4,539,507, 5,151,629, EP 0676461 and WO 98/27136. Emitting materials used are frequently organometallic complexes which exhibit phosphorescence rather than fluorescence. For quantum mechanical reasons, up to four times the energy efficiency and power efficiency is possible using organometallic compounds as phosphorescent emitters. In general terms, there is still a need for improvement in OLEDs, especially also in OLEDs which exhibit triplet emission (phosphorescence), for example with regard to efficiency, operating voltage and lifetime.

The properties of phosphorescent OLEDs are not just determined by the triplet emitters used. More particularly, the other materials used, for example matrix materials, are also of particular significance here. Improvements to these materials can thus also lead to distinct improvements in the OLED properties.

According to the prior art, among other materials, indolocarbazole derivatives (for example according to WO 2007/063754 or WO 2008/056746) or indenocarbazole derivatives (for example according to WO 2010/136109 or WO 2011/000455), especially those substituted by electron-deficient heteroaromatics such as triazine, are used as matrix materials for phosphorescent emitters. In addition, for example, bisdibenzofuran derivatives (for example according to EP 2301926) are used as matrix materials for phosphorescent emitters. However, there is still a need for improvement in the case of use of these matrix materials, especially in relation to the efficiency, the lifetime and the operating voltage of the device.

The problem addressed by the present invention is that of providing compounds suitable for use in a fluorescent or phosphorescent OLED, especially a phosphorescent OLED, for example as matrix material or as charge transport material, especially hole transport or electron blocker material. A particular problem addressed by the present invention is that of providing matrix materials which are also suitable for green- and blue-phosphorescing OLEDs, and providing novel charge transport materials.

It has been found that, surprisingly, electroluminescent devices containing compounds of the following formula (1) have improvements over the prior art, especially when used as matrix materials for phosphorescent dopants.

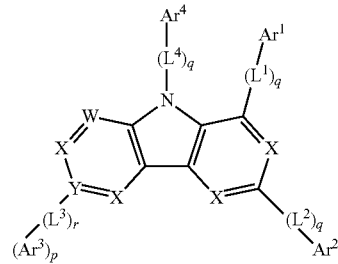

Formula (1)

where the symbols and indices used are as follows:

X is the same or different at each instance and is CR or N;
W is $CR^1$ or N;
Y is N or CR when p+r=0 and C when p+r
$L^1$, $L^2$, $L^3$, $L^4$ are the same or different at each instance and are a bivalent aromatic or heteroaromatic ring system which has 5 to 40 aromatic ring atoms and may be substituted by one or more $R^2$ radicals;
$Ar^1$, $Ar^2$, $Ar^3$, $Ar^4$ at each instance are an aromatic or heteroaromatic ring system which has 6 to 60 aromatic ring atoms and may in each case also be substituted by one or more $R^2$ radicals;
Ar is the same or different at each instance and is an aromatic or heteroaromatic ring system, preferably an aryl or heteroaryl group, which has 5 to 40 aromatic ring atoms and may be substituted by one or more $R^4$ radicals;
R, $R^2$ is the same or different at each instance and is H, D, F, Cl, Br, I, $N(R^3)_2$, $N(Ar)_2$, $C(=O)Ar$, $P(=O)Ar_2$, $S(=O)Ar$, $S(=O)_2Ar$, $CR^3=CR^3Ar$, CN, $NO_2$, $Si(R^3)_3$, $B(OR^3)_2$, $OSO_2R^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent $CH_2$ groups may be replaced by $R^3C=CR^3$, $C\equiv C$, $Si(R^3)_2$, $C=O$, $C=NR^3$, $P(=O)(R^3)$, SO, $SO_2$, $NR^3$, O, S or $CONR^3$ and where one or more hydrogen atoms may be replaced by D, F, Cl, Br, I, CN or $NO_2$, or an aromatic or heteroaromatic ring system which has 5 to 60 aromatic ring atoms, each of which may be substituted by one or more $R^3$ radicals, or an aryloxy or heteroaryloxy group which has 5 to 40 aromatic ring atoms and may be substituted by one or more $R^3$ radicals, or an aralkyl or heteroaralkyl group which has 5 to 40 aromatic ring atoms and may be substituted by one or more $R^3$ radicals, or a combination of these systems; at the same time, two or more $R^2$ substituents together with the atoms to which they are bonded and also with one another, or two adjacent R substituents, may form a mono- or polycyclic, aliphatic or aromatic ring system;
$R^1$ at each instance is H, D, F, Cl, Br, I, $N(R^5)_2$, CN, $NO_2$, $Si(R^5)_3$, $B(OR^5)_2$, $OSO_2R^5$, a straight-chain alkyl, alkoxy or thioalkoxy group having 1 to 40 carbon atoms or a branched or cyclic alkyl, alkoxy or thioalkoxy group which has 3 to 40 carbon atoms and may be substituted in each case by one or more $R^5$ radicals, where one or more nonadjacent $CH_2$ groups may be replaced by $R^5C=CR^5$, $C\equiv C$, $Si(R^5)_2$, $C=O$, $C=NR^5$, $P(=O)(R^5)$, SO, $SO_2$, $NR^5$, O, S or $CONR^5$ and where one or more hydrogen atoms may be replaced by D, F, Cl, Br, I, CN or $NO_2$;
$R^3$ is the same or different at each instance and is H, D, F, Cl, Br, I, $N(R^4)_2$, $C(=O)Ar$, $P(=O)Ar_2$, $S(=O)Ar$, $S(=O)_2Ar$, $CR^3=CR^3Ar$, CN, $NO_2$, $Si(R^4)_3$, $B(OR^4)_2$, OSO$_2$R$^4$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R$^3$ radicals, where one or more nonadjacent CH$_2$ groups may be replaced by R$^4$C=CR$^4$, CC, Si(R$^4$)$_2$, C=O, C=NR$^4$, P(=O)(R$^4$), SO, SO$_2$, NR$^4$, O, S or CONR$^4$ and where one or more hydrogen atoms may be replaced by D, F, Cl, Br, I, CN or NO$_2$, or an aromatic or heteroaromatic ring system which has 5 to 60 aromatic ring atoms, each of which may be substituted by one or more R$^4$ radicals, or an aryloxy or heteroaryloxy group which has 5 to 40 aromatic ring atoms and may be substituted by one or more R$^3$ radicals, or an aralkyl or heteroaralkyl group which has 5 to 40 aromatic ring atoms and may be substituted by one or more R$^4$ radicals, or a combination of these systems;

R$^4$ is the same or different at each instance and is H, D, F or an aliphatic hydrocarbyl radical having 1 to 20 carbon atoms or an aryl or heteroaryl group which has 5 to 40 ring atoms and may be substituted by one or more R$^5$ radicals, or a combination of these groups;

R$^5$ is the same or different at each instance and is H, D, F or an aliphatic hydrocarbyl radical having 1 to 20 carbon atoms;

q is the same or different at each instance and is 0 or 1;
r is 0 or 1;
p is 0 or 1, where p≥r;
where
Ar$^1$ and Ar$^2$ do not comprise any structure of formula (2):

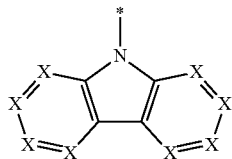

Formula (2)

where * indicates the bond to L$^1$ or L$^2$ or the base skeleton; and at least two groups selected from the (L$^1$)$_q$Ar$^1$, (L$^2$)$_q$Ar$^2$, and (L$^3$)$_r$(Ar$^3$)$_p$ groups are the same.

An aryl group in the context of this invention contains 6 to 60 carbon atoms; a heteroaryl group in the context of this invention contains 2 to 60 carbon atoms and at least one heteroatom, with the proviso that the sum total of carbon atoms and heteroatoms is at least 5. The heteroatoms are preferably selected from N, O and/or S. An aryl group or heteroaryl group is understood here to mean a simple aromatic cycle, i.e. benzene, or a simple heteroaromatic cycle, for example thiophene, etc., or a condensed (fused) aryl or heteroaryl group, for example naphthalene, anthracene, phenanthrene, dibenzofuran, etc. Aromatic systems joined to one another by a single bond, for example biphenyl, by contrast, are not referred to as an aryl or heteroaryl group but as an aromatic ring system.

An aromatic ring system in the context of this invention contains 6 to 80 carbon atoms in the ring system. A heteroaromatic ring system in the context of this invention contains 2 to 60 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention is understood to mean a system which does not necessarily contain only aryl or heteroaryl groups, but in which it is also possible for two or more aryl or heteroaryl groups to be joined by a nonaromatic unit (preferably less than 10% of the atoms other than H), for example a carbon, nitrogen or oxygen atom. For example, systems such as fluorene, 9,9'-spirobifluorene, 9,9-diarylfluorene, triarylamine, diaryl ethers, stilbene, etc. shall also be regarded as aromatic ring systems in the context of this invention, and likewise systems in which two or more aryl groups are joined, for example, by a short alkyl group. In addition, aromatic systems joined to one another by a single bond, for example biphenyl, are referred to as aromatic ring system in the context of this application.

An electron-deficient heteroaryl group in the context of the present invention is defined as a 5-membered heteroaryl group having at least two heteroatoms, for example imidazole, oxazole, oxadiazole, etc., or as a 6-membered heteroaryl group having at least one heteroatom, for example pyridine, pyrimidine, pyrazine, triazine, etc. It is also possible for further 6-membered aryl or 6-membered heteroaryl groups to be fused onto these groups, as, for example, in benzimidazole or quinoline.

In the context of the present invention, an aliphatic hydrocarbyl radical or an alkyl group or an alkenyl or alkynyl group which may typically contain 1 to 40 or else 1 to 20 carbon atoms and in which individual hydrogen atoms or CH$_2$ groups may also be replaced by the abovementioned groups are preferably understood to mean the methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkenyl, alkynyl, alkoxy or thioalkyl groups according to the present invention may be straight-chain, branched or cyclic, where one or more nonadjacent CH$_2$ groups may be replaced by the abovementioned groups; in addition, it is also possible for one or more hydrogen atoms to be replaced by D, F, Cl, Br, I, CN or NO$_2$, preferably F, Cl or CN, further preferably F or CN, especially preferably CN.

An aromatic or heteroaromatic ring system which has 5-80 aromatic ring atoms and may also be substituted in each case by the abovementioned radicals and which may be joined to the aromatic or heteroaromatic system via any desired positions is especially understood to mean groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from combinations of these systems. These groups may each be substituted by the abovementioned radicals.

An aryloxy group as defined in the present invention is understood to mean an aryl group as defined above bonded via an oxygen atom. An analogous definition applies to heteroaryloxy groups.

An electron-deficient heteroaryl group in the context of present invention is defined as a 5-membered heteroaryl group having at least two heteroatoms, for example imidazole, oxazole, oxadiazole, etc., or as a 6-membered heteroaryl group having at least one heteroatom, for example pyridine, pyrimidine, pyrazine, triazine, etc. It is also possible for further 6-membered aryl or 6-membered heteroaryl groups to be fused onto these groups, as, for example, in benzimidazole or quinoline.

The wording that two or more radicals together may form a ring, in the context of the present description, shall be understood to mean, inter alia, that the two radicals are joined to one another by a chemical bond. This is illustrated by the following scheme: Ring formation

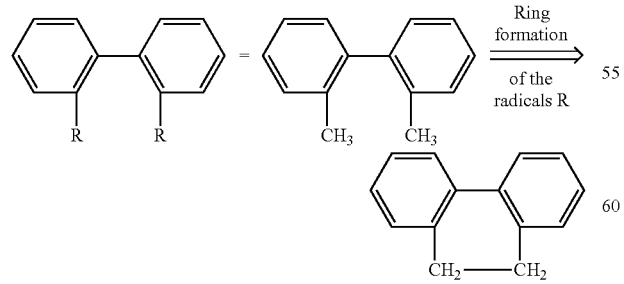

In addition, however, the abovementioned wording shall also be understood to mean that, if one of the two radicals is hydrogen, the second radical binds to the position to which the hydrogen atom was bonded, forming a ring. This shall be illustrated by the following scheme:

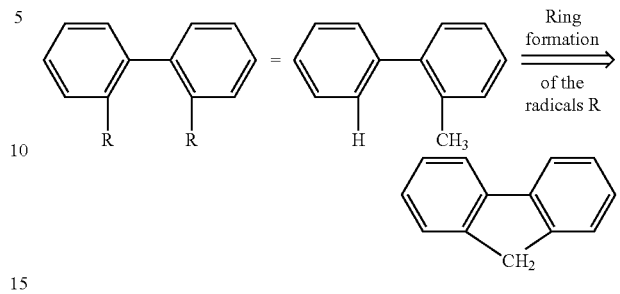

In a further embodiment of the invention, a 6-membered cycle in formula (1) comprises not more than one N as aromatic ring atom, meaning that only one X, Y or W is N. More preferably, none of the X, Y or W symbols in formula (1) is N.

A preferred embodiment of the compound of the formula (1) is a compound of the following formula (3):

Formula (3)

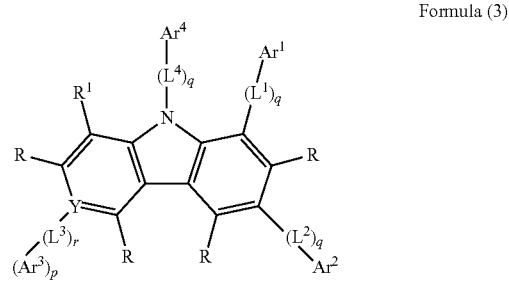

where Y is CR when p+r=0 and C when p+r 0. The other symbols and indices used correspond to those of formula (1).

In a preferred embodiment of the invention, the compound is a compound of one of the following formulae (4) to (7):

Formula (4)

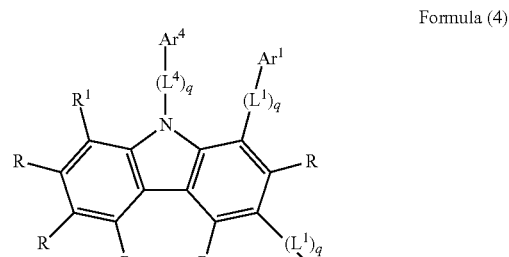

Formula (5)

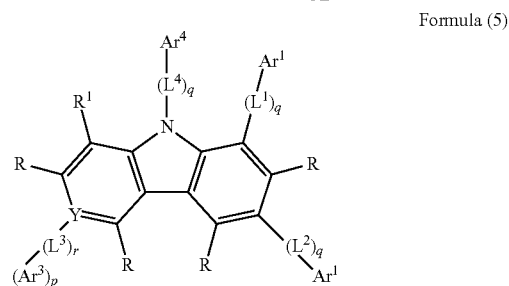

Formula (6)

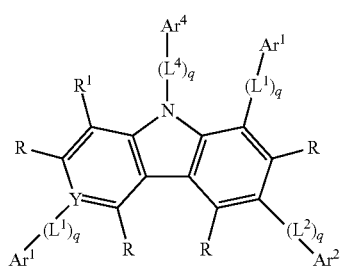

Formula (7)

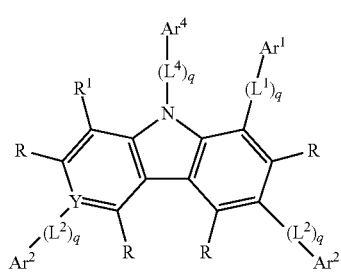

The symbols and indices here correspond to the symbols and indices of the formula (3).

Preference is given here to a compound of one of the formulae (4) and (5). According to the above definitions, the carbazole base skeleton of the compounds of the invention does not have any further rings fused to the base skeleton. It has only one aromatic ring system in the ortho position.

In a preferred embodiment of the invention, R is the same or different at each instance and is H, D, F or an aliphatic hydrocarbyl radical having 1 to 20 carbon atoms, more preferably H, D or F.

In a preferred embodiment of the invention, $R^1$ is the same or different at each instance and is H, D, F or an aliphatic hydrocarbyl radical having 1 to 20 carbon atoms, more preferably H, D or F, most preferably H or D.

In a preferred embodiment of the invention, the Ai1 and $Ar^2$ groups at each instance are selected from the groups having the following formulae (Ar-1) to (Ar-14):

Formula (Ar-1)

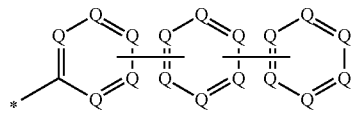

Formula (Ar-2)

Formula (Ar-3)

Formula (Ar-4)

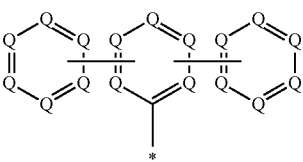

Formula (Ar-5)

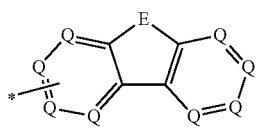

Formula (Ar-6)

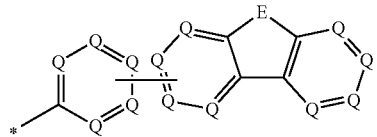

Formula (Ar-7)

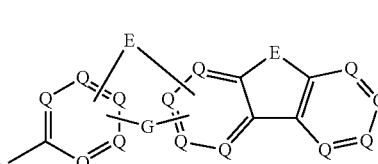

Formula (Ar-8)

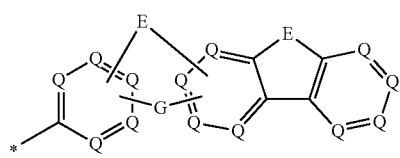

Formula (Ar-9)

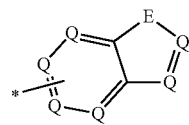

Formula (Ar-10)

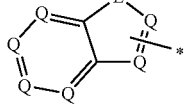

Formula (Ar-11)

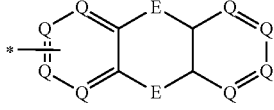

Formula (Ar-12)

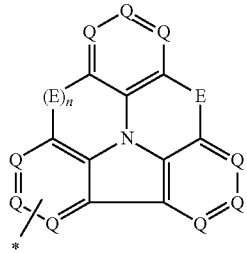

Formula (Ar-13)

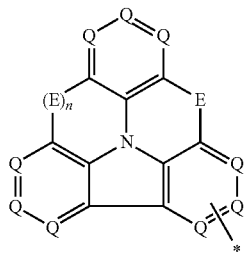

Formula (Ar-14)

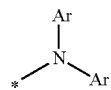

where the symbols and indices correspond to the symbols and indices of formula (1) and, in addition:
Q is the same or different at each instance and is $CR^2$ or N, where not more than 3 Q symbols per cycle are N;
E is the same or different at each instance and is $(CR^2)_2$, $NR^2$, O, S or C=O;
G at each instance is a single bond, $(CR^2)_2$, $NR^2$, O, S or C=O;
n is 0 or 1, where n=0 means that no E group is bonded at this position and $R^2$ radicals are bonded to the corresponding carbon atoms instead; and
* represents the bond to $L^1$ or $L^2$ or the base skeleton.

In a further embodiment of the invention, the $Ar^3$ and $Ar^4$ groups are the same or different at each instance and are selected from the formulae (Ar-1) to (Ar-14) and the following formulae (Ar-15) to (Ar-19):

Formula (Ar-15)

Formula (Ar-16)

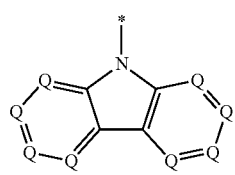

Formula (Ar-17)

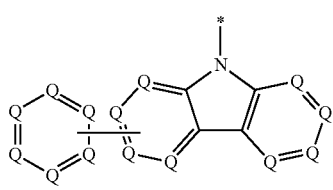

Formula (Ar-18)

Formula (Ar-19)

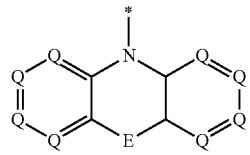

where the symbols and indices correspond to the symbols and indices of formula (1) and, in addition, for the formulae (Ar-15) to (Ar-19):
Q is the same or different at each instance and is $CR^2$ or N, where not more than 2 Q symbols per cycle are N;
E is the same or different at each instance and is $(CR^2)_2$, $NR^2$, O, S or C=O;
G at each instance is a single bond, $(CR^2)_2$, $NR^2$, O, S or C=O;
n is 0 or 1, where n=0 means that no E group is bonded at this position and $R^2$ radicals are bonded to the corresponding carbon atoms instead;
* represents the bond, in the case of $Ar^3$, to $L^3$ or to the base skeleton and, in the case of $Ar^4$, to $L^4$.

In a further preferred embodiment of the invention, at least one of the $Ar^1$, $Ar^2$, $Ar^3$ or $Ar^4$ groups is selected from one of the formulae (Ar-1), (Ar-5), (Ar-6), (Ar-8) or (Ar-10), preferably selected from one of the formulae (Ar-1-2), (Ar-1-3), (Ar-1-4), (Ar-1-5), (Ar-5), (Ar-6), (Ar-8) or (Ar-10).

In a further particularly preferred embodiment of the invention, at least one $Ar^1$, $Ar^2$, $Ar^3$ or $Ar^4$ group comprises an electron-deficient heteroaryl group. Preferably, at least one of the $Ar^1$, $Ar^2$, $Ar^3$ or $Ar^4$ groups is selected from one of the formulae (Ar-1-2), (Ar-1-3), (Ar-1-4) and (Ar-1-5), more preferably from one of the formulae (Ar-1-2) and (Ar-1-5).

In a further particularly preferred embodiment of the invention, at least one $Ar^1$, $Ar^2$, $Ar^3$ or $Ar^4$ group is selected from one of the formulae (Ar-5), (Ar-6), (Ar-8) and (Ar-10).

In a further preferred embodiment, in the formula (Ar-1), 0, 2 or 3 Q symbols are N.

Preferred embodiments of the formula (Ar-8) are shown by the following formulae (Ar-8-1) to (Ar-8-7):

Formula (Ar-8-1)

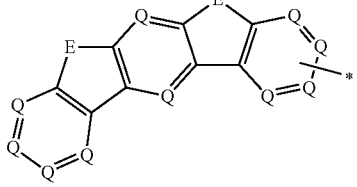

Formula (Ar-8-2)

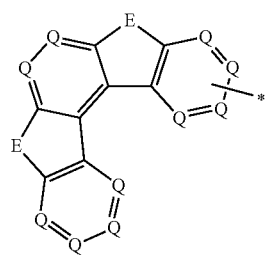

Formula (Ar-8-3)

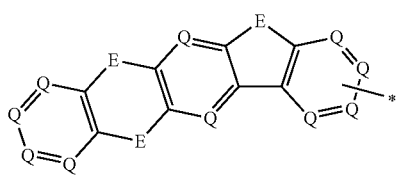

Formula (Ar-8-4)

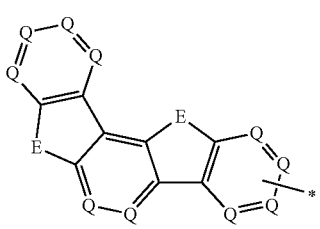

Formula (Ar-8-5)

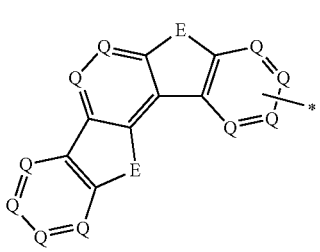

Formula (Ar-8-6)

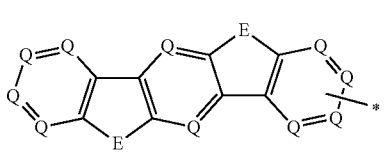

Formula (Ar-8-7)

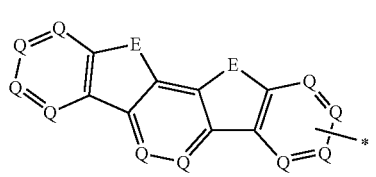

where the symbols correspond to the symbols of the formula (Ar-8). More preferably, Q is always $CR^2$.

In a further preferred embodiment, the $Ar^1$ and $Ar^2$ groups are the same or different at each instance and are selected from the groups having the structures of formulae (Ar-1) to (Ar-14), preferably (Ar-1) to (Ar-13), where the general formulae are replaced by the respective particularly preferred embodiments of the following formulae (Ar-1-1) to (Ar-13-1) (for example, formula (Ar-1) is replaced by one of the formulae (Ar-1-1) to (Ar-1-9)):

Formula (Ar-1-1)

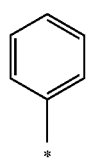

Formula (Ar-1-2)

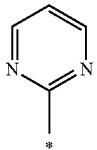

Formula (Ar-1-3)

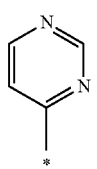

Formula (Ar-1-4)

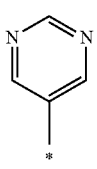

Formula (Ar-1-5)

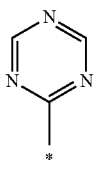

Formula (Ar-1-6)

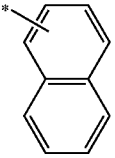

Formula (Ar-1-7)

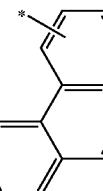

Formula (Ar-1-8)

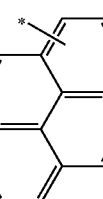

Formula (Ar-1-9)

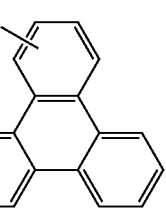

Formula (Ar-2-1)
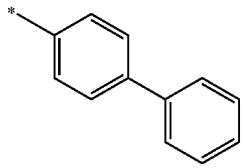
Formula (Ar-2-2)
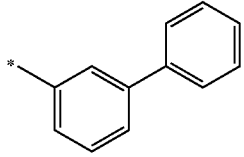
Formula (Ar-2-3)
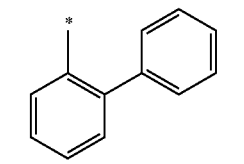
Formula (Ar-3-1)
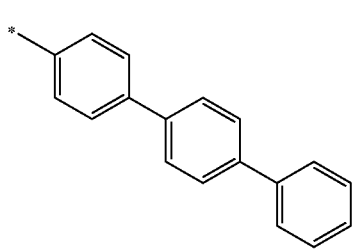
Formula (Ar-3-2)
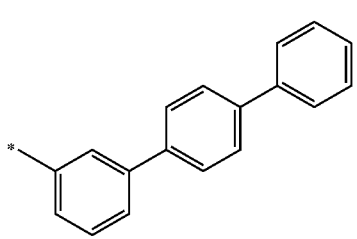
Formula (Ar-3-3)
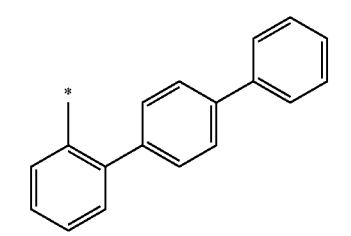
Formula (Ar-3-4)
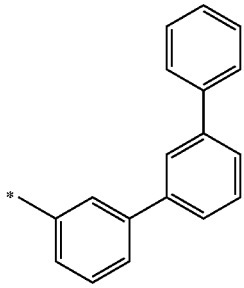
Formula (Ar-3-5)
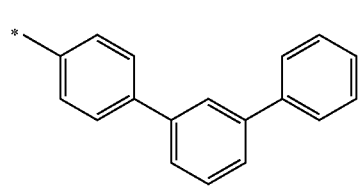
Formula (Ar-3-6)
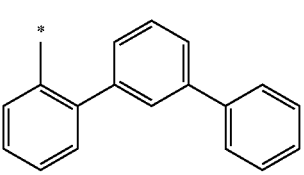
Formula (Ar-3-7)
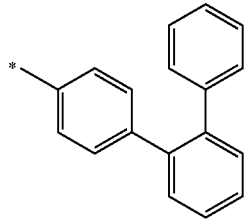
Formula (Ar-3-8)
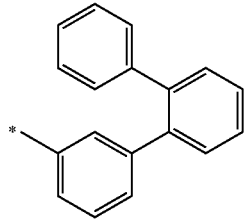
Formula (Ar-3-9)
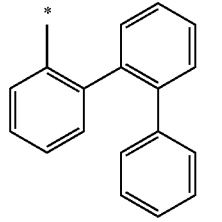
Formula (Ar-4-1)
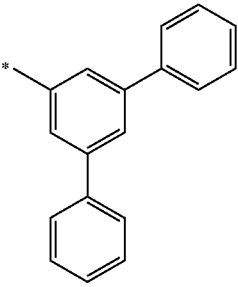

Formula (Ar-4-2)
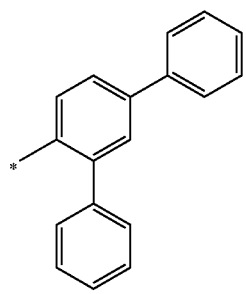
Formula (Ar-5-1)
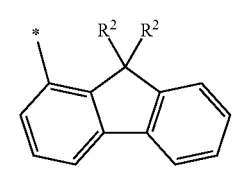
Formula (Ar-5-2)
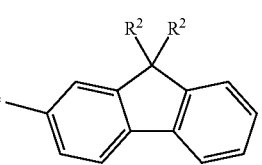
Formula (Ar-5-3)
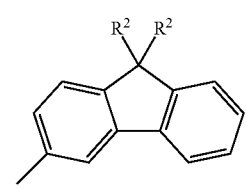
Formula (Ar-5-4)
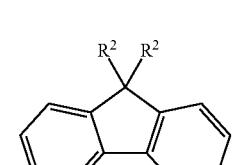
Formula (Ar-5-5)
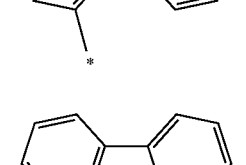
Formula (Ar-5-6)
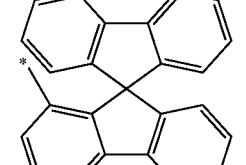
Formula (Ar-5-7)
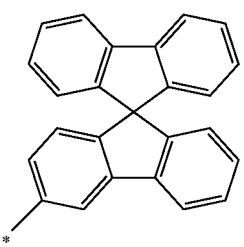
Formula (Ar-5-8)
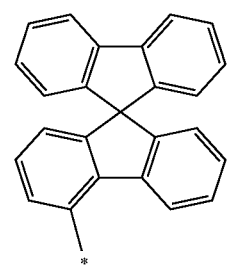
Formula (Ar-5-9)
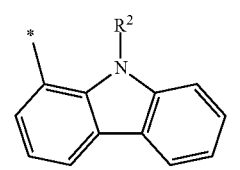
Formula (Ar-5-10)
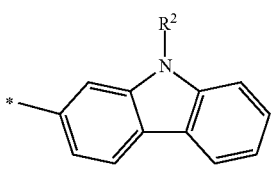
Formula (Ar-5-11)
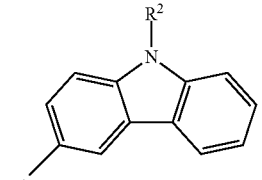
Formula (Ar-5-12)
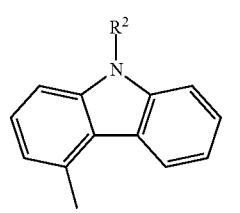
Formula (Ar-5-13)
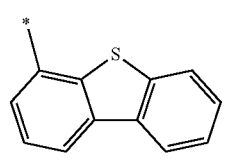

Formula (Ar-5-14)
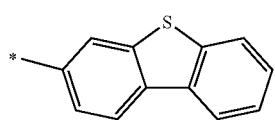
Formula (Ar-5-15)
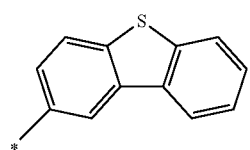
Formula (Ar-5-16)
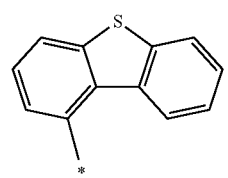
Formula (Ar-5-17)
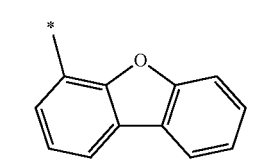
Formula (Ar-5-18)
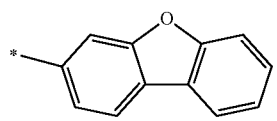
Formula (Ar-5-19)
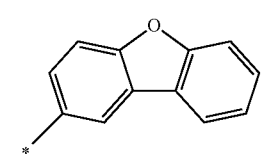
Formula (Ar-5-20)
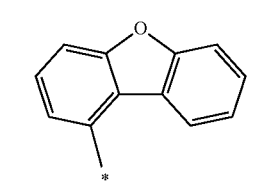
Formula (Ar-6-1)
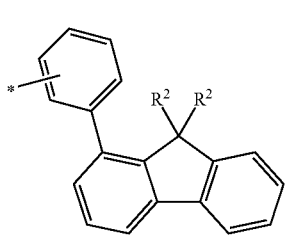
Formula (Ar-6-2)
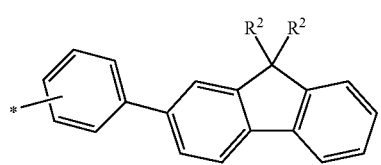
Formula (Ar-6-3)
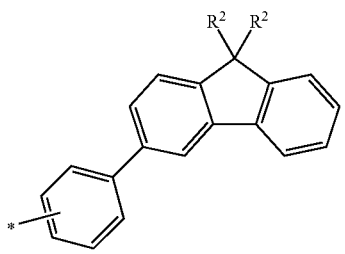
Formula (Ar-6-4)
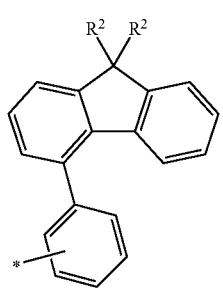
Formula (Ar-6-5)
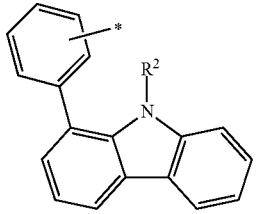
Formula (Ar-6-6)
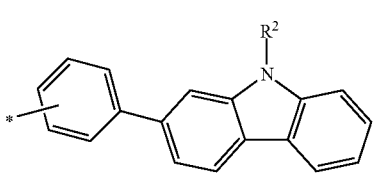
Formula (Ar-6-7)
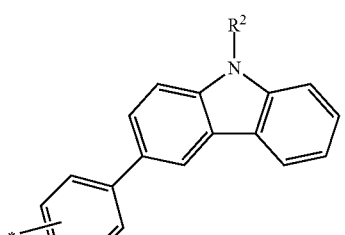
Formula (Ar-6-8)
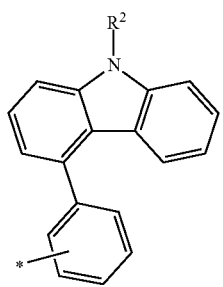

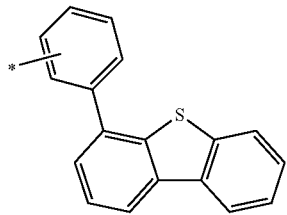
Formula (Ar-6-9)
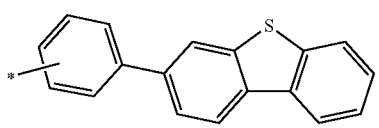
Formula (Ar-6-10)
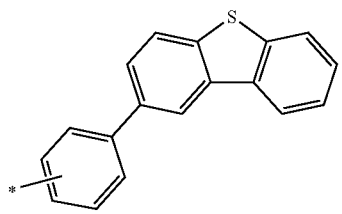
Formula (Ar-6-11)
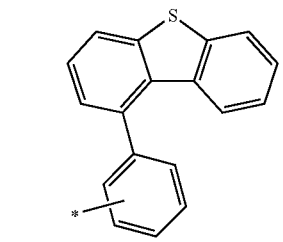
Formula (Ar-6-12)
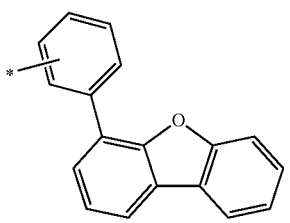
Formula (Ar-6-13)
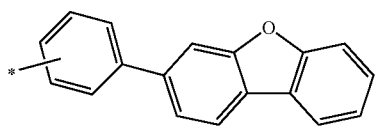
Formula (Ar-6-14)
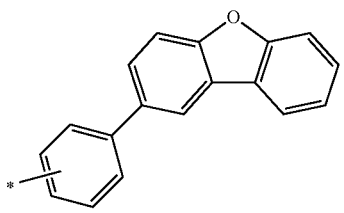
Formula (Ar-6-15)
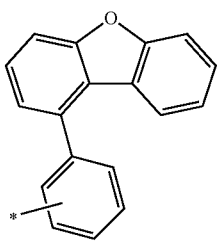
Formula (Ar-6-16)
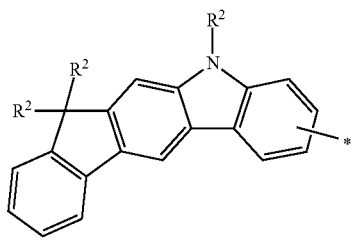
Formula (Ar-8-1-1)
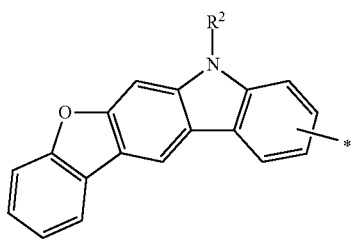
Formula (Ar-8-1-2)
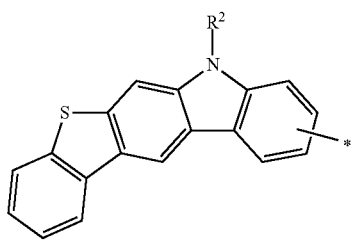
Formula (Ar-8-1-3)
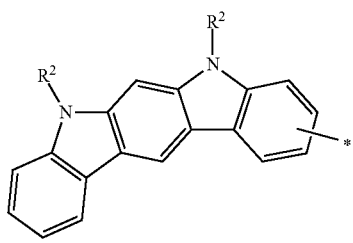
Formula (Ar-8-1-4)
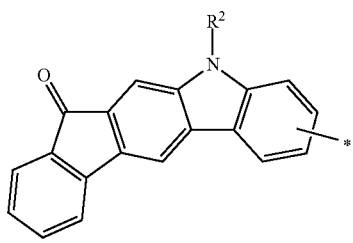
Formula (Ar-8-1-5)

Formula (Ar-8-1-6)
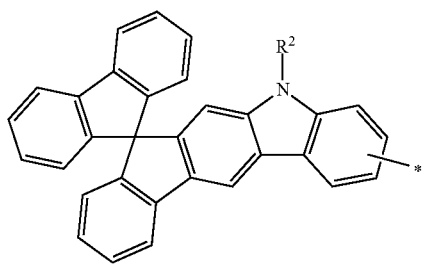
Formula (Ar-8-2-1)
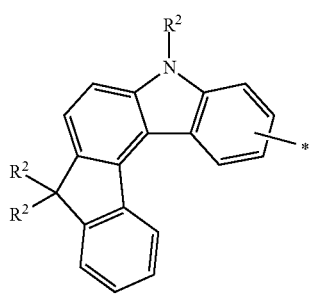
Formula (Ar-8-2-2)
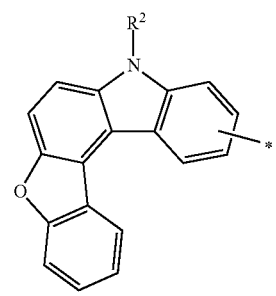
Formula (Ar-8-2-3)
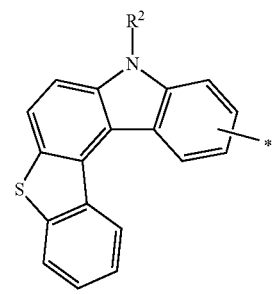
Formula (Ar-8-2-4)
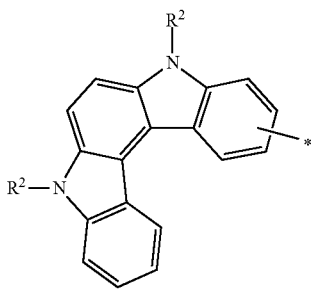
Formula (Ar-8-2-5)
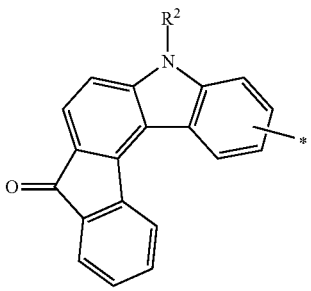
Formula (Ar-8-2-6)
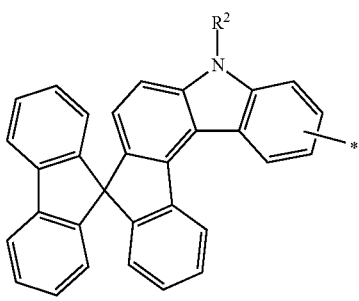
Formula (Ar-8-3-1)
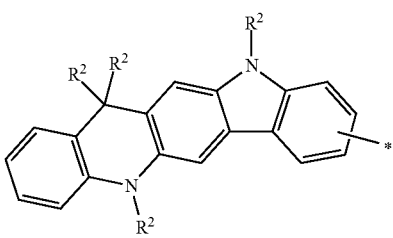
Formula (Ar-8-3-2)
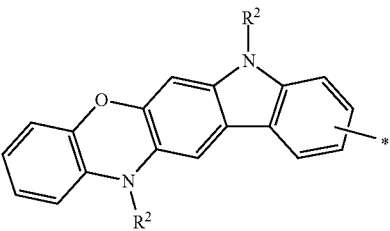
Formula (Ar-8-3-3)
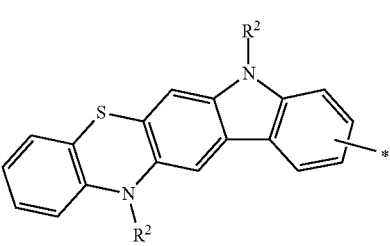

Formula (Ar-8-3-4)
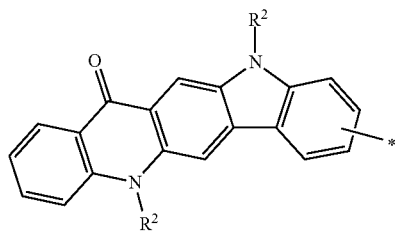
Formula (Ar-8-4-1)
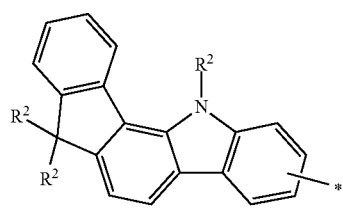
Formula (Ar-8-4-2)
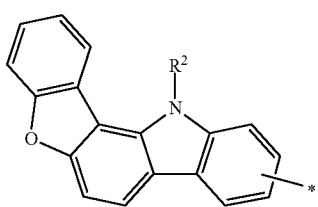
Formula (Ar-8-4-3)
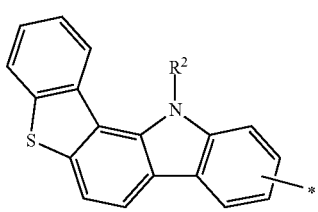
Formula (Ar-8-4-4)
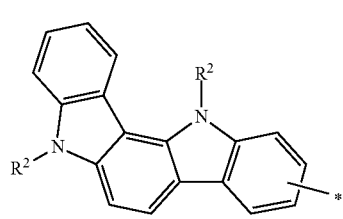
Formula (Ar-8-4-5)
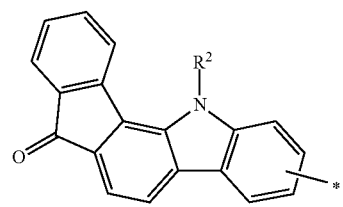
Formula (Ar-8-4-6)
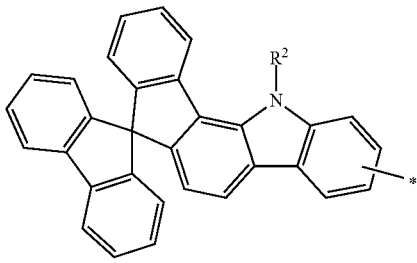
Formula (Ar-8-5-1)
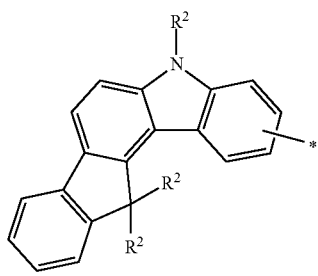
Formula (Ar-8-5-2)
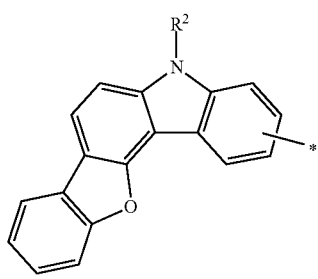
Formula (Ar-8-5-3)
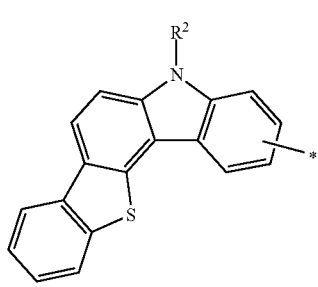
Formula (Ar-8-5-4)
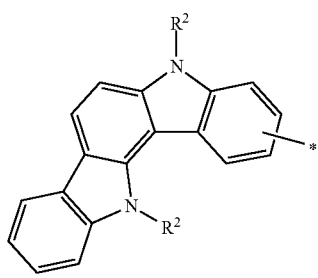

Formula (Ar-8-5-5)
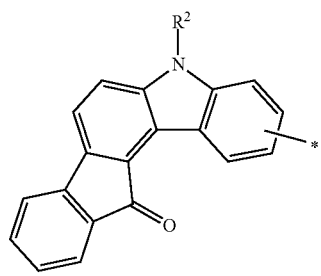
Formula (Ar-8-5-6)
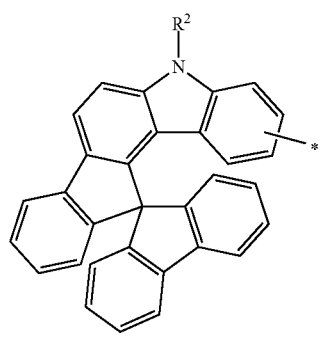
Formula (Ar-8-6-1)
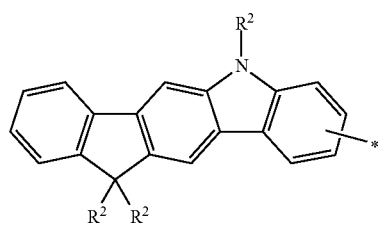
Formula (Ar-8-6-2)
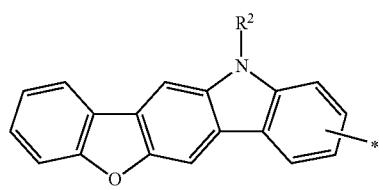
Formula (Ar-8-6-3)
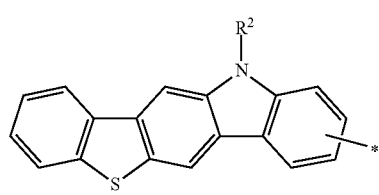
Formula (Ar-8-6-4)
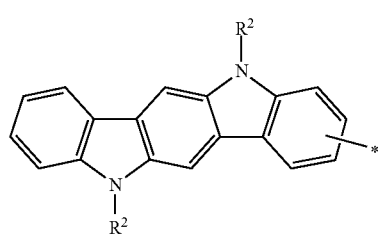
Formula (Ar-8-6-5)
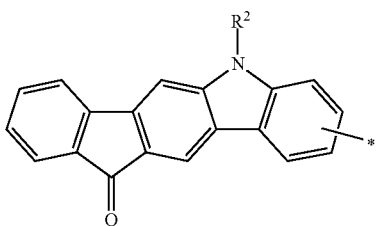
Formula (Ar-8-6-6)
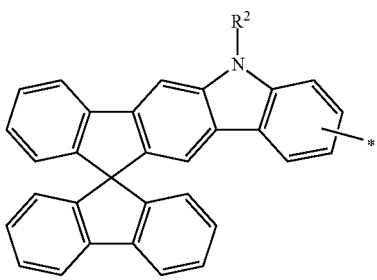
Formula (Ar-8-7-1)
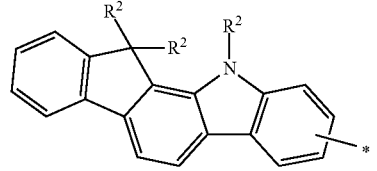
Formula (Ar-8-7-2)
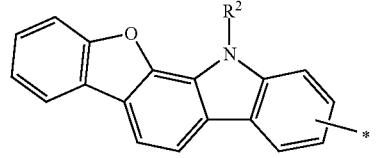
Formula (Ar-8-7-3)
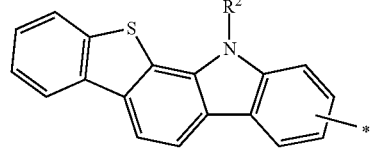
Formula (Ar-8-7-4)
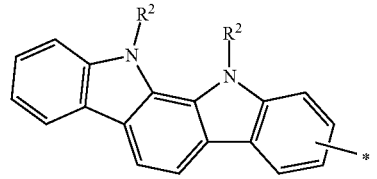
Formula (Ar-8-7-5)
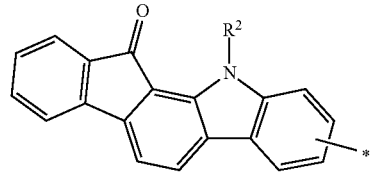

Formula (Ar-8-7-6)

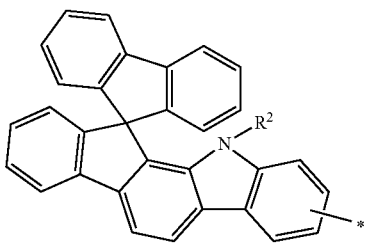

Formula (Ar-9-1)

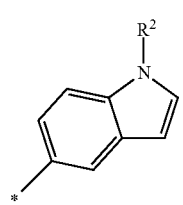

Formula (Ar-10-1)

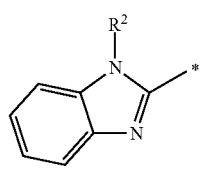

Formula (Ar-11-1)

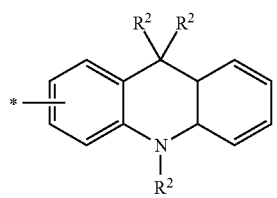

Formula (Ar-11-2)

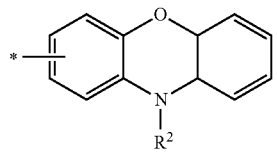

Formula (Ar-11-3)

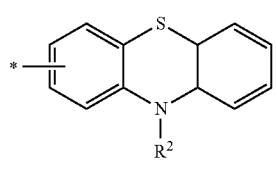

Formula (Ar-11-4)

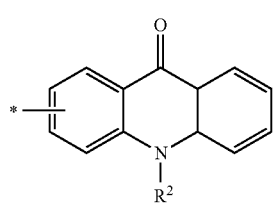

Formula (Ar-13-1)

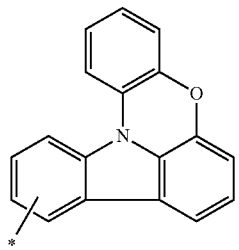

where the symbols correspond to the symbols in formula (1). The formulae may be substituted by $R^2$ at the free positions.

In a further embodiment of the invention, the $Ar^3$ and $Ar^4$ groups are the same or different at each instance and are selected from the formulae (Ar-1) to (Ar-14), preferably from the formulae (Ar-1) to (Ar-13), or the preferred formulae (Ar-1-1) to (Ar-13-1), and the following preferred formulae (Ar-15-1) to (Ar-19-4):

Formula (Ar-15-1)

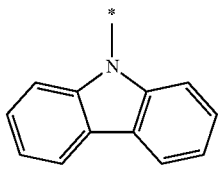

Formula (Ar-16-1)

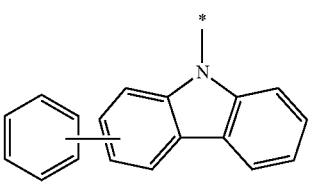

Formula (Ar-17-1)

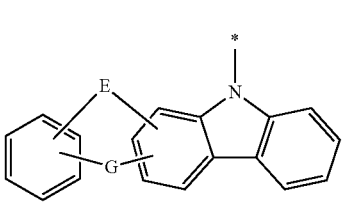

Formula (Ar-18-1)

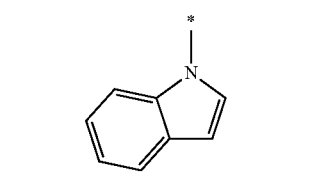

Formula (Ar-19-1)

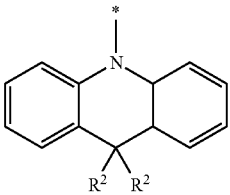

Formula (Ar-19-2)

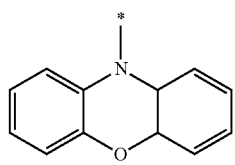

Formula (Ar-19-3)

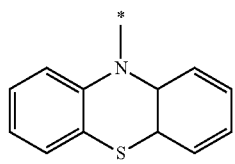

Formula (Ar-19-4)

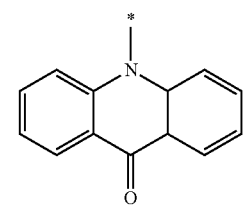

where the symbols correspond to the symbols in the formulae (Ar-15) to (Ar-19). The formulae may be substituted by $R^2$ at the free positions.

In a further embodiment of the invention, the groups of formula (Ar-8) or preferred embodiments thereof are selected from the groups of one of the formulae (Ar-8-1-1a) to (Ar-8-7-6a):

Formula (Ar-8-1-1a)

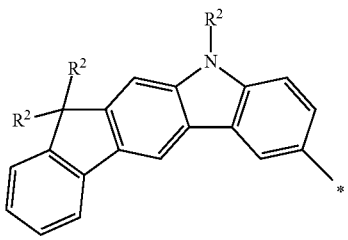

Formula (Ar-8-1-2a)

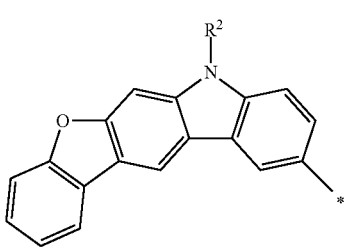

Formula (Ar-8-1-3a)

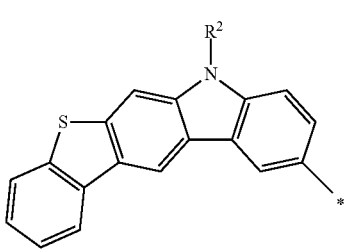

Formula (Ar-8-1-4a)

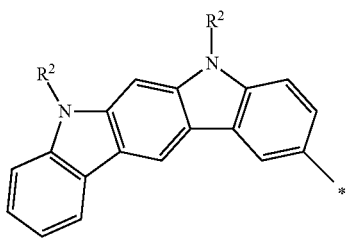

Formula (Ar-8-1-5a)

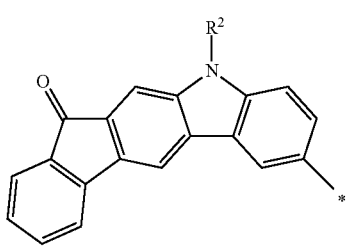

Formula (Ar-8-1-6a)

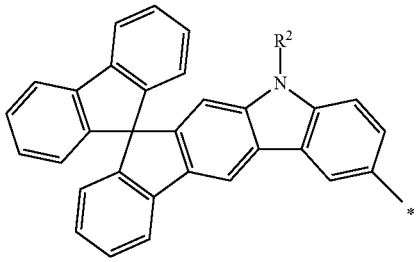

Formula (Ar-8-2-1a)

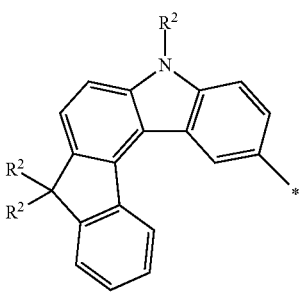

Formula (Ar-8-2-2a)

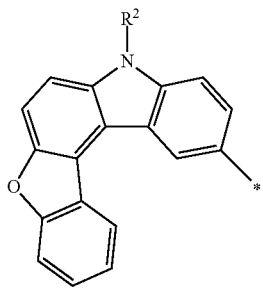

Formula (Ar-8-2-3a)
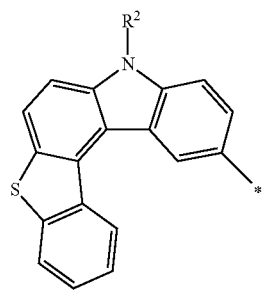
Formula (Ar-8-2-4a)
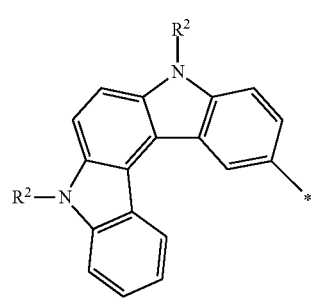
Formula (Ar-8-2-5a)
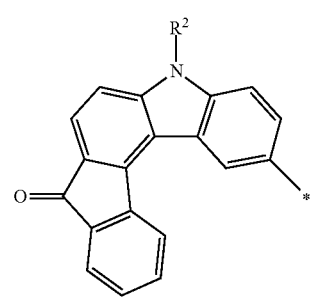
Formula (Ar-8-2-6a)
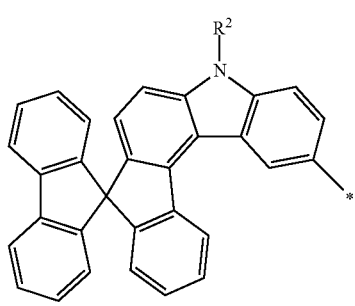
Formula (Ar-8-3-1a)
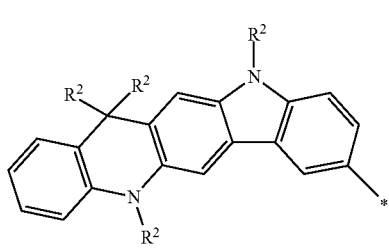
Formula (Ar-8-3-2a)
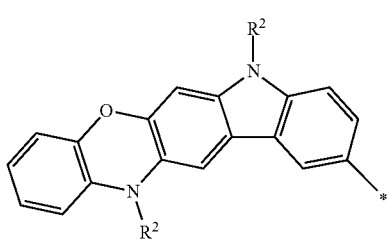
Formula (Ar-8-3-3a)
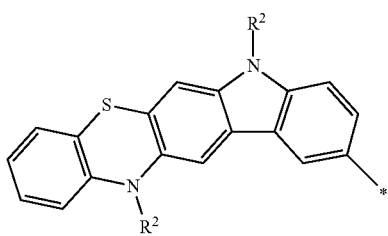
Formula (Ar-8-3-4a)
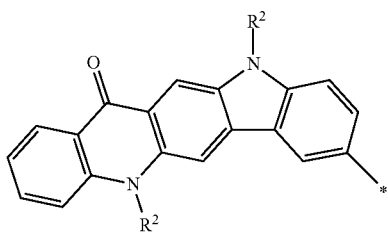
Formula (Ar-8-4-1a)
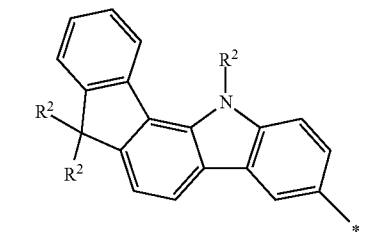
Formula (Ar-8-4-2a)
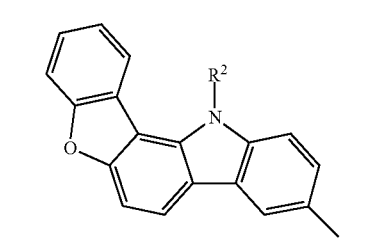
Formula (Ar-8-4-3a)
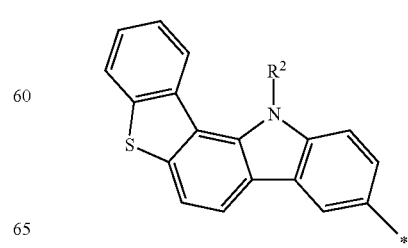

Formula (Ar-8-4-4a)
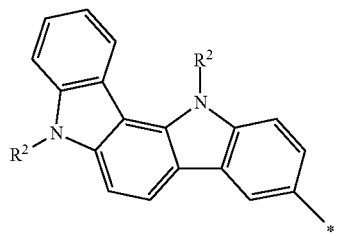
Formula (Ar-8-4-5a)
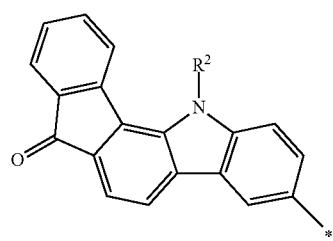
Formula (Ar-8-4-6a)
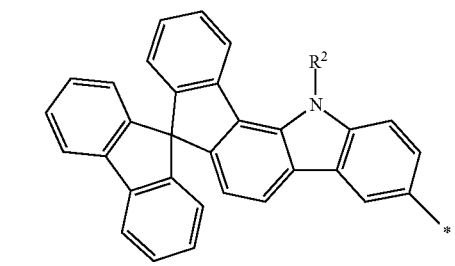
Formula (Ar-8-5-1a)
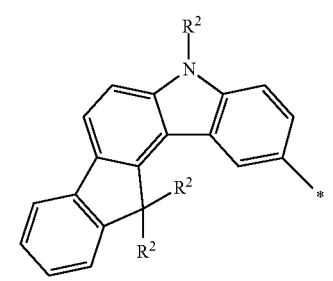
Formula (Ar-8-5-2a)
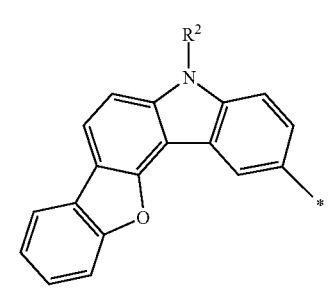
Formula (Ar-8-5-3a)
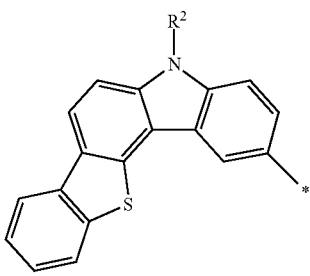
Formula (Ar-8-5-4a)
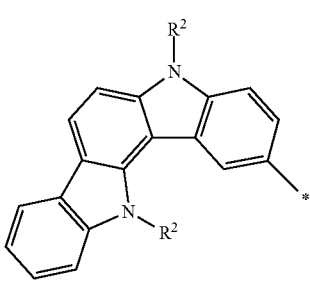
Formula (Ar-8-5-5a)
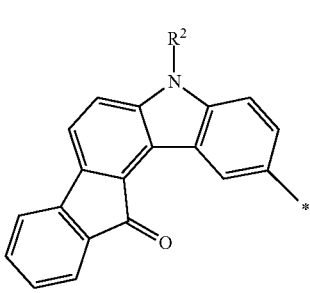
Formula (Ar-8-5-6a)
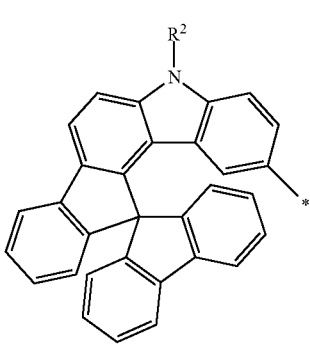
Formula (Ar-8-6-1a)
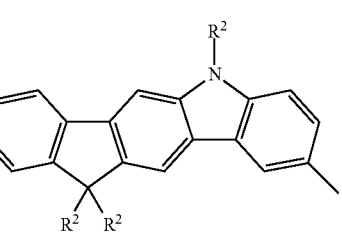
Formula (Ar-8-6-2a)
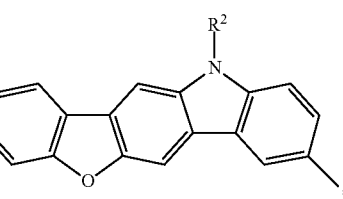

-continued

Formula (Ar-8-6-3a)
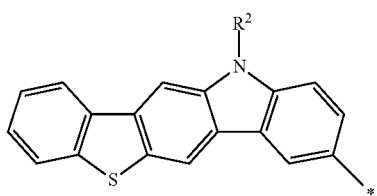

Formula (Ar-8-6-4a)
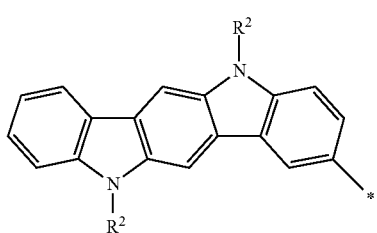

Formula (Ar-8-6-5a)
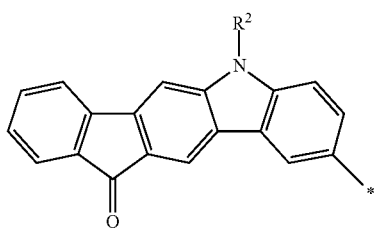

Formula (Ar-8-6-6a)
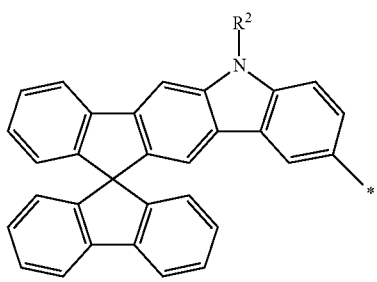

Formula (Ar-8-7-1a)
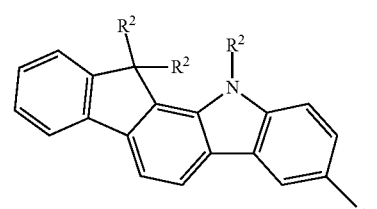

Formula (Ar-8-7-2a)
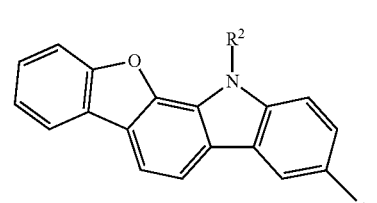

Formula (Ar-8-7-3a)
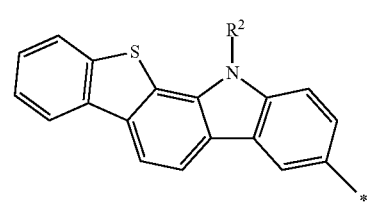

Formula (Ar-8-7-4a)
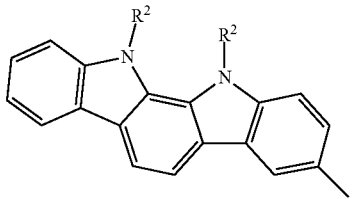

Formula (Ar-8-7-5a)
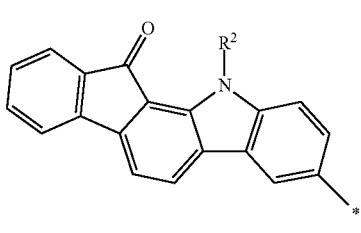

Formula (Ar-8-7-6a)
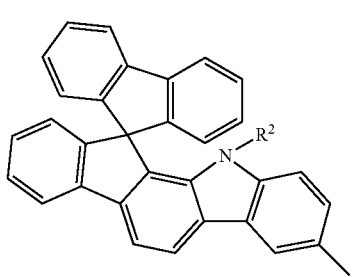

where the symbols correspond to the symbols in formula (1). The formulae may be substituted by $R^2$ at the free positions.

In a further particularly preferred embodiment of the invention, at least one $Ar^1$, $Ar^2$, $Ar^3$ or $Ar^4$ group is selected from one of the formulae (Ar-8-1-1) to (Ar-8-7-6), preferably from one of the formulae (Ar-8-1-1a) to (Ar-8-7-6a).

When one or more $L^1$, $L^2$, $L^3$ and/or $L^4$ groups are present, they are preferably a bivalent aromatic or heteroaromatic ring system having 6 to 24 aromatic ring atoms, preferably not containing any fused aryl or heteroaryl group having more than two six-membered rings fused directly to one another. Preferred $L^1$, $L^2$, $L^3$ and/or $L^4$ groups are the same or different and are selected from the group consisting of ortho-, meta- or para-benzene, ortho-, meta- or para-biphenyl, terphenyl, especially ortho-, meta- or para-terphenyl, quaterphenyl, especially ortho-, meta- or para-quaterphenyl, fluorene, 9,9'-spirobifluorene, furan, benzofuran, dibenzofuran, dibenzothiophene, pyrrole, indole or carbazole, where the divalent bond to the base skeleton in the case of carbazole is not via the nitrogen atom. These groups may be substituted by one or more $R^2$ radicals, but are preferably unsubstituted. When $L^1$, $L^2$, $L^3$ and/or $L^4$ are fluorene, they are preferably substituted in the 9 position by two alkyl groups each having 1 to 10 carbon atoms.

In a further embodiment of the invention, the $L^1$, $L^2$, $L^3$ and/or $L^4$ groups are selected from the formulae (Ar2-1) to (Ar2-12):

Formula (Ar2-1)
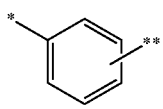

-continued

Formula (Ar2-2)

Formula (Ar2-3)

Formula (Ar2-4)

Formula (Ar2-5)

Formula (Ar2-6)

Formula (Ar2-7)

Formula (Ar2-8)

Formula (Ar2-9)

Formula (Ar2-10)

Formula (Ar2-11)

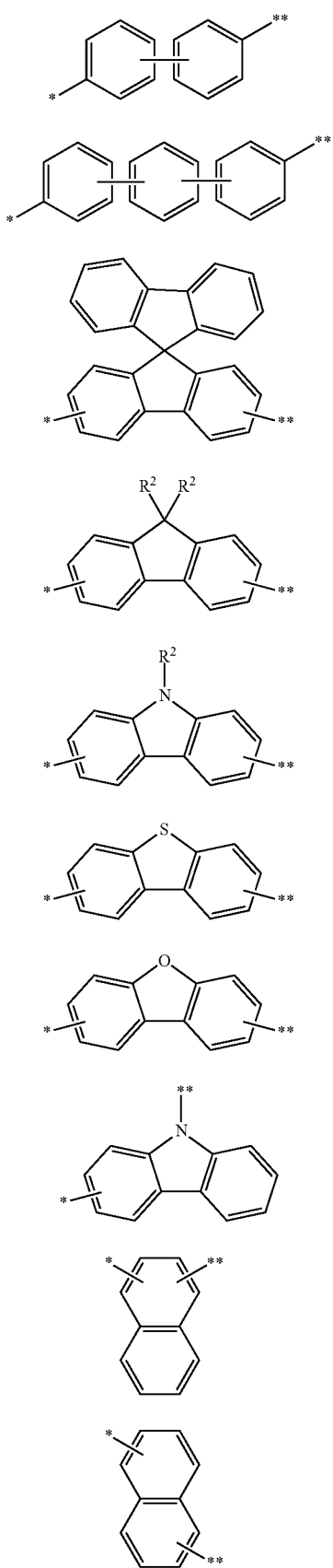

-continued

Formula (Ar2-12)

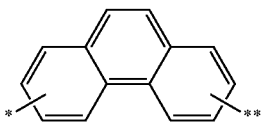

where the symbols used for formula (1) have the definitions given, and the bond identified by * indicates the bond to the base skeleton, the bond identified by ** the bond to the corresponding $Ar^1$, $Ar^2$, $Ar^3$ or $A^4$ radical. The groups may be substituted by $R^2$ at the free positions. They are preferably unsubstituted.

In one embodiment of the invention, at least two groups selected from the $(L^1)_q Ar^1$, $(L^2)_q Ar^2$ and $(L^3)_r (Ar^3)_p$ groups are the same. Preferably, the $(L^1)_q Ar^1$ and $(L^2)_q Ar^2$ groups are the same.

In a further embodiment of the invention, the compound of the formula (1) does not comprise two dibenzofuran derivatives and/or dibenzothiophene derivatives. These may be unsubstituted dibenzofurans (e.g. formulae (Ar-5-17), (Ar-5-18), (Ar-5-19), (Ar-5-20), (Ar2-8)) or substituted dibenzofurans (e.g. formulae (Ar-6-13), (Ar-6-14), (Ar-6-15), (Ar-6-16)). Alternatively, the dibenzofuran structure may be part of a fused heteroaromatic ring system (e.g. formulae (Ar-8-1-2), (Ar-8-4-2), (Ar-8-5-2), (Ar-8-6-2), (Ar-8-7-2)). These may be unsubstituted dibenzothiophenes (e.g. formula (Ar-5-13), (Ar-5-14), (Ar-5-15), (Ar-5-16)) or substituted dibenzothiophenes (e.g. formula (Ar-6-9), (Ar-6-10), (Ar-6-11), (Ar-6-12), (Ar2-7)). Alternatively, the dibenzothiophene structure may be part of a fused heteroaromatic ring system (e.g. formulae (Ar-8-1-3), (Ar-8-2-3), (Ar-8-4-3), (Ar-8-5-3), (Ar-8-6-3) or (Ar-8-7-3)).

In a further embodiment of the invention, the $Ar^1$ and $Ar^2$ groups are the same or different at each instance and are selected from the formulae (Ar-1) to (Ar-14), preferably (Ar-1) to (Ar-13) or their preferred embodiments, and the $Ar^3$ and $Ar^4$ groups, where present, are the same or different and are selected from the formulae (Ar-1) to (Ar-19) or their preferred embodiments, and the $L^1$, $L^2$, $L^3$ and/or $L^4$ groups, where present, are the same or different and are selected from the formulae (Ar2-1) to (Ar2-12).

In a preferred embodiment of the invention, $R^2$ is the same or different at each instance and is selected from the group consisting of H, D, F, $Si(R^3)_3$, CN, a straight-chain alkyl or alkoxy group having 1 to 10 carbon atoms or a branched or cyclic alkyl or alkoxy group having 3 to 10 carbon atoms, each of which may be substituted by one or more $R^3$ radicals, where one or more nonadjacent $CH_2$ groups may be replaced by 0 and where one or more hydrogen atoms may be replaced by D or F, an aromatic or heteroaromatic ring system which has 6 to 60 aromatic ring atoms and may be substituted in each case by one or more $R^3$ radicals, where two or more adjacent $R^2$ substituents may optionally form a mono- or polycyclic aliphatic ring system which may be substituted by one or more $R^3$ radicals.

In a particularly preferred embodiment of the invention, $R^2$ is the same or different at each instance and is selected from the group consisting of H, D, F, a straight-chain alkyl group having 1 to 10 carbon atoms or a branched or cyclic alkyl group having 3 to 10 carbon atoms, each of which may be substituted by one or more $R^3$ radicals, an aromatic or heteroaromatic ring system which has 6 to 60 carbon atoms and may be substituted in each case by one or more $R^3$ radicals, where two or more adjacent $R^2$ substituents may optionally form a mono- or polycyclic aliphatic ring system which may be substituted by one or more R³ radicals.

In a further preferred embodiment, R² which binds to a carbon bridge in an aromatic or heteroaromatic ring system, as, for example, in the formulae (Ar-5-1), (Ar-5-2), (Ar-5-3), (Ar-5-4), (Ar-6-1), (Ar-6-2), (Ar-6-3), (Ar-6-4), (Ar-8-3-1), (Ar-11-1), (Ar-18-1) or (Ar2-8b), is the same or different at each instance and is selected from the group consisting of a straight-chain alkyl group having 1 to 10 carbon atoms, a branched or cyclic alkyl group having 3 to 10 carbon atoms or an aromatic ring system having 6 to 30 carbon atoms which is as defined above and which may be substituted by one or more R³ radicals. In this case, the two R² groups may also form a ring system with one another, which may be aliphatic or, in addition to the definition of R² given above, may also be aromatic. Ring formation forms a Spiro system.

In a further preferred embodiment, R² which binds to a nitrogen atom is selected from the group consisting of a straight-chain alkyl group having 1 to 10 carbon atoms, a branched or cyclic alkyl group having 3 to 10 carbon atoms or an aromatic ring system having 6 to 30 carbon atoms, especially an aromatic ring system having 6 to 24 carbon atoms which is as defined above and which may be substituted by one or more R³ radicals.

The abovementioned embodiments may be combined with one another as desired. More particularly, it is preferable to combine the preferred embodiments detailed above with one another.

Examples of preferred compounds of the above-detailed embodiments or compounds as usable with preference in organic electronic devices are the following compounds:

(1)

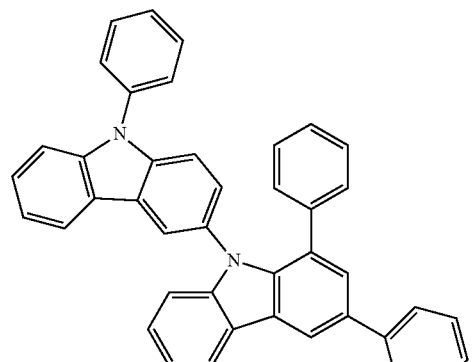

(2)

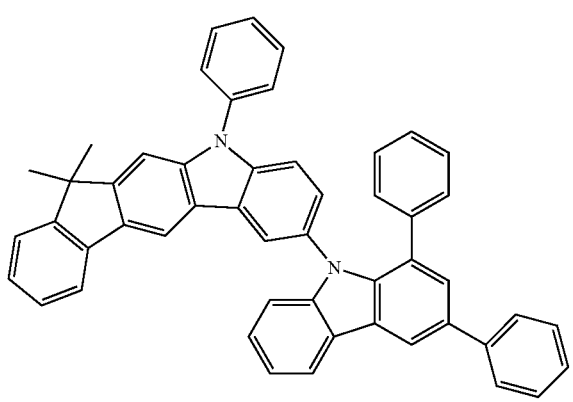

(3)

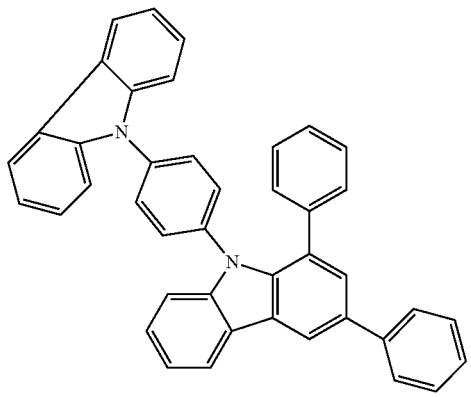

(4)

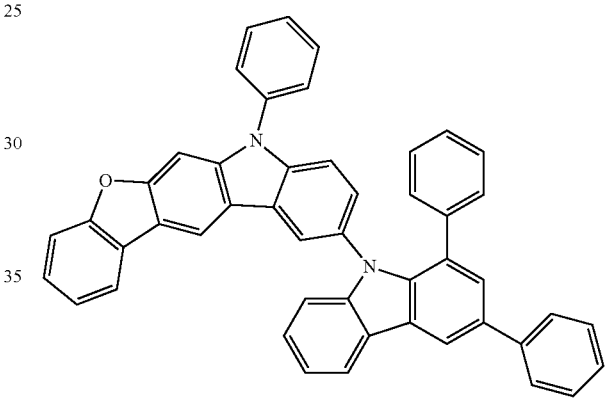

(5)

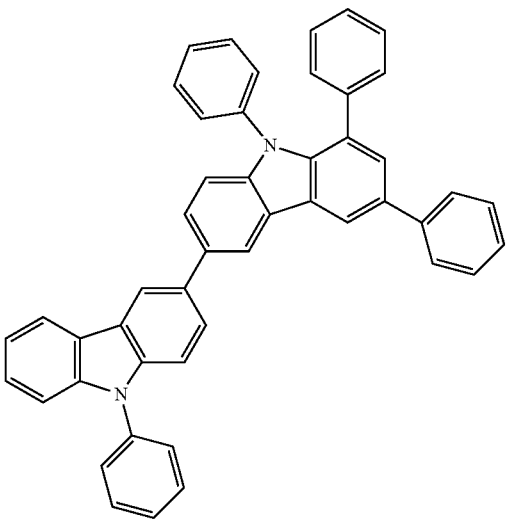

(6)
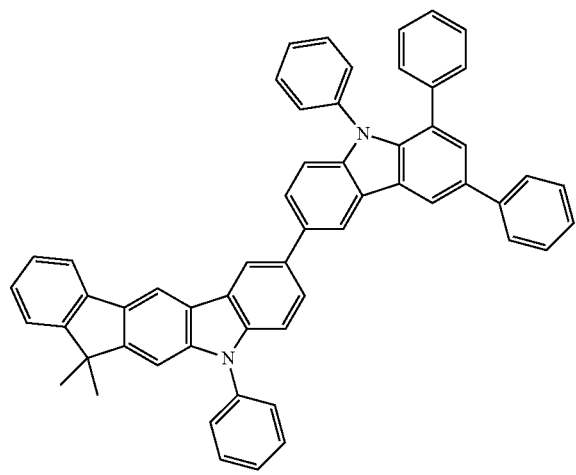
(7)
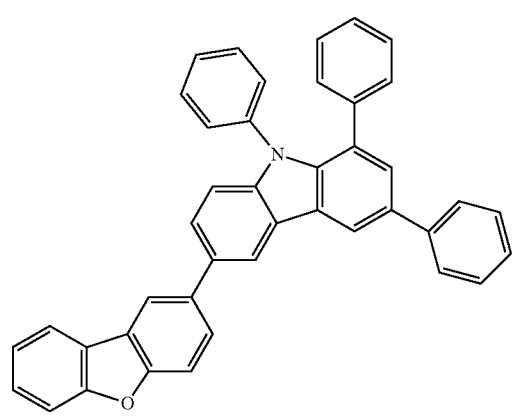
(8)
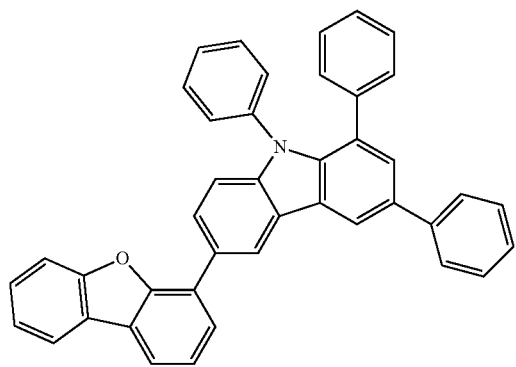
(9)
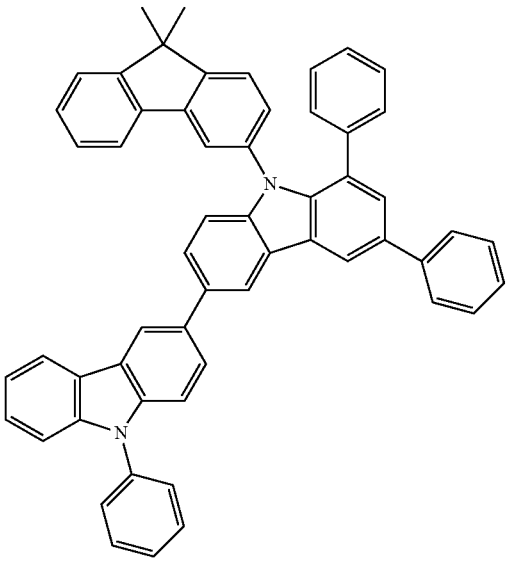
(10)
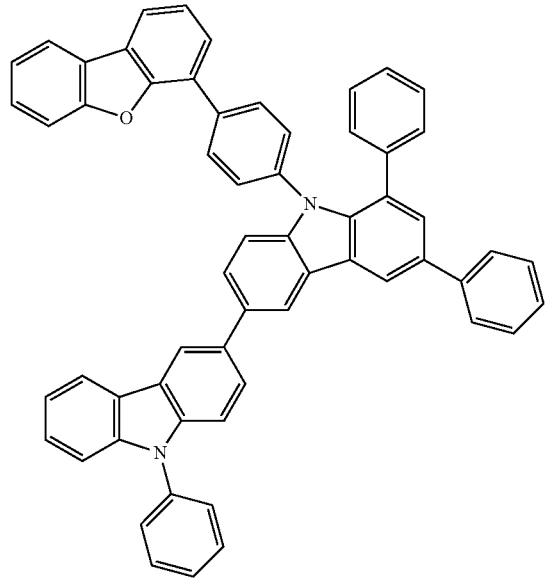
(11)
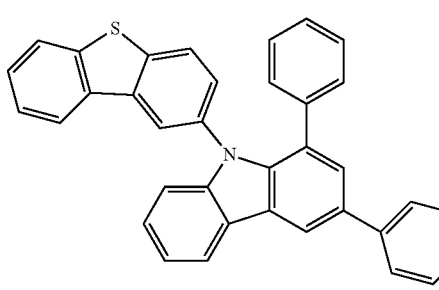

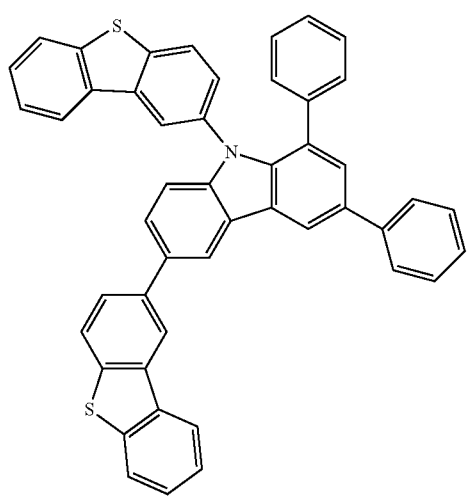
(12)
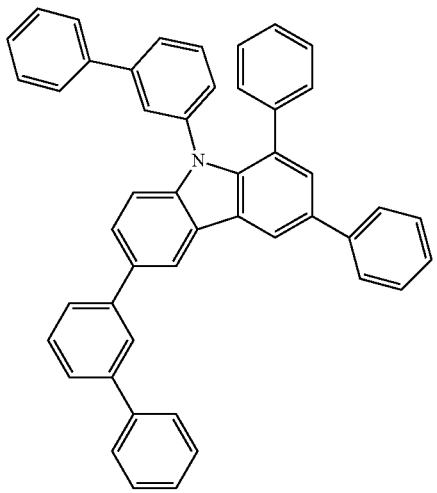
(15)
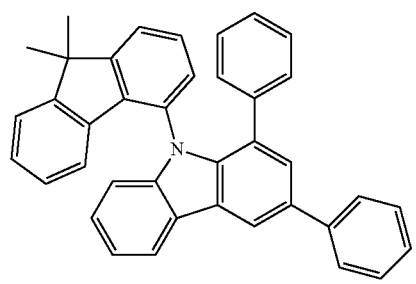
(13)
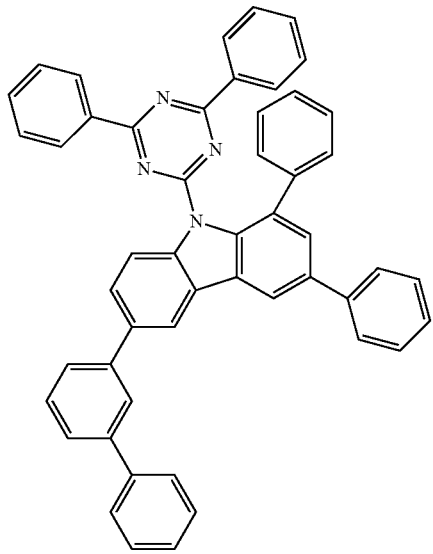
(16)
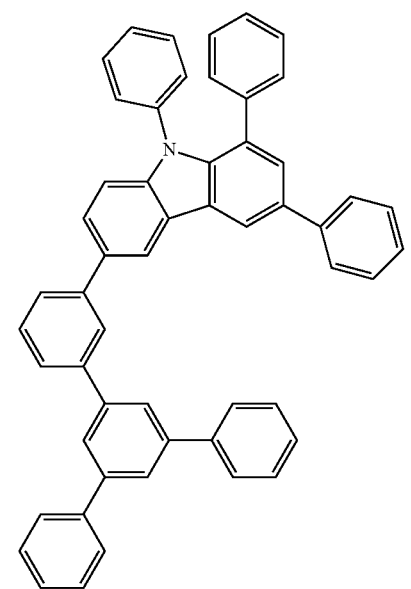
(14)
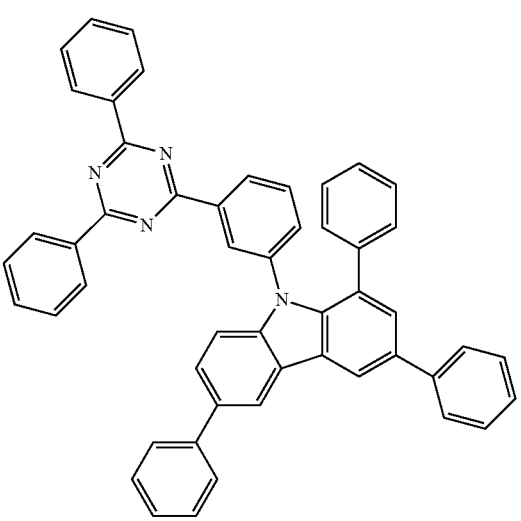
(17)

(18)
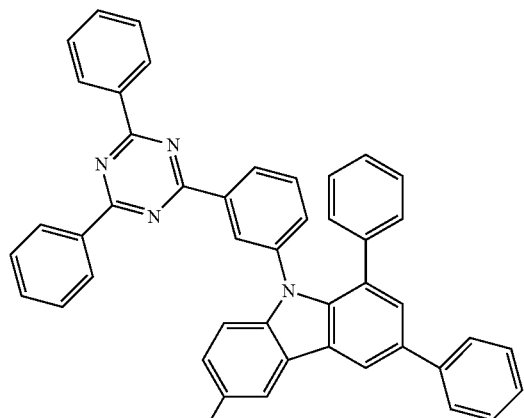
(19)
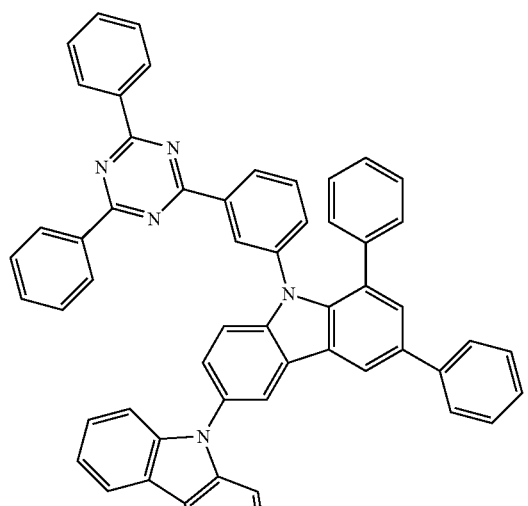
(20)
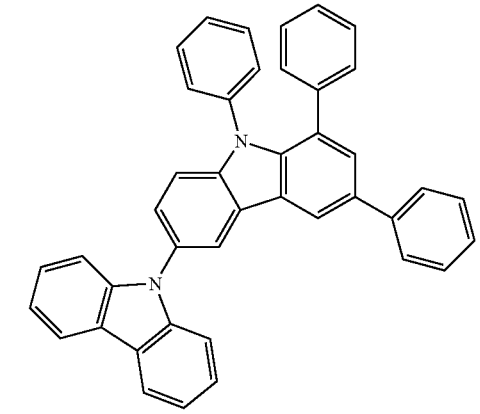
(21)
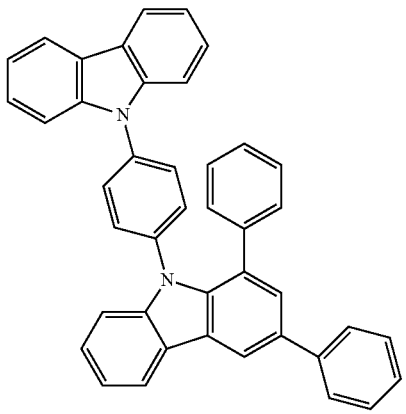
(22)
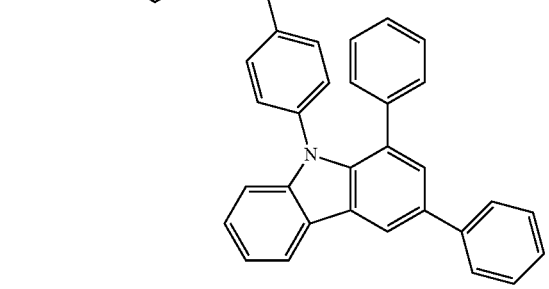
(23)
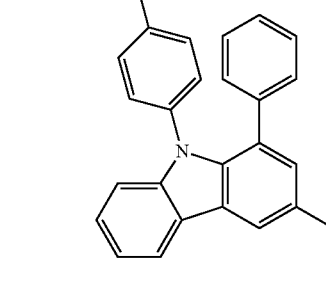

(24)
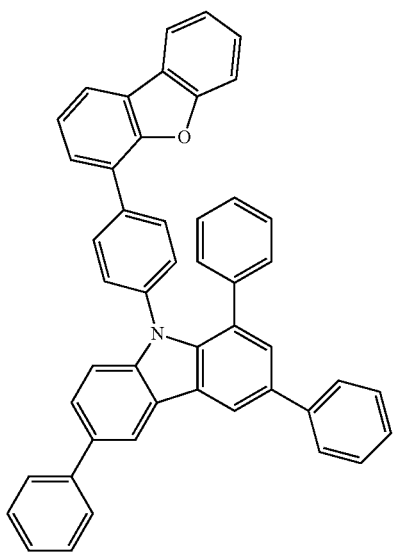
(27)
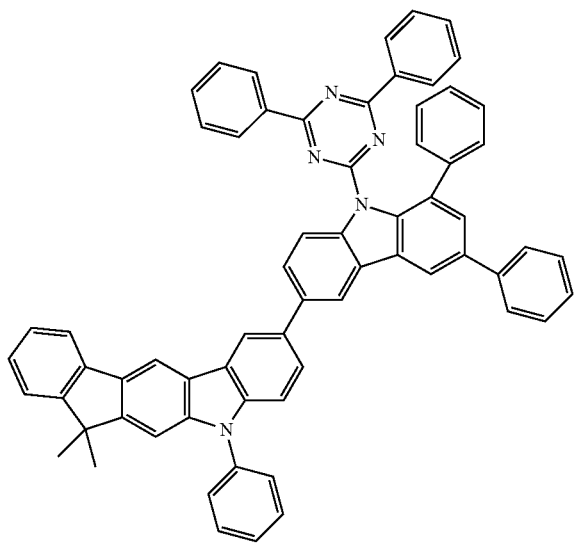
(25)
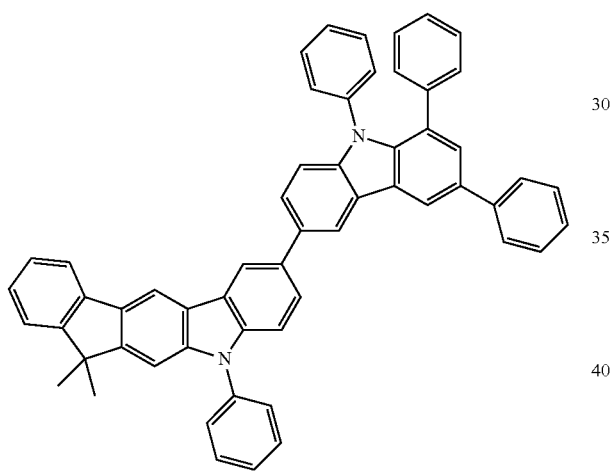
(28)
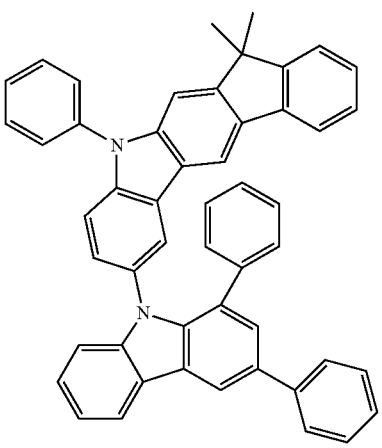
(26)
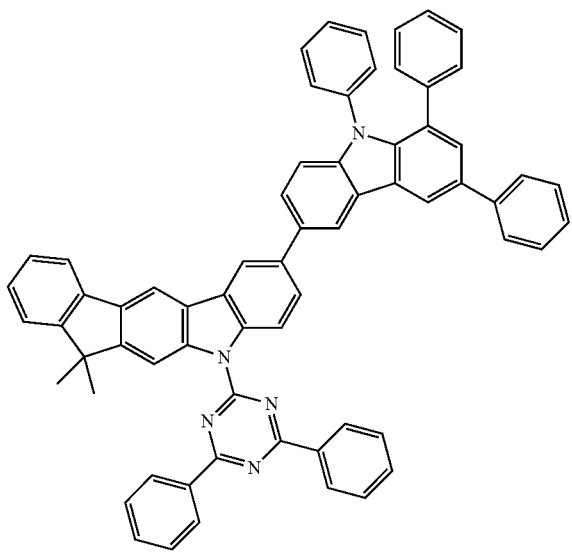
(29)
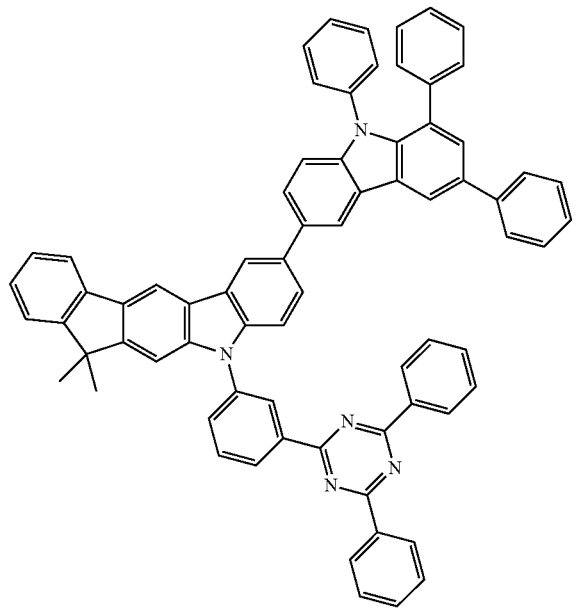

(30)
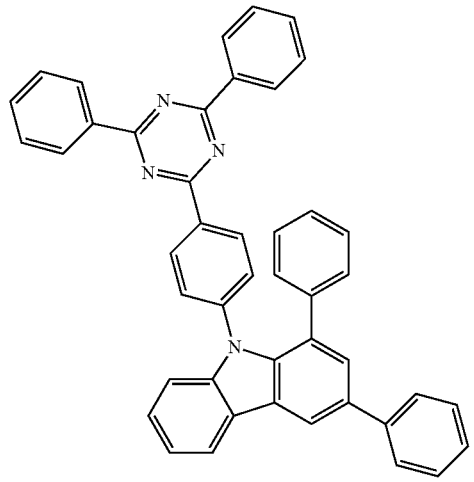
(31)
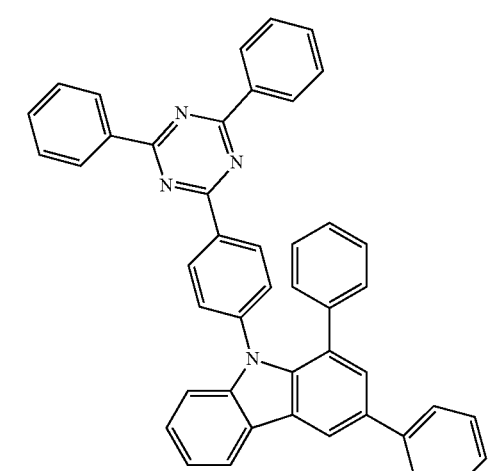
(32)
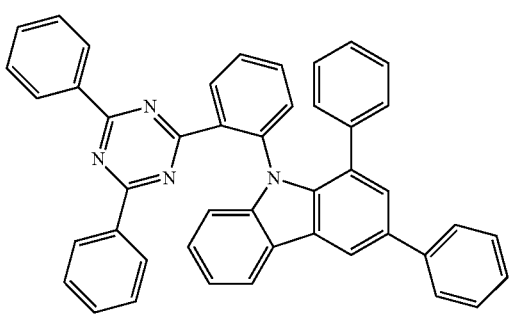
(33)
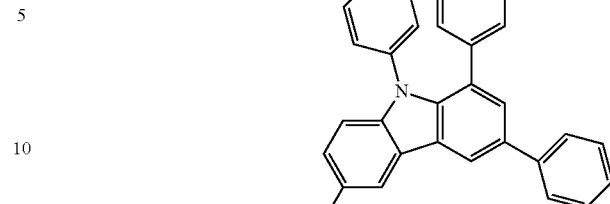
(34)
(35)
(36)
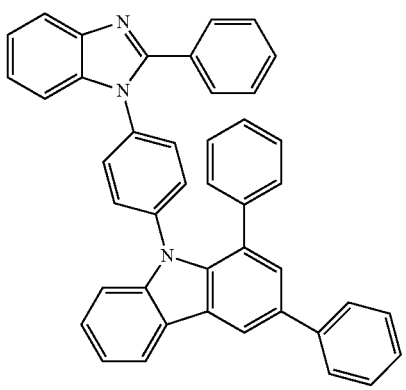

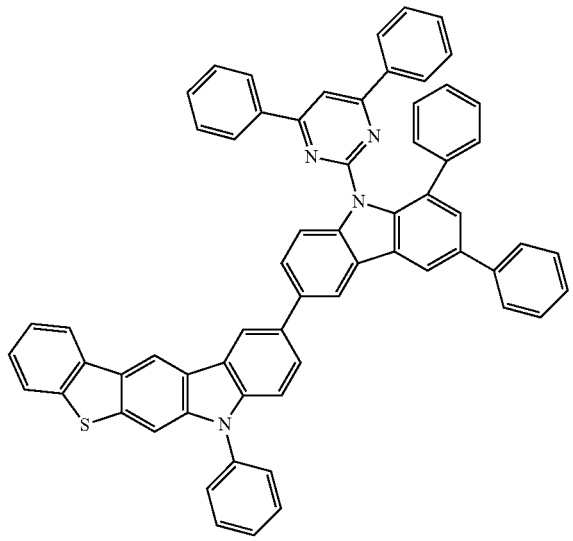
(37)
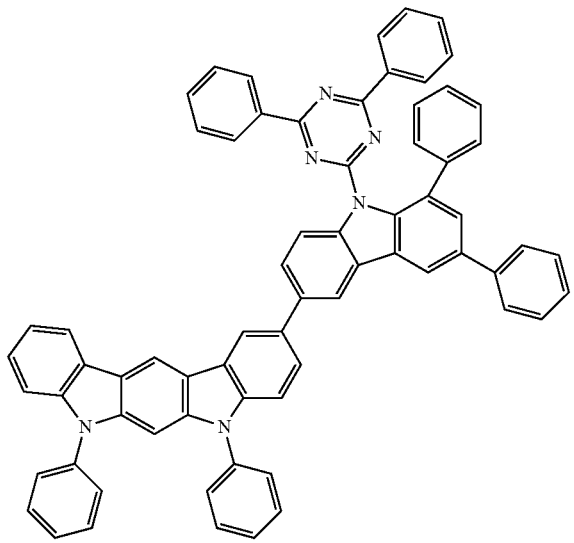
(39)
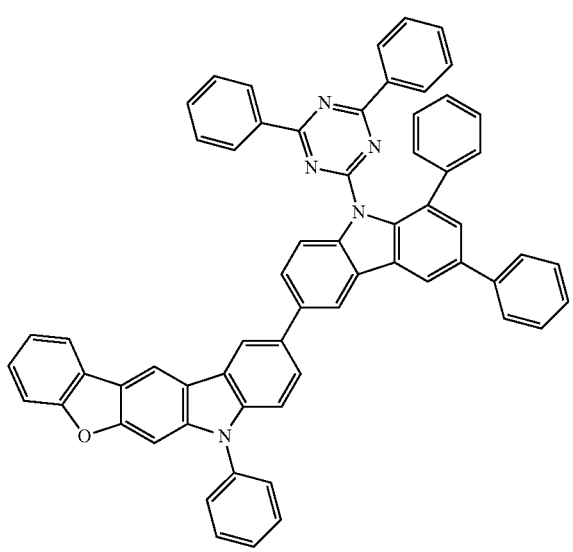
(38)
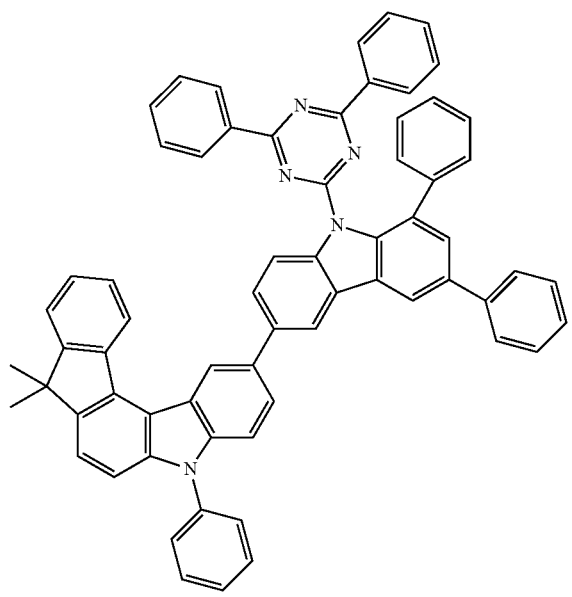
(40)

(41)
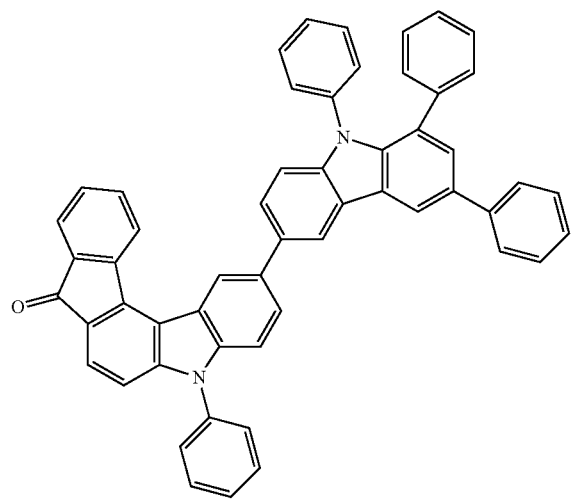
(42)
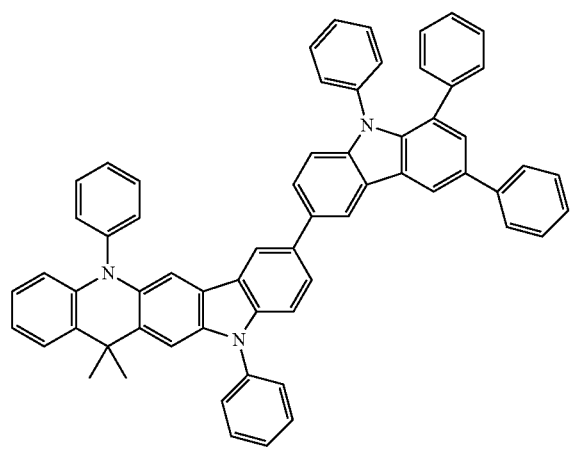
(43)
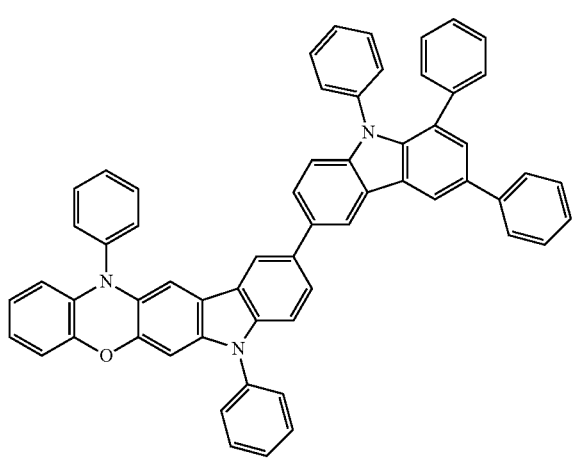
(44)
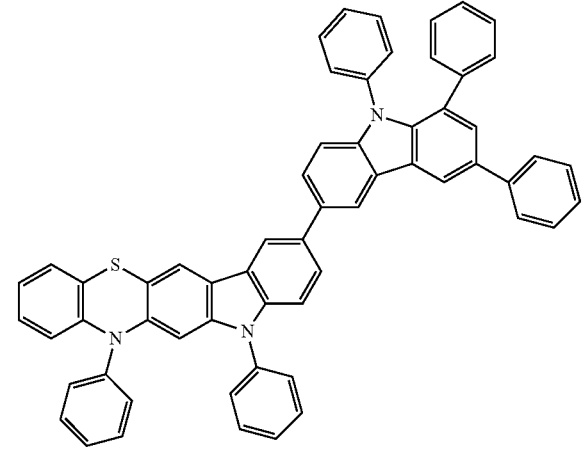
(45)
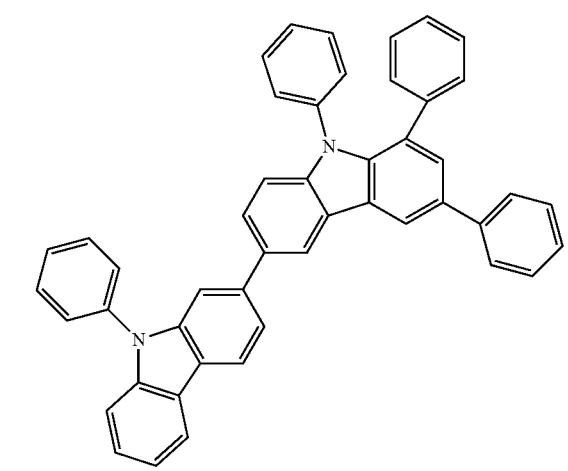
(46)
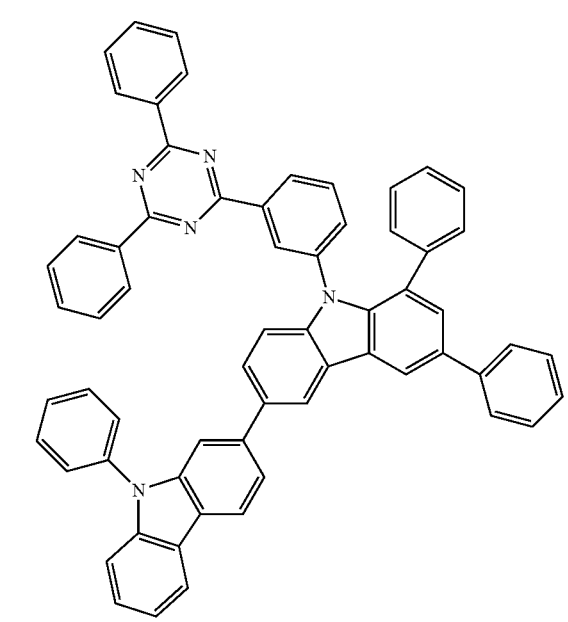

(47)
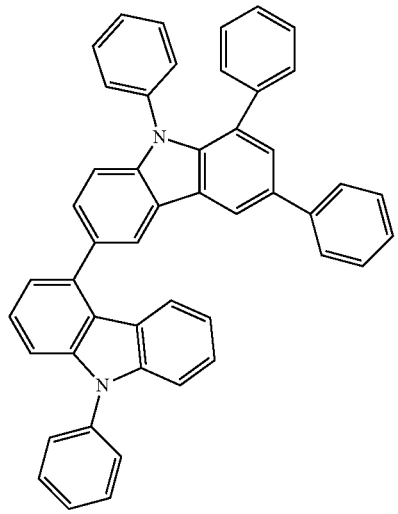
(48)
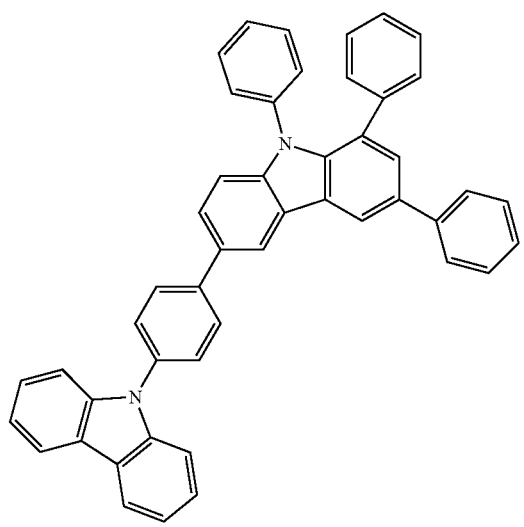
(49)
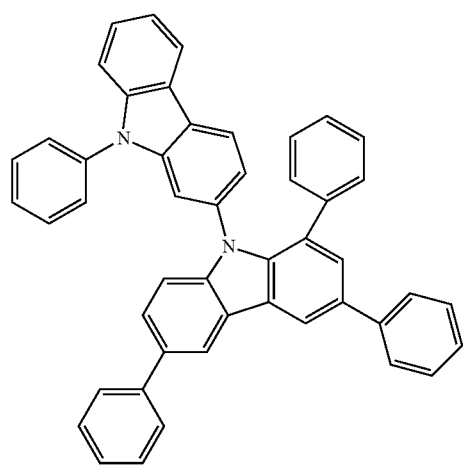
(50)
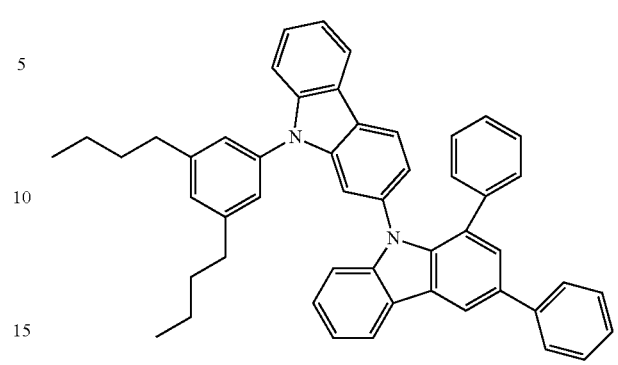
(51)
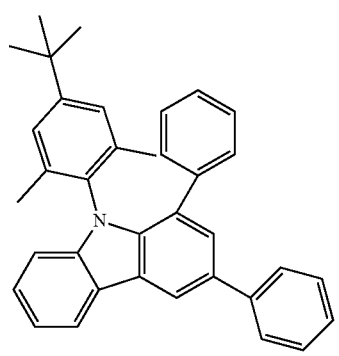
(52)
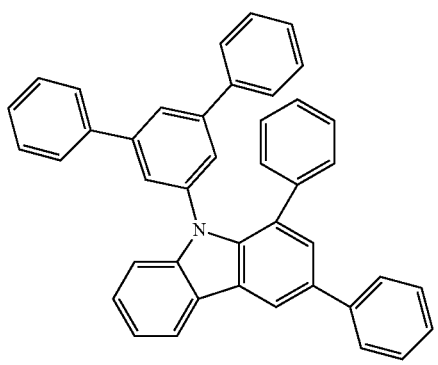
(53)
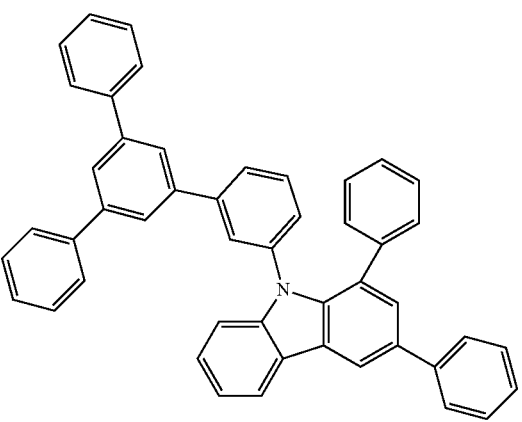

(54)
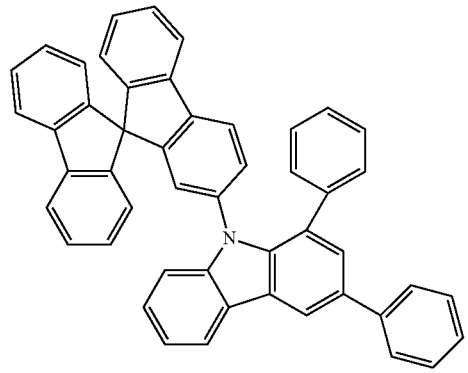
(55)
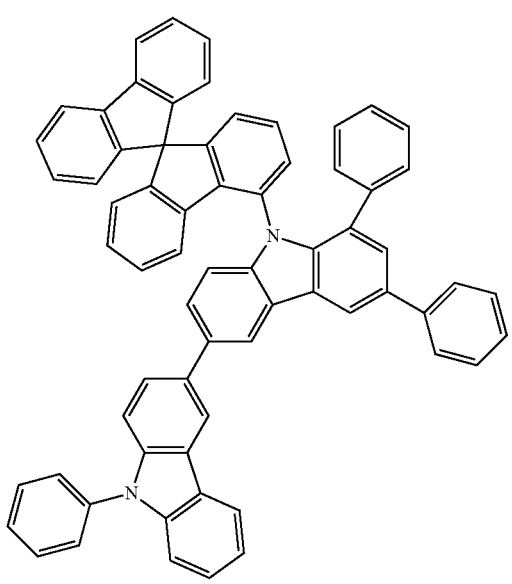
(56)
(57)
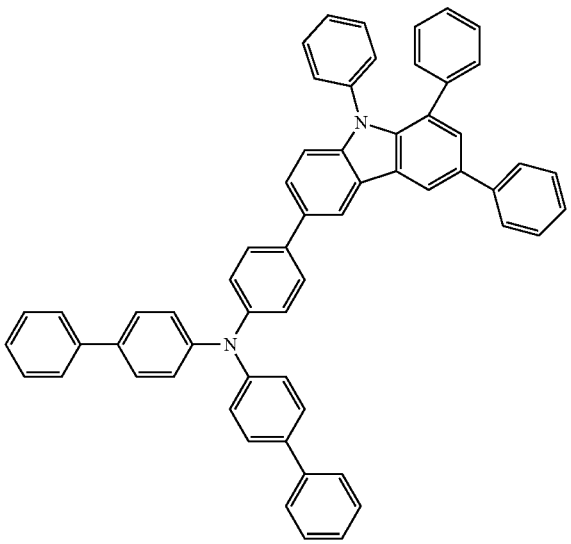
(58)
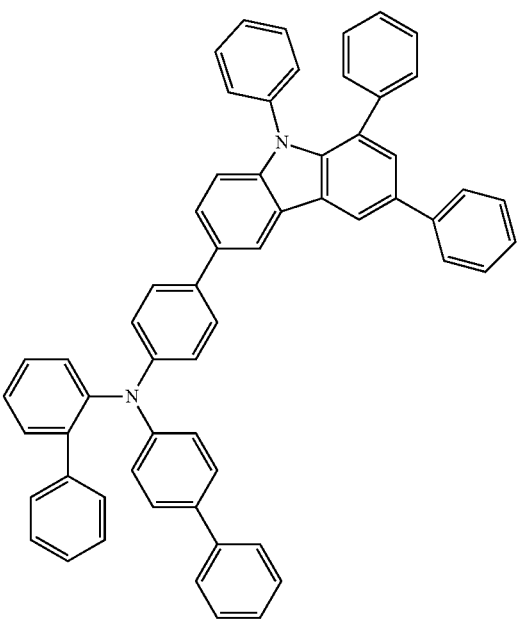

(59)
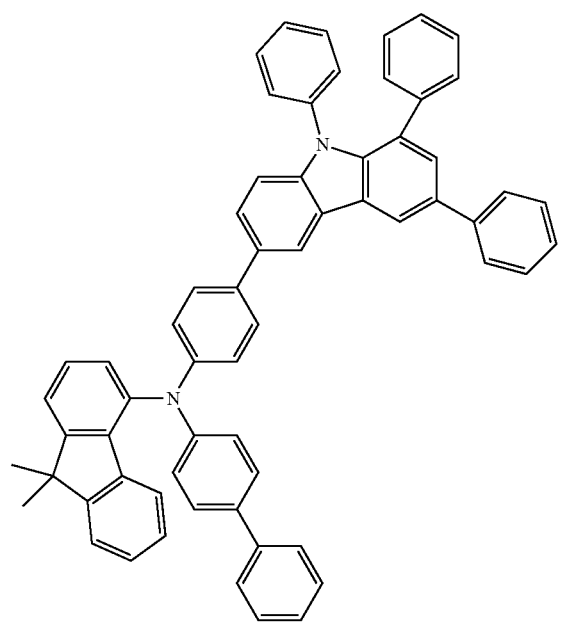
(60)
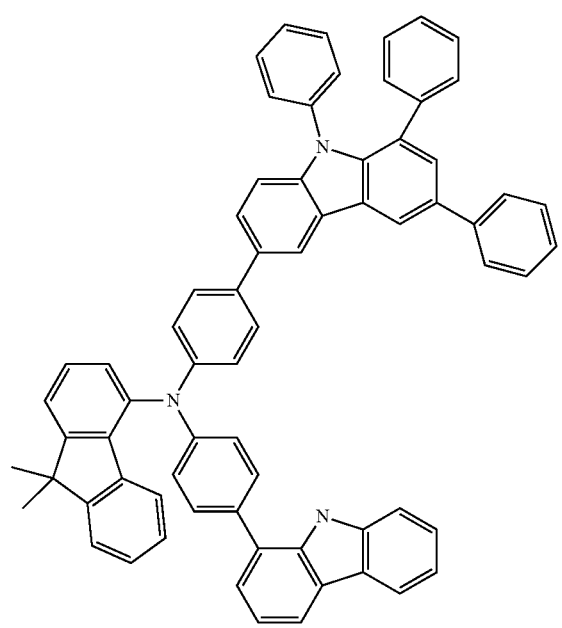
(61)
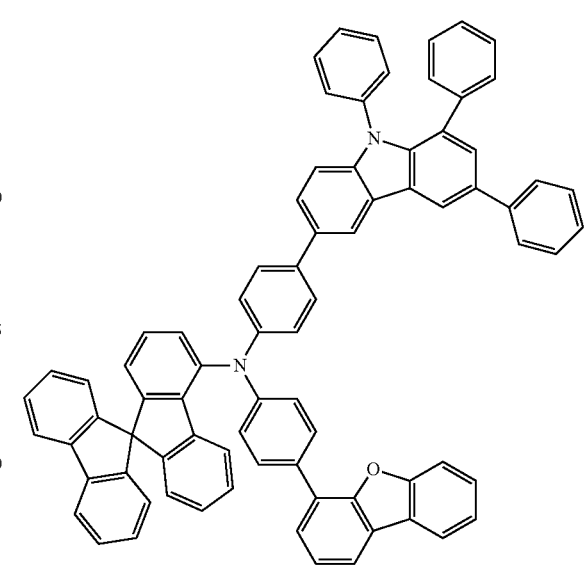
(62)
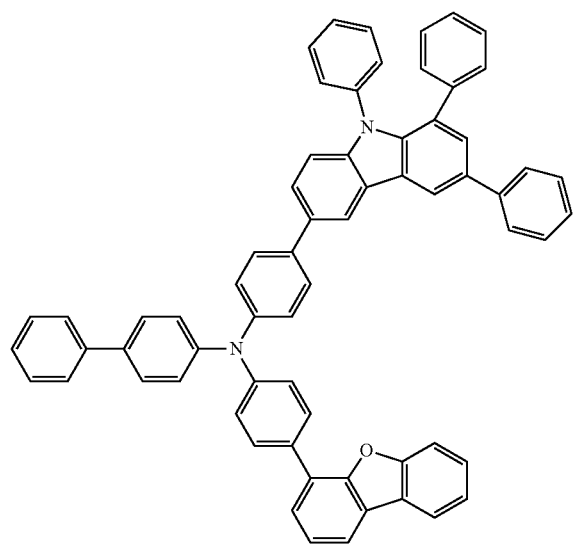

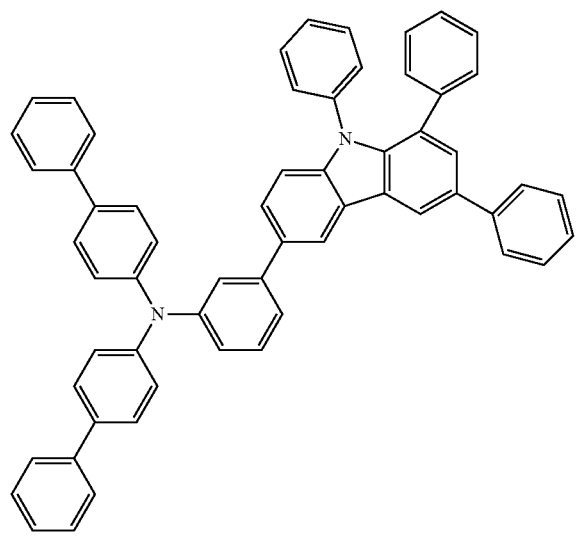
(63)
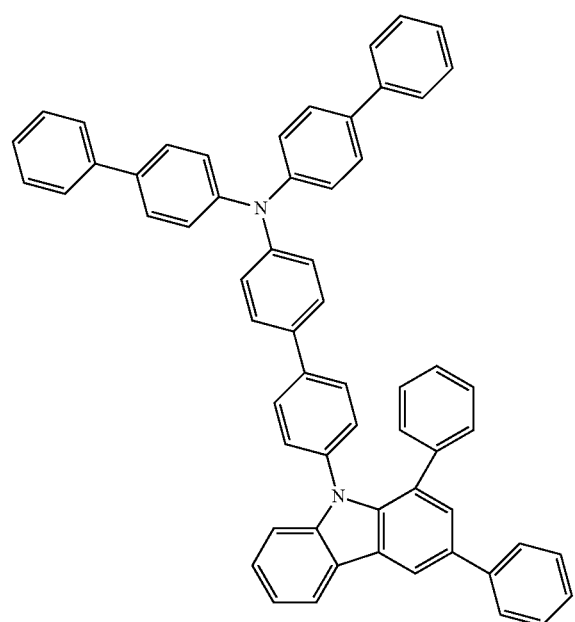
(64)
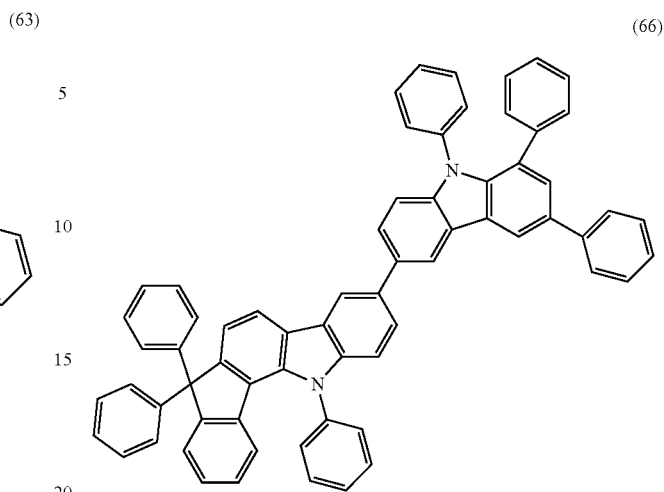
(65)
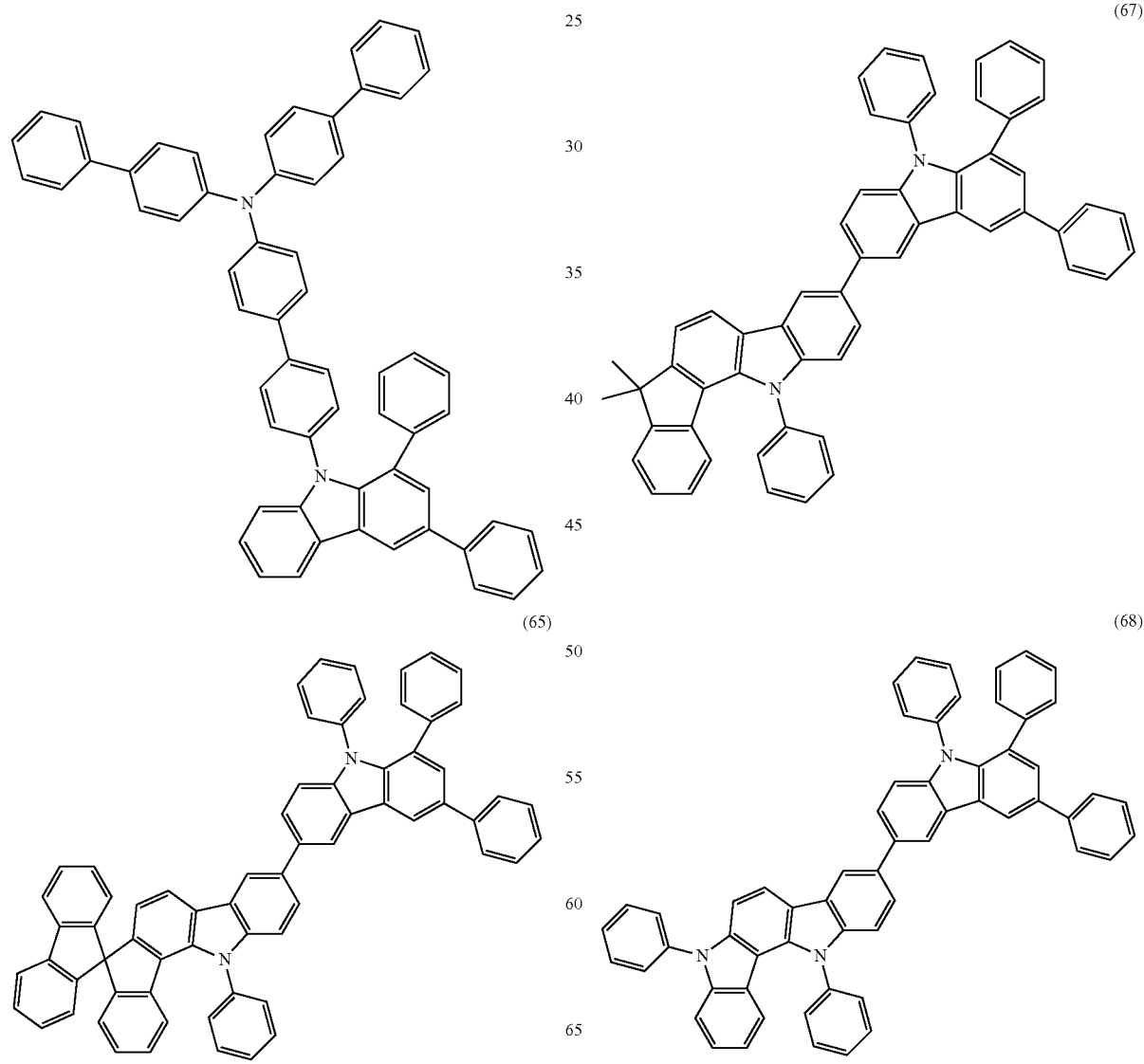
(66)
(67)
(68)

(69)
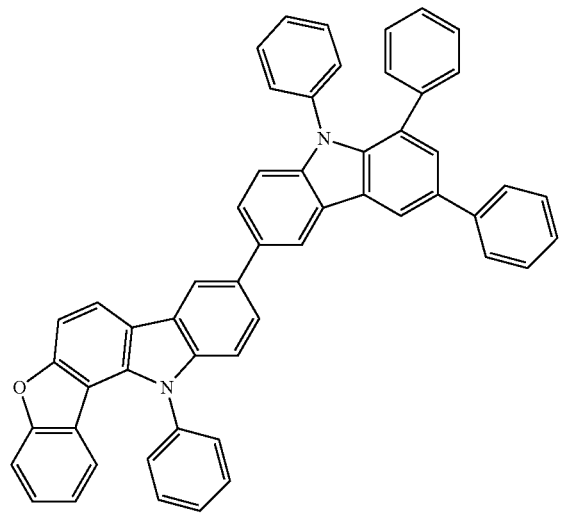
(70)
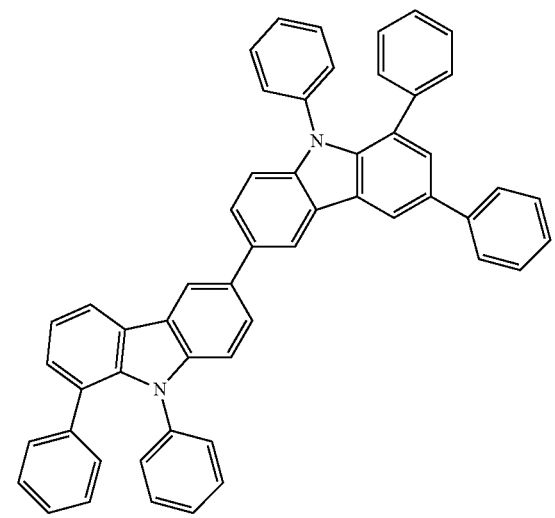
(71)
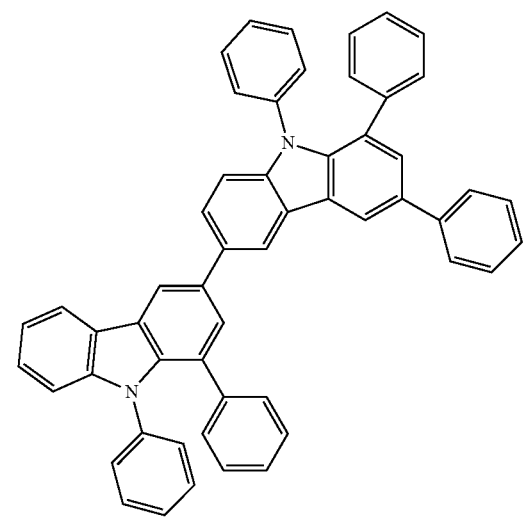
(72)
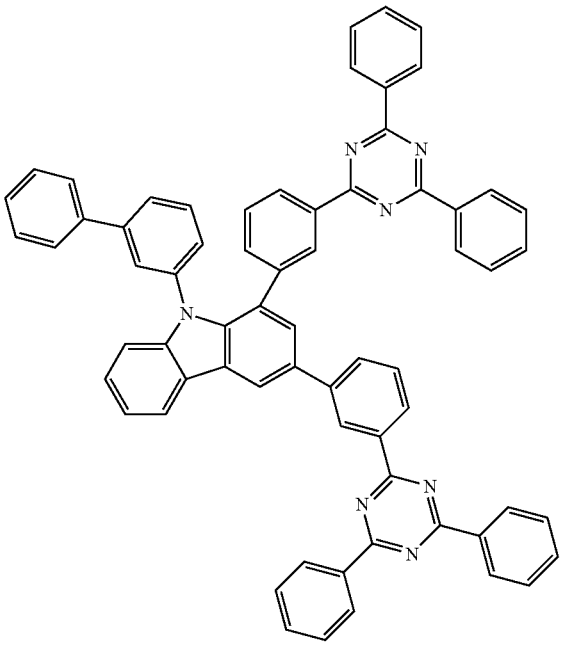
(73)
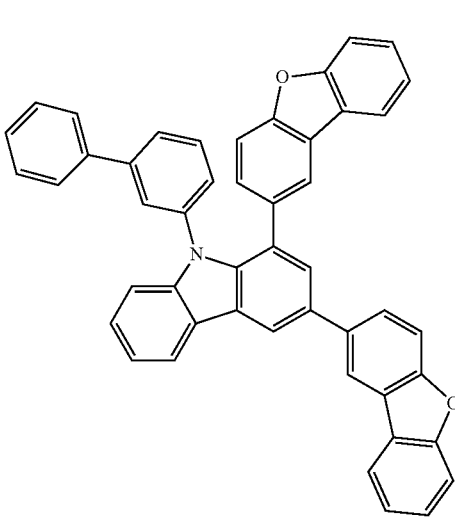

-continued
(74)
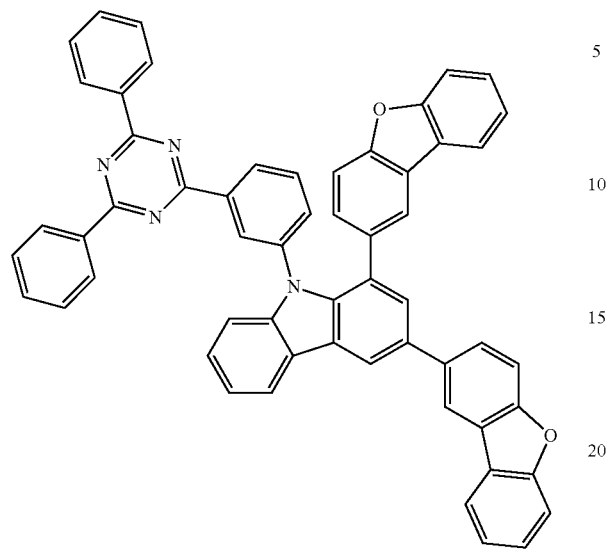
(75)
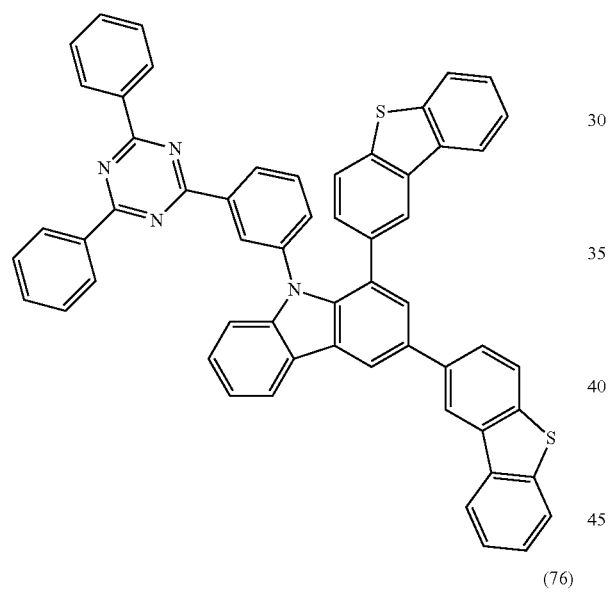
(76)
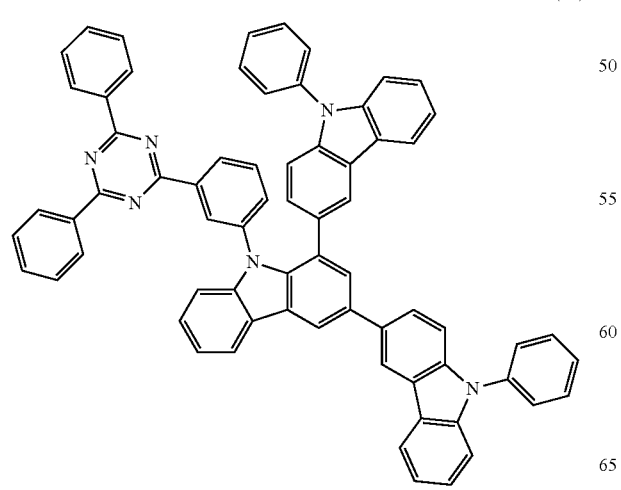
-continued
(77)
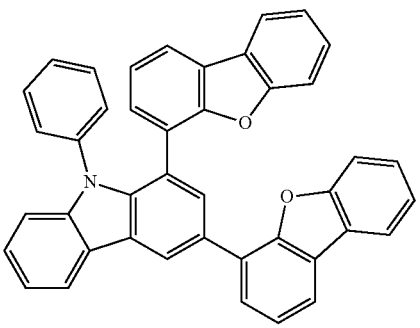
(78)
(79)
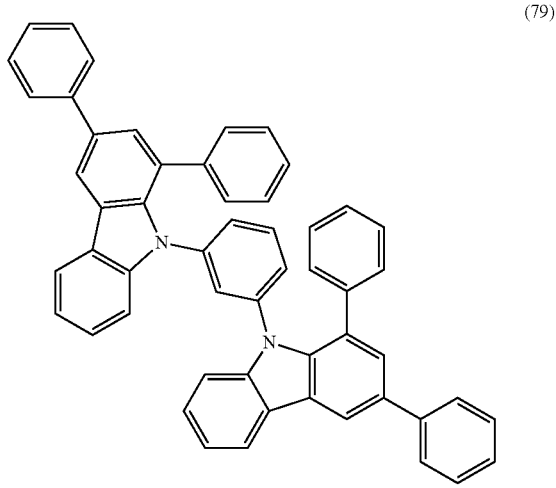
(80)
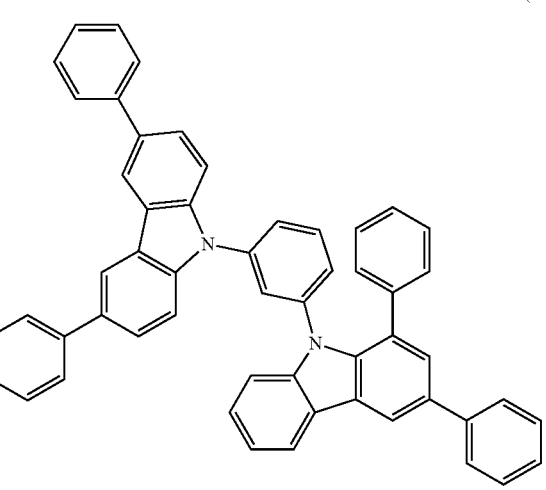

(81)
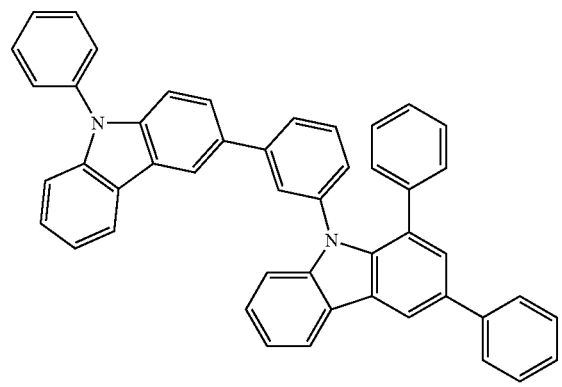
(82)
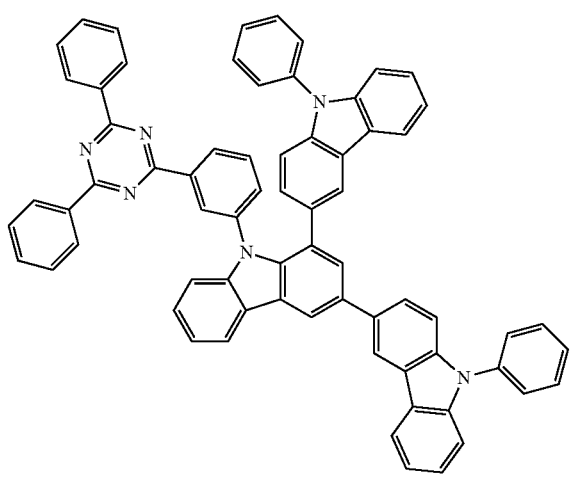
(83)
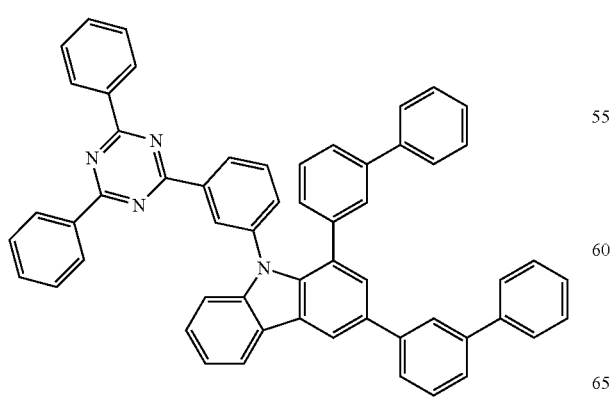
(84)
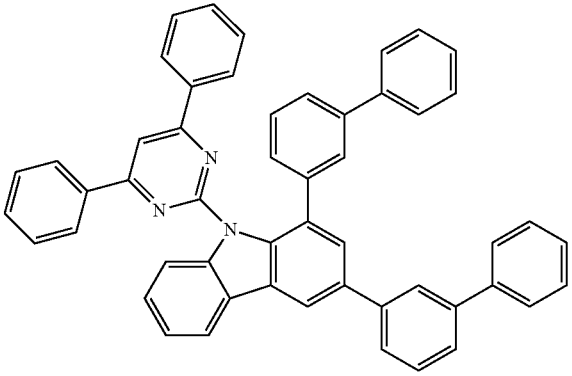
(85)
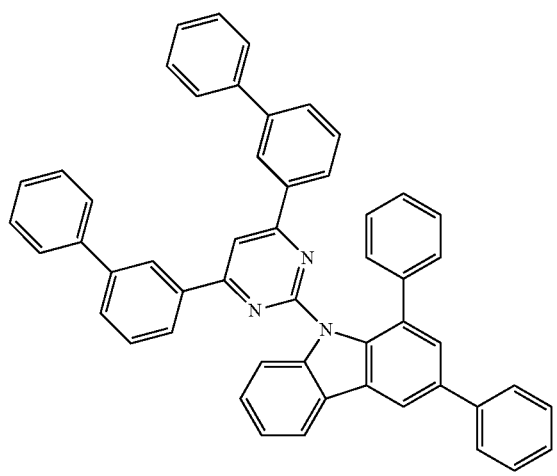
(86)
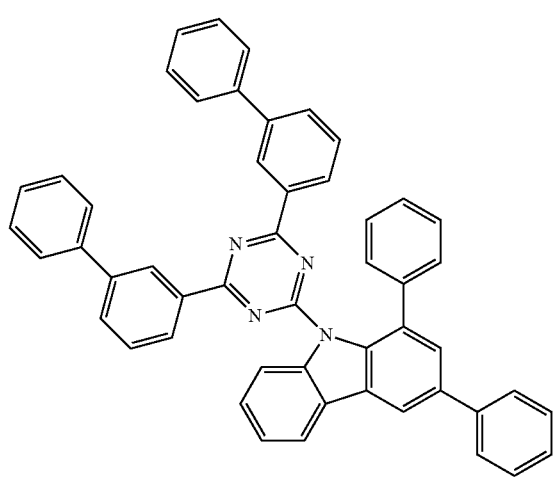

(87)
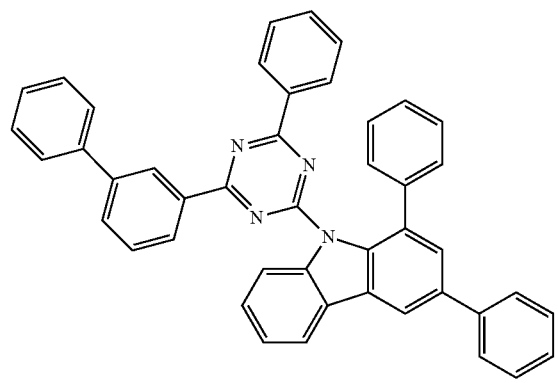
(88)
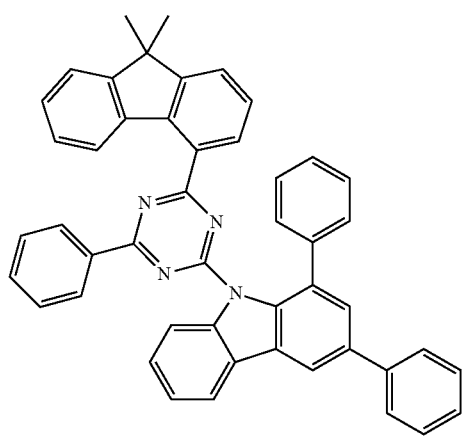
(89)
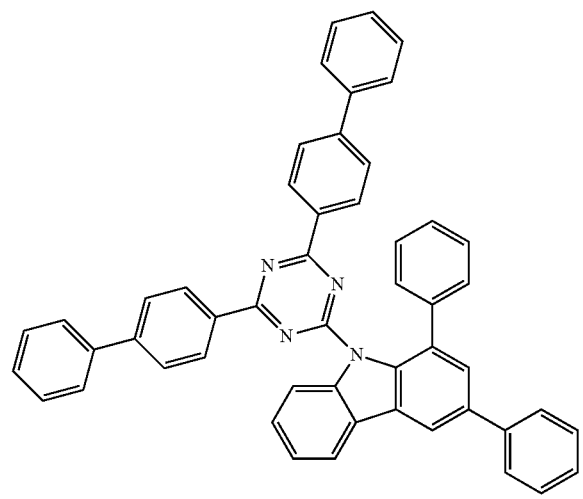
(90)
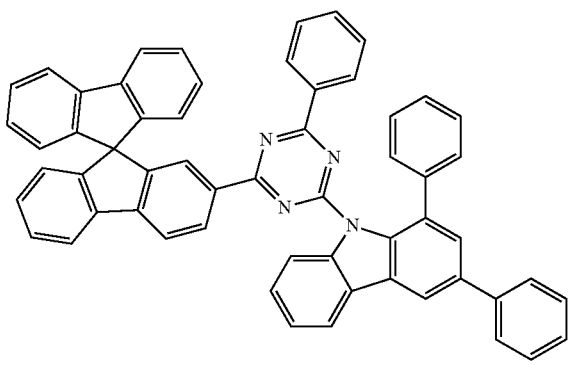
(91)
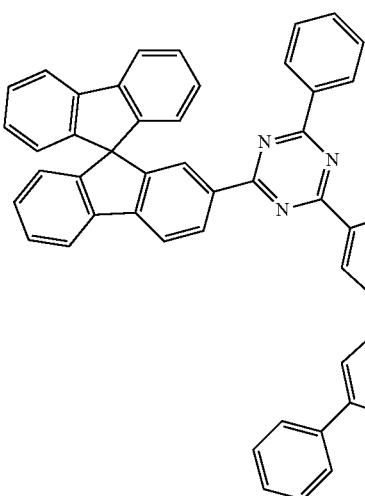
(92)
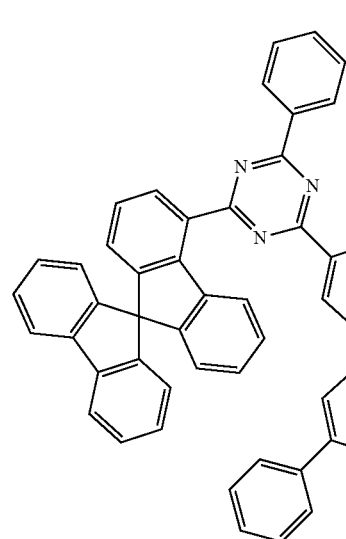

(93)
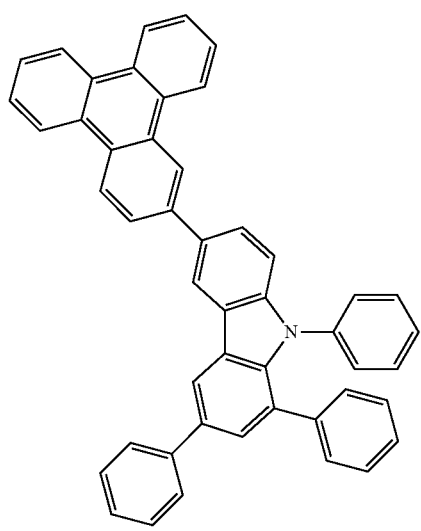
(94)
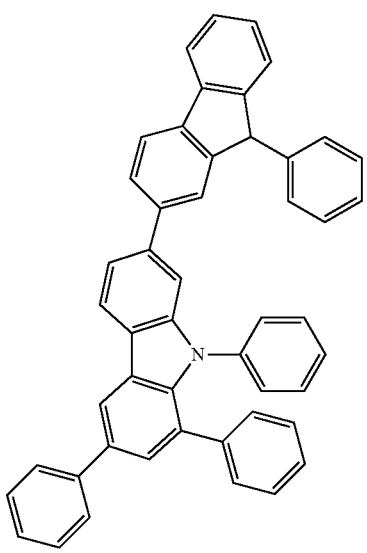
(95)
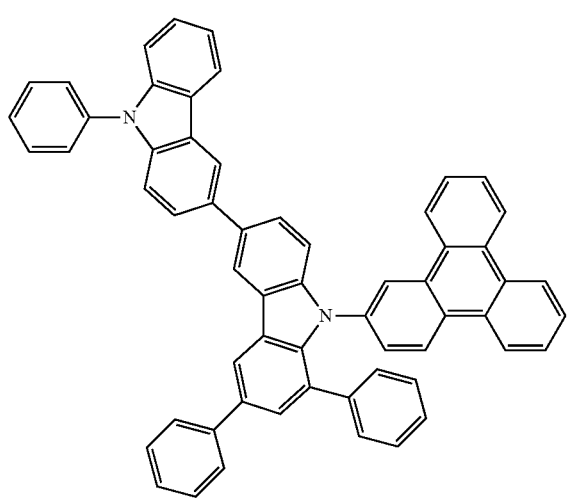
(96)
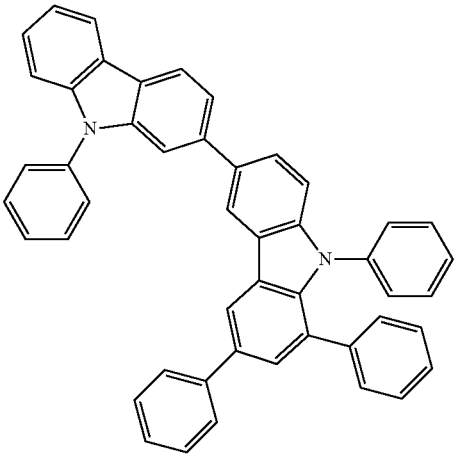
(97)
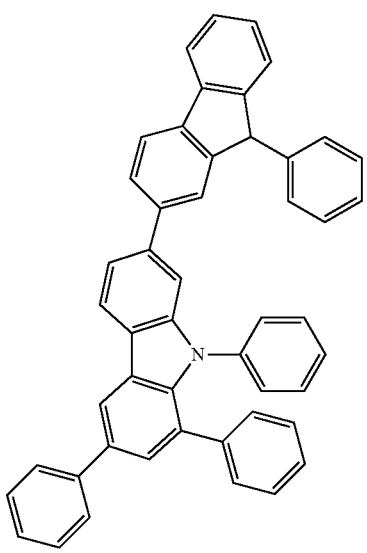
(98)
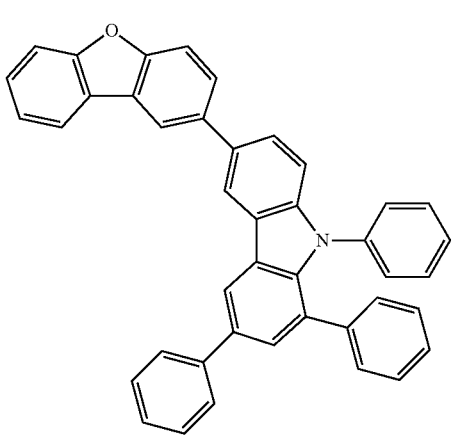

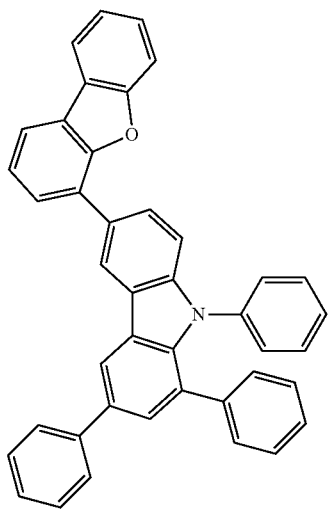
(99)
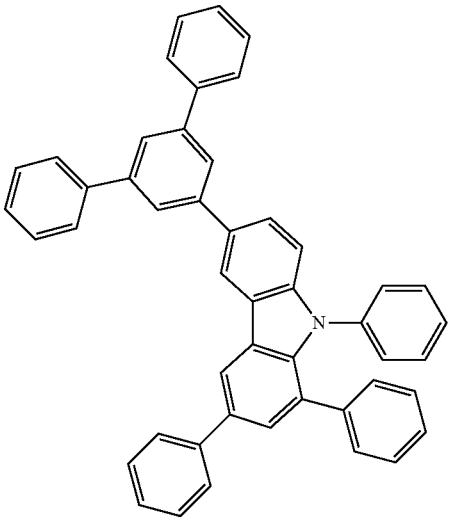
(102)
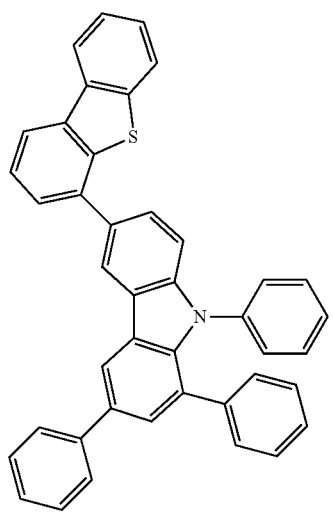
(100)
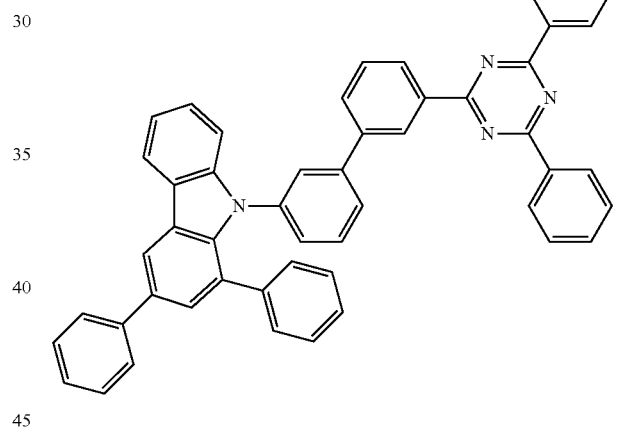
(103)
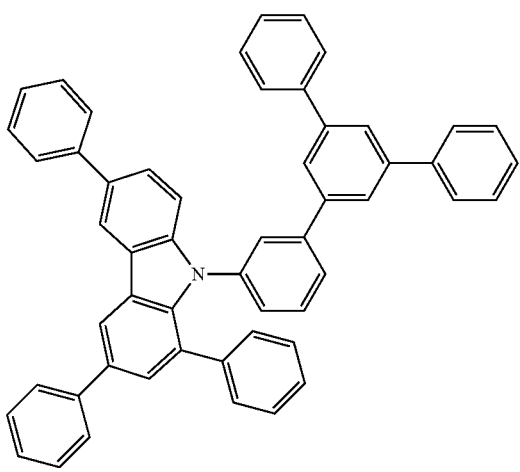
(101)
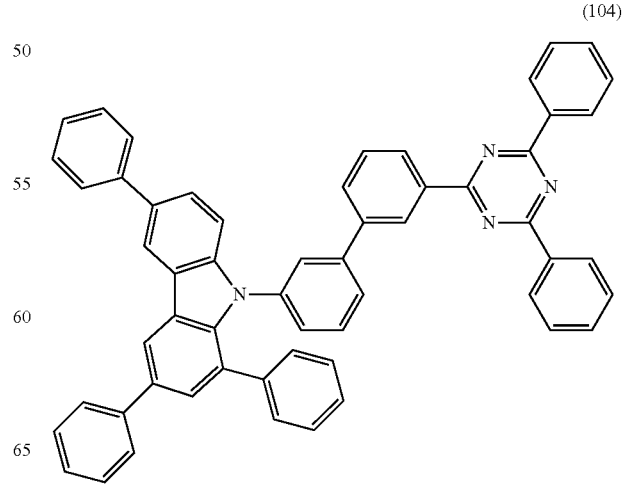
(104)

-continued
(105)
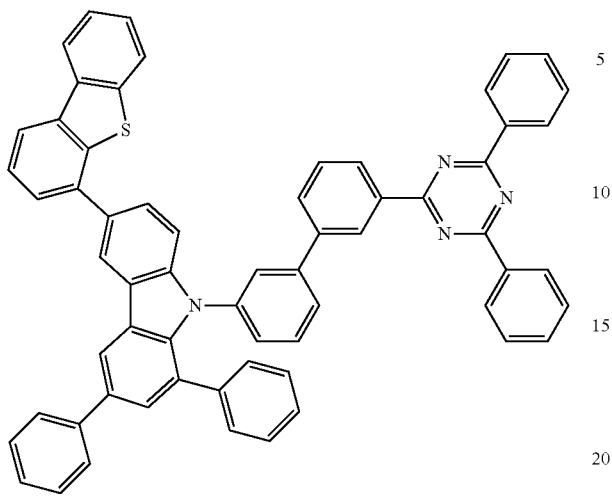
(106)
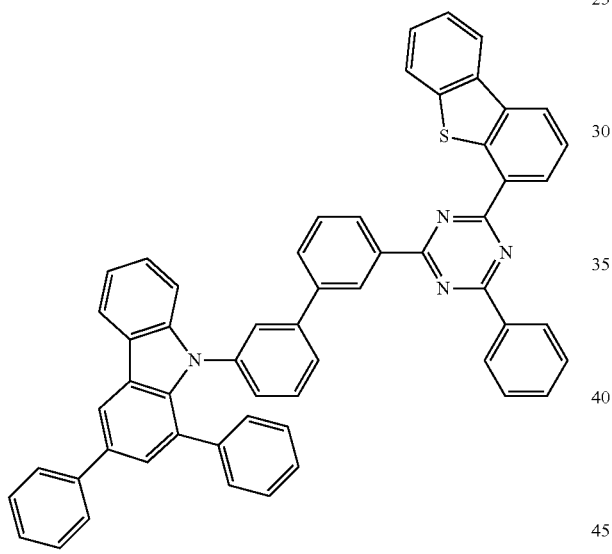
(107)
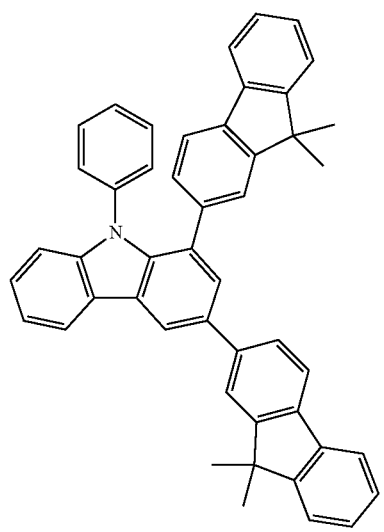
-continued
(108)
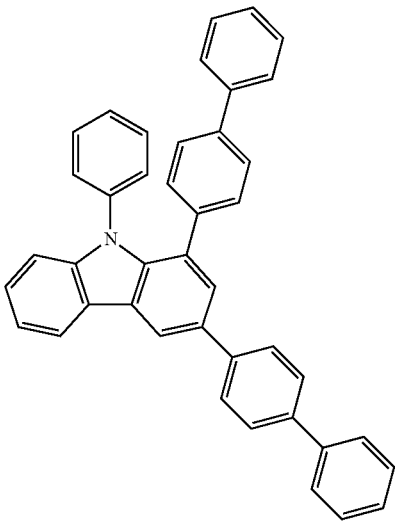
(109)
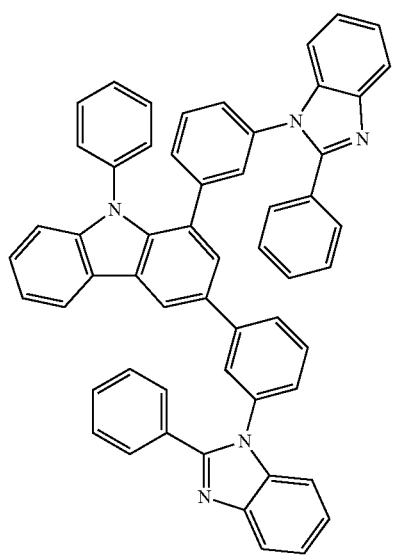

-continued
(110)
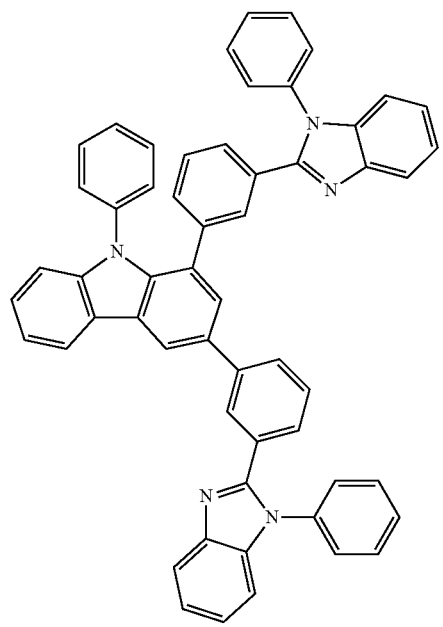
(111)
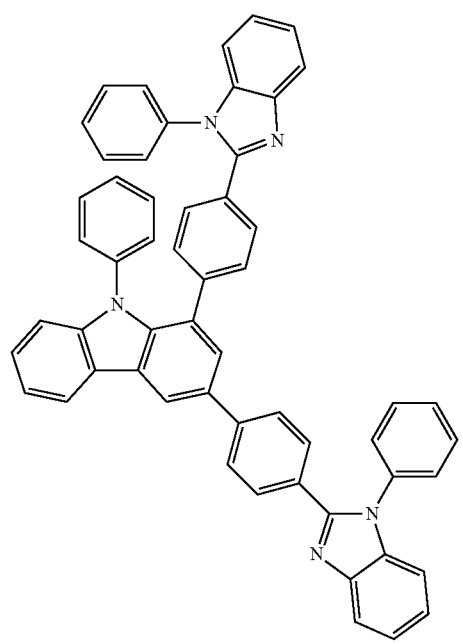
(112)
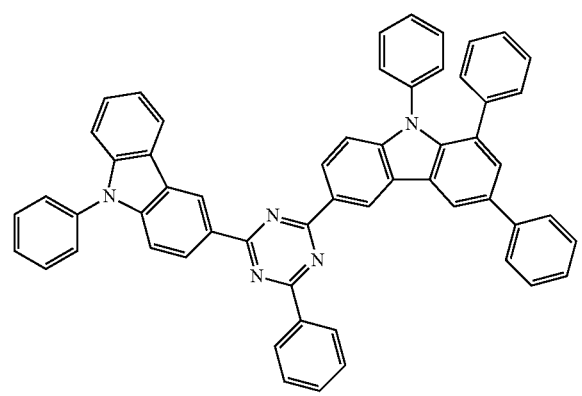
-continued
(113)
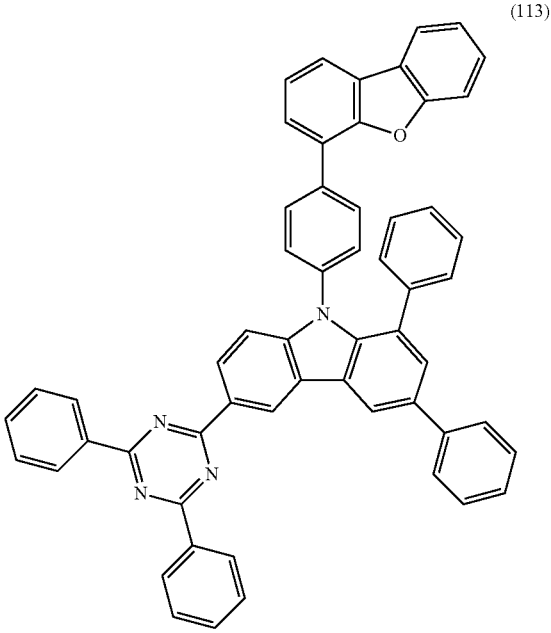
(114)
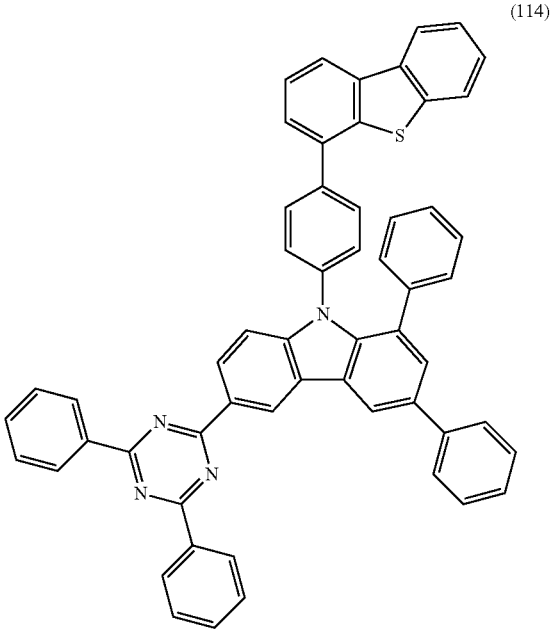

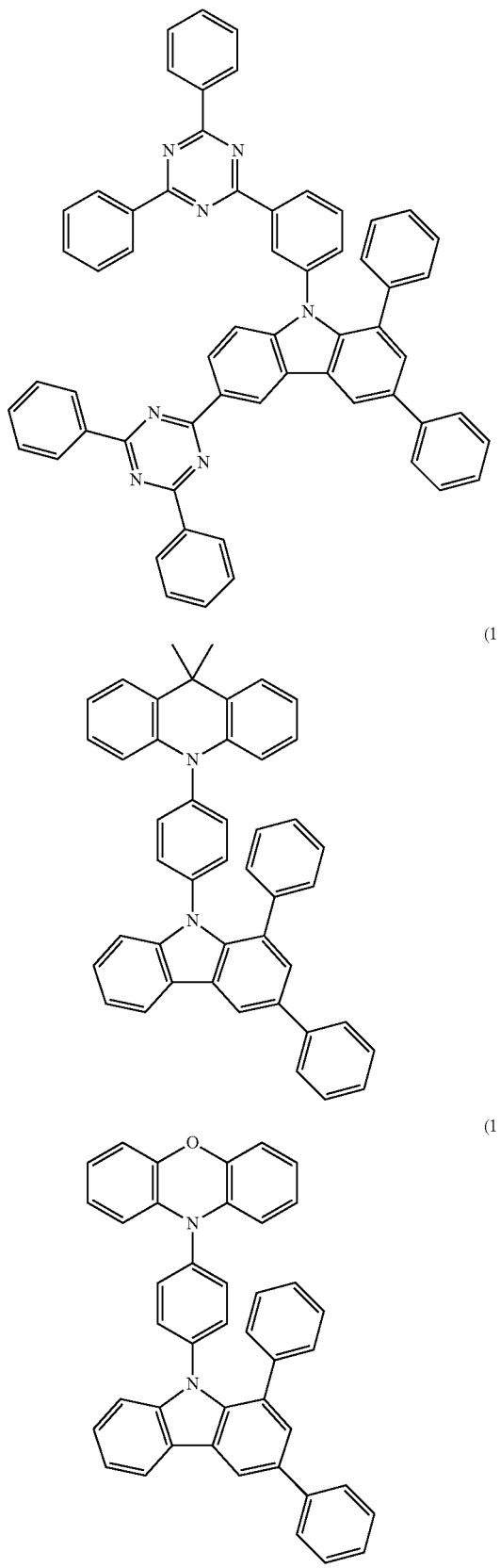
(115)
(116)
(117)
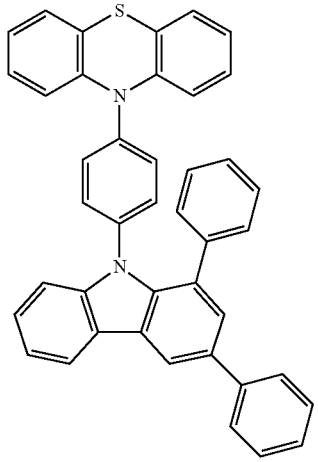
(118)
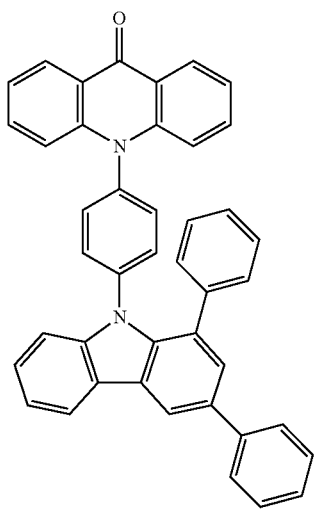
(119)
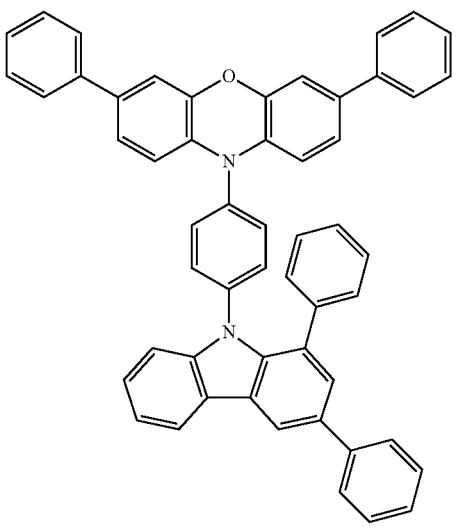
(120)

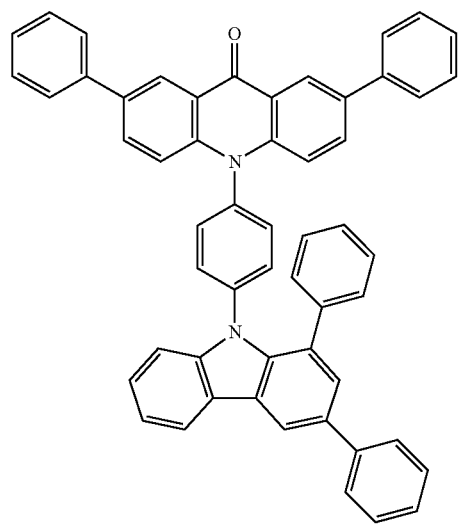
(121)
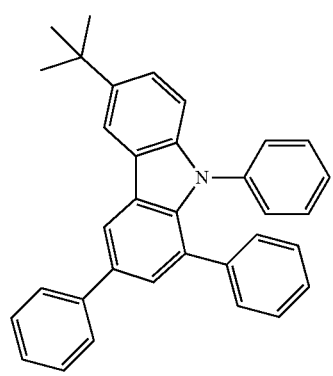
(122)
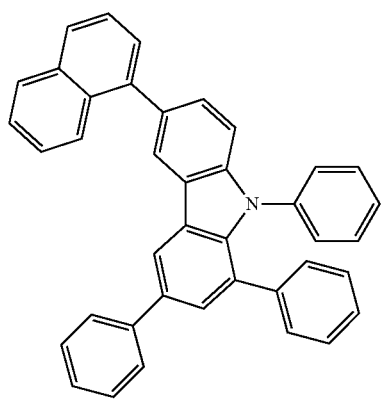
(123)
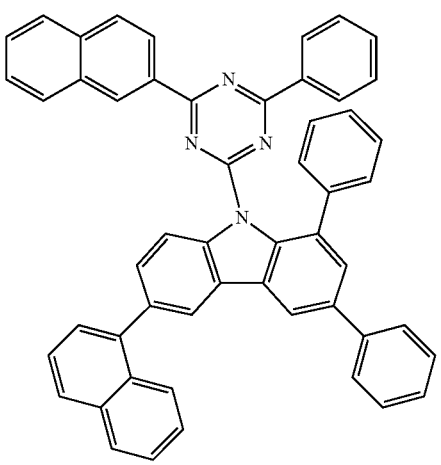
(124)
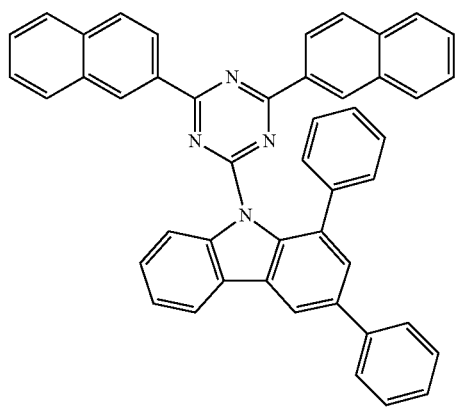
(125)
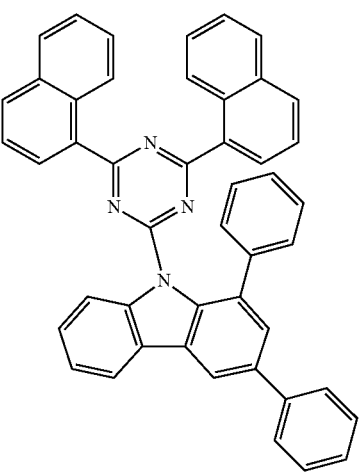
(126)

(127)
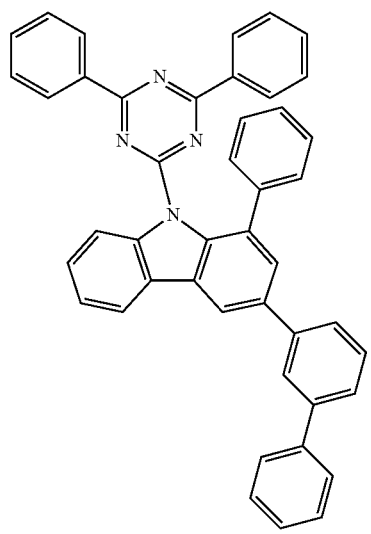
(128)
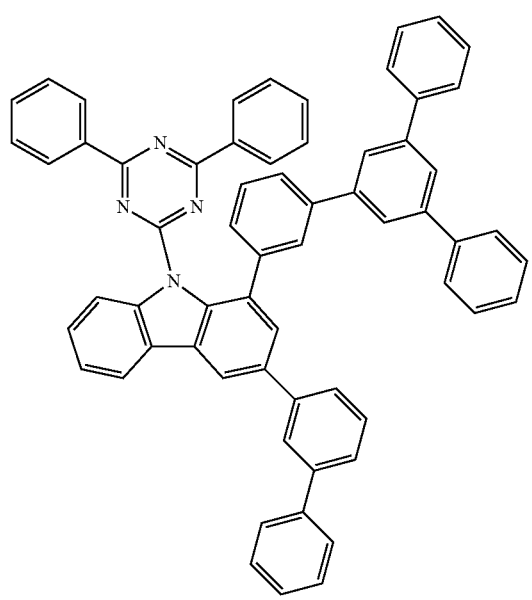
(129)
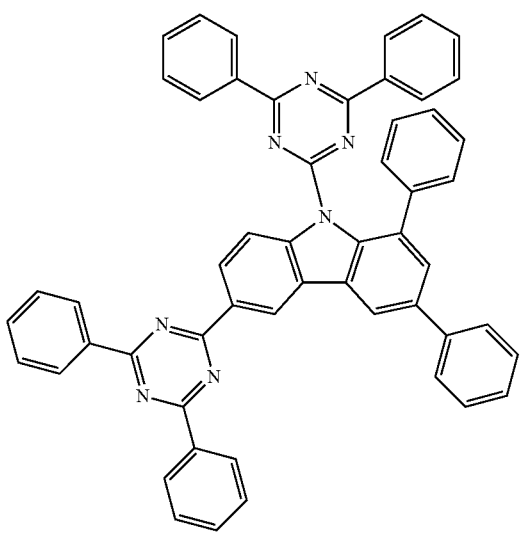
(130)
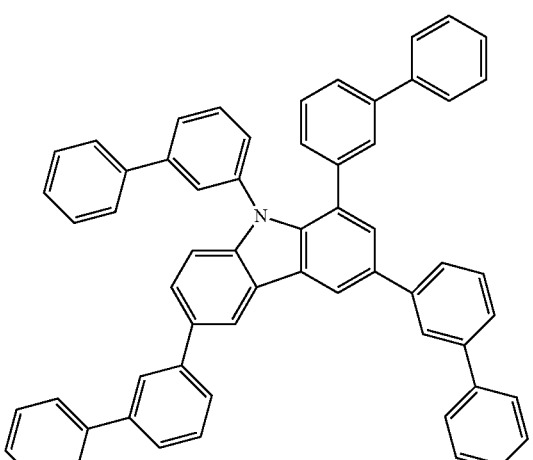
(131)
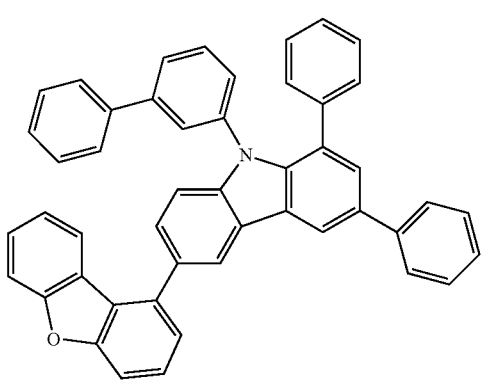

(132)
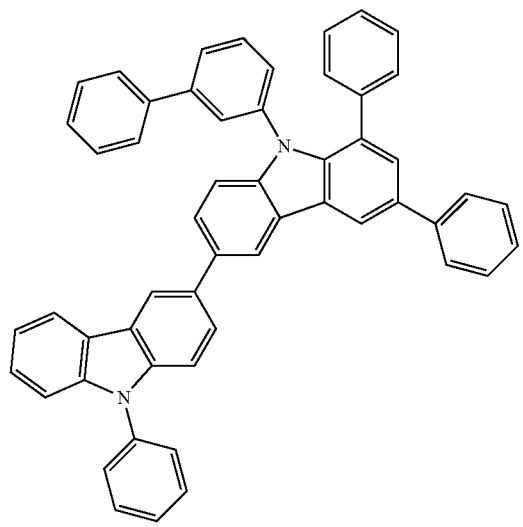
(133)
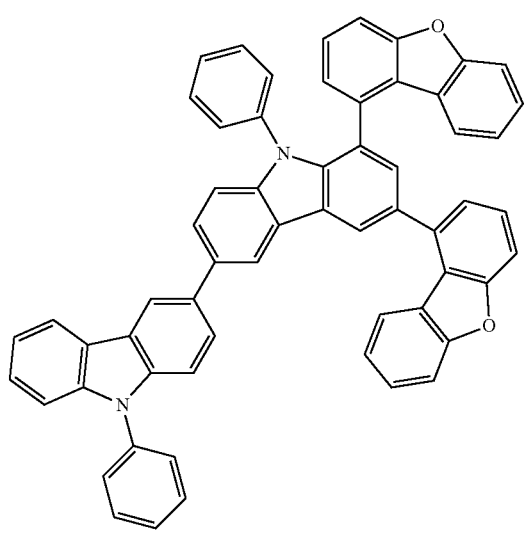
(134)
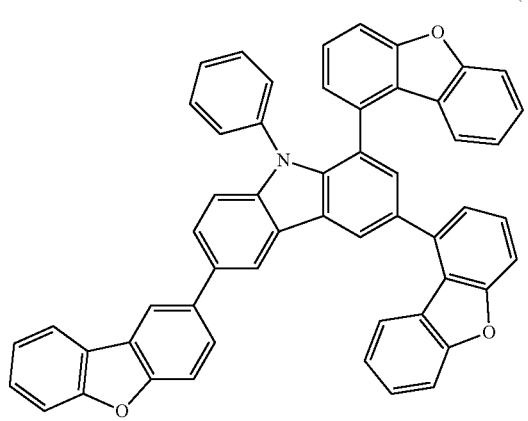
(135)
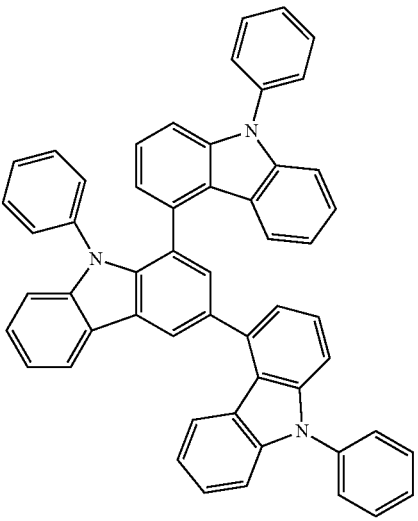
(136)
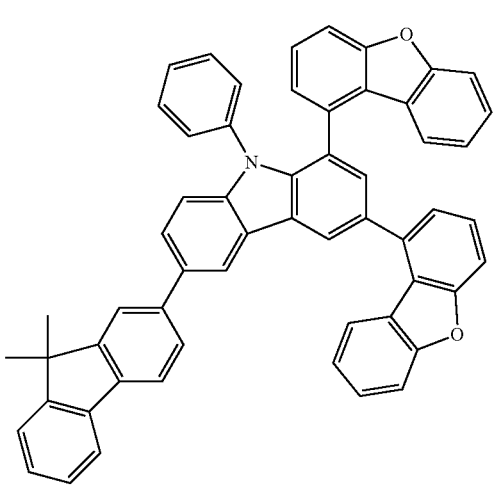
(137)
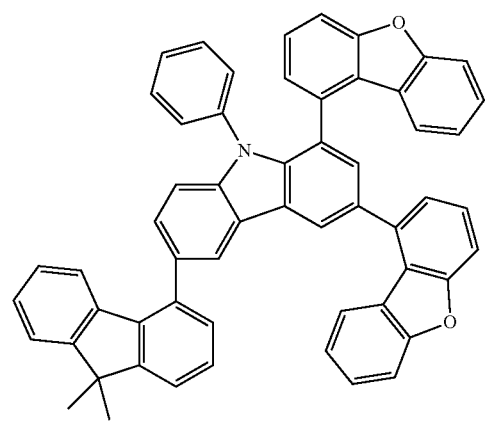

(138)
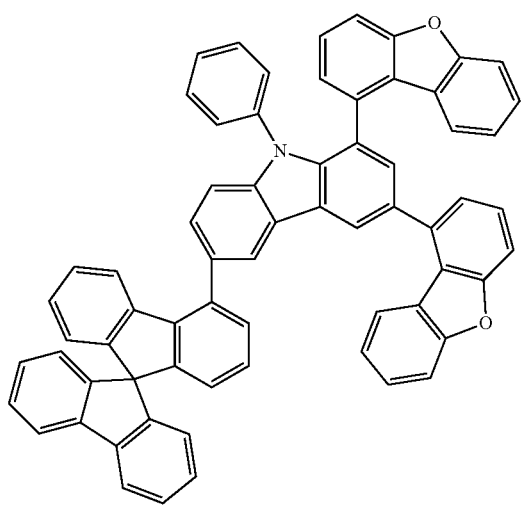
(139)
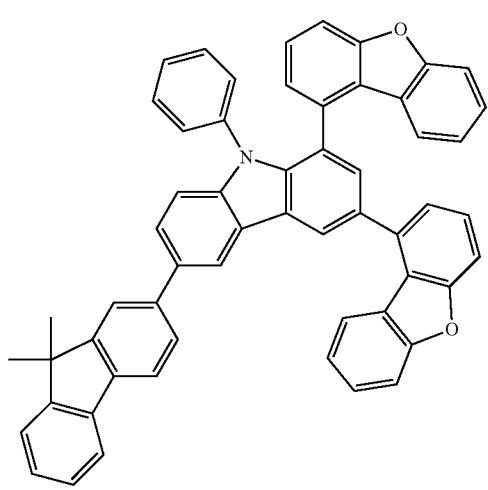
(140)
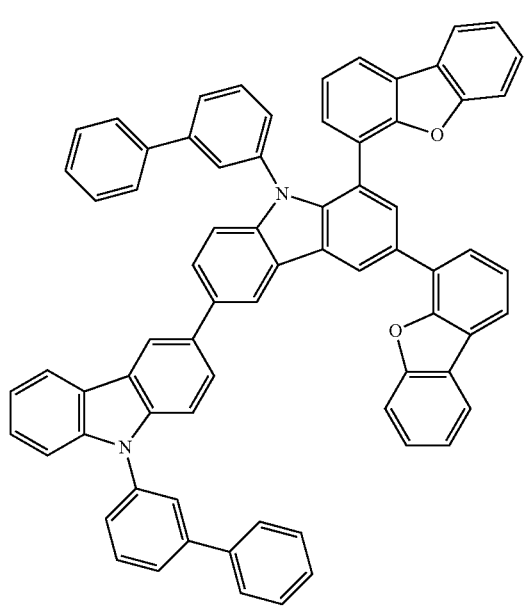
(141)
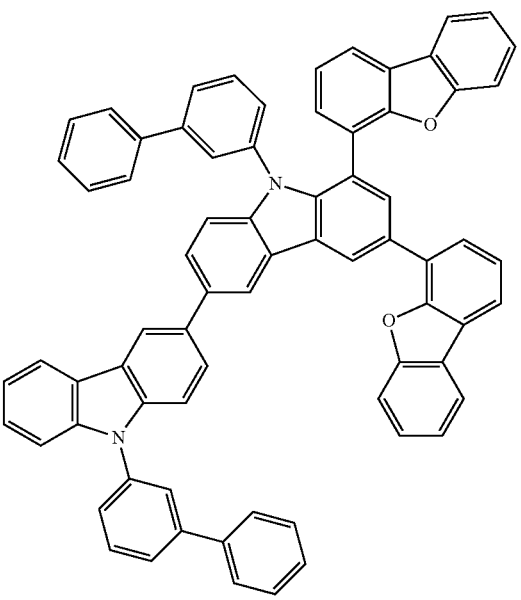
(142)
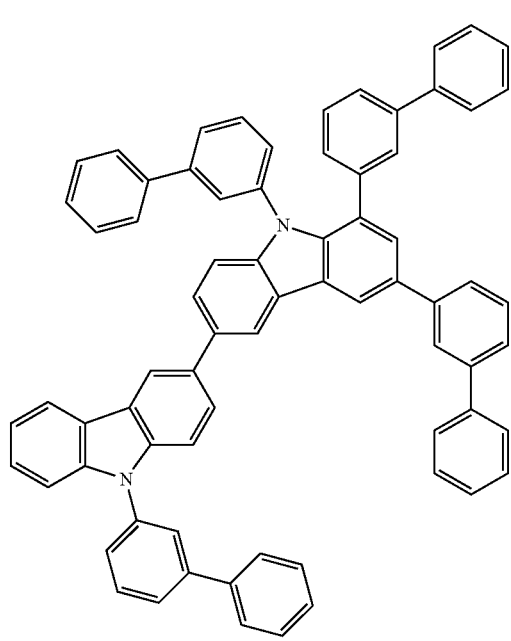

-continued
(143)
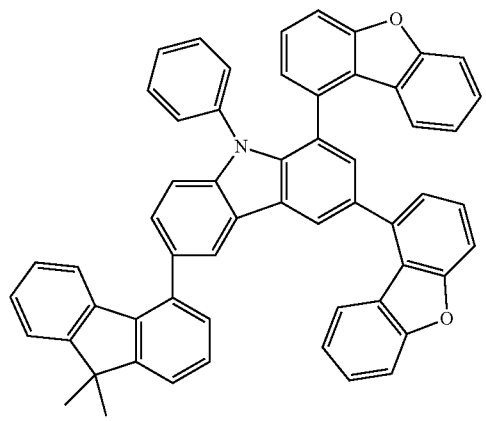
(144)
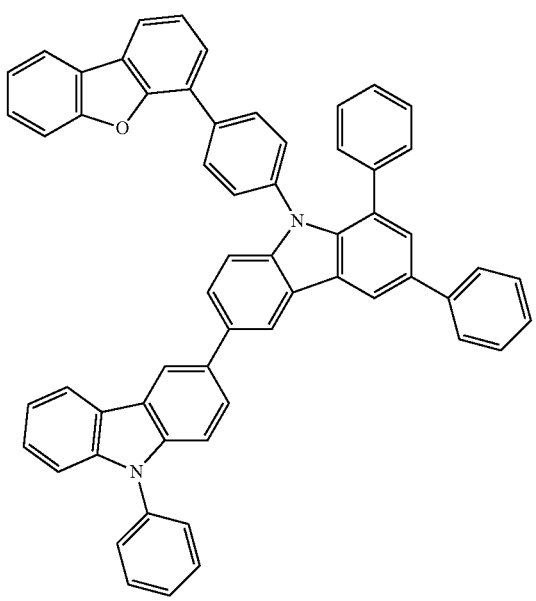
(145)
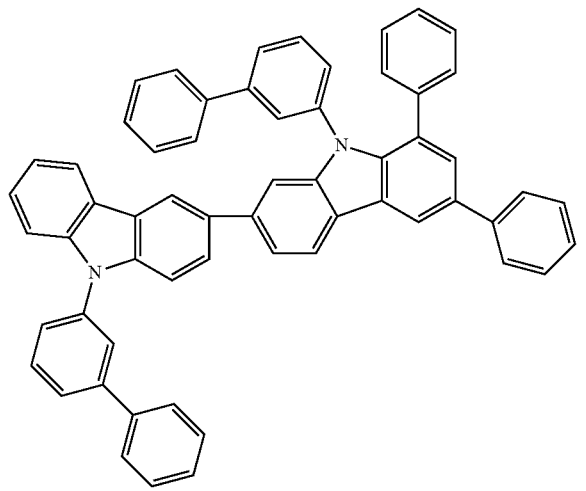
-continued
(146)
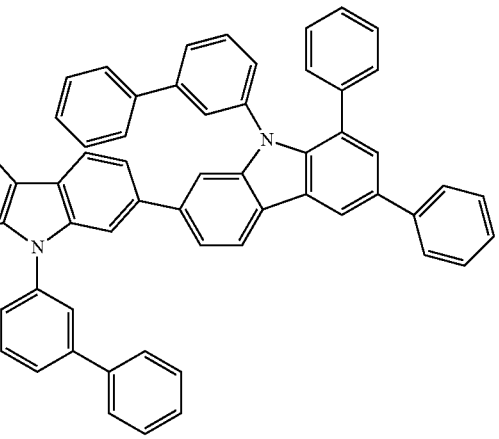
(147)
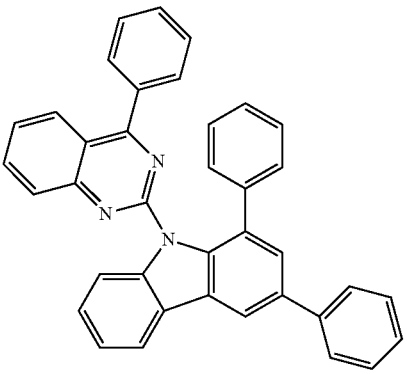
(148)
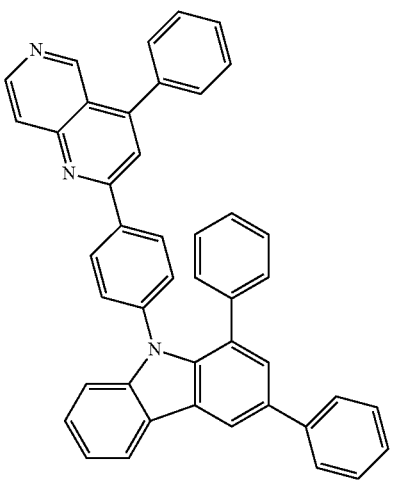

-continued
(149)
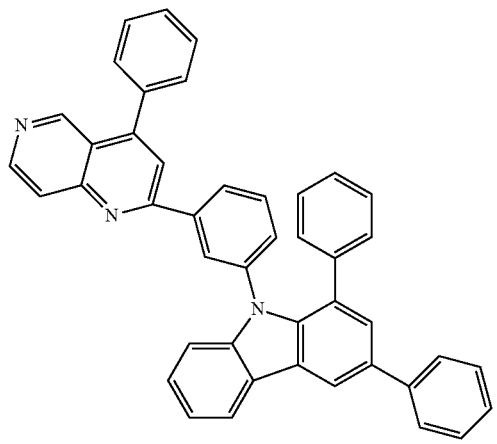
(150)
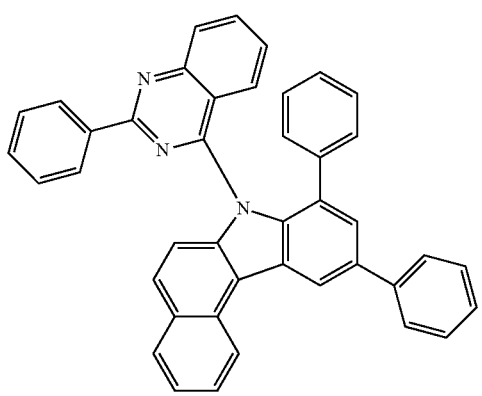
(151)
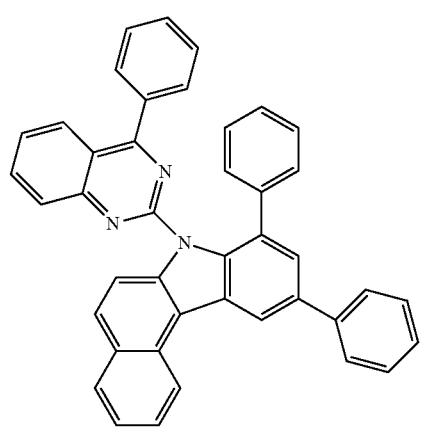
-continued
(152)
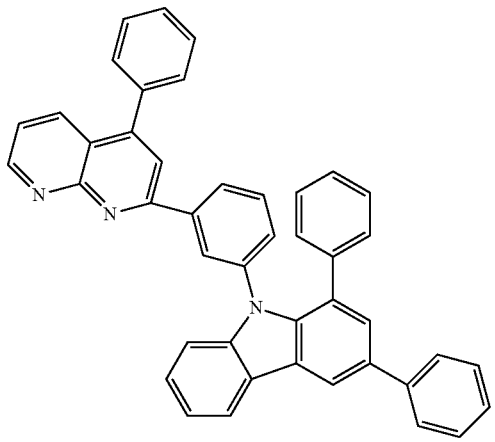
(153)
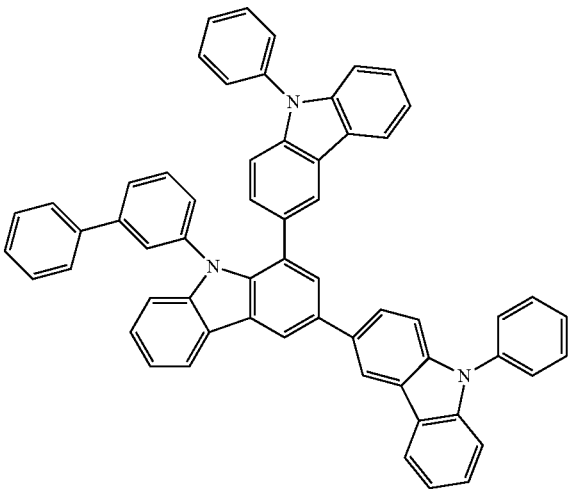
(154)
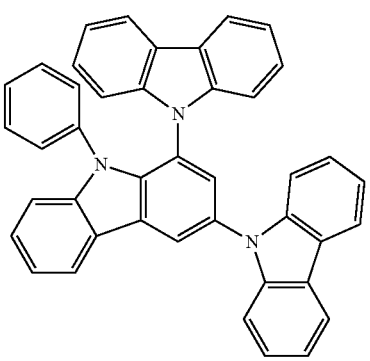

(155)
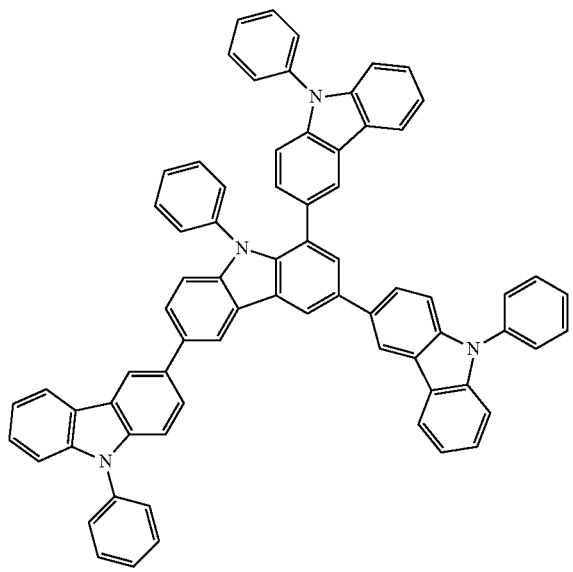
(157)
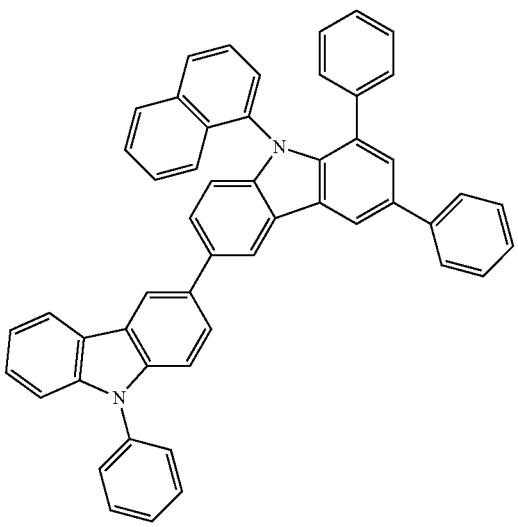
(158)
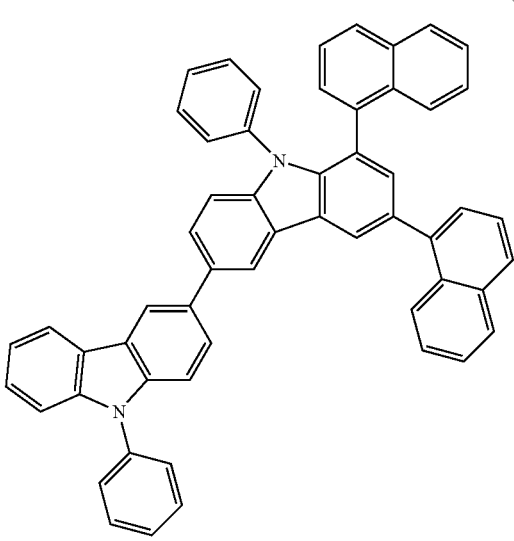
(156)
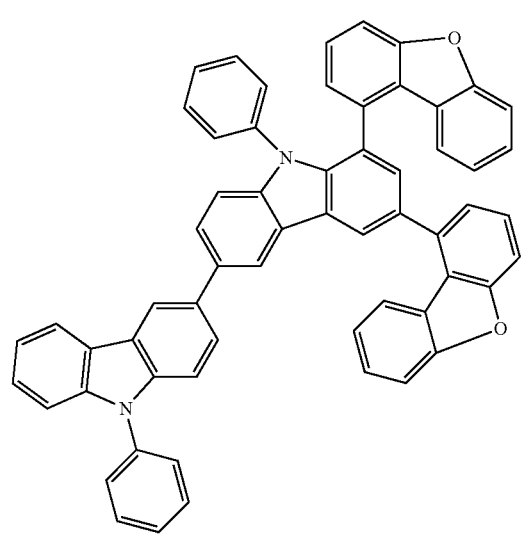
(159)
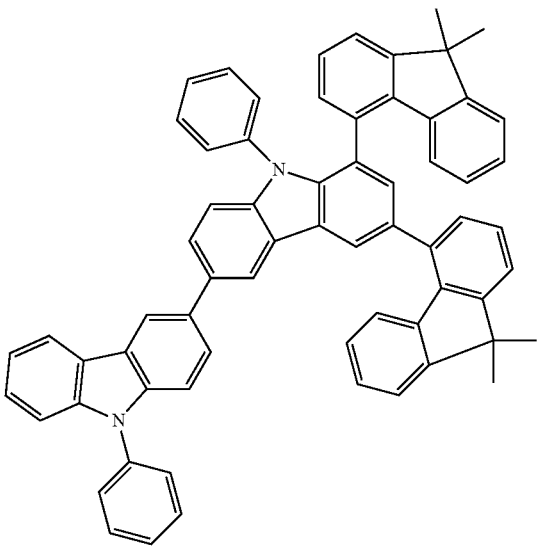

-continued (160)

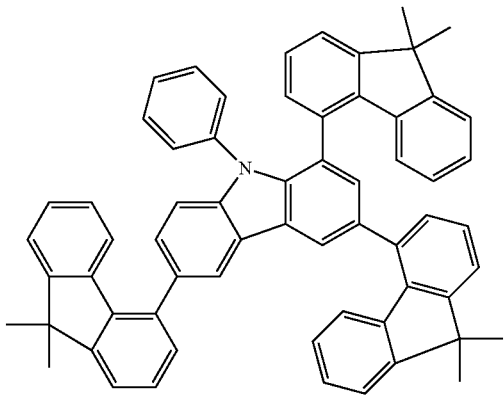

(161)

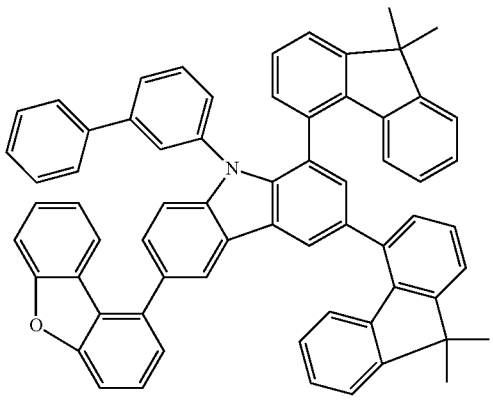

(162)

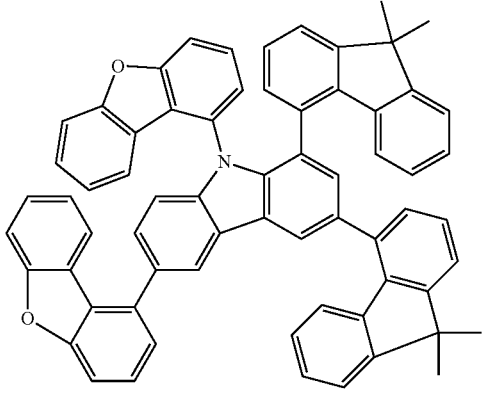

The compounds of the invention can be prepared by synthesis steps known to those skilled in the art, for example bromination, Suzuki coupling, Ullmann coupling, Hartwig-Buchwald coupling, etc.

The synthesis of the compounds of the invention proceeds, for example, from a 1,3,5-tribromobenzene optionally having further substitution. Rather than bromine, it is also possible to use other reactive leaving groups, for example iodine, chlorine or triflate. In that case, this compound is coupled with the corresponding $(L^1)_q Ar^1$ and $(L^2)_q Ar^2$ groups at two positions. Especially suitable for this purpose are transition metal-catalyzed coupling reactions (e.g. Suzuki coupling or Stille coupling). For this purpose, the group to be coupled also has to have a correspondingly suitable leaving group, especially chlorine, bromine, iodine, triflate or a boronic acid derivative, especially boronic acid or a boronic ester.

In a next step, it is then possible to react the at least disubstituted benzene derivative with a further aromatic bearing a nitro group in the ortho position to the coupling position by a further coupling reaction. The nitrobiphenyl derivative thus obtained can then be cyclized to give the carbazole base skeleton. In further steps, by further coupling reactions, it is possible to introduce the groups on the nitrogen atom of the carbazole (e.g. Buchwald coupling or Ullmann coupling). In addition, still further groups may be introduced by selective bromination and subsequent coupling.

The present invention therefore further provides a process for preparing, a compound of formula (1) wherein the compound of the formula (1) is formed by one or more coupling reactions and/or cyclizations.

The synthesis methods shown above are of illustrative character and can be modified in a suitable manner by the person skilled in the art in the field of organic synthesis if this is advantageous for the synthesis of particular embodiments of compounds of the invention.

The above-described compounds of the invention, especially compounds substituted by reactive leaving groups, such as bromine, iodine, chlorine, boronic acid or boronic ester, may find use as monomers for production of corresponding oligomers, dendrimers or polymers. Suitable reactive leaving groups are, for example, bromine, iodine, chlorine, boronic acids, boronic esters, amines, alkenyl or alkynyl groups having a terminal C—C double bond or C—C triple bond, oxiranes, oxetanes, groups which enter into a cycloaddition, for example a 1,3-dipolar cycloaddition, for example dienes or azides, carboxylic acid derivatives, alcohols and silanes.

The invention therefore further provides oligomers, polymers or dendrimers containing one or more compounds of formula (1), wherein the bond(s) to the polymer, oligomer or dendrimer, may be localized at any free positions in formula (1). According to the linkage of the compound of the invention, the compound is part of a side chain of the oligomer or polymer or part of the main chain.

An oligomer in the context of this invention is understood to mean a compound formed from at least three monomer units. A polymer in the context of the invention is understood to mean a compound formed from at least ten monomer units.

The polymers, oligomers or dendrimers of the invention may be conjugated, partly conjugated or nonconjugated. The oligomers or polymers of the invention may be linear, branched or dendritic.

In the structures having linear linkage, the units of formula (1) may be joined directly to one another, or they may be joined to one another via a bivalent group, for example via a substituted or unsubstituted alkylene group, via a heteroatom or via a bivalent aromatic or heteroaromatic group.

In branched and dendritic structures, it is possible, for example, for 3, 5 or more units of formula (1) to be joined via a trivalent or higher-valency group, for example via a trivalent or higher-valency aromatic or heteroaromatic group, to give a branched or dendritic oligomer or polymer.

For the repeat units of formula (1) in oligomers, dendrimers and polymers, the same preferences apply as described above for the compounds of the invention.

For preparation of the oligomers or polymers, the monomers of the invention are homopolymerized or copolymerized with further monomers. Suitable and preferred comonomers are chosen from fluorenes (for example according to EP 842208 or WO 2000/22026), spirobifluorenes (for example according to EP 707020, EP 894107 or WO 2006/061181), paraphenylenes (for example according to WO 1992/18552), carbazoles (for example according to WO 2004/070772 or WO 2004/113468), thiophenes (for example according to EP 1028136), dihydrophenanthrenes (for example according to WO 2005/014689 or WO 2007/006383), cis- and trans-indenofluorenes (for example according to WO 2004/041901 or WO 2004/113412), ketones (for example according to WO2005/040302), phenanthrenes (for example according to WO 2005/104264 or WO 2007/017066) or else a plurality of these units. The polymers, oligomers and dendrimers typically contain still further units, for example emitting (fluorescent or phosphorescent) units, for example vinyltriarylamines (for example according to WO 2007/068325) or phosphorescent metal complexes (for example according to WO 2006/003000), and/or charge transport units, especially those based on triarylamines.

The polymers, oligomers and dendrimers of the invention have advantageous properties, especially high lifetimes, high efficiencies and good color coordinates.

The polymers and oligomers of the invention are generally prepared by polymerization of one or more monomer types, of which at least one monomer leads to repeat units of the formula (1) in the polymer. Suitable polymerization reactions are known to those skilled in the art and are described in the literature. Particularly suitable and preferred polymerization reactions which lead to C—C and C—N bonds are as follows (A) SUZUKI polymerization
(B) YAMAMOTO polymerization
(C) STILLE polymerization and
(D) HARTWIG-BUCHWALD polymerization.

How the polymerization can be conducted by these methods and how the polymers can then be separated from the reaction medium and purified is known to those skilled in the art and is described in detail in the literature, for example in WO 2003/048225, WO 2004/037887 and WO 2004/037887.

The present invention thus also provides a process for preparing the polymers, oligomers and dendrimers of the invention, which is characterized in that they are prepared by polymerization according to SUZUKI, polymerization according to YAMAMOTO, polymerization according to STILLE or polymerization according to HARTWIG-BUCHWALD. The dendrimer of the invention can be prepared by processes known to those skilled in the art or in analogy thereto. Suitable processes are described in the literature, for example in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 2002/067343 A1 and WO 2005/026144 A1.

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THE, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore further provides a formulation, especially a solution, dispersion or emulsion, comprising at least one compound of formula (1) or at least one polymer, oligomer or dendrimer containing at least one unit of formula (1) and at least one solvent, preferably an organic solvent. The way in which such solutions can be prepared is known to those skilled in the art and is described, for example, in WO 2002/072714, WO 2003/019694 and the literature cited therein.

The present invention further provides mixtures comprising at least one compound of the invention and at least one further compound. The further compound may, for example, be a fluorescent or phosphorescent dopant when the compound of the invention is used as matrix material, especially a phosphorescent dopant. Suitable dopants are detailed below in connection with the organic electroluminescent devices and are also preferred for the mixtures of the invention.

The compounds of the invention and mixtures are suitable for use in an electronic device. An electronic device is understood to mean a device containing at least one layer containing at least one organic compound. This component may also comprise inorganic materials or else layers formed entirely from inorganic materials.

The present invention therefore further provides for the use of the compounds or mixtures of the invention in an electronic device, especially in an organic electroluminescent device.

The present invention still further provides an electronic device comprising at least one of the above-detailed compounds or mixtures of the invention. In this case, the preferences detailed above for the compound also apply to the electronic devices.

The electronic device is preferably selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitized solar cells, organic optical detectors, organic photoreceptors, organic field-quench devices (O-FQDs), light-emitting electrochemical cells (LECs), organic laser diodes (O-lasers) and organic plasmon emitting devices (D. M. Koller et al., *Nature Photonics* 2008, 1-4), preferably organic electroluminescent devices (OLEDs, PLEDs), especially phosphorescent OLEDs.

The organic electroluminescent device comprises cathode, anode and at least one emitting layer. Apart from these layers, it may also comprise further layers, for example in each case one or more hole injection layers, hole transport layers, hole blocker layers, electron transport layers, electron injection layers, exciton blocker layers, electron blacker layers and/or charge generation layers. It is likewise possible for interlayers having an exciton-blocking function, for example, to be introduced between two emitting layers. However, it should be pointed out that not necessarily every one of these layers need be present. In this case, it is possible for the organic electroluminescent device to contain an emitting layer, or for it to contain a plurality of emitting layers. If a plurality of emission layers are present, these preferably have several emission maxima between 380 nm and 750 mm overall, such that the overall result is white emission; in other words, various emitting compounds which may fluoresce or phosphoresce are used in the emitting layers. Especially preferred are systems having three emitting layers, where the three layers show blue, green and orange or red emission (for the basic construction, see, for example, WO 2005/011013). These may be fluorescent or phosphorescent emission layers or else hybrid systems in which fluorescent and phosphorescent emission layers are combined with one another.

The compound of the invention according to the above-detailed embodiments may be used in different layers, according to the exact structure. Preference is given to an organic electroluminescent device comprising a compound of formula (1) or as per the preferred embodiments as matrix material for fluorescent or phosphorescent emitters, especially for phosphorescent emitters, and/or in an electron transport layer and/or in an electron-blocking or exciton-blocking layer and/or in a hole transport layer, according to the exact substitution. In this context, the above-detailed preferred embodiments also apply to the use of the materials in organic electronic devices.

In a preferred embodiment of the invention, the compound of formula (1) or according to the preferred embodiments is used as matrix material for a fluorescent or phosphorescent compound, especially for a phosphorescent compound, in an emitting layer. In this case, the organic electroluminescent device may contain an emitting layer, or it may contain a plurality of emitting layers, where at least one emitting layer contains at least one compound of the invention as matrix material.

A further preferred embodiment of the present invention is the use of the compound of formula (1) or according to the preferred embodiments as matrix material for a phosphorescent emitter in combination with a further matrix material. Particularly suitable matrix materials which can be used in combination with the compounds of formula (1) or according to the preferred embodiments are aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109 and WO 2011/000455, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or according to the unpublished application EP 11003232.3, triphenylene derivatives, for example according to WO 2012/048781, or lactams, for example according to WO 2011/116865 or WO 2011/137951. It is likewise possible for a further phosphorescent emitter which emits at a shorter wavelength than the actual emitter to be present as co-host in the mixture.

The mixture of the compound of formula (1) or according to the preferred embodiments and the emitting compound contains between 99% and 1% by volume, preferably between 98% and 10% by volume, more preferably between 97% and 60% by volume and especially between 95% and 80% by volume of the compound of formula (1) or according to the preferred embodiments, based on the overall mixture of emitter and matrix material. Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material.

The term "phosphorescent dopants (emitters)" typically encompasses compounds where the emission of light is effected through a spin-forbidden transition, for example a transition from an excited triplet state or a state having a higher spin quantum number, for example a quintet state.

Suitable phosphorescent dopants are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent dopants, compounds containing copper, molybdenum, tungsten, rhenium, ruthenium, osmium, rhodium, iridium, palladium, platinum, silver, gold or europium, especially compounds containing iridium, platinum or copper.

In the context of the present invention, all luminescent iridium, platinum or copper complexes are considered to be phosphorescent compounds.

Examples of phosphorescent dopants can be found in applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used for phosphorescent OLEDs according to the prior art and as known to those skilled in the art in the field of organic electroluminescent devices are suitable for use in the devices of the invention. It is also possible for the person skilled in the art, without exercising inventive skill, to use further phosphorescent complexes in combination with the compounds of the invention in OLEDs.

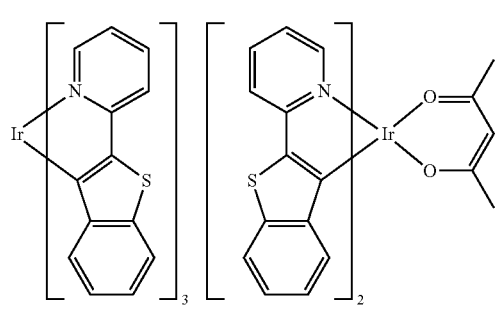

101
-continued
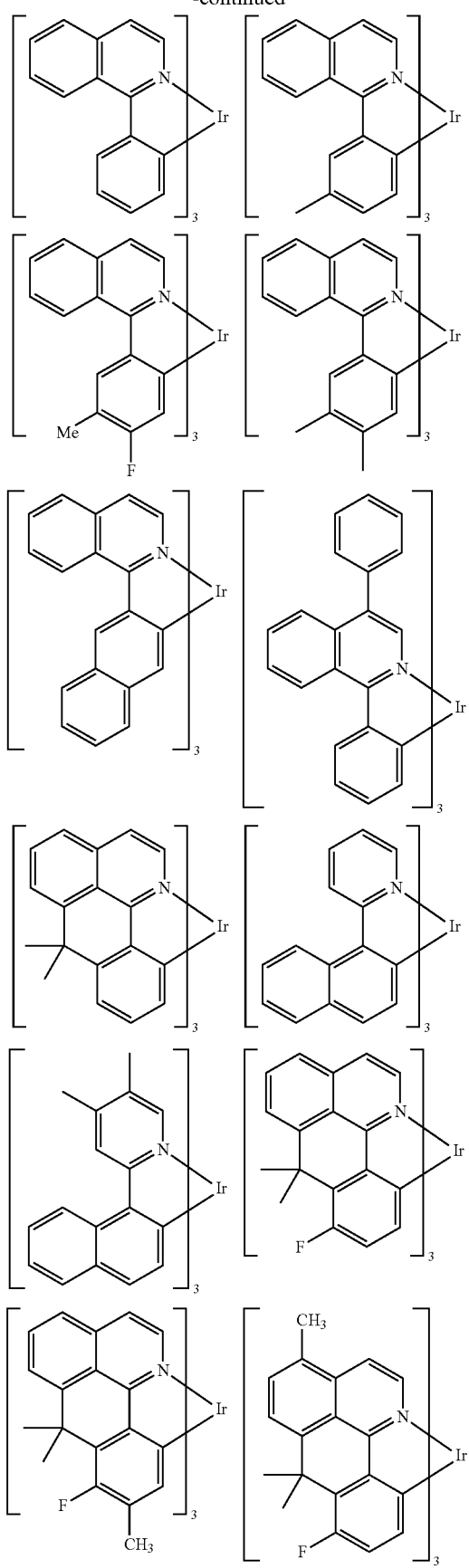
102
-continued
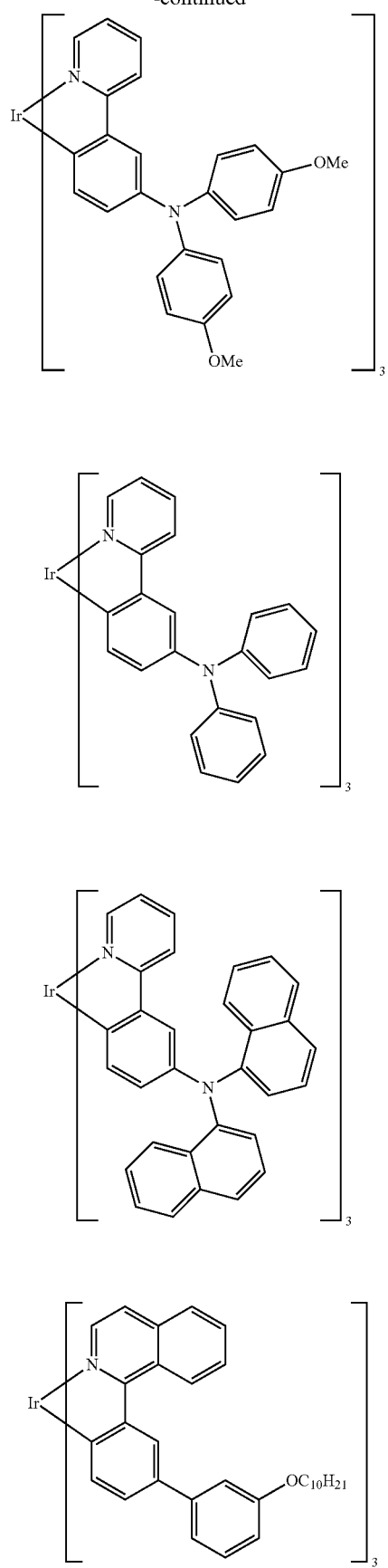

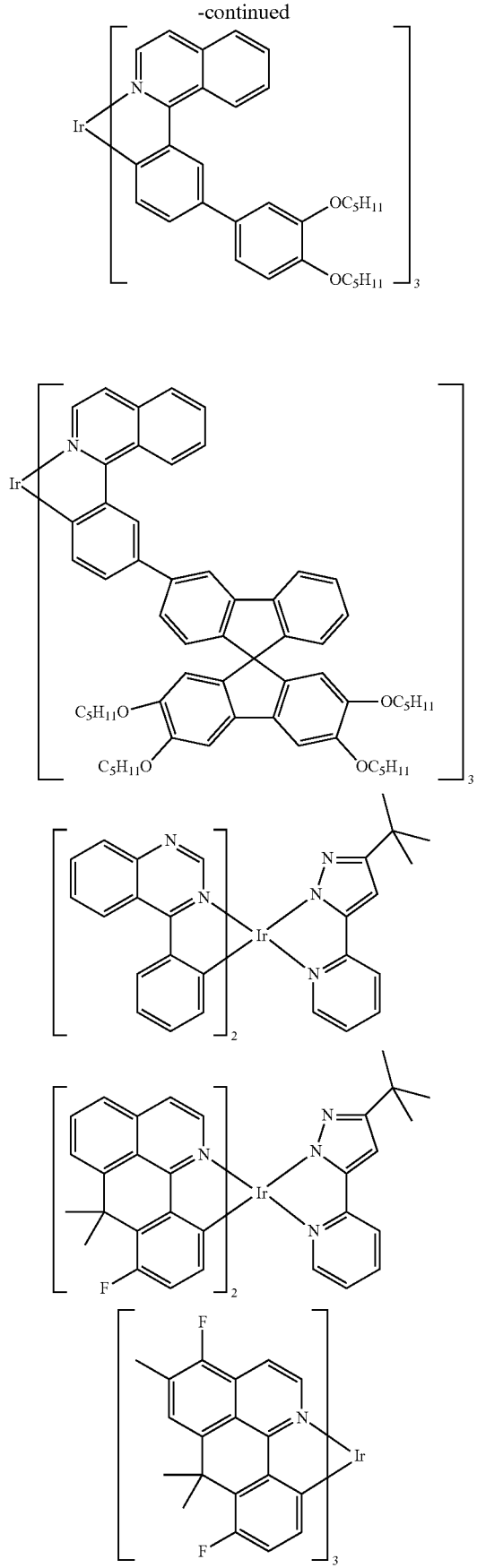
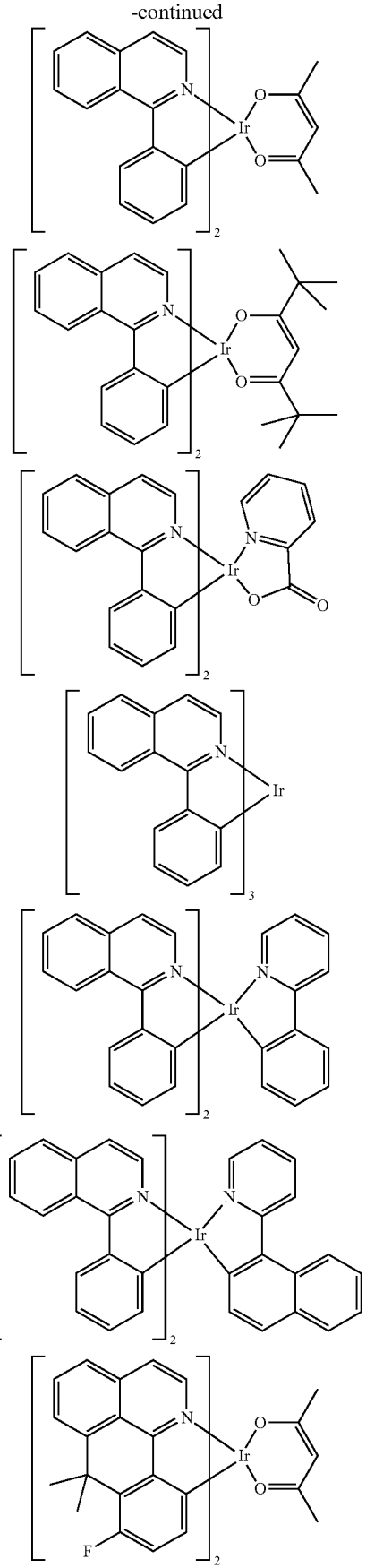

105
-continued
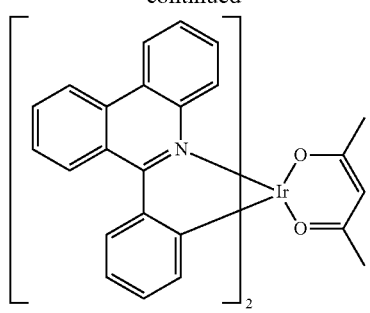
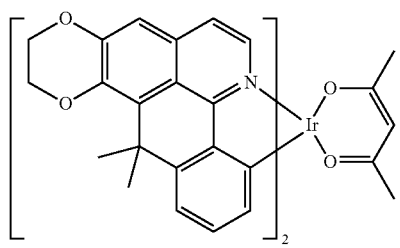
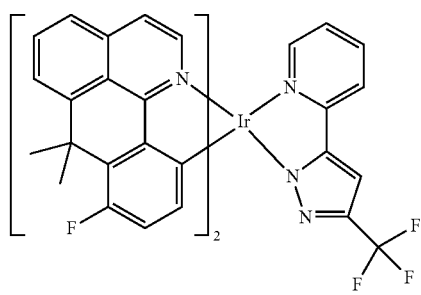
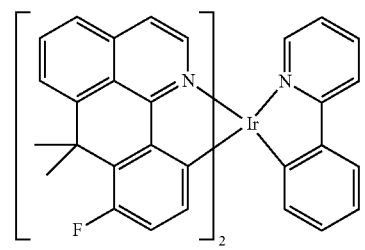
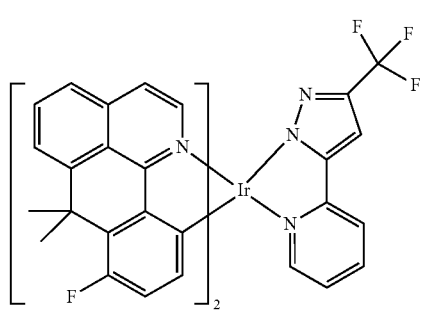
106
-continued
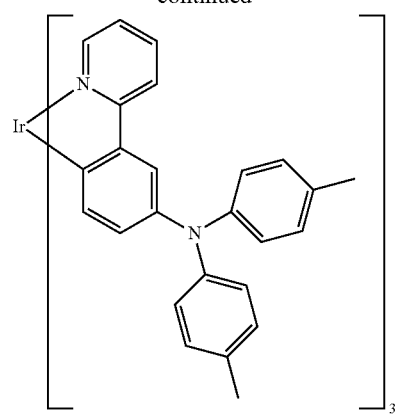
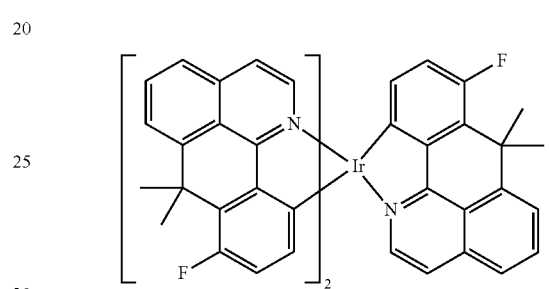
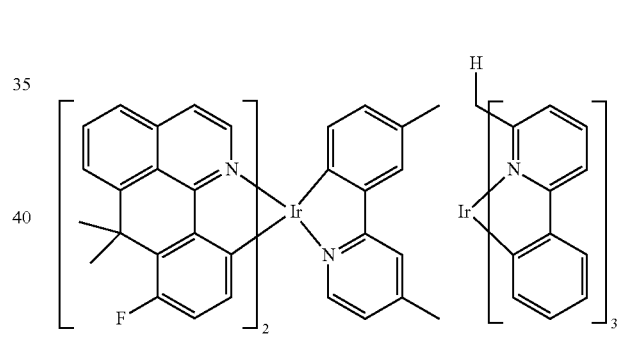
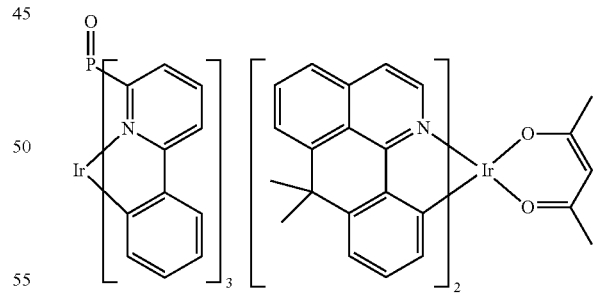
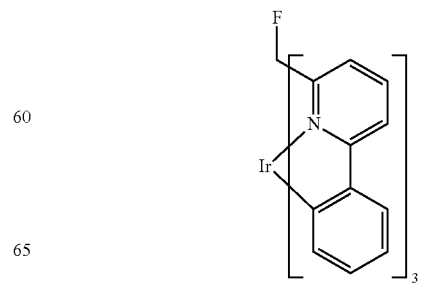

107
-continued
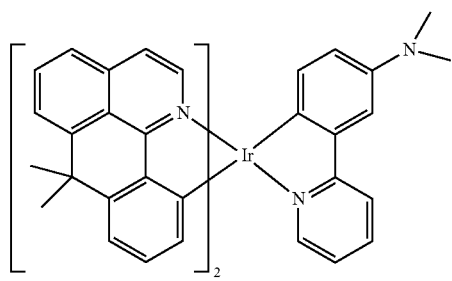
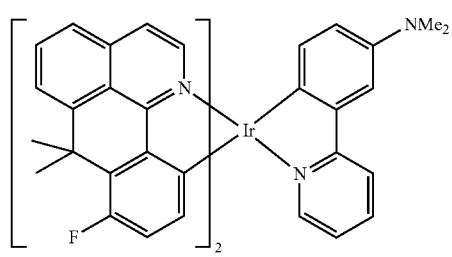
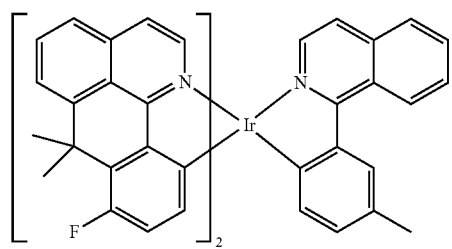
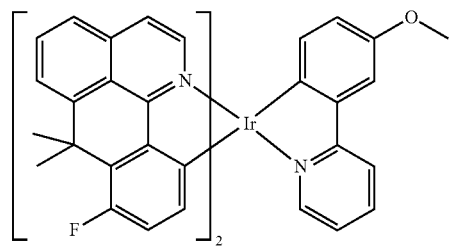
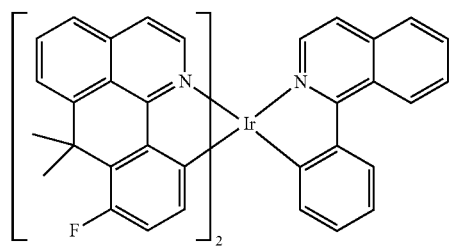
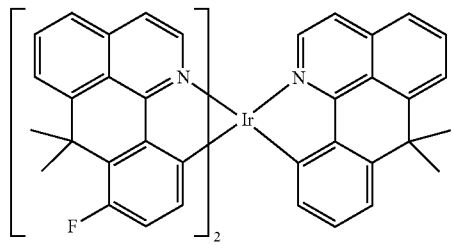
108
-continued
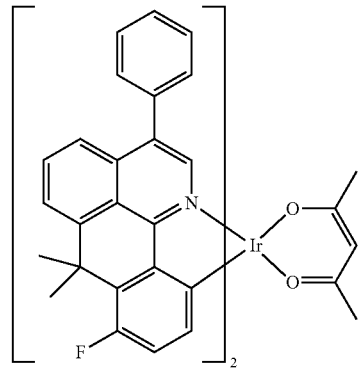
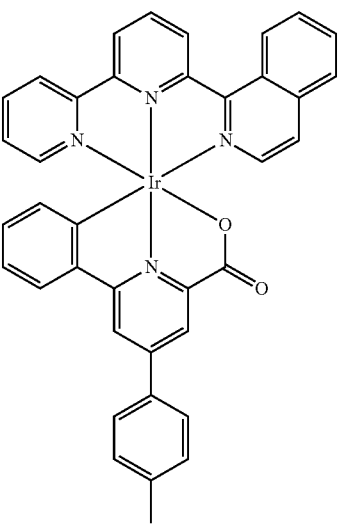
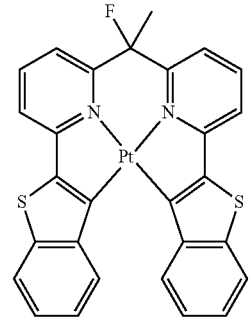

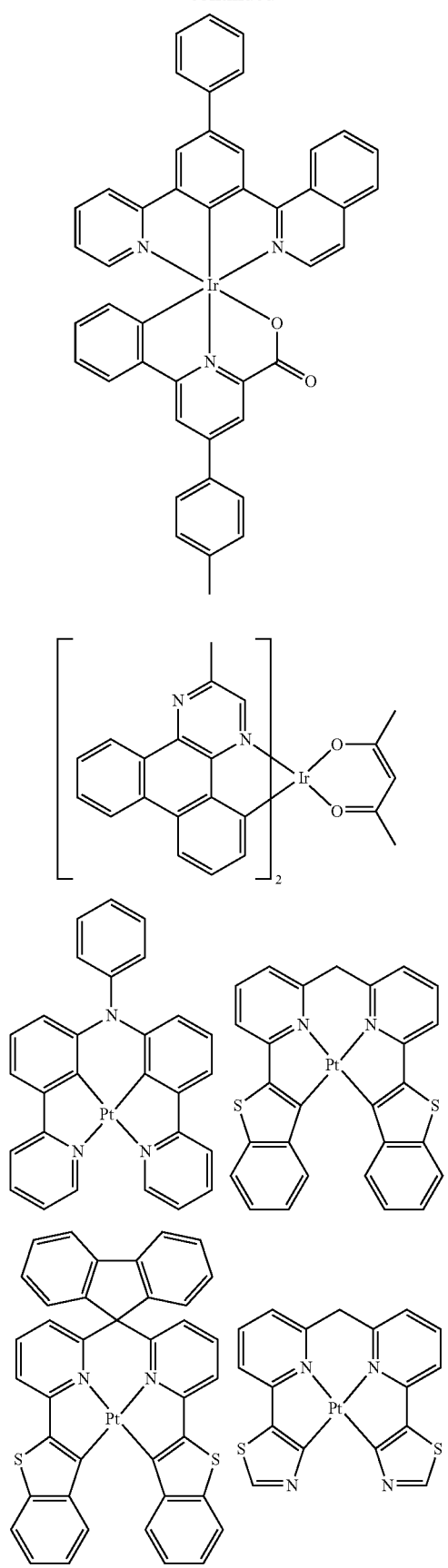

111
-continued
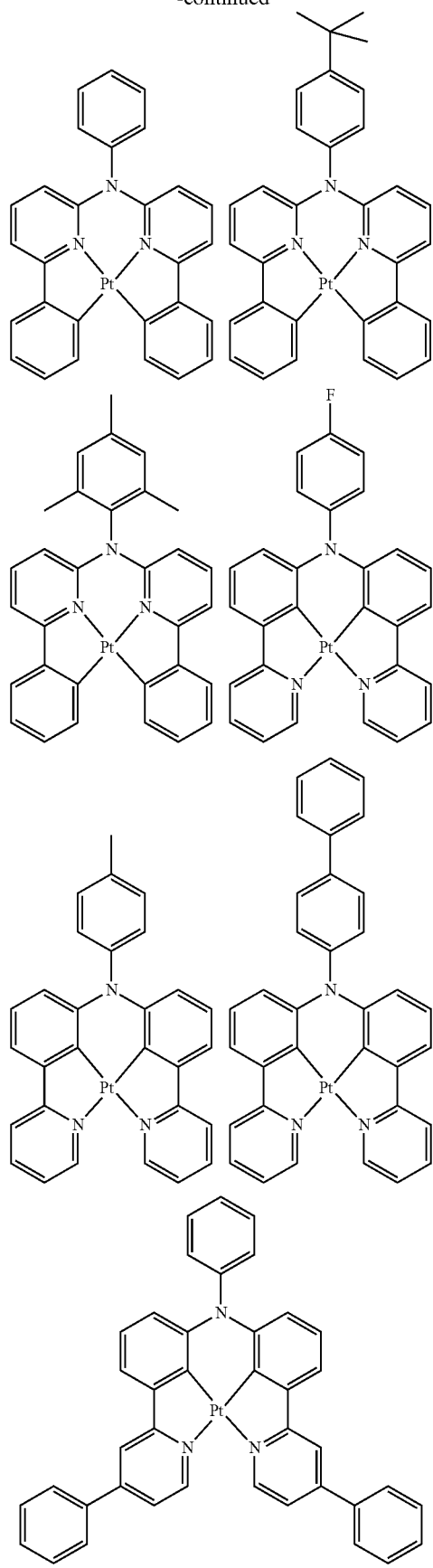
112
-continued
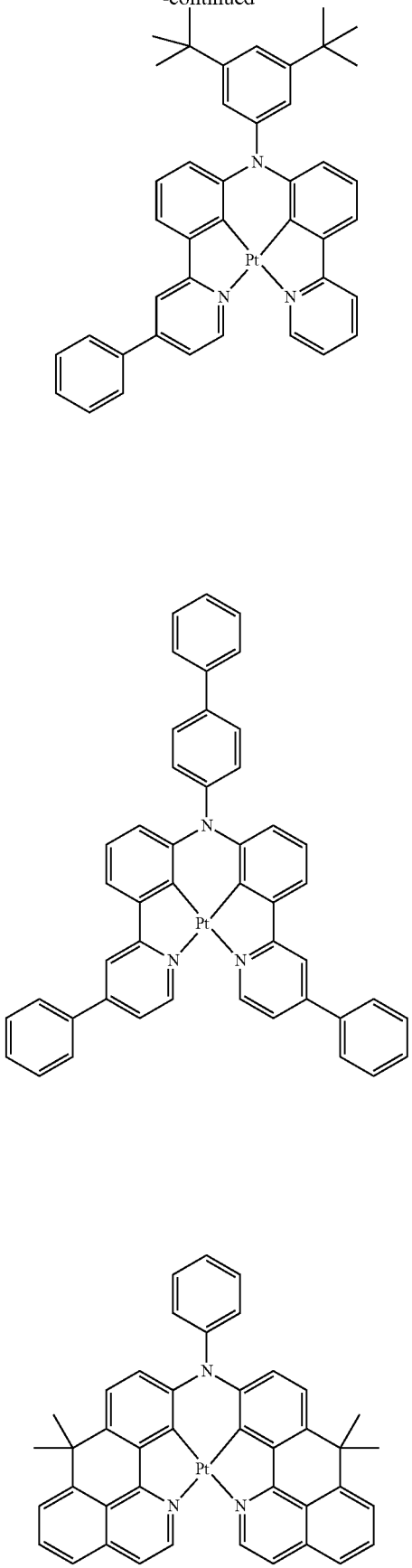

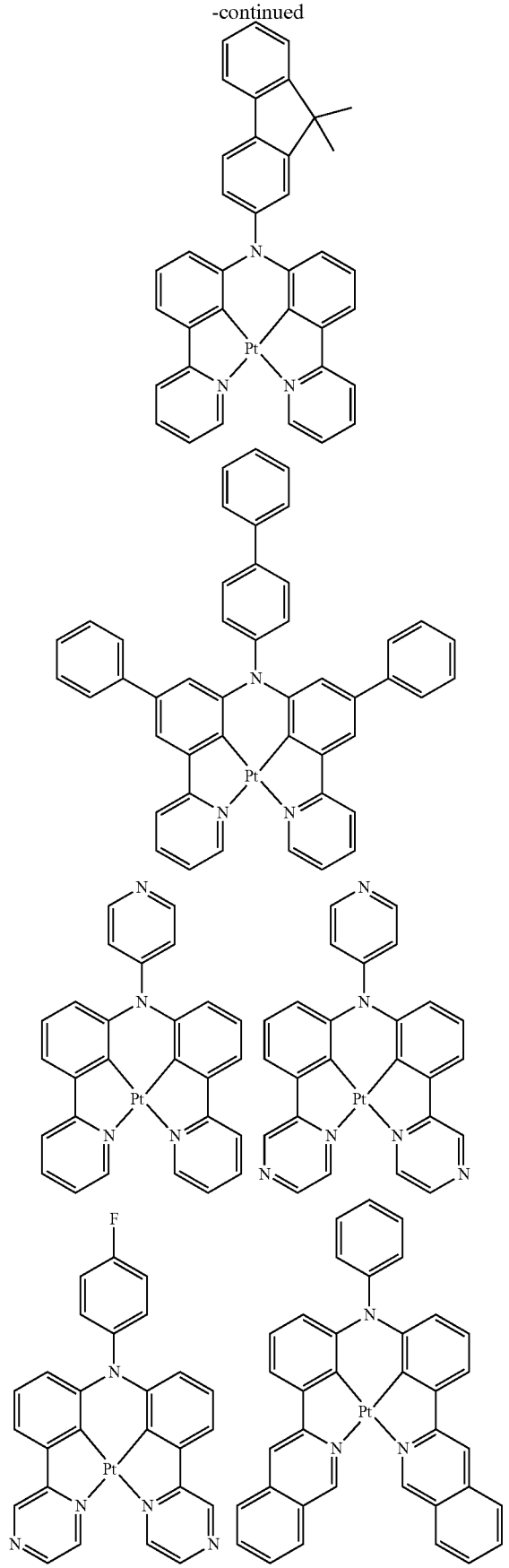
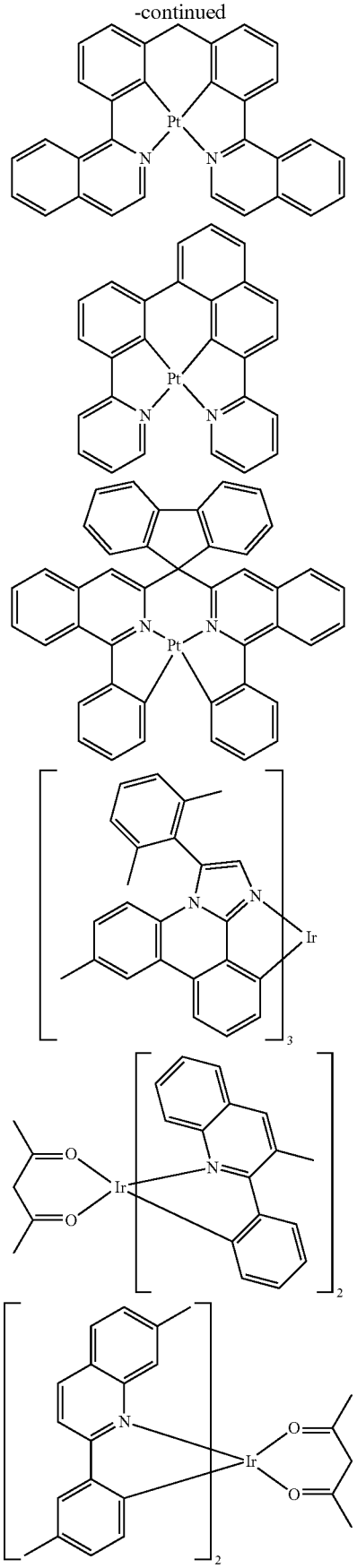

115
-continued
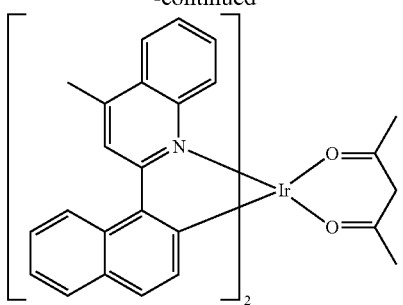
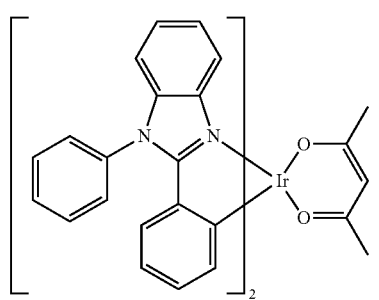
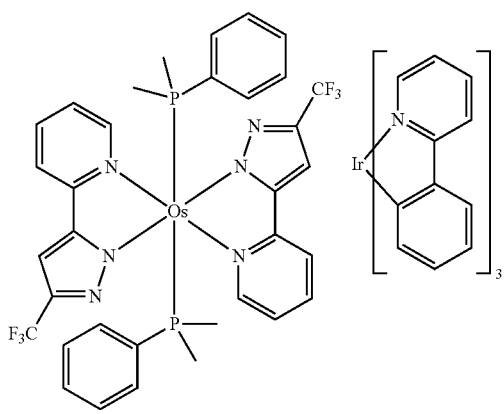
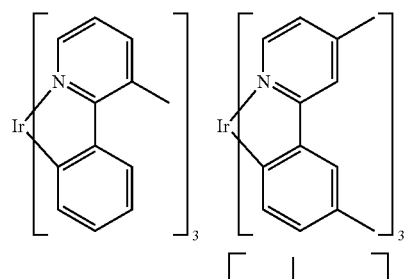
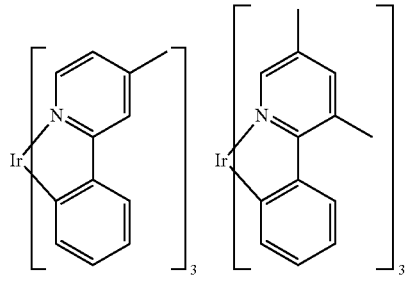
116
-continued
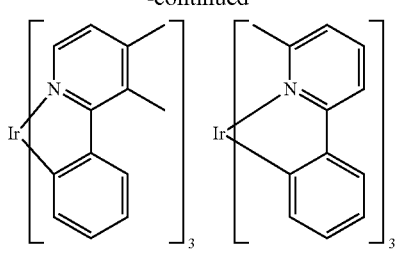
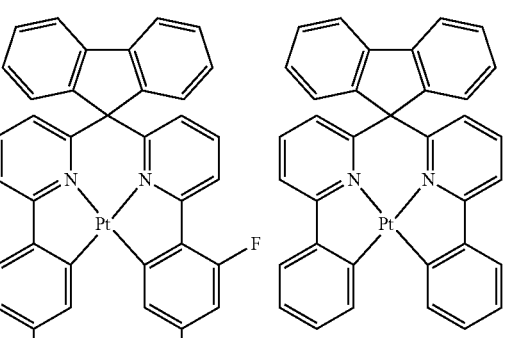
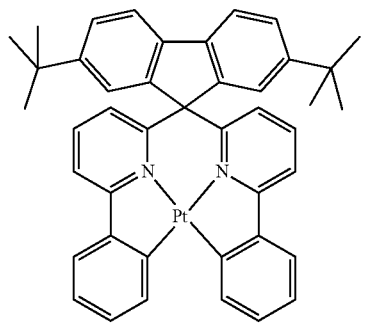
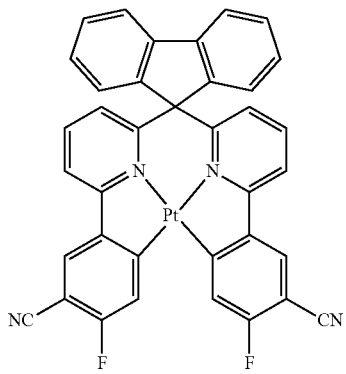

117
-continued
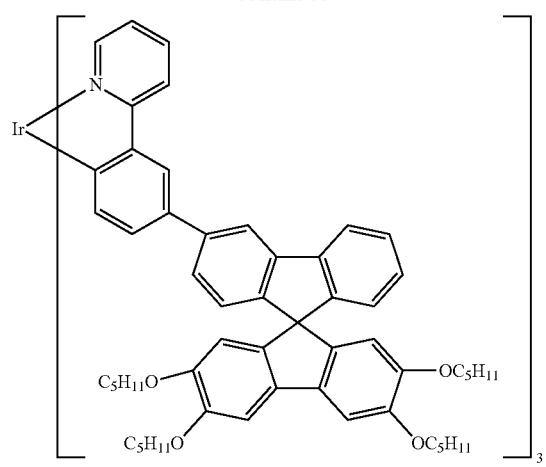
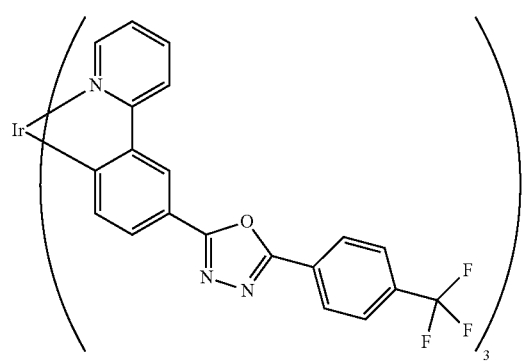
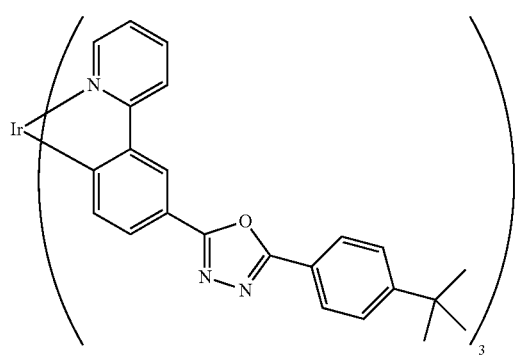
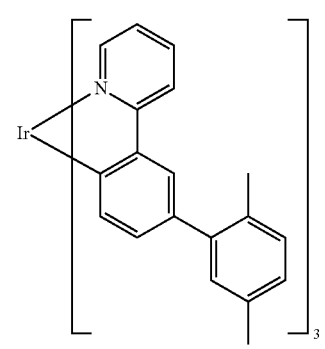
118
-continued
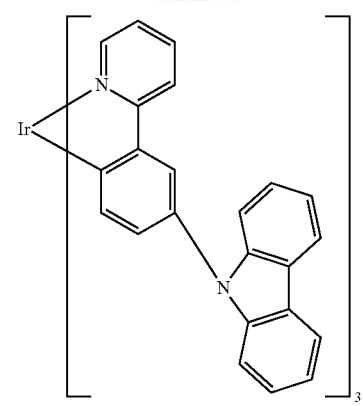
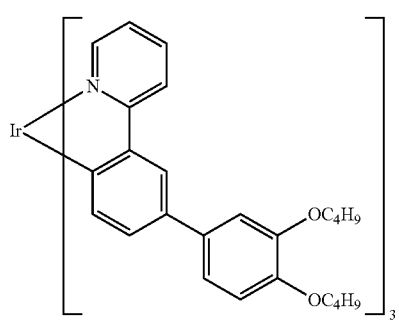
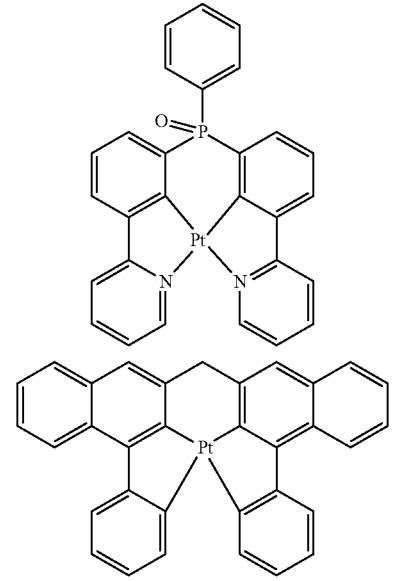
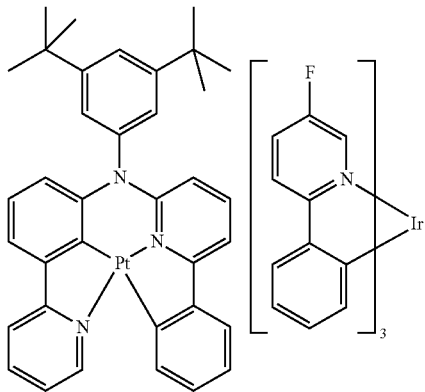

119
-continued
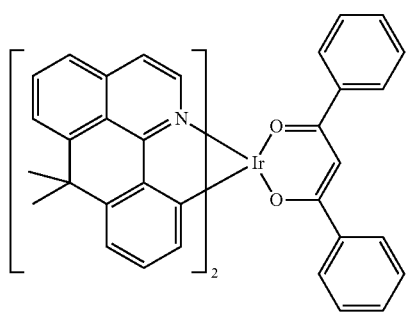
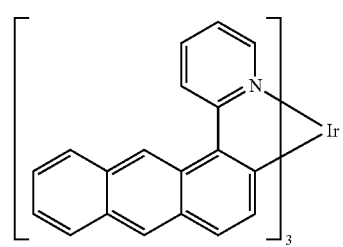
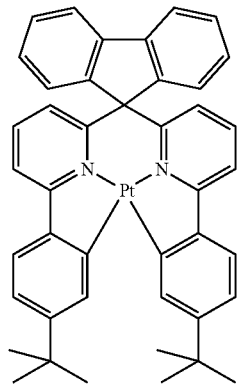
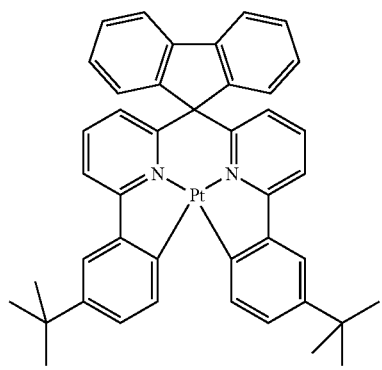
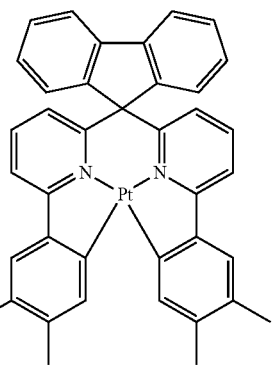
120
-continued
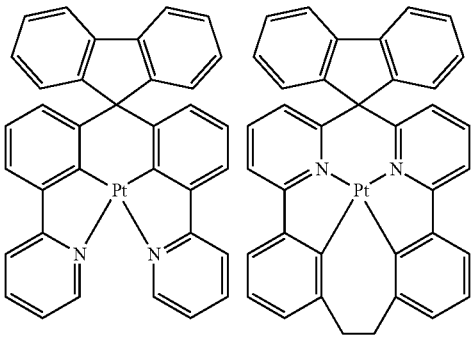
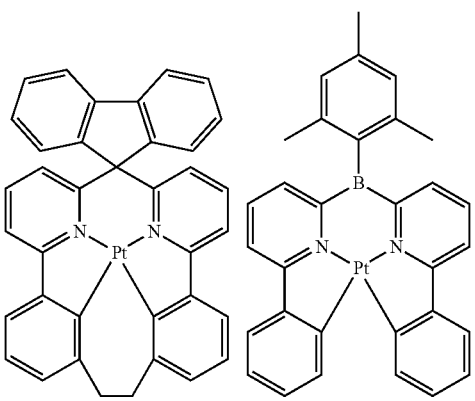
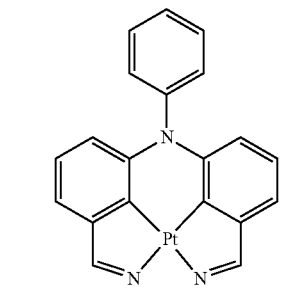
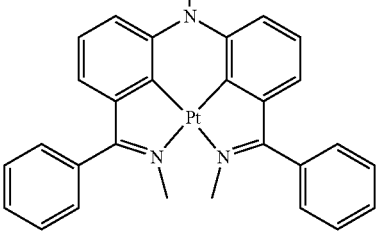

121
-continued
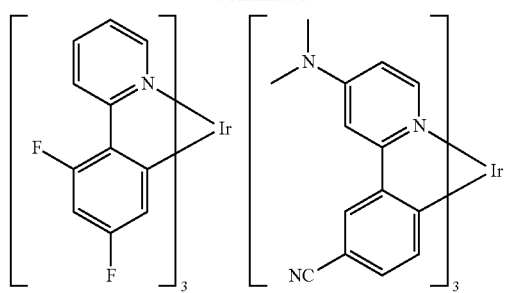
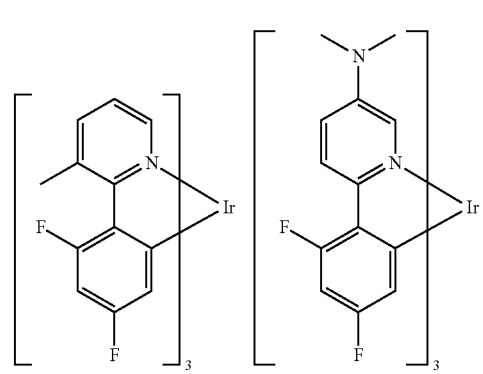
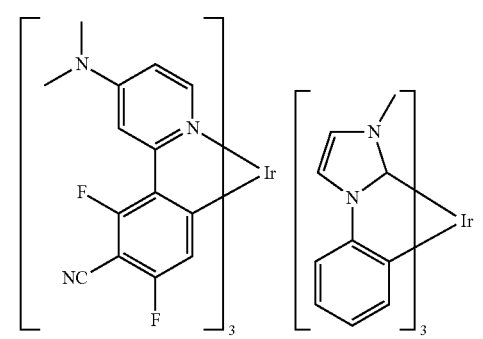
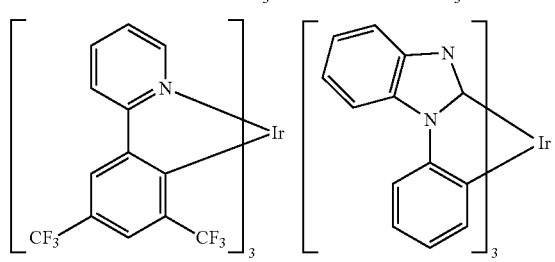
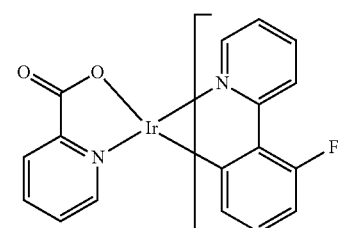
122
-continued
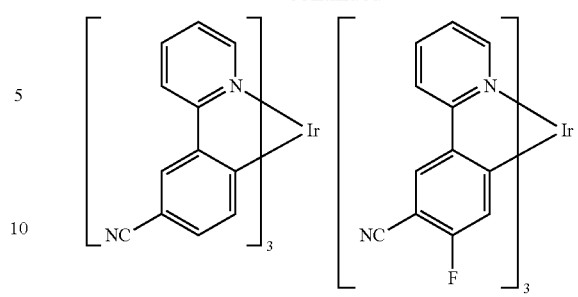
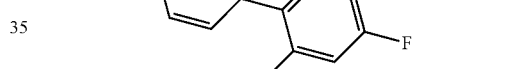
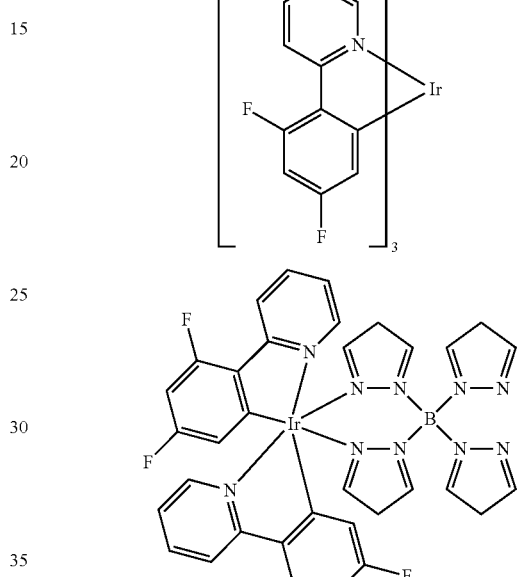
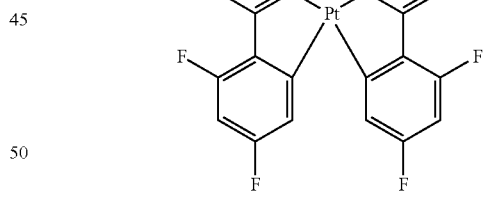
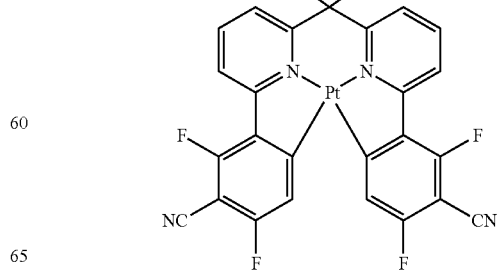

123
-continued
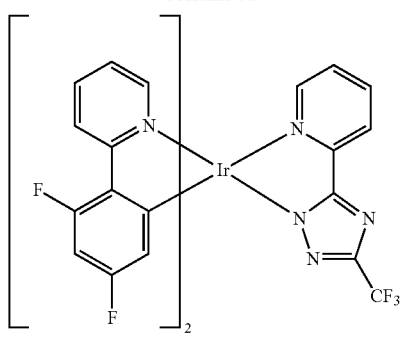
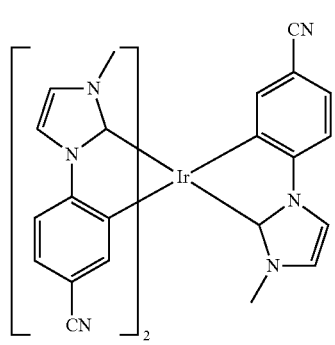
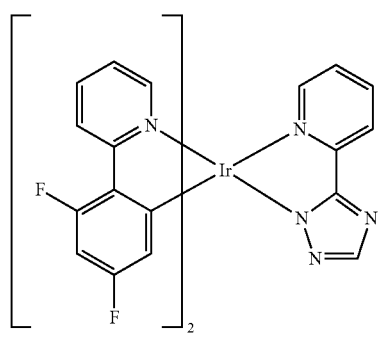
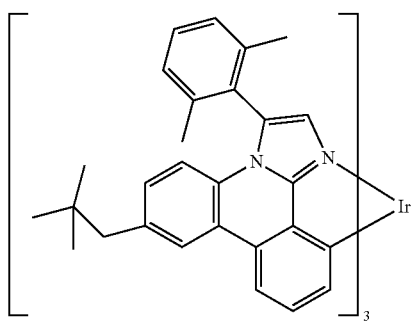
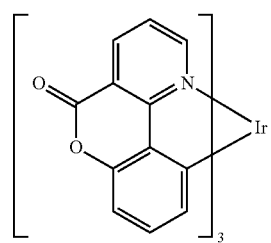
124
-continued
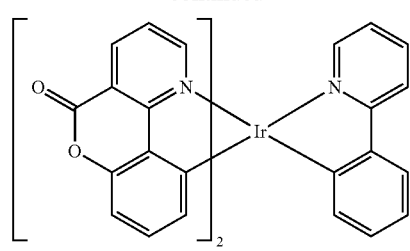
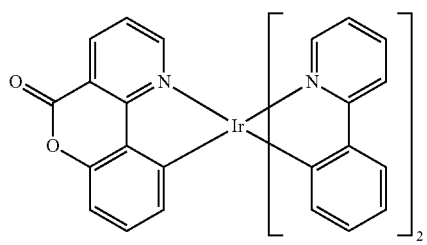
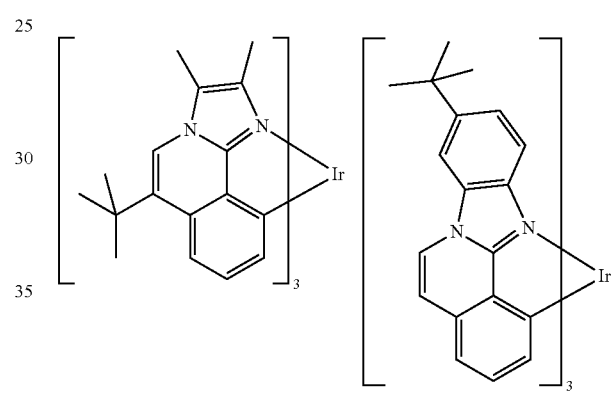
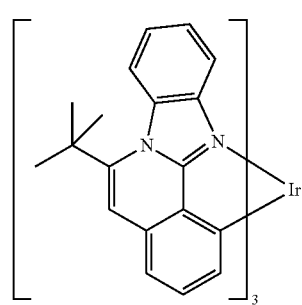
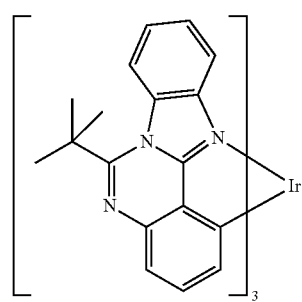

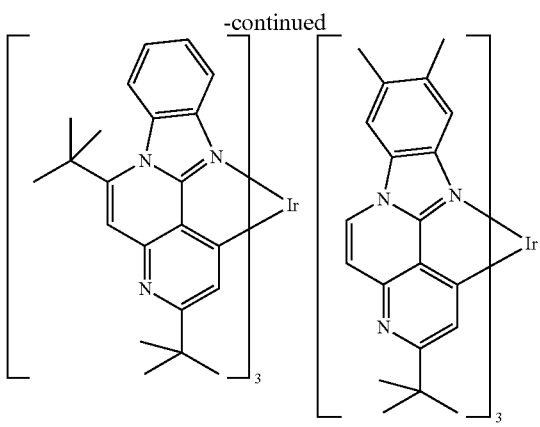

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

It is additionally possible to use the compounds of the invention in a hole transport layer or in a hole injection layer or in an exciton or electron blocker layer.

In the further layers of the organic electroluminescent device of the invention, it is possible to use any materials as typically used according to the prior art. The person skilled in the art is therefore able, without exercising inventive skill, to use any materials known for organic electroluminescent devices in combination with the inventive compounds of formula (1) or according to the preferred embodiments.

Additionally preferred is an organic electroluminescent device, characterized in that one or more layers are coated by a sublimation process. In this case, the materials are applied by vapor deposition in vacuum sublimation systems at an initial pressure of less than $10^{-5}$ mbar, preferably less than $10^{-6}$ mbar. It is also possible that the initial pressure is even lower or higher, for example less than $10^{-7}$ mbar.

Preference is likewise given to an organic electroluminescent device, characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured (for example, M. S. Arnold et al., *Appl. Phys. Lett.* 2008, 92, 053301).

Preference is additionally given to an organic electroluminescent device, characterized in that one or more layers are produced from solution, for example by spin-coating, or by any printing method, for example inkjet printing, LITI (light-induced thermal imaging, thermal transfer printing), screen printing, flexographic printing, offset printing or nozzle printing. For this purpose, soluble compounds are needed, which are obtained, for example, through suitable substitution. These methods are especially also suitable for oligomers, dendrimers and polymers.

In addition, hybrid methods are possible, in which, for example, one or more layers are applied from solution and one or more further layers are applied by vapor deposition. For example, it is possible to apply the emitting layer from solution and to apply the electron transport layer by vapor deposition.

These methods are known in general terms to those skilled in the art and can be applied by those skilled in the art without exercising inventive skill to organic electroluminescent devices comprising the compounds of the invention.

The compounds of the invention, when used in organic electroluminescent devices, have one or more of the following surprising advantages over the prior art:

1. Higher power efficiency of corresponding devices compared to systems according to the prior art.
2. Higher stability of corresponding devices compared to systems according to the prior art, which is manifested particularly in a much longer lifetime.
3. The organic electroluminescent devices of the invention have a reduced operating voltage.
4. When the compounds of the invention are used as matrix material for phosphorescent emitters, it is already possible to achieve very good results with only a low emitter concentration in the region of less than 10% by volume.
5. The compounds of the invention have a very good thermal stability.

The invention is now illustrated in detail by the examples which follow, without any intention of restricting it thereby.

WORKING EXAMPLES

A) Synthesis Examples

The syntheses which follow, unless stated otherwise, are conducted under a protective gas atmosphere in dried solvents. The solvents and reagents can be purchased, for example, from Sigma-ALDRICH or ABCR. For the compounds known from the literature, the corresponding CAS numbers are also reported in each case.

Example 1: 3,3-(5-chloro-1,3-phenylene)bis[9-phenyl-9H-carbazole]

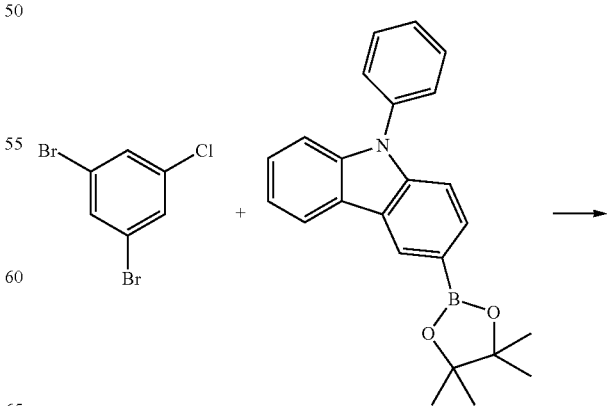

[1126522-69-7]

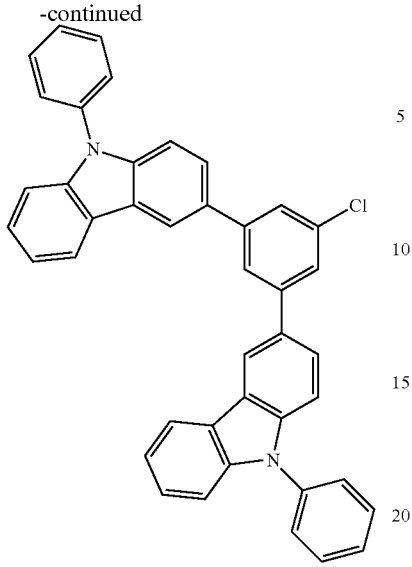

50 g (185 mmol) of 1,3-dibromo-5-chlorobenzene, 143 g (388 mmol) of phenylboronic acid and 78 g (369 mmol) of potassium phosphate are suspended in 250 mL of water and 500 mL of dioxane. 830 mg (3.6 mmol) of Pd(OAC)$_2$ and 3.3 g (11 mmol) of P(o-Tol)$_3$ are added to this suspension, and the reaction mixture is heated under reflux for 16 h. The mixture is subsequently partitioned between ethyl acetate and water, and the organic phase is washed three times with water and dried over Na$_2$SO$_4$ and concentrated by rotary evaporation. The remaining residue is recrystallized from heptane/toluene. The yield is 104 g (175 mmol, 95%).

In an analogous manner, it is possible to obtain the following compounds:

| | Reactant 1 | Reactant 2 | Product | Yield |
|---|---|---|---|---|
| 1a | ![Br,Cl,Br structure] | ![boronic acid phenanthrene] [1188094-10-1] | ![product 1a] | 89% |
| 1b | ![Br,Cl,Br structure] | ![diphenyl triazine boronic acid] [1251825-65-6] | ![product 1b] | 88% |

-continued
| Reactant 1 | Reactant 2 | Product | Yield |
|---|---|---|---|
| 1c 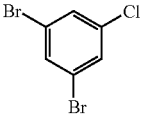 | 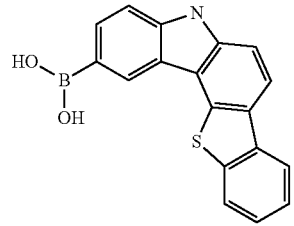 [1350842-21-5] | 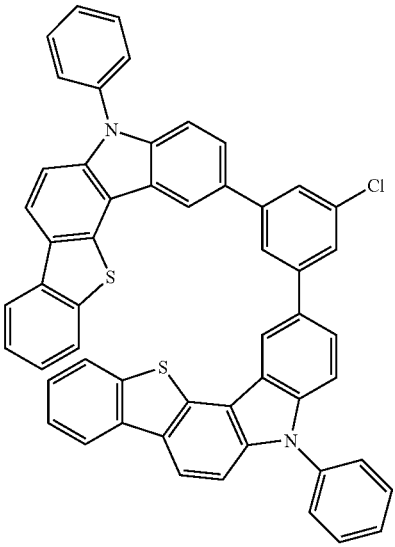 [SMILES: Clc1cc(-c2ccc3c(c2)c2c4sc5ccccc5c4ccc2n3-c2ccccc2)cc(-c2ccc3c(c2)c2c4sc5ccccc5c4ccc2n3-c2ccccc2)c1] | 75% |
| 1e  | 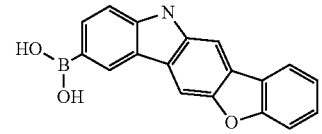 [1377576-52-7] | 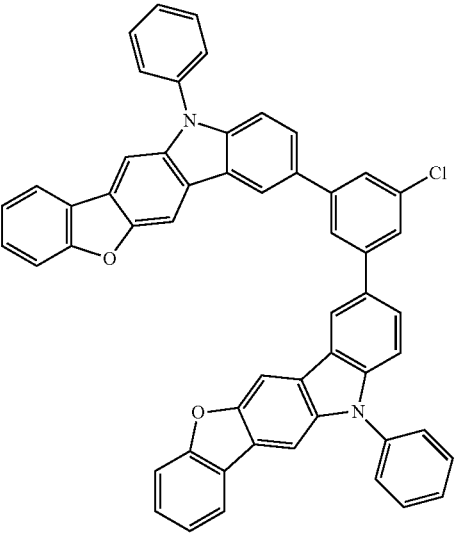 [SMILES: Clc1cc(-c2ccc3c(c2)c2cc4oc5ccccc5c4cc2n3-c2ccccc2)cc(-c2ccc3c(c2)c2cc4oc5ccccc5c4cc2n3-c2ccccc2)c1] | 78% |

-continued
| | Reactant 1 | Reactant 2 | Product | Yield |
|---|---|---|---|---|
| 1f | 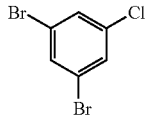 | 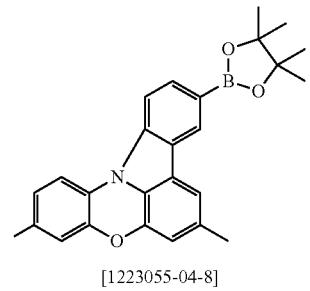
[1223055-04-8] | 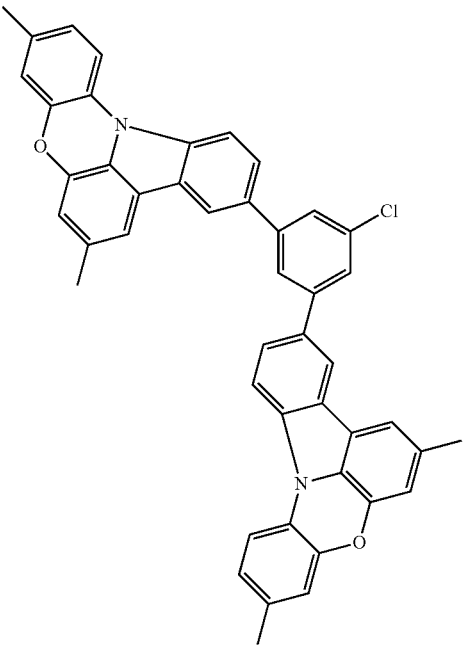 | 69% |
| 1g | 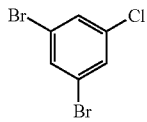 | 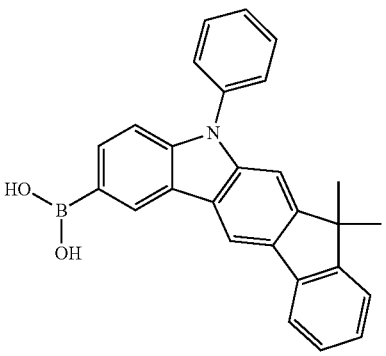
[1379585-25-7] | 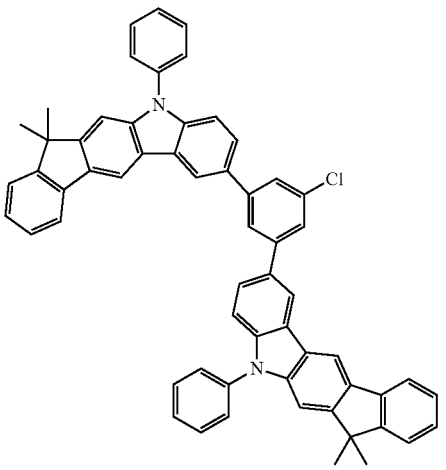 [SMILES: CC1(C)c2ccccc2-c2cc3c4cc(-c5cc(Cl)cc(-c6ccc7c(c6)c6cc8c(cc6n7-c6ccccc6)C(C)(C)c6ccccc6-8)c5)ccc4n(-c4ccccc4)c3cc21] | 89% |
| 1h | 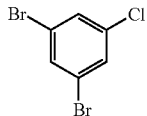 | 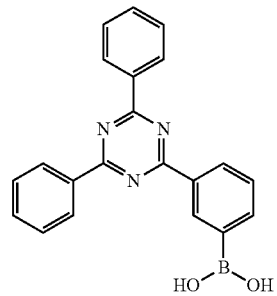
[1269508-31-7] | 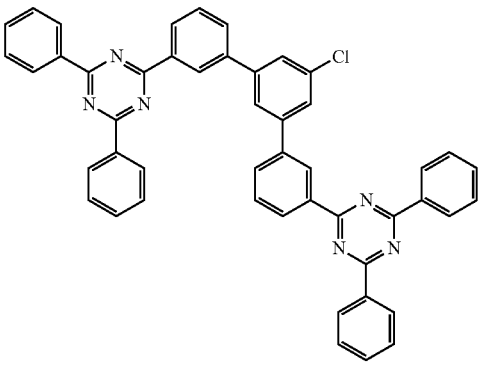 [SMILES: Clc1cc(-c2cccc(-c3nc(-c4ccccc4)nc(-c4ccccc4)n3)c2)cc(-c2cccc(-c3nc(-c4ccccc4)nc(-c4ccccc4)n3)c2)c1] | 87% |

-continued
| | Reactant 1 | Reactant 2 | Product | Yield |
|---|---|---|---|---|
| 1i | 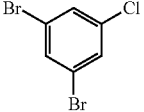 | 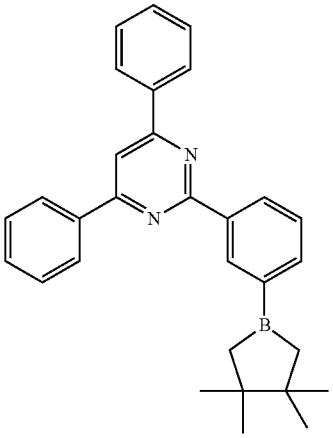  [1381862-91-4] | 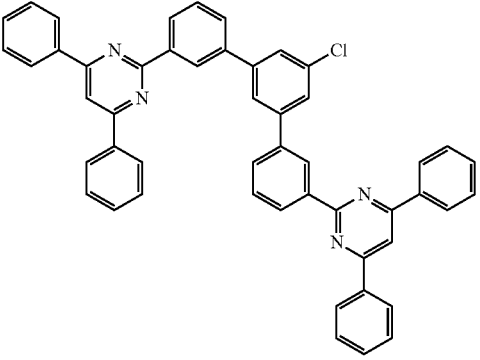 [SMILES: Clc1cc(-c2cccc(-c3nc(-c4ccccc4)cc(-c4ccccc4)n3)c2)cc(-c2cccc(-c3nc(-c4ccccc4)cc(-c4ccccc4)n3)c2)c1] | 82% |
| 1j | 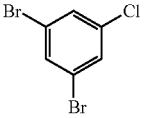 | 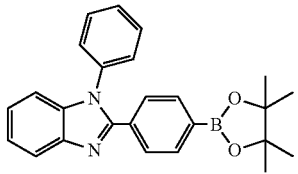  [1146340-38-8] | 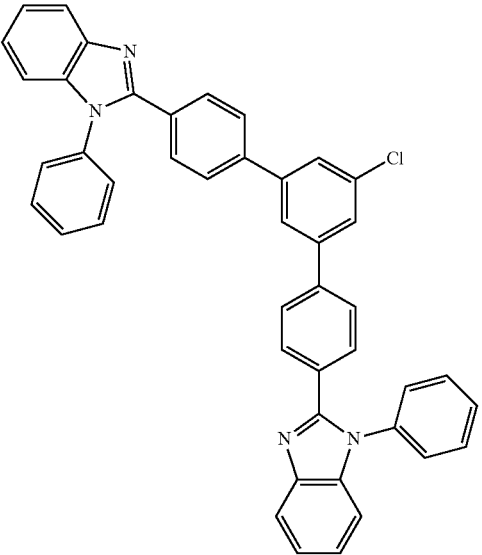 [SMILES: Clc1cc(-c2ccc(-c3nc4ccccc4n3-c3ccccc3)cc2)cc(-c2ccc(-c3nc4ccccc4n3-c3ccccc3)cc2)c1] | 87% |
| 1k | 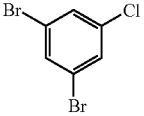 | 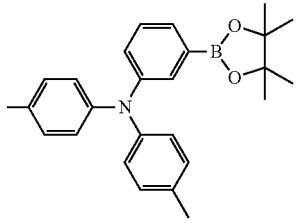  [1162753-18-5] | 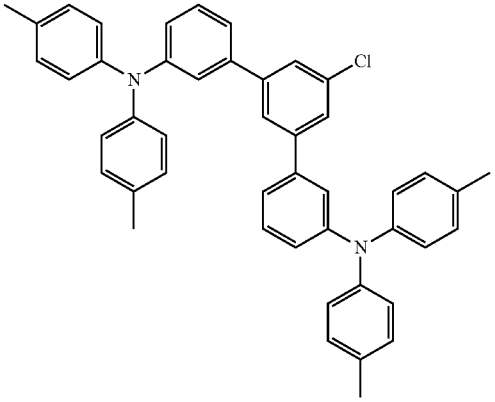 | 88% |

| | Reactant 1 | Reactant 2 | Product | Yield |
|---|---|---|---|---|
| 11 | 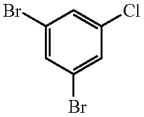 | 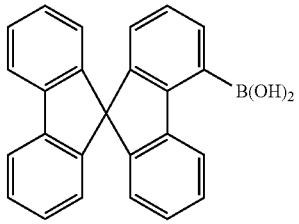<br>[1421789-05-0] | 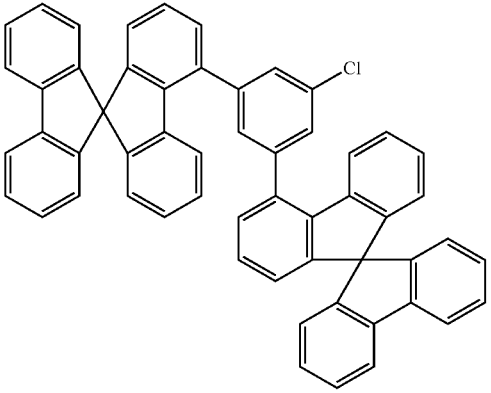 [SMILES: Clc1cc(-c2cccc3c2-c2ccccc2C32c3ccccc3-c3ccccc32)cc(-c2cccc3c2-c2ccccc2C32c3ccccc3-c3ccccc32)c1] | 85% |
| 1i | 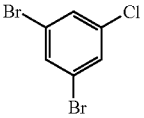 | 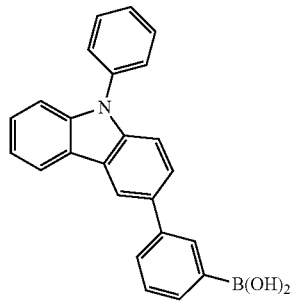<br>854952-60-6 | 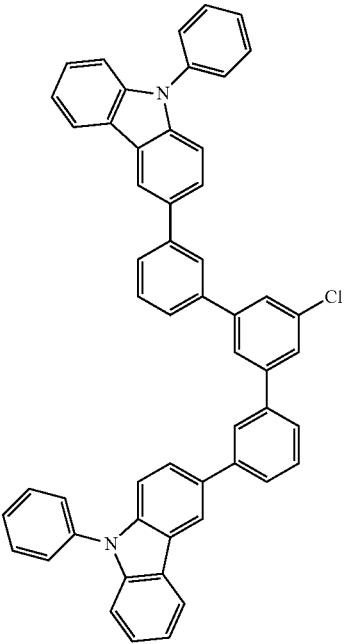 [SMILES: Clc1cc(-c2cccc(-c3ccc4c(c3)c3ccccc3n4-c3ccccc3)c2)cc(-c2cccc(-c3ccc4c(c3)c3ccccc3n4-c3ccccc3)c2)c1] | 78% |

| | Reactant 1 | Reactant 2 | Product | Yield |
|---|---|---|---|---|
| 1j | 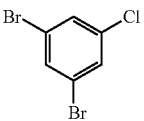 | 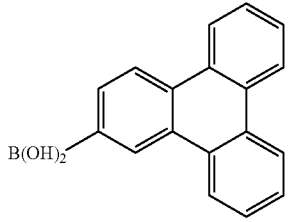[654664-63-8] | 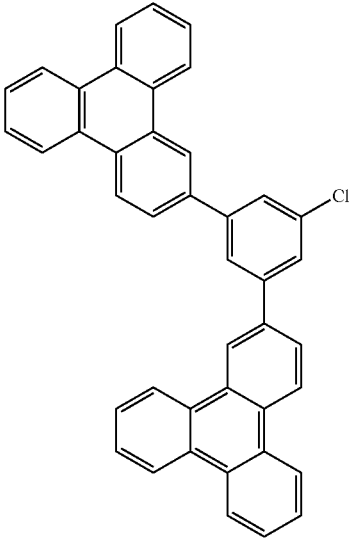 [SMILES: Clc1cc(-c2ccc3c4ccccc4c4ccccc4c3c2)cc(-c2ccc3c4ccccc4c4ccccc4c3c2)c1] | 77% |

Example 2: 3,3-[5(4,4,5,5-tetramethyl-[1,3,2]dioxaborolanyl-2yl)-1,3-phenylene]bis[9-phenyl-9H-carbazole]

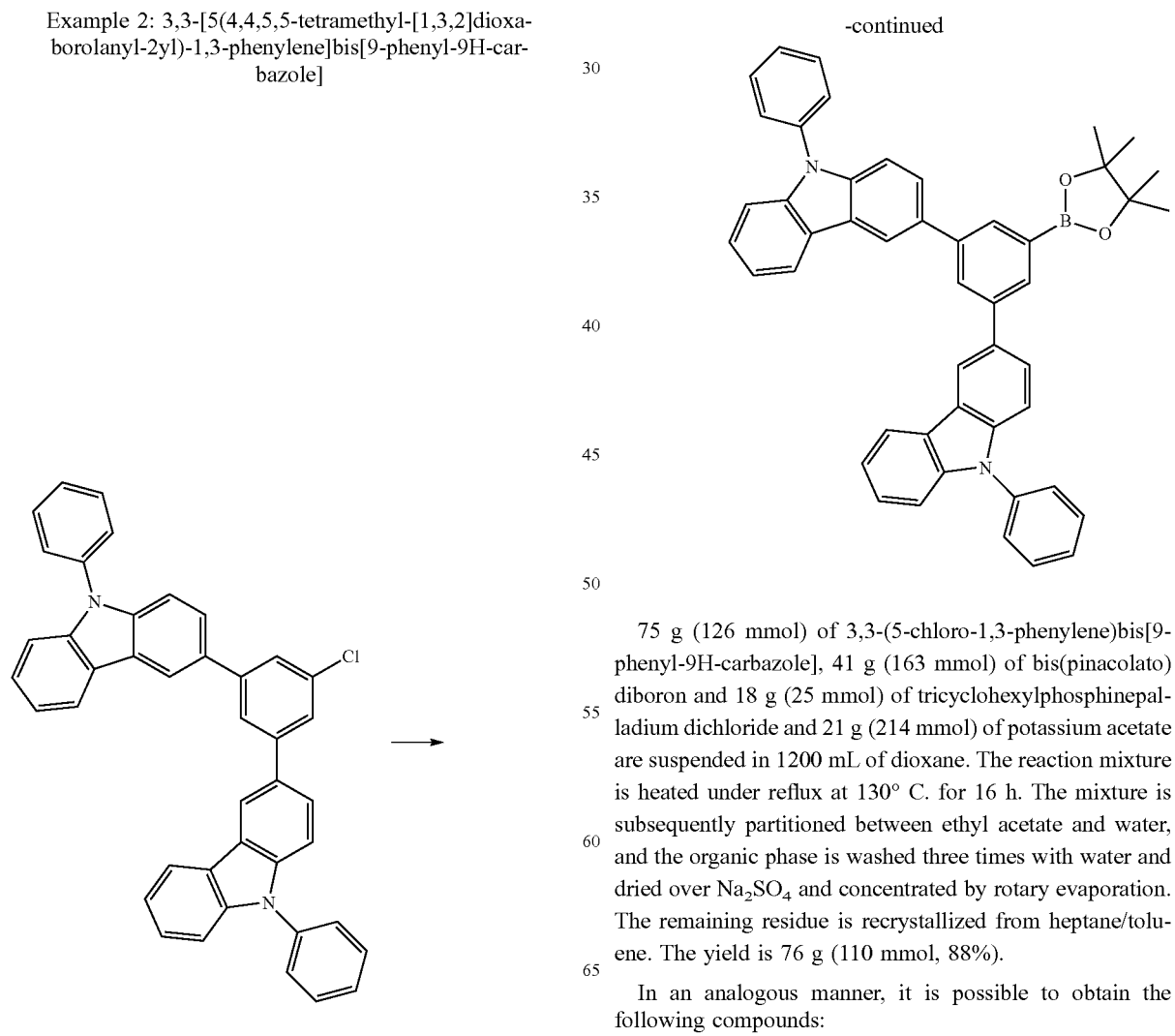

75 g (126 mmol) of 3,3-(5-chloro-1,3-phenylene)bis[9-phenyl-9H-carbazole], 41 g (163 mmol) of bis(pinacolato)diboron and 18 g (25 mmol) of tricyclohexylphosphinepalladium dichloride and 21 g (214 mmol) of potassium acetate are suspended in 1200 mL of dioxane. The reaction mixture is heated under reflux at 130° C. for 16 h. The mixture is subsequently partitioned between ethyl acetate and water, and the organic phase is washed three times with water and dried over $Na_2SO_4$ and concentrated by rotary evaporation. The remaining residue is recrystallized from heptane/toluene. The yield is 76 g (110 mmol, 88%).

In an analogous manner, it is possible to obtain the following compounds:

| Reactant 1 | Product | Yield |
|---|---|---|
| 2a 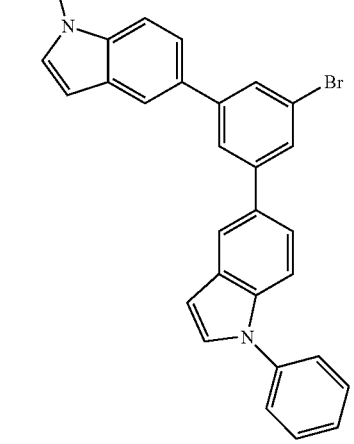 [1462961-95-0] | 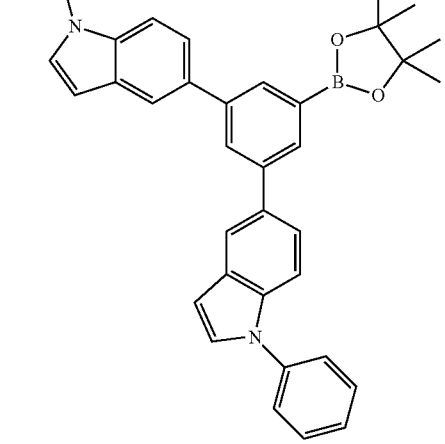 | 77% |
| 2b 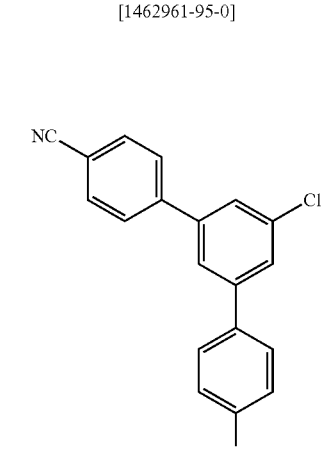 [1445904-36-8]] | 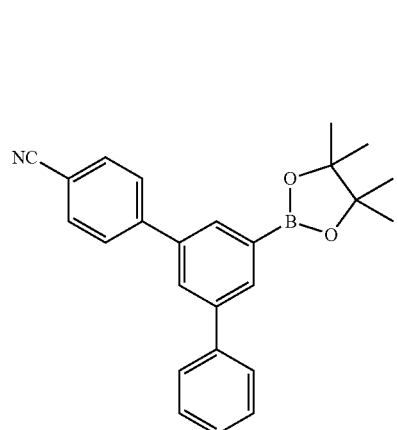 | 78% |
| 2c 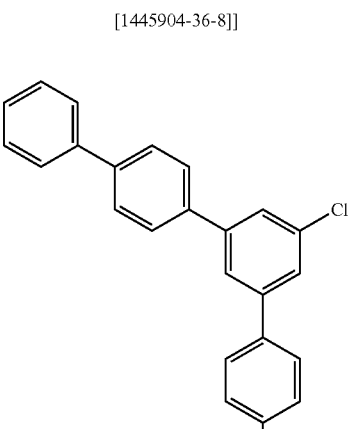 [1247176-23-3] | 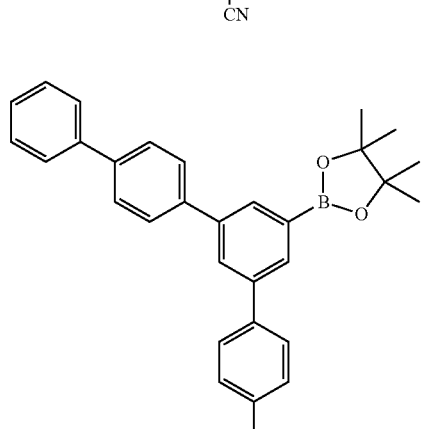 | 65% |

| Reactant 1 | Product | Yield |
|---|---|---|
| 2d 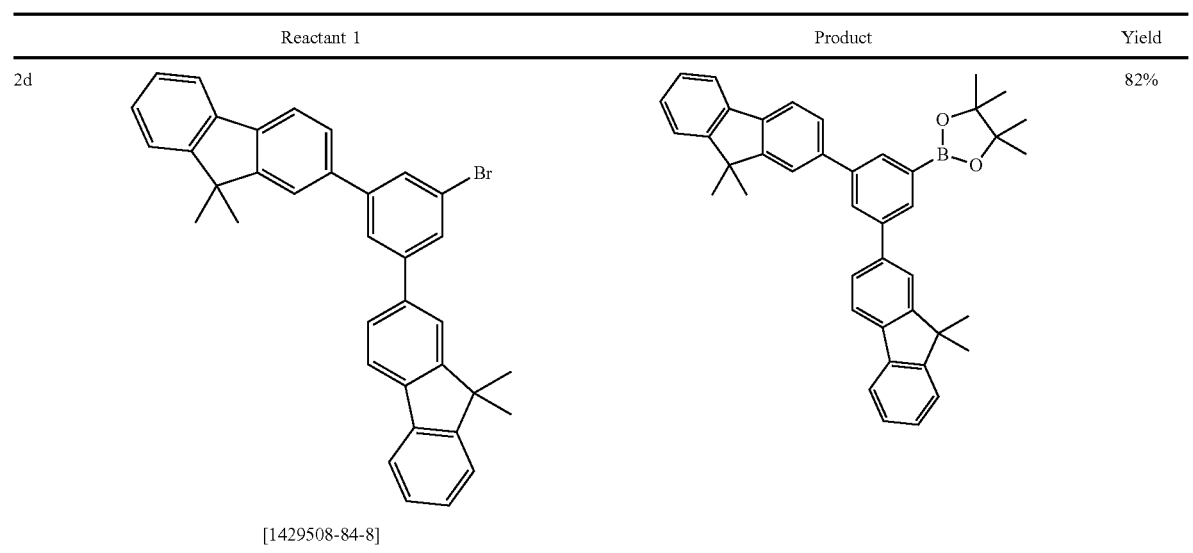 [1429508-84-8] | | 82% |
| 2e 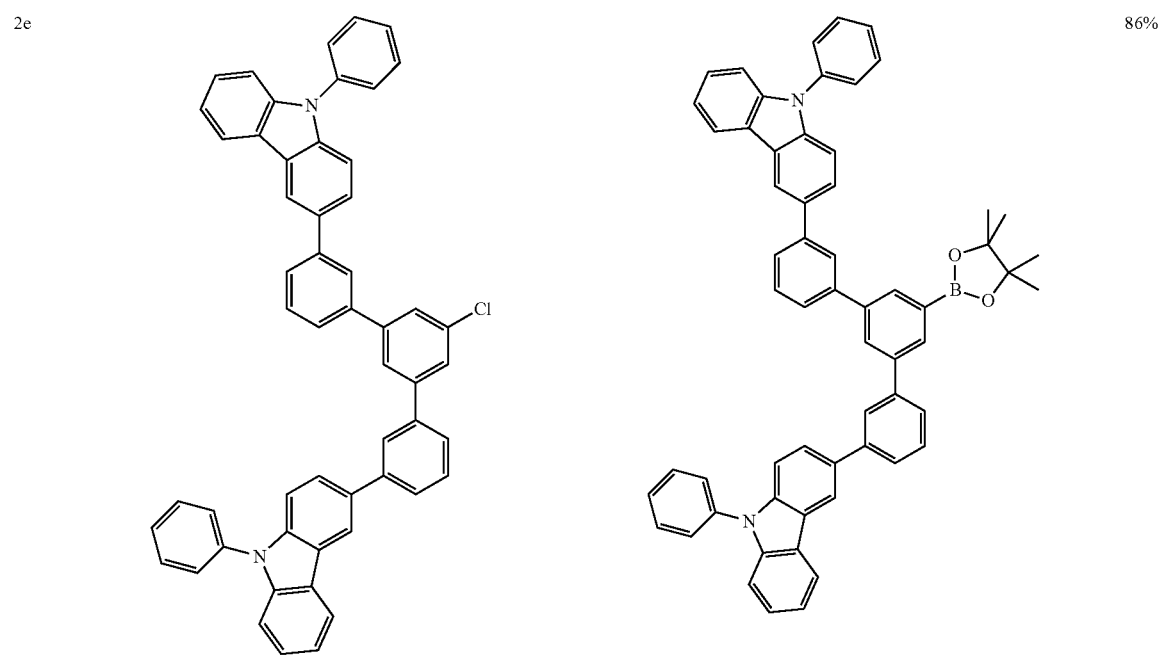 | | 86% |

| Reactant 1 | Product | Yield |
|---|---|---|
| 2f 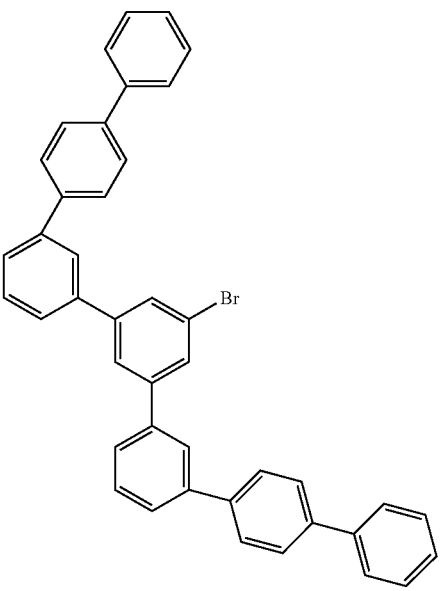 [1401577-24-9] | 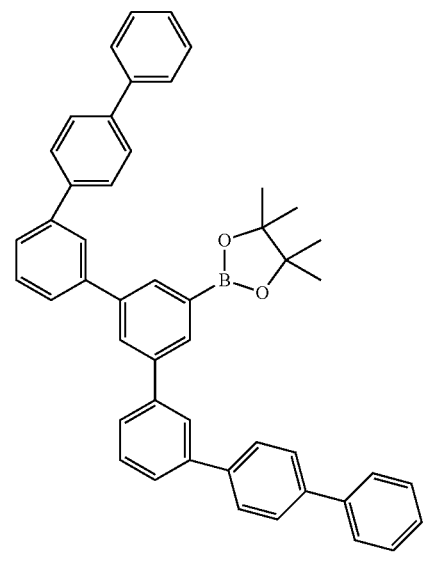 [SMILES: CC1(C)OB(c2cc(-c3cccc(-c4ccc(-c5ccccc5)cc4)c3)cc(-c3cccc(-c4ccc(-c5ccccc5)cc4)c3)c2)OC1(C)C] | 90% |
| 2h 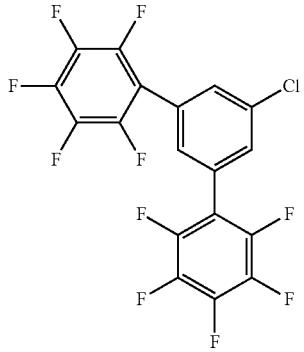 [1357178-34-7] | 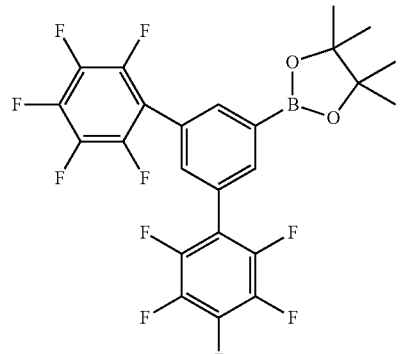 | 93% |
| 2i 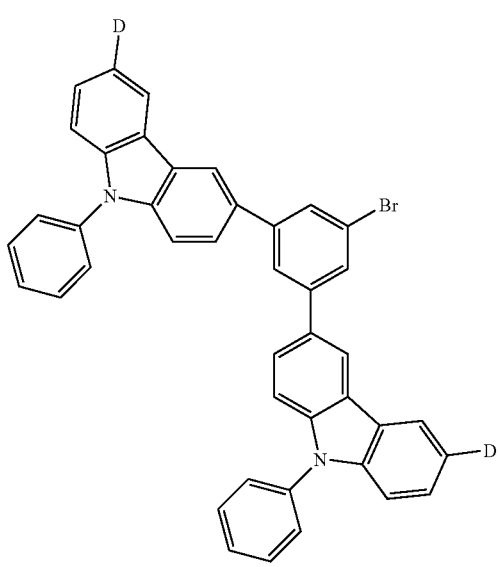 [1345860-61-8] | 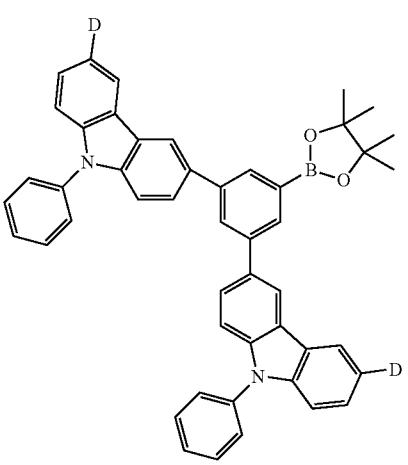 [SMILES: [2H]c1ccc2c(c1)c1cc(-c3cc(B4OC(C)(C)C(C)(C)O4)cc(-c4ccc5c(c4)c4cc([2H])ccc4n5-c4ccccc4)c3)ccc1n2-c1ccccc1] | 81% |

-continued

| Reactant 1 | Product | Yield |
|---|---|---|
| 2j [1271836-77-1] | | 90% |
| 2k [1247176-30-2] | | 96% |
| 2l | | 87% |

-continued
| | Reactant 1 | Product | Yield |
|---|---|---|---|
| 2m | 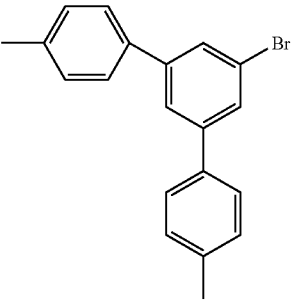 [918964-52-0] | 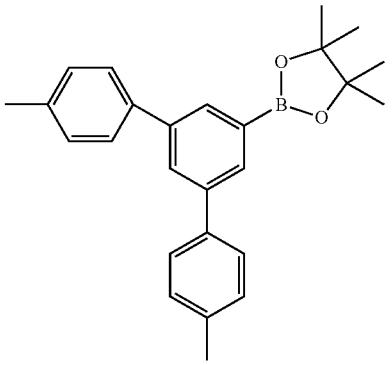 | 95% |
| 2n | 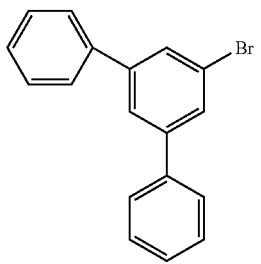 [103068-20-8] | 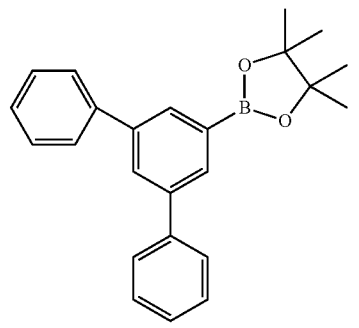 [SMILES: CC1(C)OB(c2cc(-c3ccccc3)cc(-c3ccccc3)c2)OC1(C)C] | 97% |
| 2o | 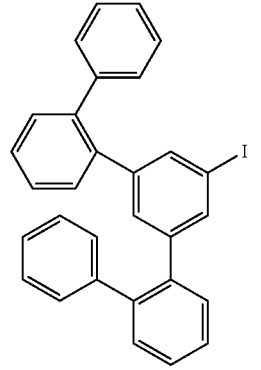 [88241-90-1] | 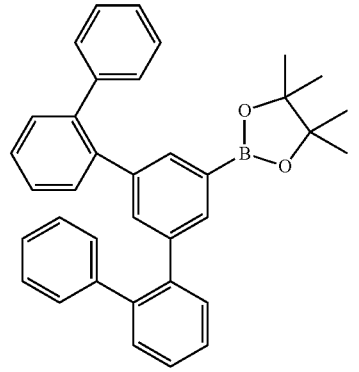 [SMILES: CC1(C)OB(c2cc(-c3ccccc3-c3ccccc3)cc(-c3ccccc3-c3ccccc3)c2)OC1(C)C] | 86% |
| 2p | 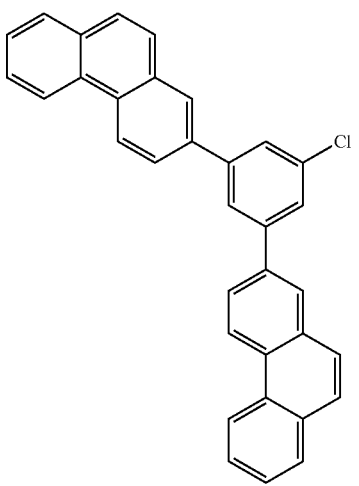 [SMILES: Clc1cc(-c2ccc3c(ccc4ccccc43)c2)cc(-c2ccc3c(ccc4ccccc43)c2)c1] | 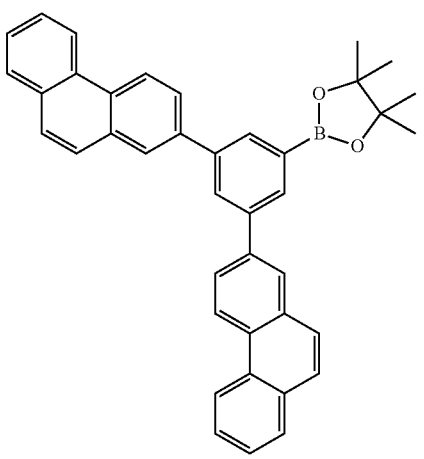 [SMILES: CC1(C)OB(c2cc(-c3ccc4c(ccc5ccccc54)c3)cc(-c3ccc4c(ccc5ccccc54)c3)c2)OC1(C)C] | 88% |

| Reactant 1 | Product | Yield |
|---|---|---|
| 2q | | 73% |
| 2r | | 70% |
| 2s | | 79% |

-continued
| Reactant 1 | Product | Yield |
|---|---|---|
| 2t 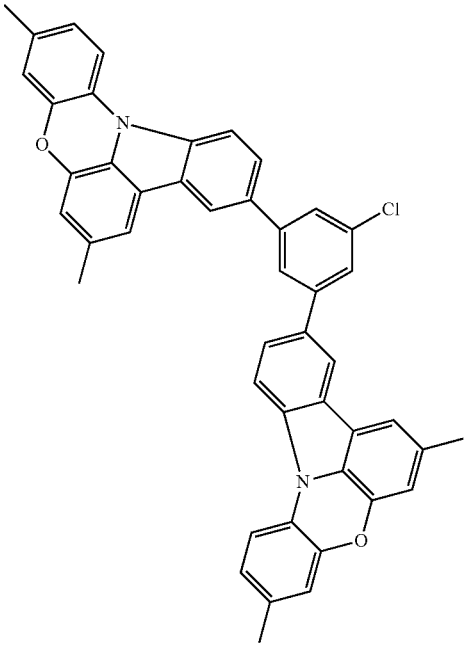 | 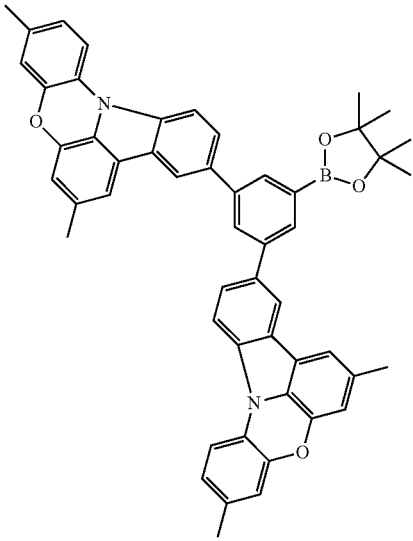 | 75% |
| 2u 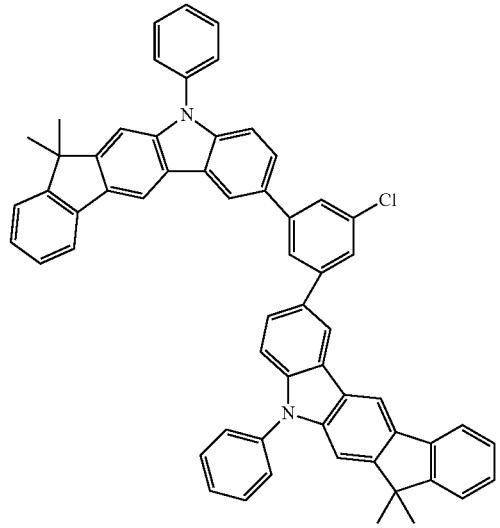 [SMILES: CC1(C)c2ccccc2-c2cc3c4cc(-c5cc(Cl)cc(-c6ccc7c(c6)c6cc8c(cc6n7-c6ccccc6)C(C)(C)c6ccccc6-8)c5)ccc4n(-c4ccccc4)c3cc21] | 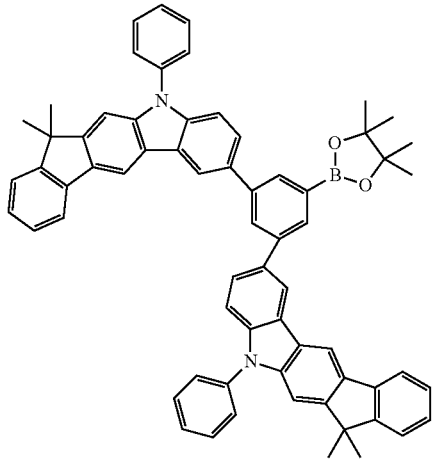 [SMILES: CC1(C)c2ccccc2-c2cc3c4cc(-c5cc(B6OC(C)(C)C(C)(C)O6)cc(-c6ccc7c(c6)c6cc8c(cc6n7-c6ccccc6)C(C)(C)c6ccccc6-8)c5)ccc4n(-c4ccccc4)c3cc21] | 78% |
| 2v 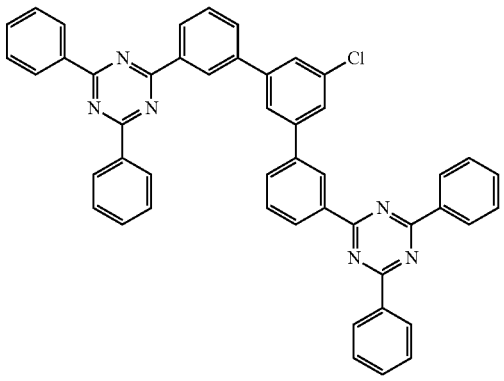 [SMILES: Clc1cc(-c2cccc(-c3nc(-c4ccccc4)nc(-c4ccccc4)n3)c2)cc(-c2cccc(-c3nc(-c4ccccc4)nc(-c4ccccc4)n3)c2)c1] | 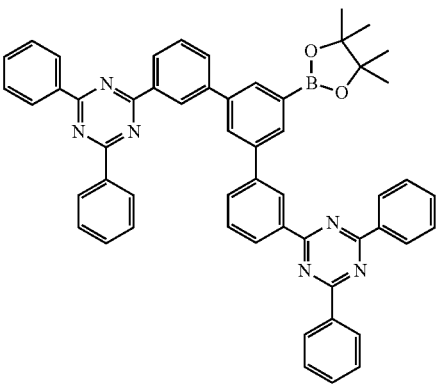 [SMILES: CC1(C)OB(c2cc(-c3cccc(-c4nc(-c5ccccc5)nc(-c5ccccc5)n4)c3)cc(-c3cccc(-c4nc(-c5ccccc5)nc(-c5ccccc5)n4)c3)c2)OC1(C)C] | 69% |

| Reactant 1 | Product | Yield |
|---|---|---|
| 2w | | 74% |
| 2x | | 86% |
| 2z | | 89% |

| Reactant 1 | Product | Yield |
|---|---|---|
| 2aa 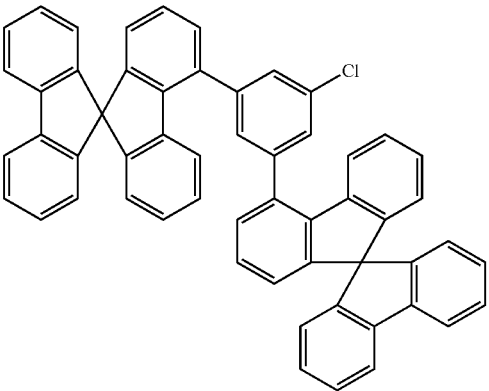 [SMILES: Clc1cc(-c2cccc3c2-c2ccccc2C32c3ccccc3-c3ccccc32)cc(-c2cccc3c2-c2ccccc2C32c3ccccc3-c3ccccc32)c1] | 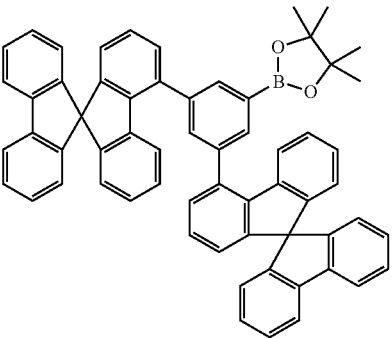 [SMILES: CC1(C)OB(c2cc(-c3cccc4c3-c3ccccc3C43c4ccccc4-c4ccccc43)cc(-c3cccc4c3-c3ccccc3C43c4ccccc4-c4ccccc43)c2)OC1(C)C] | 76% |

Example 3: Reaction with 1-bromo-2-nitrobenzene

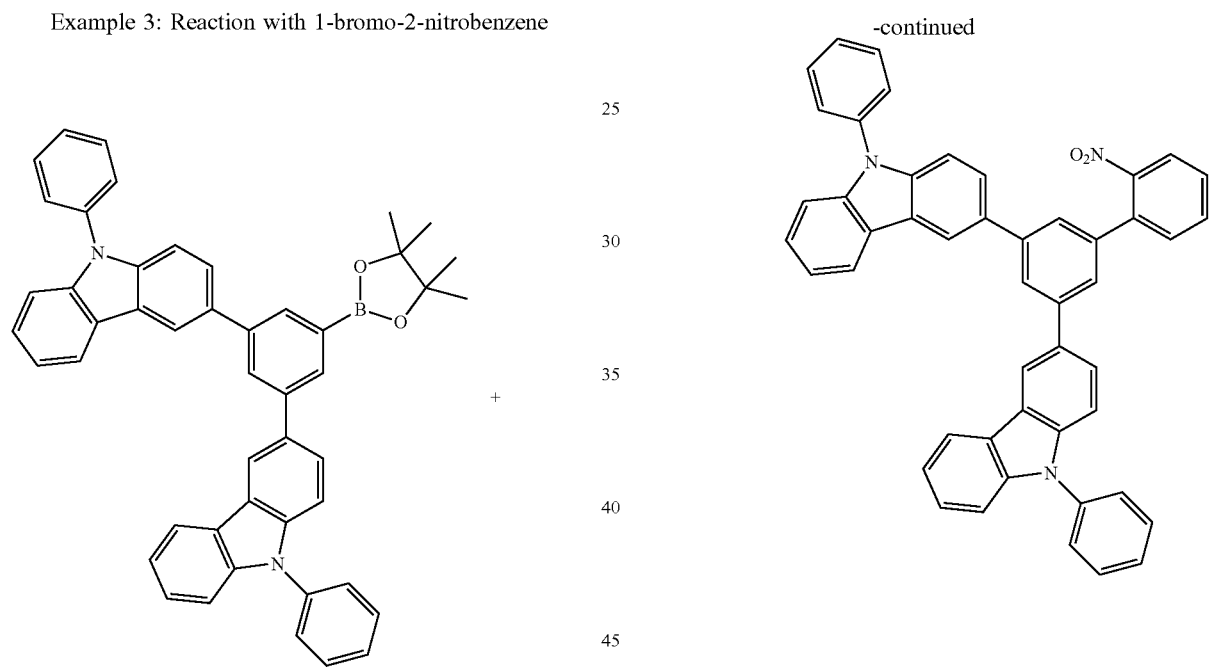

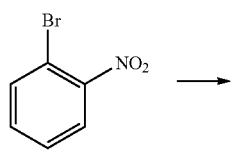

46 g (67 mmol) of 3,3-[5-(4,4,5,5-tetramethyl-[1,3,2]dioxaborolanyl-2-yl)-1,3-phenylene]bis[9-phenyl-9H-carbazole], 16 g (81 mmol) of 1-bromo-2-nitrobenzene and 152 mg (0.67 mmol) of Pd(OAC)$_2$ and 178 mg (0.67 mmol) of P(o-Tol)$_3$ and 136 g (980 mmol) of potassium carbonate are suspended in 1000 mL of THF and 300 mL of water. The reaction mixture is heated under reflux at 130° C. for 16 h. The mixture is subsequently partitioned between ethyl acetate and water, and the organic phase is washed three times with water and dried over Na$_2$SO$_4$ and concentrated by rotary evaporation. The remaining residue is recrystallized from heptane/toluene. The yield is 42 g (62 mmol, 91%).

In an analogous manner, it is possible to obtain the following compounds:

|     | Reactant 1 | Reactant 2 |
| --- | --- | --- |
| 3a | 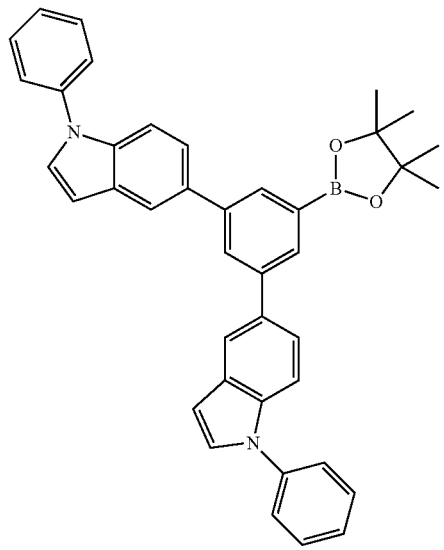 [SMILES: CC1(C)OB(c2cc(-c3ccc4c(ccn4-c4ccccc4)c3)cc(-c3ccc4c(ccn4-c4ccccc4)c3)c2)OC1(C)C] | 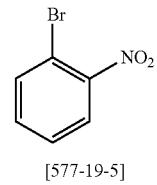<br>[577-19-5] |
| 3b | 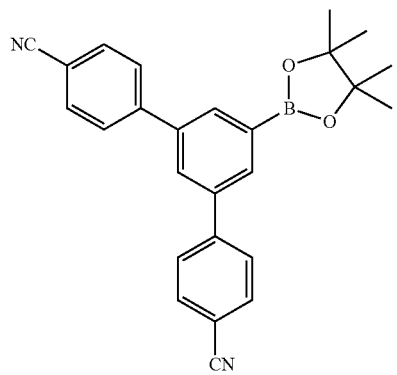 [SMILES: CC1(C)OB(c2cc(-c3ccc(C#N)cc3)cc(-c3ccc(C#N)cc3)c2)OC1(C)C] | 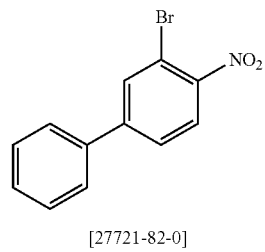 [SMILES: O=[N+]([O-])c1ccc(-c2ccccc2)cc1Br]<br>[27721-82-0] |
| 3c | 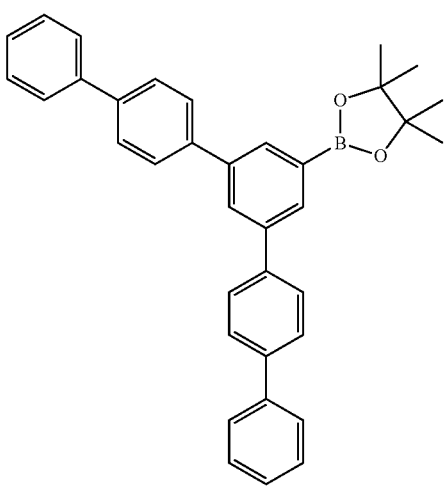 [SMILES: CC1(C)OB(c2cc(-c3ccc(-c4ccccc4)cc3)cc(-c3ccc(-c4ccccc4)cc3)c2)OC1(C)C] | 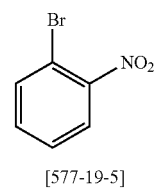<br>[577-19-5] |

| | | |
|---|---|---|
| 3d | 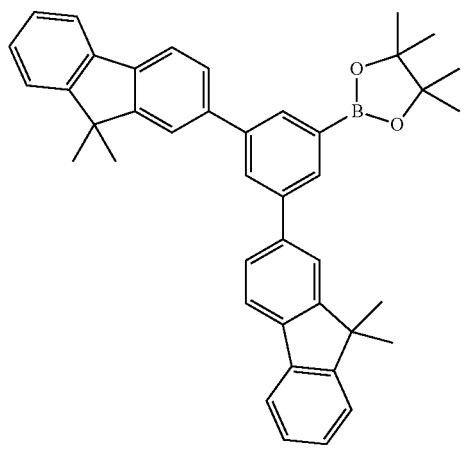 [SMILES: CC1(C)c2ccccc2-c2ccc(-c3cc(B4OC(C)(C)C(C)(C)O4)cc(-c4ccc5c(c4)C(C)(C)c4ccccc4-5)c3)cc21] | 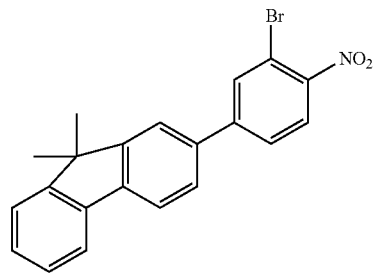
[1373131-68-0] |
| 3e | 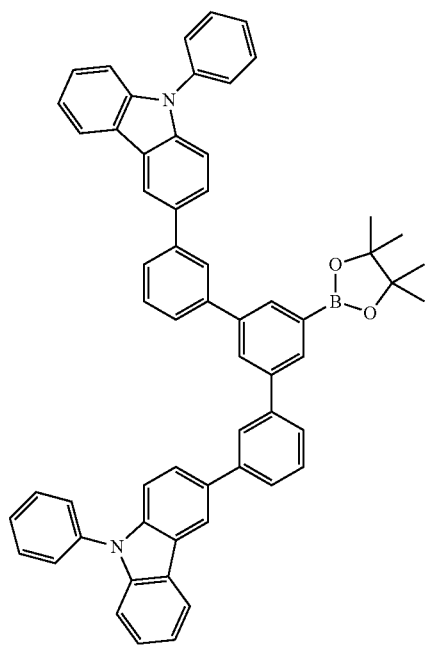 [SMILES: CC1(C)OB(c2cc(-c3cccc(-c4ccc5c(c4)c4ccccc4n5-c4ccccc4)c3)cc(-c3cccc(-c4ccc5c(c4)c4ccccc4n5-c4ccccc4)c3)c2)OC1(C)C] | 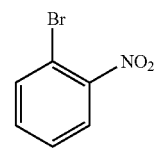
[577-19-5] |

| | | |
|---|---|---|
| 3f | 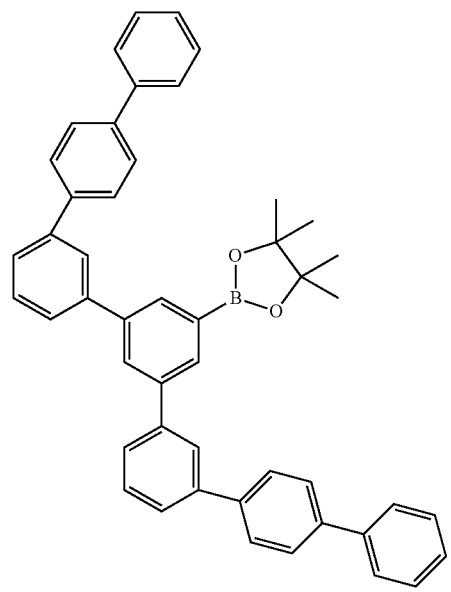 [SMILES: CC1(C)OB(c2cc(-c3cccc(-c4ccc(-c5ccccc5)cc4)c3)cc(-c3cccc(-c4ccc(-c5ccccc5)cc4)c3)c2)OC1(C)C] | 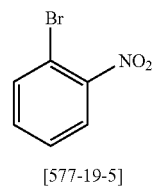[577-19-5] |
| 3h | 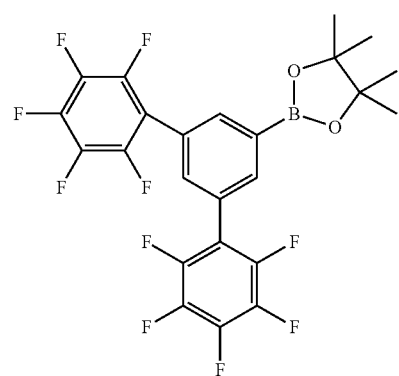 [SMILES: CC1(C)OB(c2cc(-c3c(F)c(F)c(F)c(F)c3F)cc(-c3c(F)c(F)c(F)c(F)c3F)c2)OC1(C)C] | 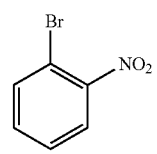[577-19-5] |
| 3i | 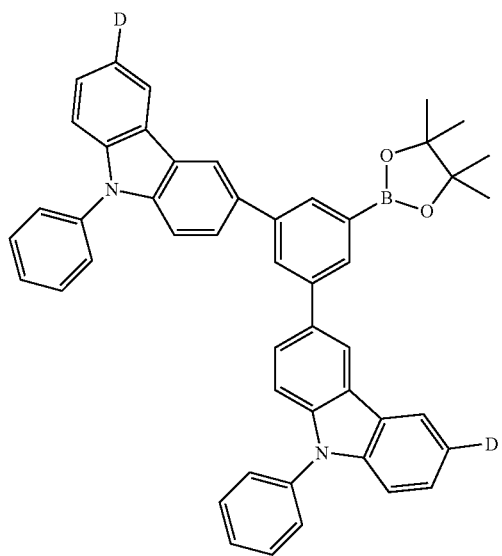 [SMILES: [2H]c1ccc2c(c1)c1cc(-c3cc(B4OC(C)(C)C(C)(C)O4)cc(-c4ccc5c(c4)c4cc([2H])ccc4n5-c4ccccc4)c3)ccc1n2-c1ccccc1] | [577-19-5] |

| | | |
|---|---|---|
| 3j | 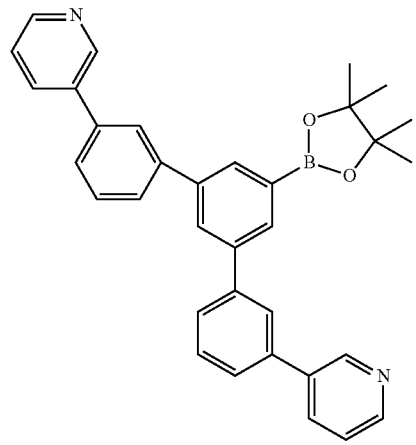 [SMILES: CC1(C)OB(c2cc(-c3cccc(-c4cccnc4)c3)cc(-c3cccc(-c4cccnc4)c3)c2)OC1(C)C] | 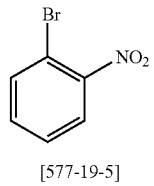
[577-19-5] |
| 3k | 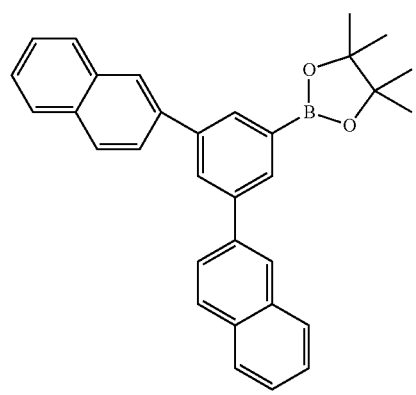 [SMILES: CC1(C)OB(c2cc(-c3ccc4ccccc4c3)cc(-c3ccc4ccccc4c3)c2)OC1(C)C] | 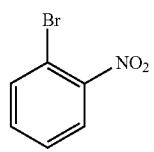
[577-19-5] |
| 3l | 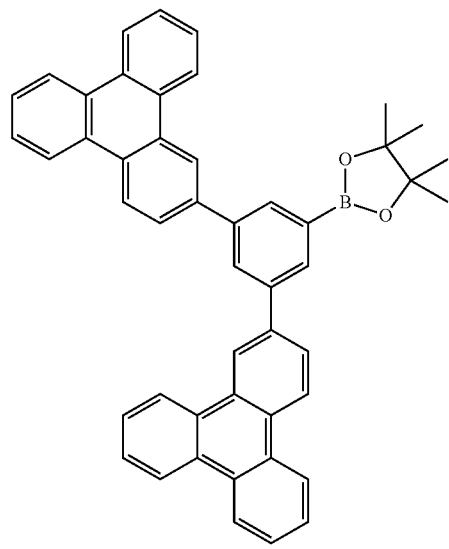 [SMILES: CC1(C)OB(c2cc(-c3ccc4c5ccccc5c5ccccc5c4c3)cc(-c3ccc4c5ccccc5c5ccccc5c4c3)c2)OC1(C)C] | 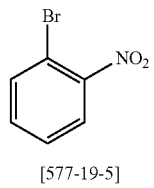
[577-19-5] |

| | | |
|---|---|---|
| 3m | 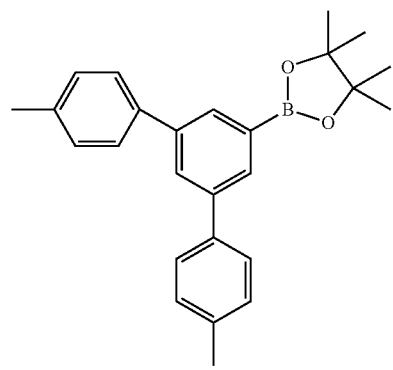 | 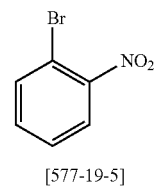
[577-19-5] |
| 3n | 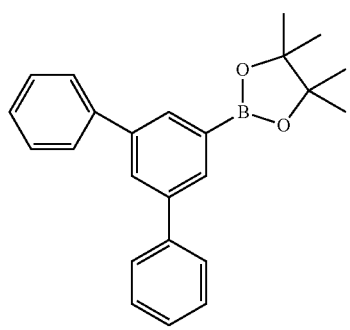 [SMILES: CC1(C)OB(c2cc(-c3ccccc3)cc(-c3ccccc3)c2)OC1(C)C] | 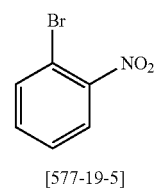
[577-19-5] |
| 3o | 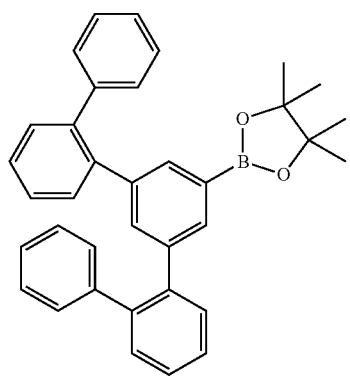 [SMILES: CC1(C)OB(c2cc(-c3ccccc3-c3ccccc3)cc(-c3ccccc3-c3ccccc3)c2)OC1(C)C] | 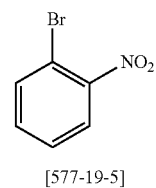
[577-19-5] |
| 3p | 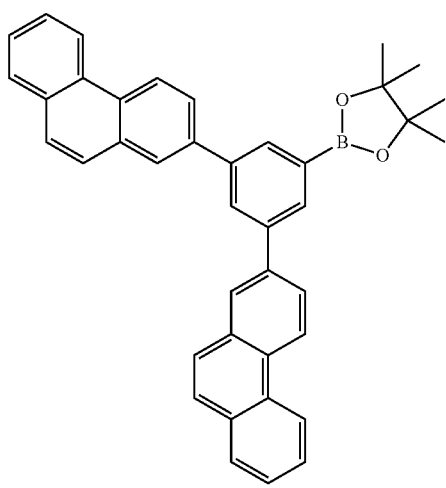 [SMILES: CC1(C)OB(c2cc(-c3ccc4c(ccc5ccccc54)c3)cc(-c3ccc4c(ccc5ccccc54)c3)c2)OC1(C)C] | 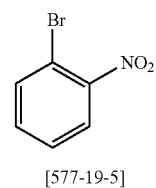
[577-19-5] |

| | | |
|---|---|---|
| 3q | 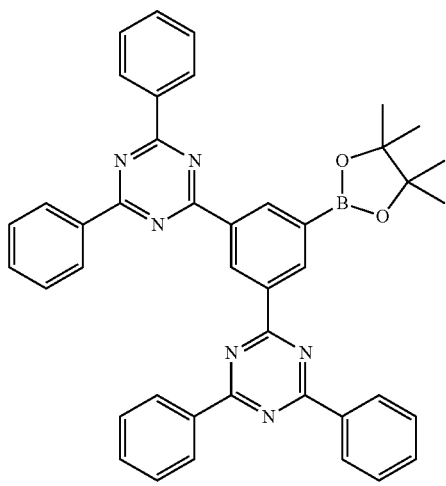 [SMILES: CC1(C)OB(c2cc(-c3nc(-c4ccccc4)nc(-c4ccccc4)n3)cc(-c3nc(-c4ccccc4)nc(-c4ccccc4)n3)c2)OC1(C)C] | 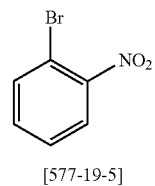
[577-19-5] |
| 3r | 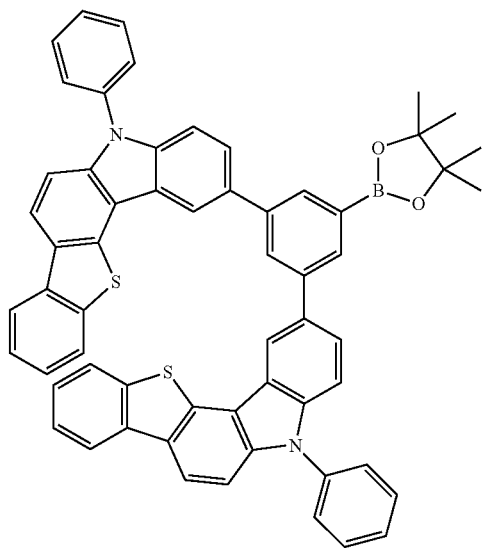 [SMILES: CC1(C)OB(c2cc(-c3ccc4c(c3)c3c5sc6ccccc6c5ccc3n4-c3ccccc3)cc(-c3ccc4c(c3)c3c5sc6ccccc6c5ccc3n4-c3ccccc3)c2)OC1(C)C] | 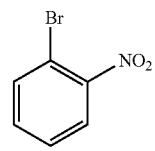
[577-19-5] |
| 3s | 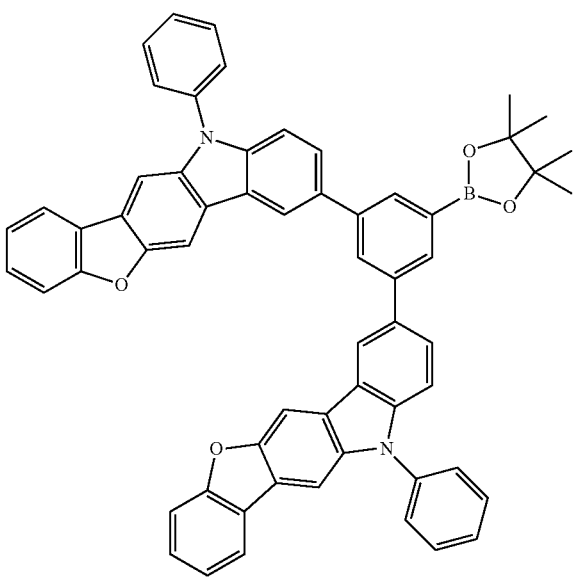 [SMILES: CC1(C)OB(c2cc(-c3ccc4c(c3)c3cc5oc6ccccc6c5cc3n4-c3ccccc3)cc(-c3ccc4c(c3)c3cc5oc6ccccc6c5cc3n4-c3ccccc3)c2)OC1(C)C] | 
[577-19-5] |

-continued
3t 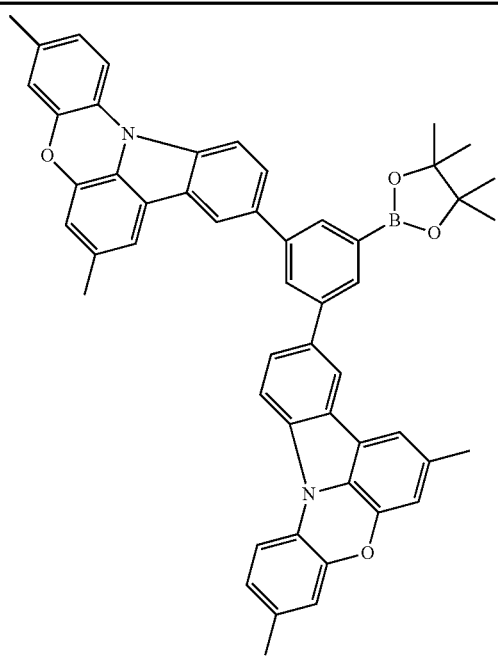  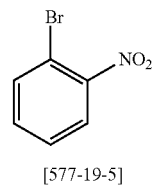
[577-19-5]
3u 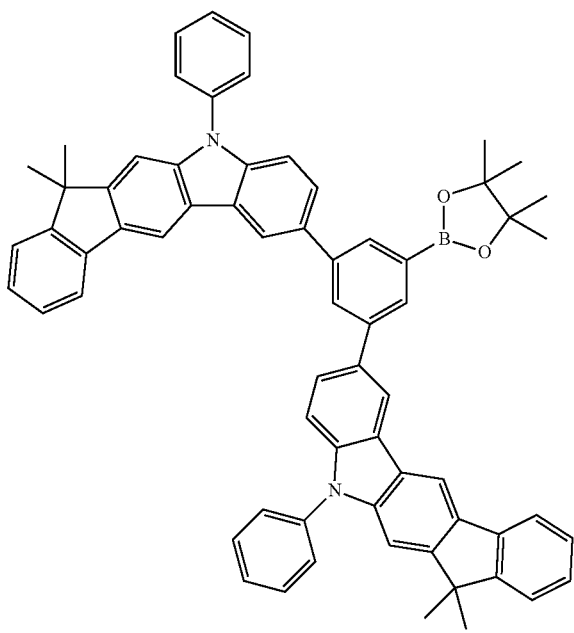 [SMILES: CC1(C)c2ccccc2-c2cc3c4cc(-c5cc(B6OC(C)(C)C(C)(C)O6)cc(-c6ccc7c(c6)c6cc8c(cc6n7-c6ccccc6)C(C)(C)c6ccccc6-8)c5)ccc4n(-c4ccccc4)c3cc21]  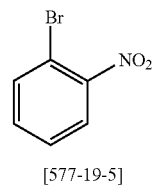
[577-19-5]

-continued
| | | |
|---|---|---|
| 3v | 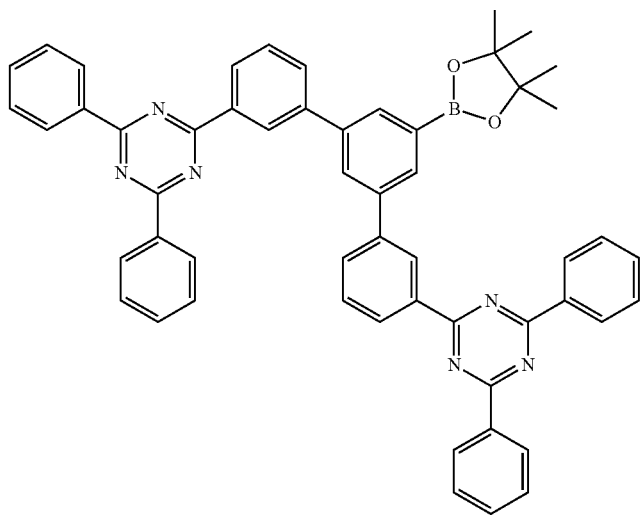 [SMILES: CC1(C)OB(c2cc(-c3cccc(-c4nc(-c5ccccc5)nc(-c5ccccc5)n4)c3)cc(-c3cccc(-c4nc(-c5ccccc5)nc(-c5ccccc5)n4)c3)c2)OC1(C)C] | 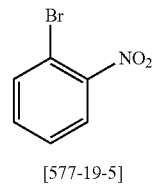
[577-19-5] |
| 3w | 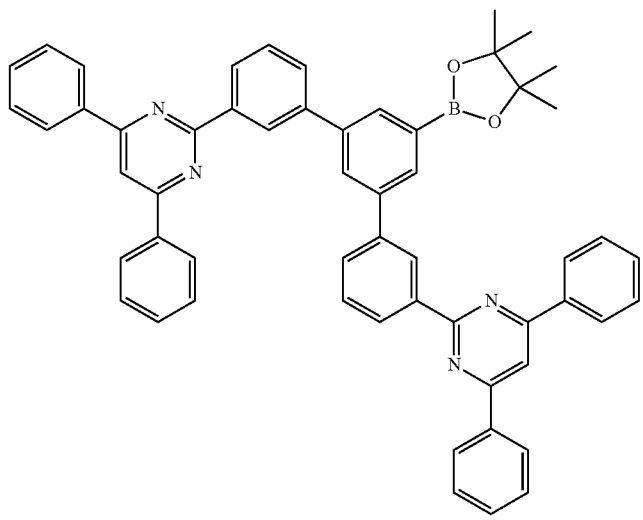 [SMILES: CC1(C)OB(c2cc(-c3cccc(-c4nc(-c5ccccc5)cc(-c5ccccc5)n4)c3)cc(-c3cccc(-c4nc(-c5ccccc5)cc(-c5ccccc5)n4)c3)c2)OC1(C)C] | 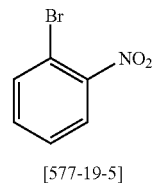
[577-19-5] |
| 3x | 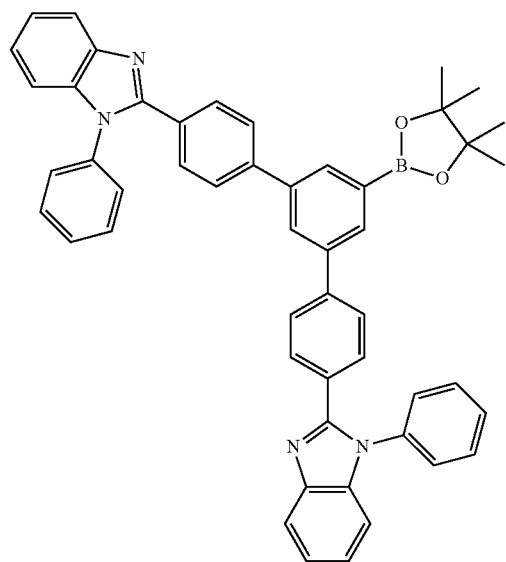 [SMILES: CC1(C)OB(c2cc(-c3ccc(-c4nc5ccccc5n4-c4ccccc4)cc3)cc(-c3ccc(-c4nc5ccccc5n4-c4ccccc4)cc3)c2)OC1(C)C] | 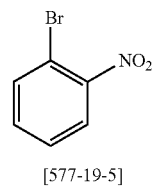
[577-19-5] |

| | | |
|---|---|---|
| 3z | 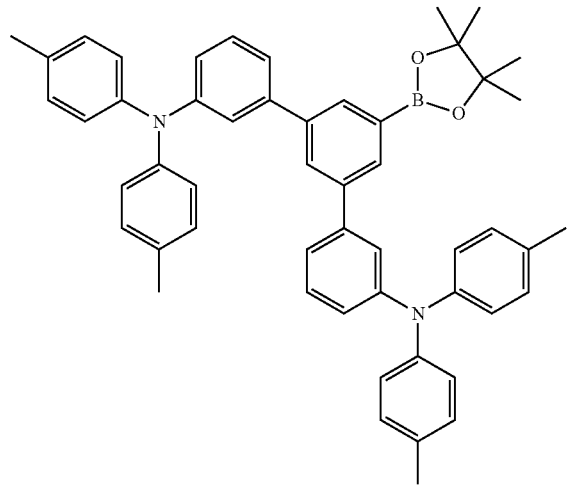 | 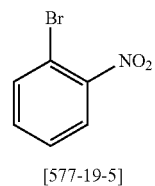
[577-19-5] |
| 3aa | 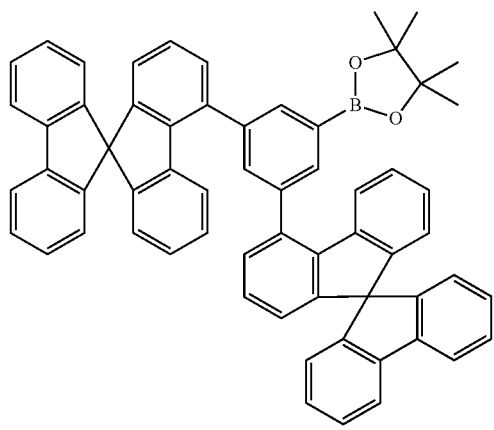 [SMILES: CC1(C)OB(c2cc(-c3cccc4c3-c3ccccc3C43c4ccccc4-c4ccccc43)cc(-c3cccc4c3-c3ccccc3C43c4ccccc4-c4ccccc43)c2)OC1(C)C] | 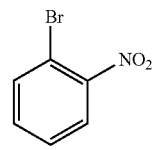
[577-19-5] |
| 3ab | 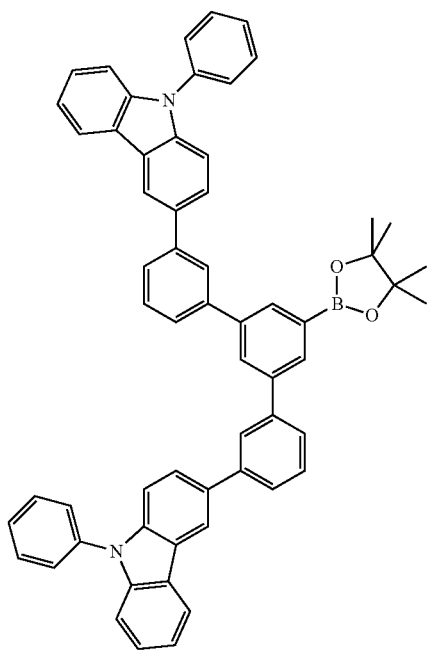 [SMILES: CC1(C)OB(c2cc(-c3cccc(-c4ccc5c(c4)c4ccccc4n5-c4ccccc4)c3)cc(-c3cccc(-c4ccc5c(c4)c4ccccc4n5-c4ccccc4)c3)c2)OC1(C)C] | 
[577-19-5] |

-continued

| | Product | Yield |
|---|---|---|
| 3a | (1-phenyl-1H-indol-5-yl) substituted benzene with 2-nitrophenyl and 1-phenyl-1H-indol-5-yl groups | 90% |
| 3b | 4'-cyano-5'-(4-cyanophenyl)-2-nitro-5-phenyl-1,1':3',1''-terphenyl derivative | 92% |
| 3c | 5'-(2-nitrophenyl)-1,1':3',1''-terphenyl with biphenyl substituents | 97% |

3d 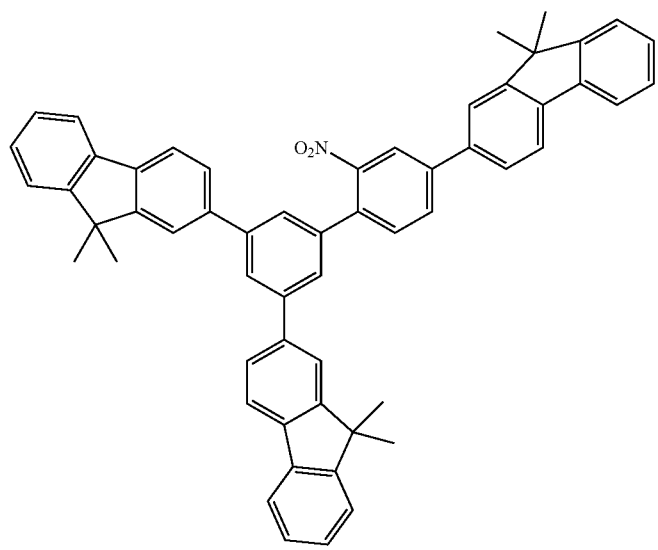 [SMILES: CC1(C)c2ccccc2-c2ccc(-c3cc(-c4ccc5c(c4)C(C)(C)c4ccccc4-5)cc(-c4ccc(-c5ccc6c(c5)C(C)(C)c5ccccc5-6)cc4[N+](=O)[O-])c3)cc21] 91%
3e 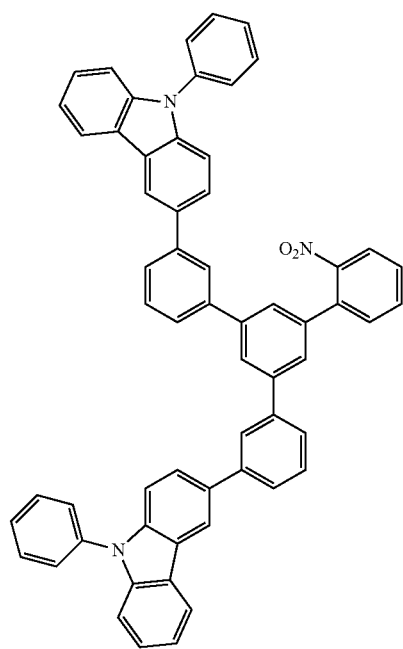 [SMILES: O=[N+]([O-])c1ccccc1-c1cc(-c2cccc(-c3ccc4c(c3)c3ccccc3n4-c3ccccc3)c2)cc(-c2cccc(-c3ccc4c(c3)c3ccccc3n4-c3ccccc3)c2)c1] 93%

3f 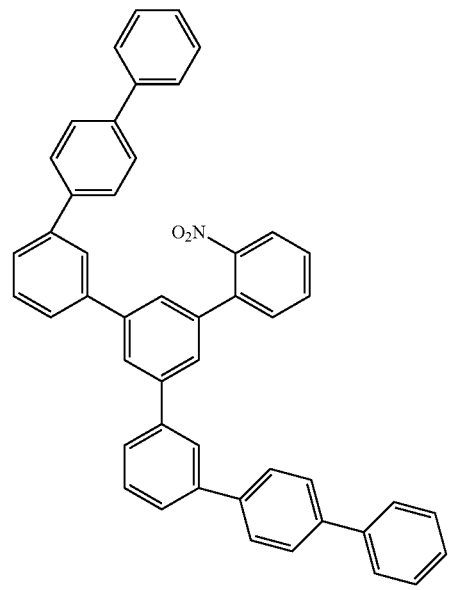 [SMILES: O=[N+]([O-])c1ccccc1-c1cc(-c2cccc(-c3ccc(-c4ccccc4)cc3)c2)cc(-c2cccc(-c3ccc(-c4ccccc4)cc3)c2)c1] 94%
3h 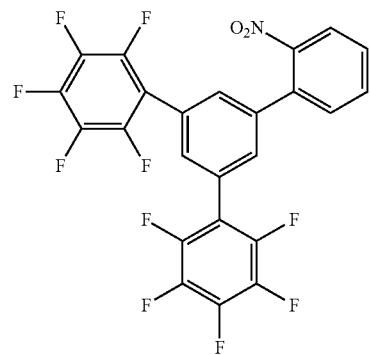 [SMILES: O=[N+]([O-])c1ccccc1-c1cc(-c2c(F)c(F)c(F)c(F)c2F)cc(-c2c(F)c(F)c(F)c(F)c2F)c1] 91%
3i 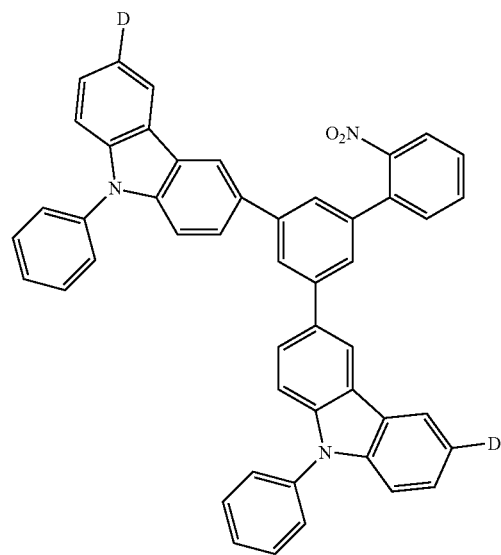 [SMILES: [2H]c1ccc2c(c1)c1cc(-c3cc(-c4ccc5c(c4)c4cc([2H])ccc4n5-c4ccccc4)cc(-c4ccccc4[N+](=O)[O-])c3)ccc1n2-c1ccccc1] 96%

| | | |
|---|---|---|
| 3j | 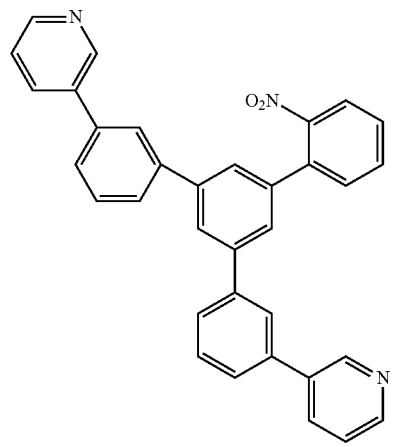 [SMILES: O=[N+]([O-])c1ccccc1-c1cc(-c2cccc(-c3cccnc3)c2)cc(-c2cccc(-c3cccnc3)c2)c1] | 95% |
| 3k | 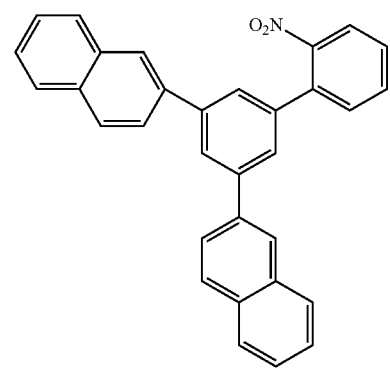 [SMILES: O=[N+]([O-])c1ccccc1-c1cc(-c2ccc3ccccc3c2)cc(-c2ccc3ccccc3c2)c1] | 93% |
| 3l | 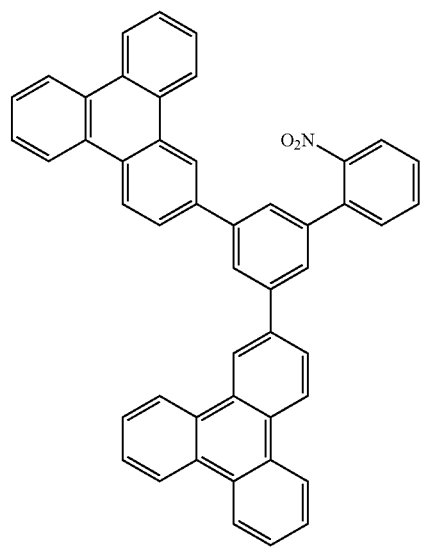 [SMILES: O=[N+]([O-])c1ccccc1-c1cc(-c2ccc3c4ccccc4c4ccccc4c3c2)cc(-c2ccc3c4ccccc4c4ccccc4c3c2)c1] | 92% |

| | | |
|---|---|---|
| 3m | 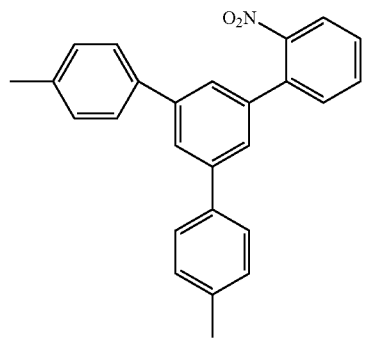 [SMILES: Cc1ccc(-c2cc(-c3ccc(C)cc3)cc(-c3ccccc3[N+](=O)[O-])c2)cc1] | 95% |
| 3n | 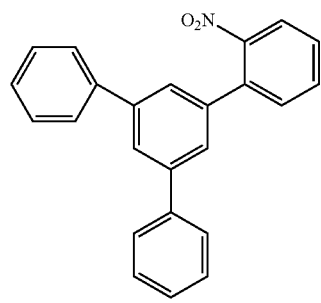 [SMILES: O=[N+]([O-])c1ccccc1-c1cc(-c2ccccc2)cc(-c2ccccc2)c1] | 98% |
| 3o | 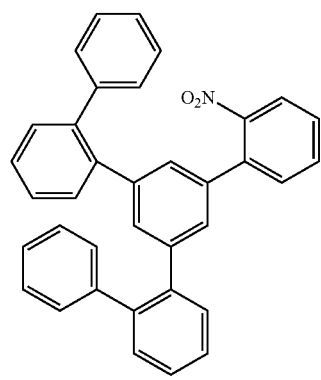 [SMILES: O=[N+]([O-])c1ccccc1-c1cc(-c2ccccc2-c2ccccc2)cc(-c2ccccc2-c2ccccc2)c1] | 90% |
| 3p | 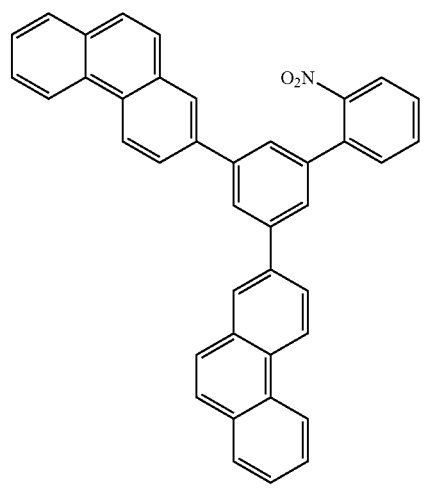 [SMILES: O=[N+]([O-])c1ccccc1-c1cc(-c2ccc3c(ccc4ccccc43)c2)cc(-c2ccc3c(ccc4ccccc43)c2)c1] | 93% |

3q 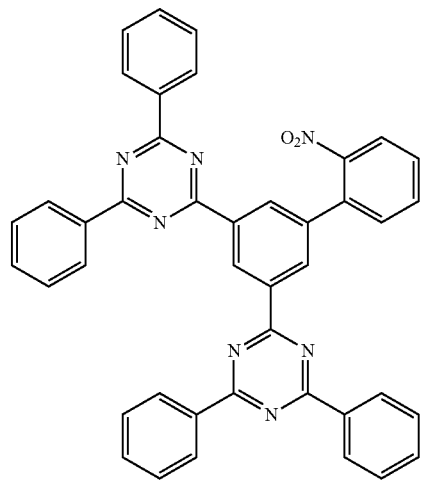 [SMILES: O=[N+]([O-])c1ccccc1-c1cc(-c2nc(-c3ccccc3)nc(-c3ccccc3)n2)cc(-c2nc(-c3ccccc3)nc(-c3ccccc3)n2)c1] 87%
3r 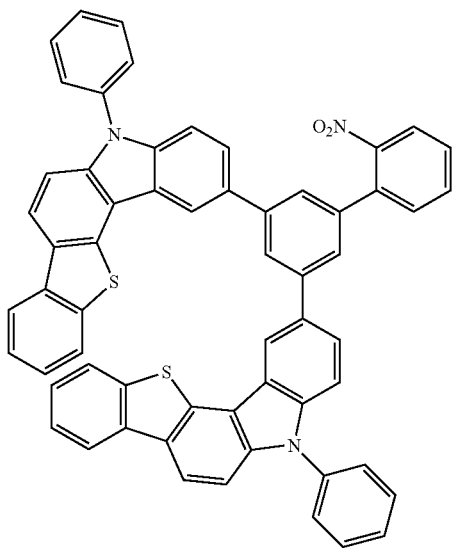 [SMILES: O=[N+]([O-])c1ccccc1-c1cc(-c2ccc3c(c2)c2c4sc5ccccc5c4ccc2n3-c2ccccc2)cc(-c2ccc3c(c2)c2c4sc5ccccc5c4ccc2n3-c2ccccc2)c1] 86%
3s 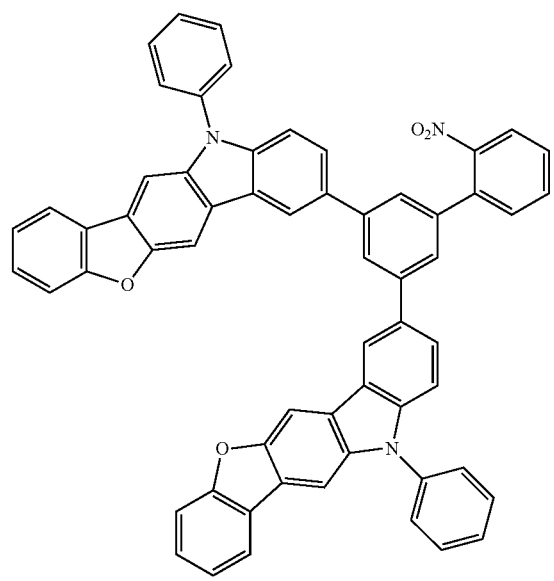 [SMILES: O=[N+]([O-])c1ccccc1-c1cc(-c2ccc3c(c2)c2cc4oc5ccccc5c4cc2n3-c2ccccc2)cc(-c2ccc3c(c2)c2cc4oc5ccccc5c4cc2n3-c2ccccc2)c1] 89%

| 3t | 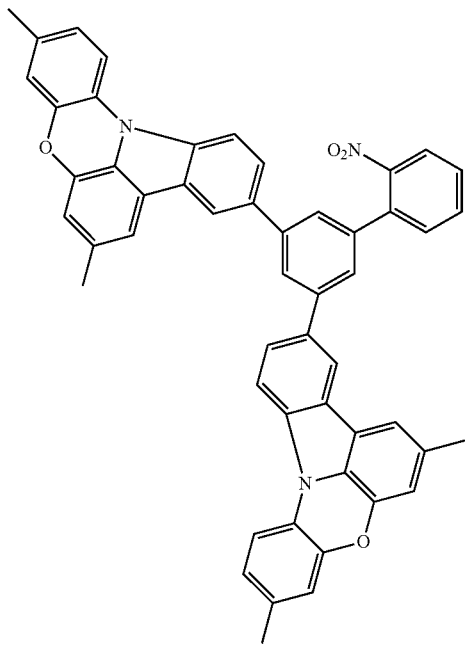 | 78% |
| 3u | 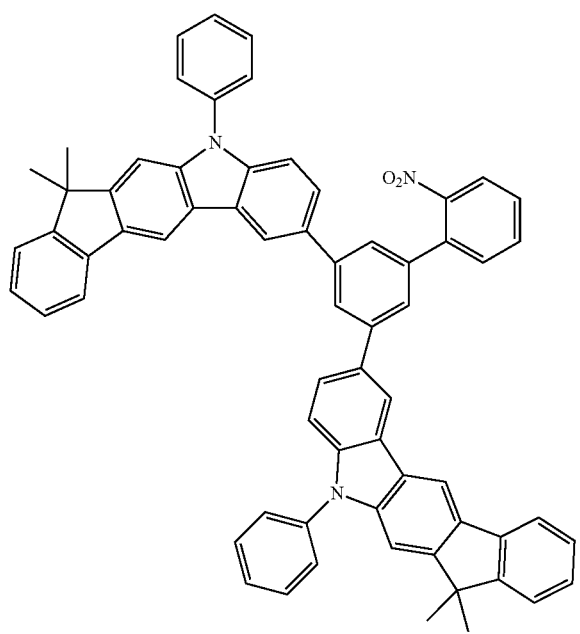 [SMILES: CC1(C)c2ccccc2-c2cc3c4cc(-c5cc(-c6ccc7c(c6)c6cc8c(cc6n7-c6ccccc6)C(C)(C)c6ccccc6-8)cc(-c6ccccc6[N+](=O)[O-])c5)ccc4n(-c4ccccc4)c3cc21] | 91% |

| | | |
|---|---|---|
| 3v | 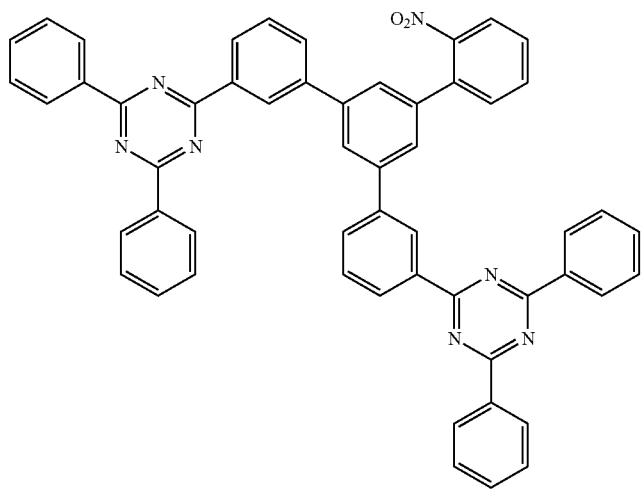 [SMILES: O=[N+]([O-])c1ccccc1-c1cc(-c2cccc(-c3nc(-c4ccccc4)nc(-c4ccccc4)n3)c2)cc(-c2cccc(-c3nc(-c4ccccc4)nc(-c4ccccc4)n3)c2)c1] | 76% |
| 3w | 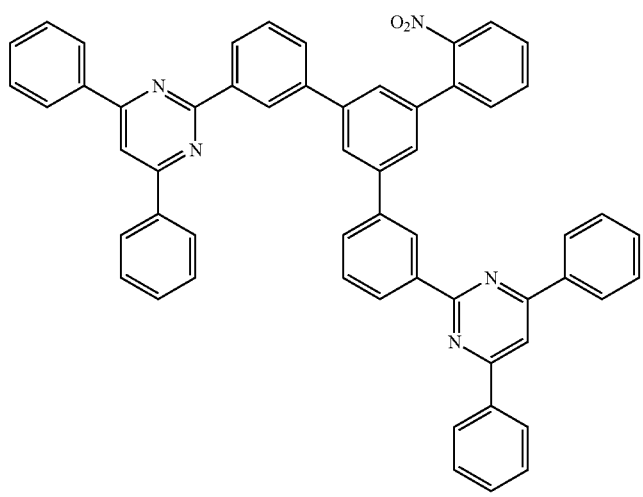 | 77% |
| 3x | 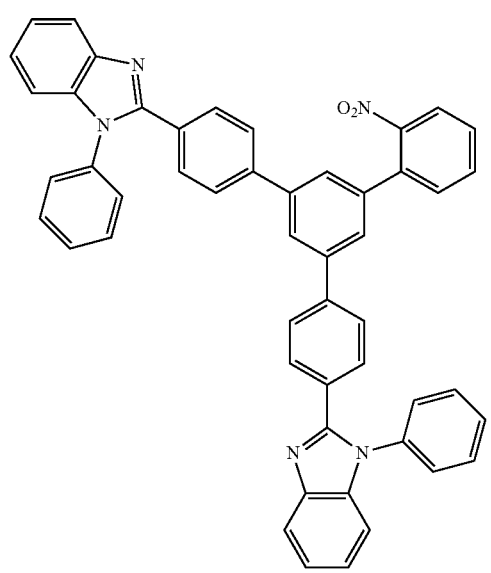 [SMILES: O=[N+]([O-])c1ccccc1-c1cc(-c2ccc(-c3nc4ccccc4n3-c3ccccc3)cc2)cc(-c2ccc(-c3nc4ccccc4n3-c3ccccc3)cc2)c1] | 89% |

| | | |
|---|---|---|
| 3z | 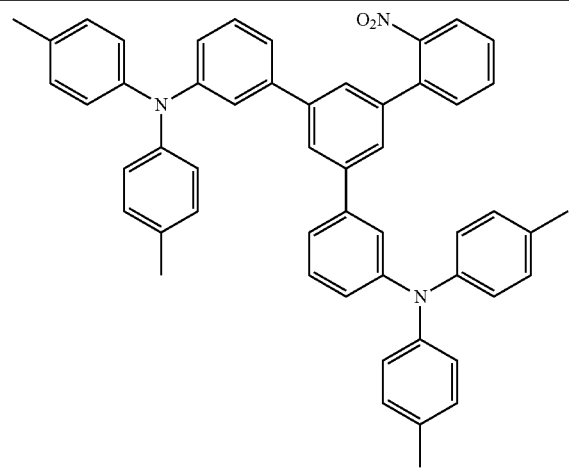 | 94% |
| 3aa | 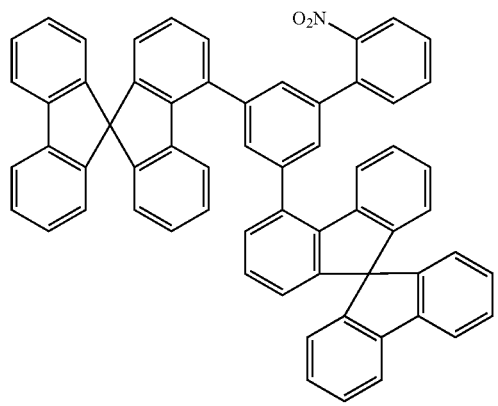 [SMILES: O=[N+]([O-])c1ccccc1-c1cc(-c2cccc3c2-c2ccccc2C32c3ccccc3-c3ccccc32)cc(-c2cccc3c2-c2ccccc2C32c3ccccc3-c3ccccc32)c1] | 78% |
| 3ab | 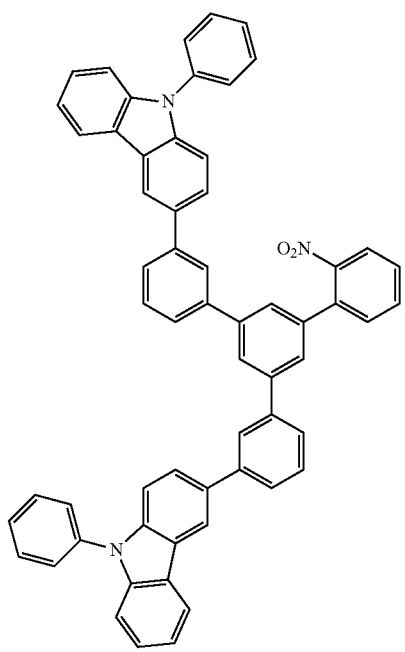 [SMILES: O=[N+]([O-])c1ccccc1-c1cc(-c2cccc(-c3ccc4c(c3)c3ccccc3n4-c3ccccc3)c2)cc(-c2cccc(-c3ccc4c(c3)c3ccccc3n4-c3ccccc3)c2)c1] | 87% |

Example 4: 9,9''-Diphenyl-9H,9'H,9''H-[3,1'; 3',3'']tercarbazole

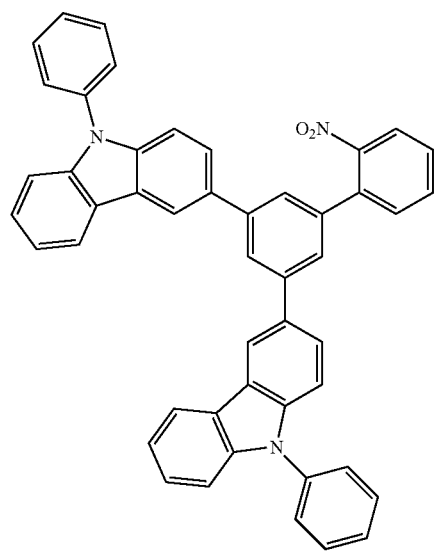

A mixture of 40 g (59 mmol) of the appropriate nitroaromatic and 239 mL (1400 mmol) of triethyl phosphite is heated under reflux to 130° C. for 12 h. Subsequently, the rest of the triethyl phosphite is distilled off (72-76° C./9 mmHg). Water/MeOH (1:1) is added to the residue, and the solids are filtered off and recrystallized. The yield is 38 g (58 mol, 99%).

In an analogous manner, it is possible to obtain the following compounds:

| | Reactant 1 | Product | Yield |
|---|---|---|---|
| 4a | | | 89% |

-continued

| | Reactant 1 | Product | Yield |
|---|---|---|---|
| 4b | | | 90% |
| 4c | | | 91% |
| 4d | | | 96% |

-continued
| | Reactant 1 | Product | Yield |
|---|---|---|---|
| 4e | 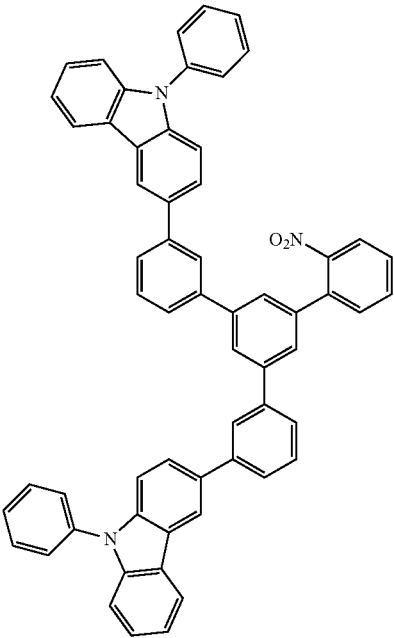 [SMILES: O=[N+]([O-])c1ccccc1-c1cc(-c2cccc(-c3ccc4c(c3)c3ccccc3n4-c3ccccc3)c2)cc(-c2cccc(-c3ccc4c(c3)c3ccccc3n4-c3ccccc3)c2)c1] | 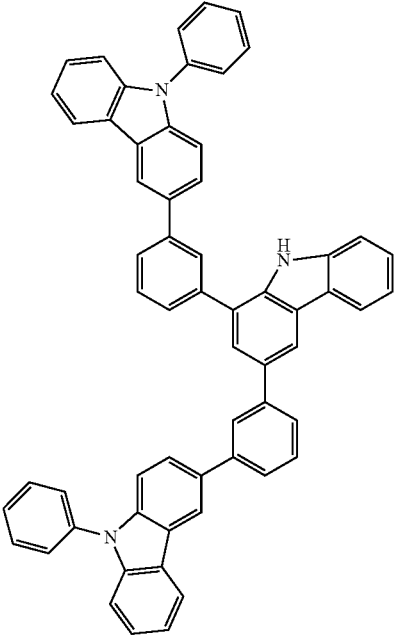 [SMILES: c1ccc(-n2c3ccccc3c3cc(-c4cccc(-c5cc(-c6cccc(-c7ccc8c(c7)c7ccccc7n8-c7ccccc7)c6)c6[nH]c7ccccc7c6c5)c4)ccc32)cc1] | 94% |
| 4f | 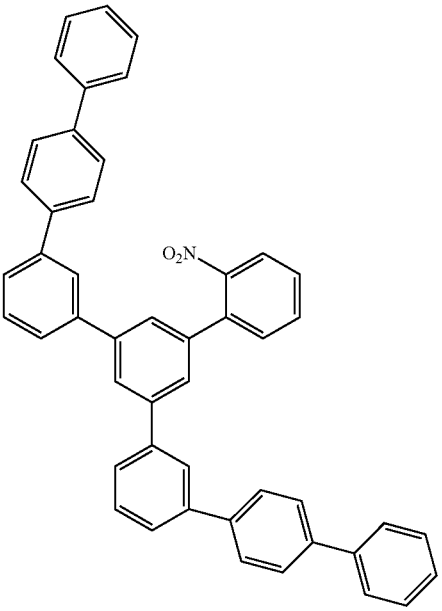 [SMILES: O=[N+]([O-])c1ccccc1-c1cc(-c2cccc(-c3ccc(-c4ccccc4)cc3)c2)cc(-c2cccc(-c3ccc(-c4ccccc4)cc3)c2)c1] | 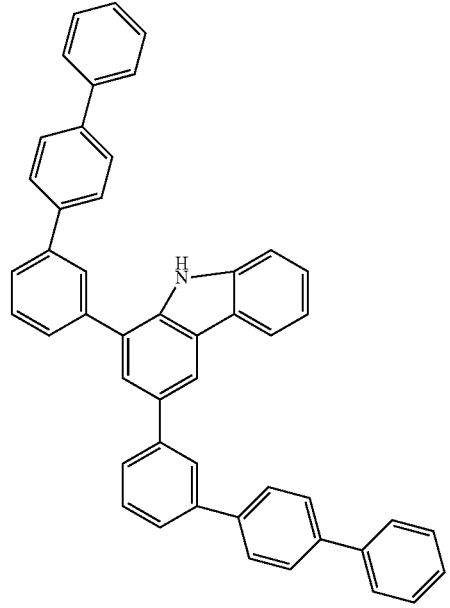 [SMILES: c1ccc(-c2ccc(-c3cccc(-c4cc(-c5cccc(-c6ccc(-c7ccccc7)cc6)c5)c5[nH]c6ccccc6c5c4)c3)cc2)cc1] | 97% |
| 4h | 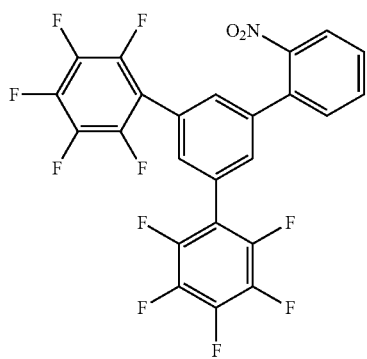 [SMILES: O=[N+]([O-])c1ccccc1-c1cc(-c2c(F)c(F)c(F)c(F)c2F)cc(-c2c(F)c(F)c(F)c(F)c2F)c1] | 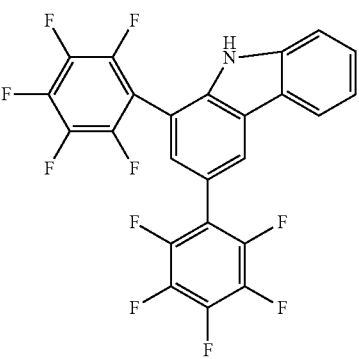 [SMILES: Fc1c(F)c(F)c(-c2cc(-c3c(F)c(F)c(F)c(F)c3F)c3[nH]c4ccccc4c3c2)c(F)c1F] | 93% |

-continued

| | Reactant 1 | Product | Yield |
|---|---|---|---|
| 4i | | | 95% |
| 4j | | | 99% |
| 4k | | | 93% |

-continued

| | Reactant 1 | Product | Yield |
|---|---|---|---|
| 4l | | | 92% |
| 4m | | | 93% |
| 4n | | | 97% |
| 4o | | | 91% |

-continued

| | Reactant 1 | Product | Yield |
|---|---|---|---|
| 4p | | | 87% |
| 4q | | | 69% |
| 4r | | | 86% |

| Reactant 1 | Product | Yield |
|---|---|---|
| 4s 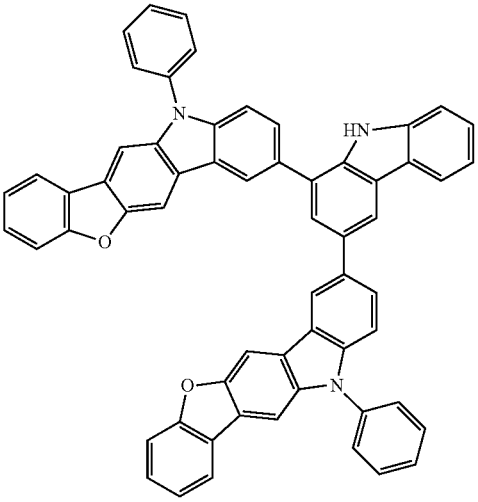 [SMILES: c1ccc(-n2c3ccc(-c4cc(-c5ccc6c(c5)c5cc7oc8ccccc8c7cc5n6-c5ccccc5)c5[nH]c6ccccc6c5c4)cc3c3cc4oc5ccccc5c4cc32)cc1] | 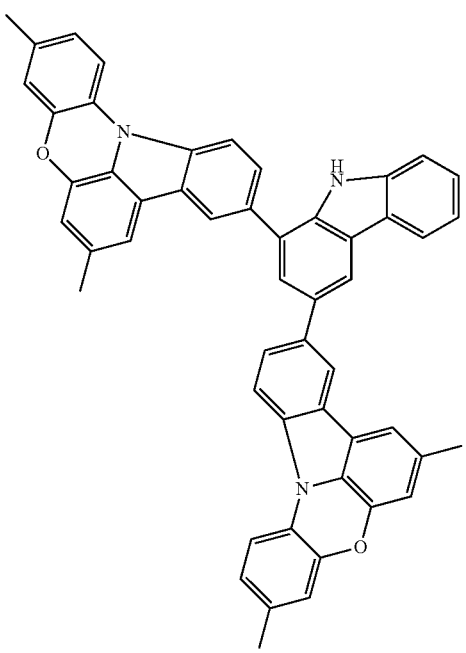 | 83% |
| 4t | | 80% |

-continued

| Reactant 1 | Product | Yield |
|---|---|---|
| 4u | | 90% |
| 4v | | 77% |
| 4w | | 75% |

-continued
| Reactant 1 | Product | Yield |
|---|---|---|
| 4x 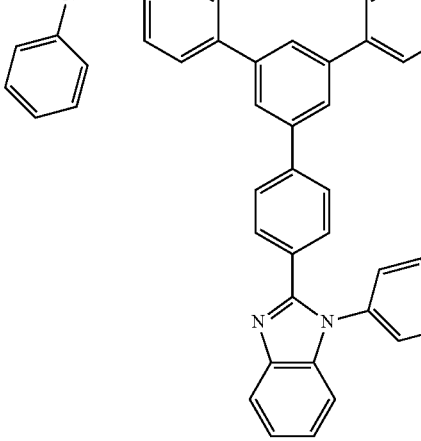 | 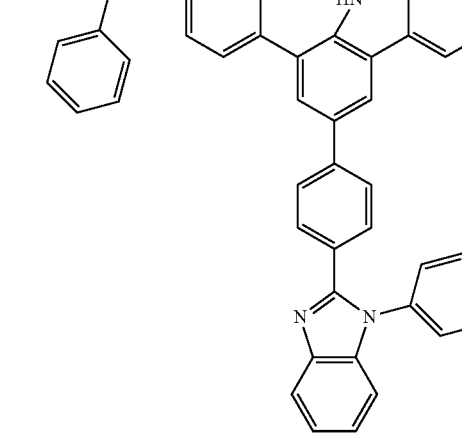 | 83% |
| 4z 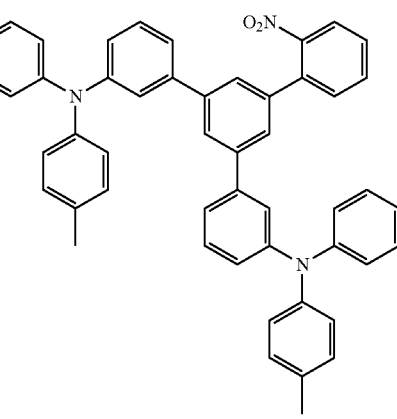 | 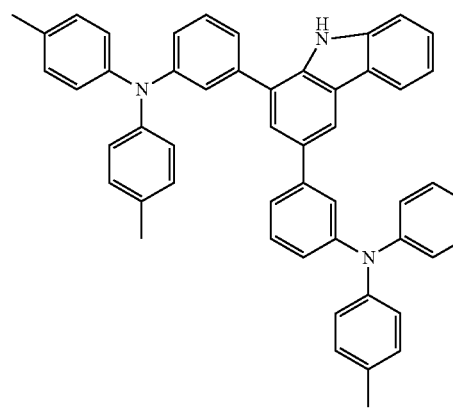 | 69% |
| 4aa 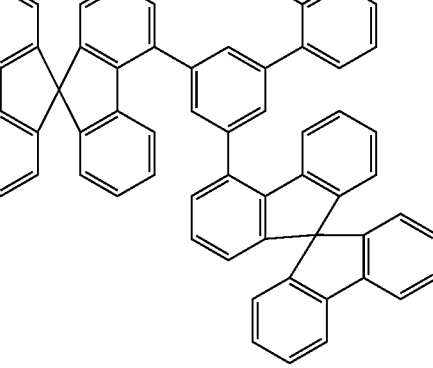 | 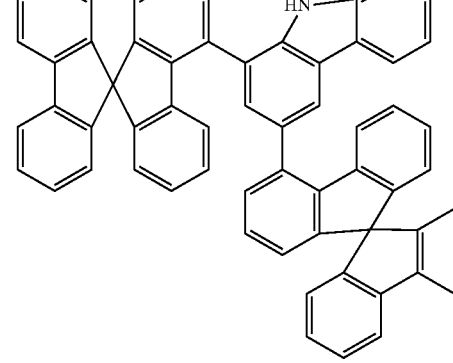 | 85% |

Example 5: 9,9',9''-Triphenyl-9H,9'H,9''H-[3,1'; 3'; 3'']tercarbazole

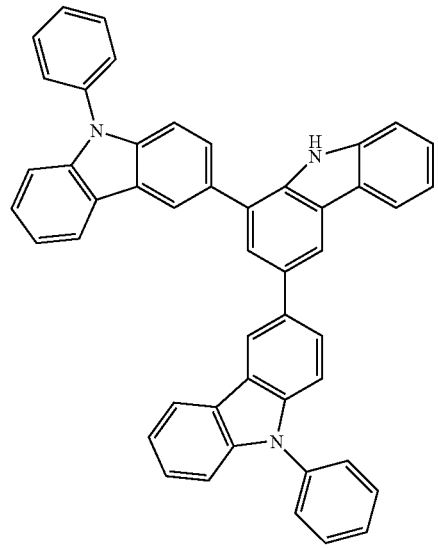

+

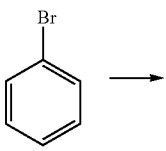

→

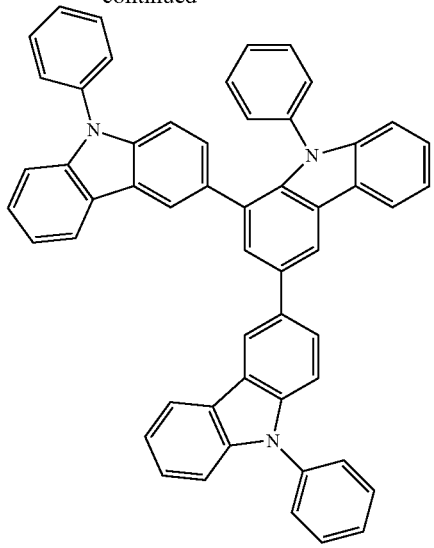

25 g (38 mmol) of 9,9''-diphenyl-9H,9'H,9''H-[3,1';3',3''] tercarbazole and 7 g (46 mmol) of bromobenzene are dissolved in 450 mL of toluene and degassed by means of a protective gas inlet. This is followed by addition of 7 mL (7 mmol, 1 M solution in toluene) of tri-tert-butylphosphine, 633.8 mg (2.82 mmol) of Pd(OAc)$_2$ and 7 g (76 mmol) of NaOtBu. The solids are degassed beforehand, and the reaction mixture is post-degassed and then stirred under reflux for 3 h. The warm reaction solution is filtered through Alox B (activity level 1), washed with water, dried and concentrated. The yield is 27 g (37 mol, 98%).

In an analogous manner, it is possible to obtain the following compounds:

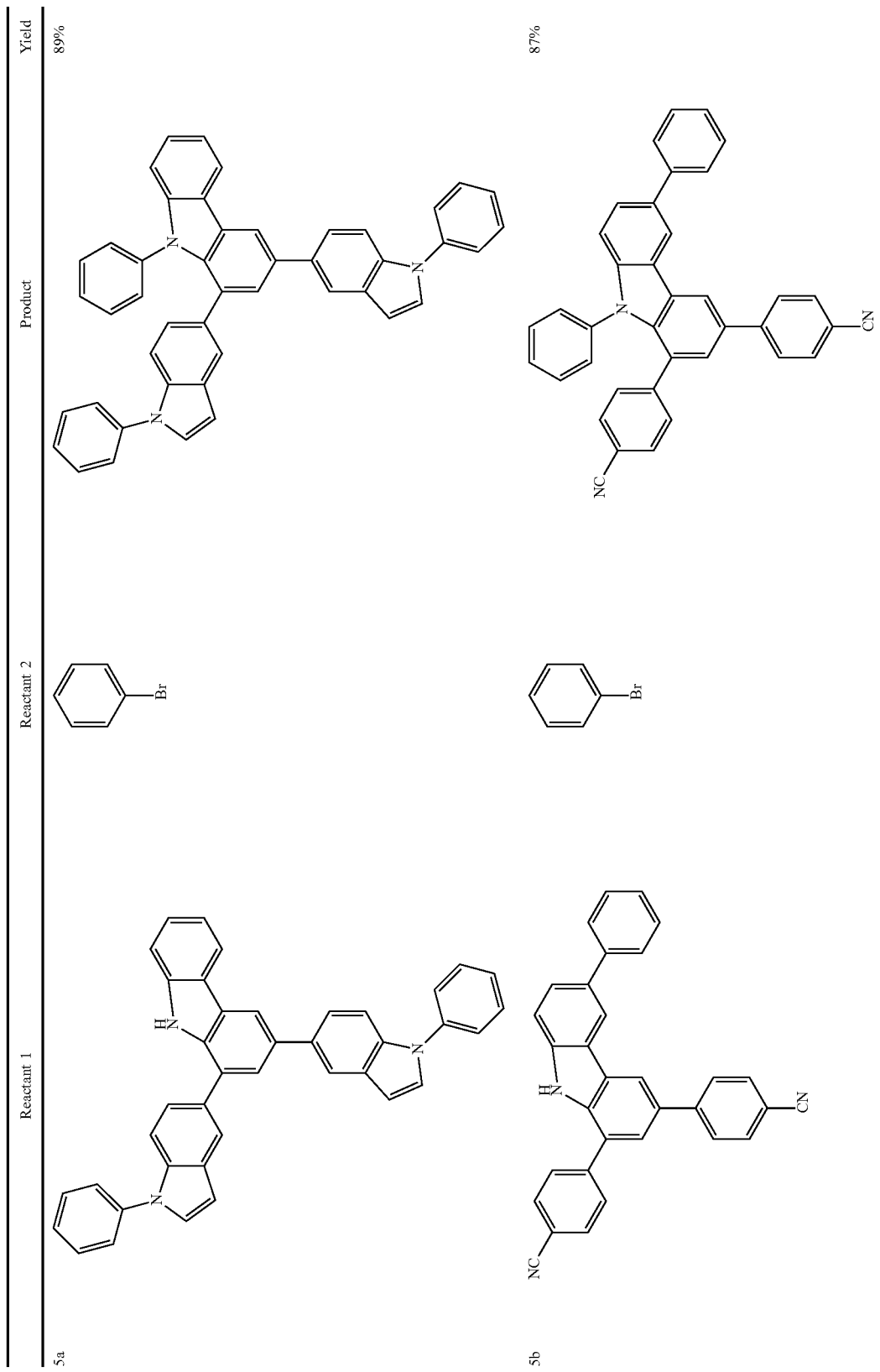

| | Reactant 1 | Reactant 2 | Product | Yield |
|---|---|---|---|---|
| 5c | 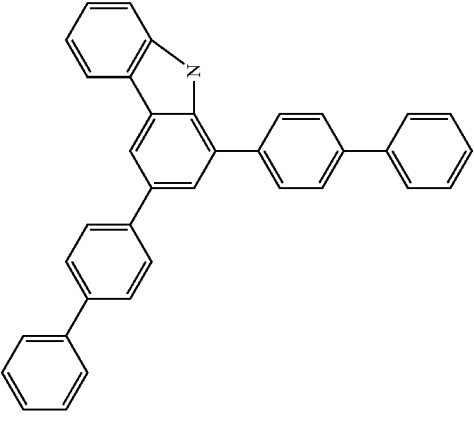 | 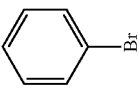 | 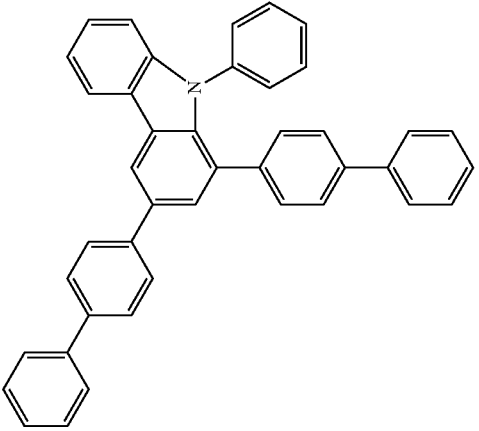 | 91% |
| 5d | 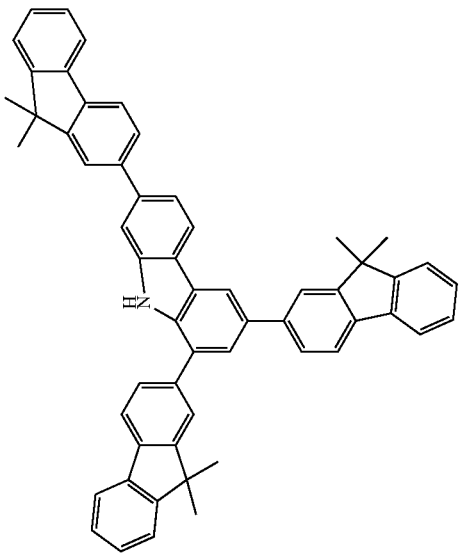 | 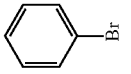 | 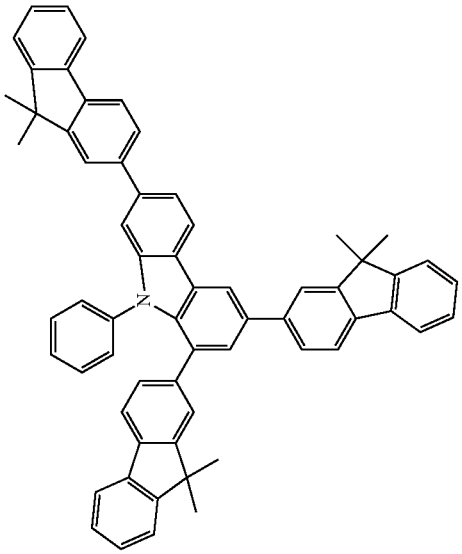 | 90% |

| Reactant 1 | Reactant 2 | Product | Yield |
|---|---|---|---|
| 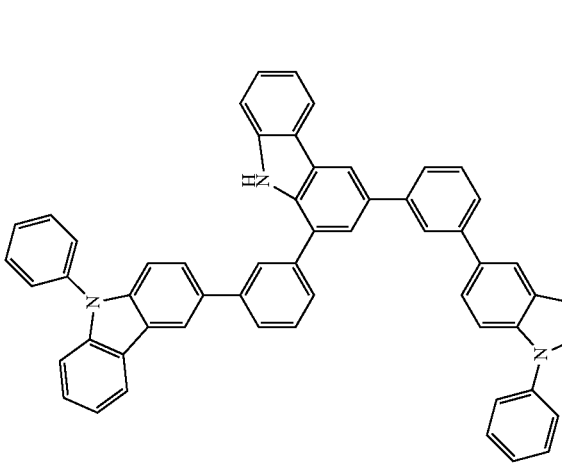 |  | 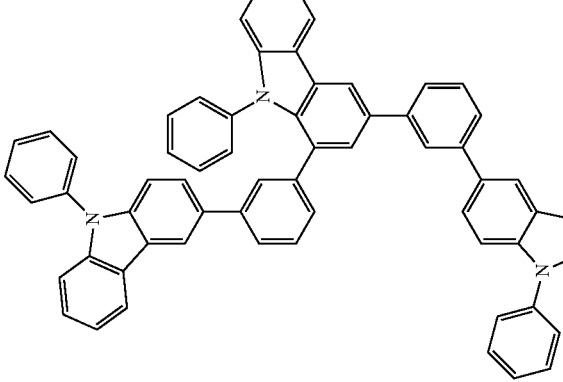 | 79% |

| | Reactant 1 | Reactant 2 | Product | Yield |
|---|---|---|---|---|
| 5f | 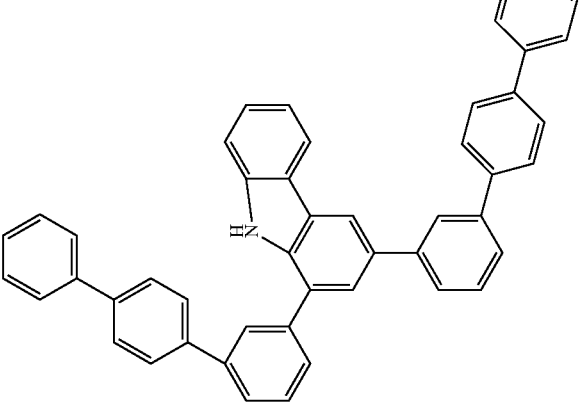 | 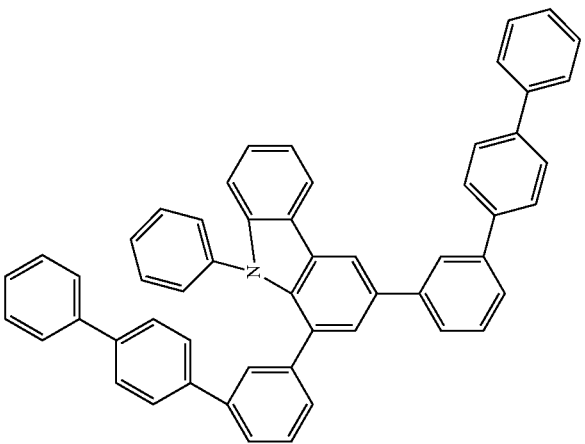 | 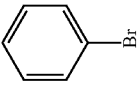 | 78% |
| 5h | 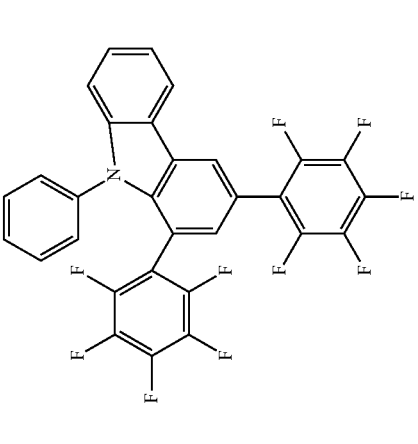 | 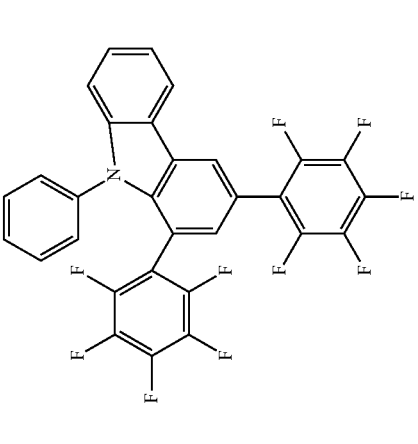 | 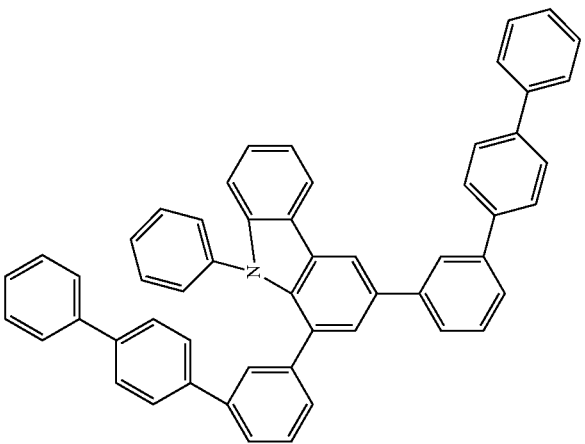 | 92% |

| | Reactant 1 | Reactant 2 | Product | Yield |
|---|---|---|---|---|
| 5i | 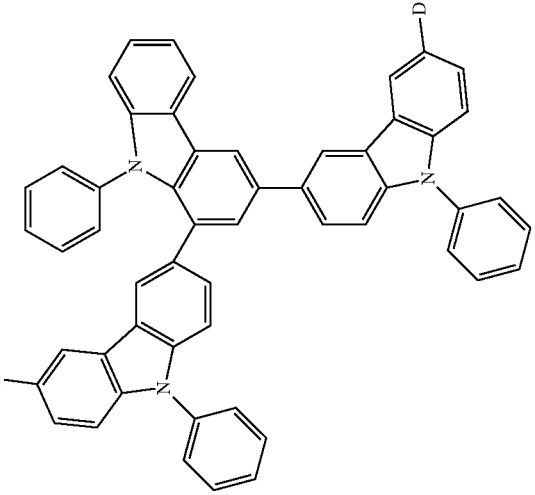 | 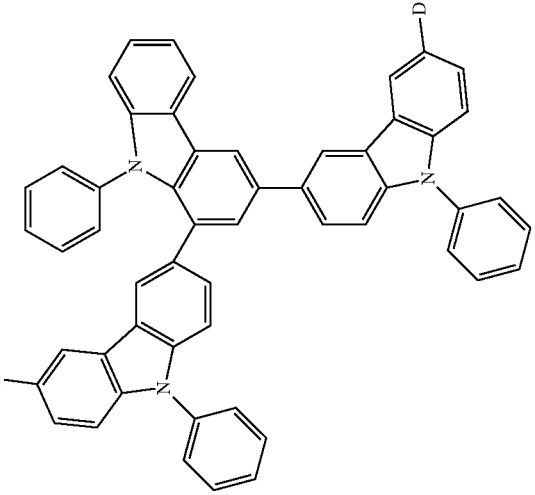 | 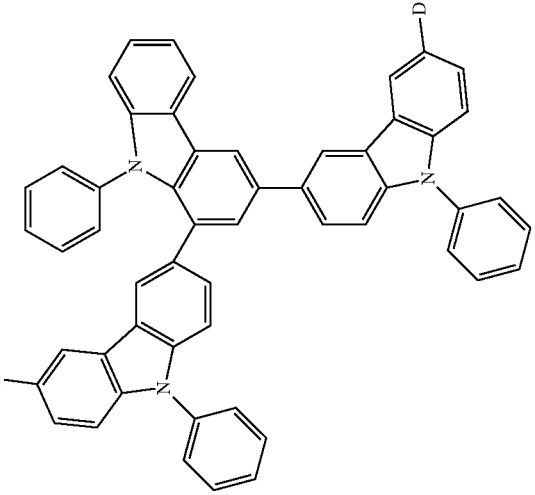 | 91% |
| 5j | 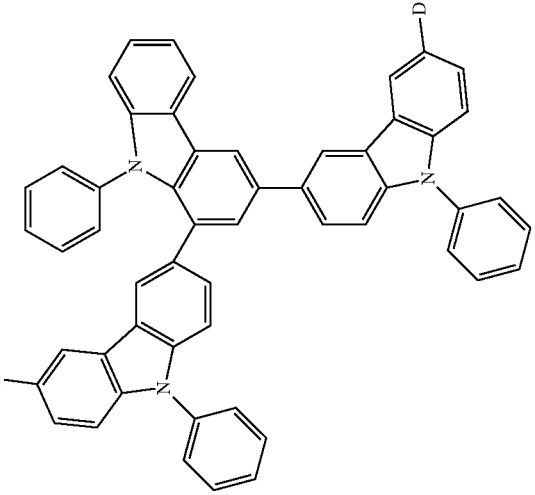 | 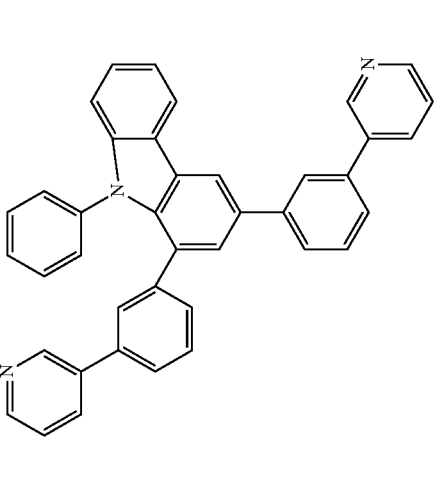 | 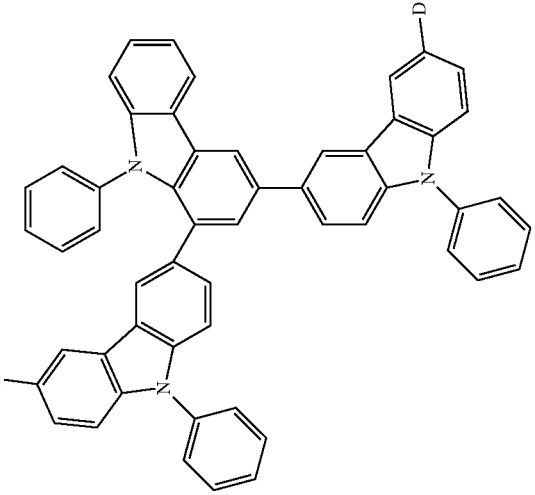 | 95% |

-continued
| | Reactant 1 | Reactant 2 | Product | Yield |
|---|---|---|---|---|
| 5k | 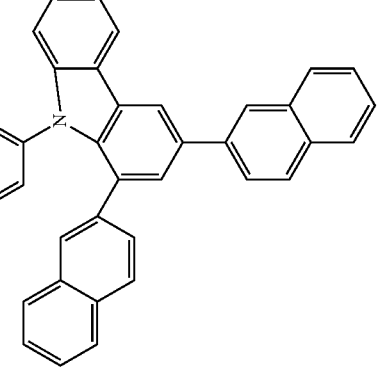 | 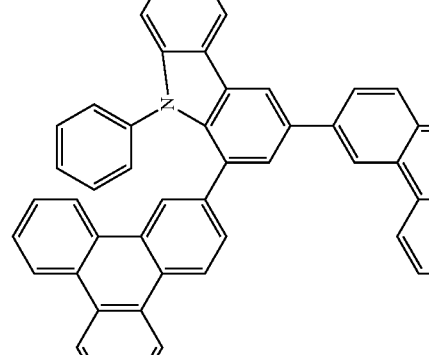 | 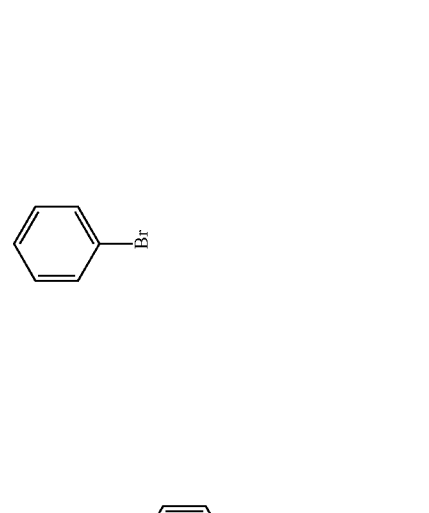 | 96% |
| 5l | 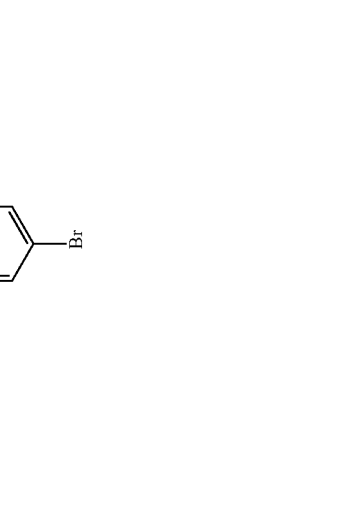 | 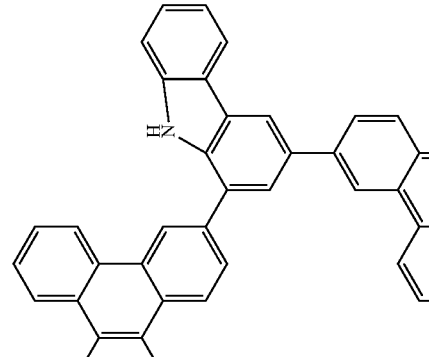 | | 93% |

-continued

| | Reactant 1 | Reactant 2 | Product | Yield |
|---|---|---|---|---|
| 5m | (carbazole substituted with two p-tolyl groups, NH) | bromobenzene | (N-phenyl carbazole substituted with two p-tolyl groups) | 94% |
| 5n | (carbazole substituted with two phenyl groups, NH) | bromobenzene | (N-phenyl carbazole substituted with two phenyl groups) | 97% |

-continued

| | Reactant 1 | Reactant 2 | Product | Yield |
|---|---|---|---|---|
| 5o | | | | 85% |
| 5p | | | | 89% |

| | Reactant 1 | Reactant 2 | Product | Yield |
|---|---|---|---|---|
| 5q | | | | 87% |
| 5r | | | | 76% |

| Reactant 1 | Reactant 2 | Product | Yield |
|---|---|---|---|
| 5s | Ph-Br | | 79% |

| | Reactant 1 | Reactant 2 | Product | Yield |
|---|---|---|---|---|
| 5t | | | | 73% |

-continued
| Reactant 1 | Reactant 2 | Product | Yield |
|---|---|---|---|
| 5u 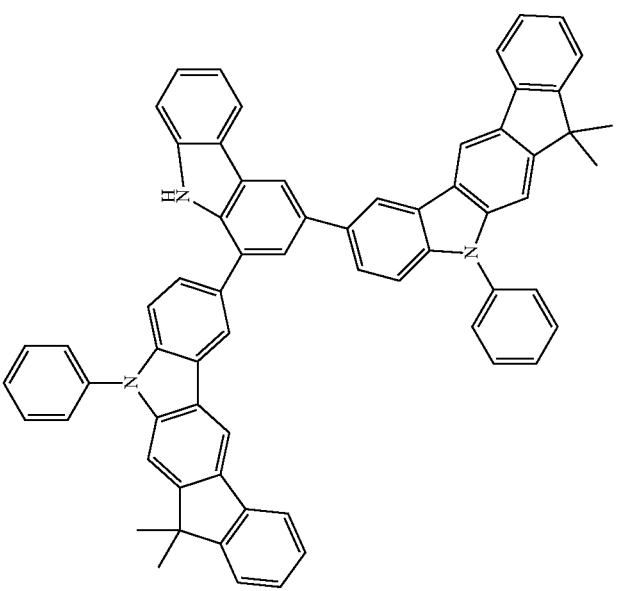 | 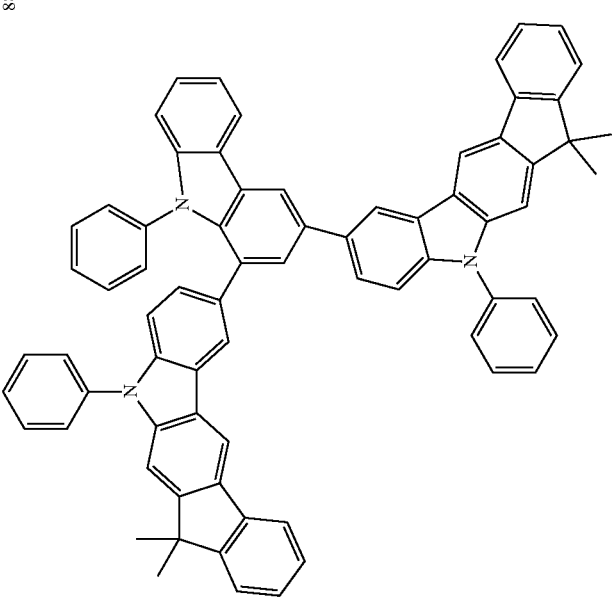 | 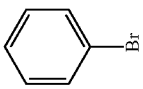 | 88% |

| | Reactant 1 | Reactant 2 | Product | Yield |
|---|---|---|---|---|
| 5v | | | | 87% |
| 5w | | | | 83% |

-continued
| Reactant 1 | Reactant 2 | Product | Yield |
|---|---|---|---|
| 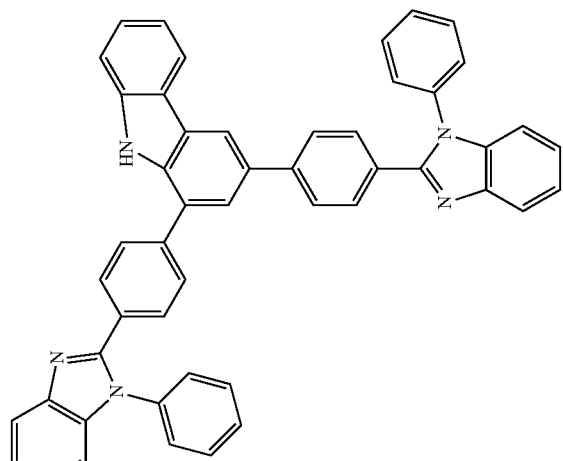 | 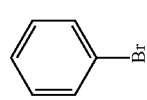 | 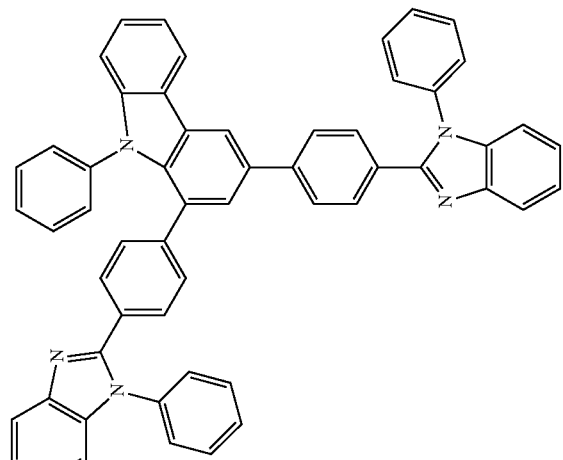 | 87% |

-continued

| | Reactant 1 | Reactant 2 | Product | Yield |
|---|---|---|---|---|
| 5z | | PhBr | | 94% |
| 5aa | | PhBr | | 86% |

| | Reactant 1 | Reactant 2 | Product | Yield |
|---|---|---|---|---|
| 5ab | | [202831-65-0] | | 87% |
| 5ac | | 864377-28-6 | | 95% |

| Reactant 1 | Reactant 2 | Product | Yield |
|---|---|---|---|
| 5ad | 864377-31-1 | | 92% |

| | Reactant 1 | Reactant 2 | Product | Yield |
|---|---|---|---|---|
| 5ae | 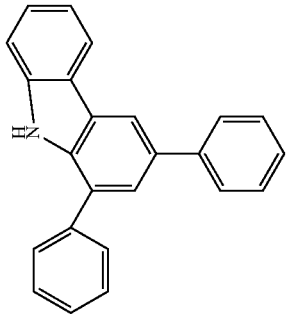 | 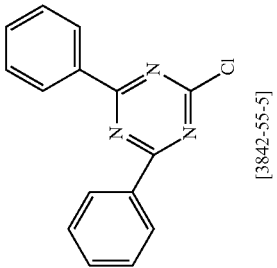  [3842-55-5] | 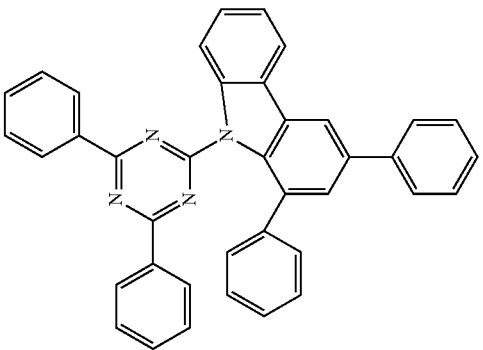 | 90% |
| 5af | 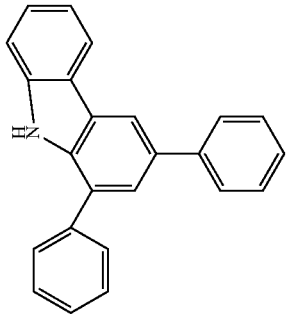 | 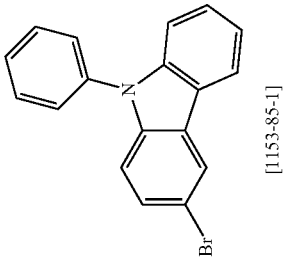  [1153-85-1] | 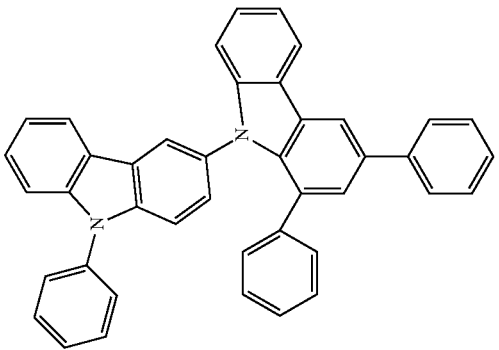 | 86% |

Example 6: 6-Bromo-1,3-diphenyl-9H-carbazole

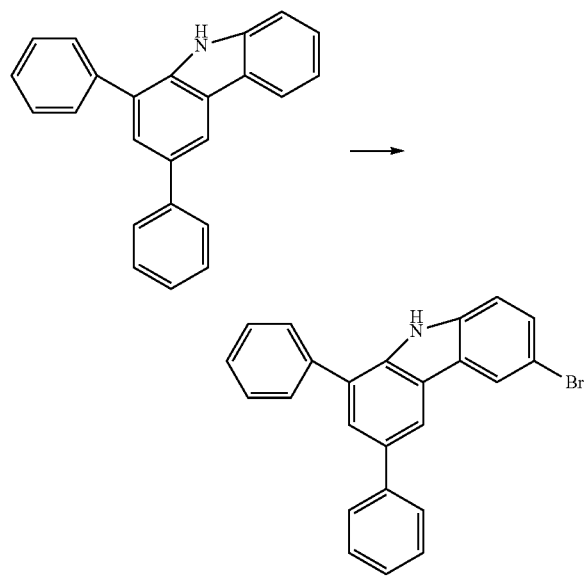

12.7 g (40 mmol) of 1,3-diphenyl-9H-carbazole are suspended in 450 mL of acetonitrile and, at −20° C., 7.15 g (40 mmol) of N-bromosuccinimide are added in portions, in such a way that the reaction temperature does not rise above −20° C. The mixture is stirred for a further 18 h, in the course of which the reaction mixture is warmed to room temperature. The reaction mixture is then concentrated by rotary evaporation, dissolved in dichloromethane and washed with water. The mixture is dried, concentrated and then recrystallized twice from toluene. The yield is 12 g (30 mol, 76%).

In an analogous manner, it is possible to obtain the following
compounds:

| | Reactant 1 | Product | Yield |
|---|---|---|---|
| 6a | | | 70% |
| 6b | | | 86% |
| [1434299-72-2] | | | |

| Reactant 1 | Product | Yield |
|---|---|---|
| 6c | | 76% |
| 6d | | 78% |

Example 7: 1,3-Diphenyl-6-(4,4,5,5-tetramethyl-[1,3,2]dioxaborolan-2-yl)-9H-carbazole

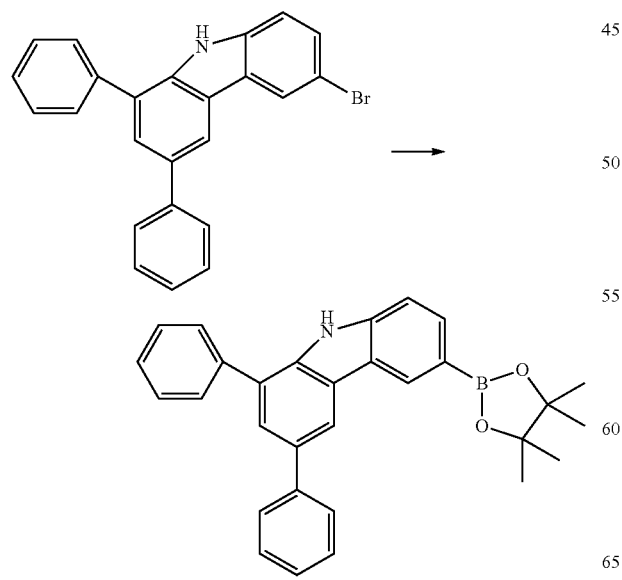

50 g (125 mmol) of 6-bromo-1,3-diphenyl-9H-carbazole, 40 g (161 mmol) of bis(pinacolato)diboron and 18 g (25 mmol) of tricyclohexylphosphinepalladium dichloride and 21 g (214 mmol) of potassium acetate are suspended in 1200 mL of dioxane. The reaction mixture is heated under reflux at 130° C. for 16 h. The mixture is subsequently partitioned between ethyl acetate and water, and the organic phase is washed three times with water and dried over $Na_2SO_4$ and concentrated by rotary evaporation. The remaining residue is recrystallized from heptane/toluene. The yield is 48 g (108 mmol, 86%).

In an analogous manner, it is possible to obtain the following compounds:

| Reactant 1 | Product | Yield |
|---|---|---|
| 7a 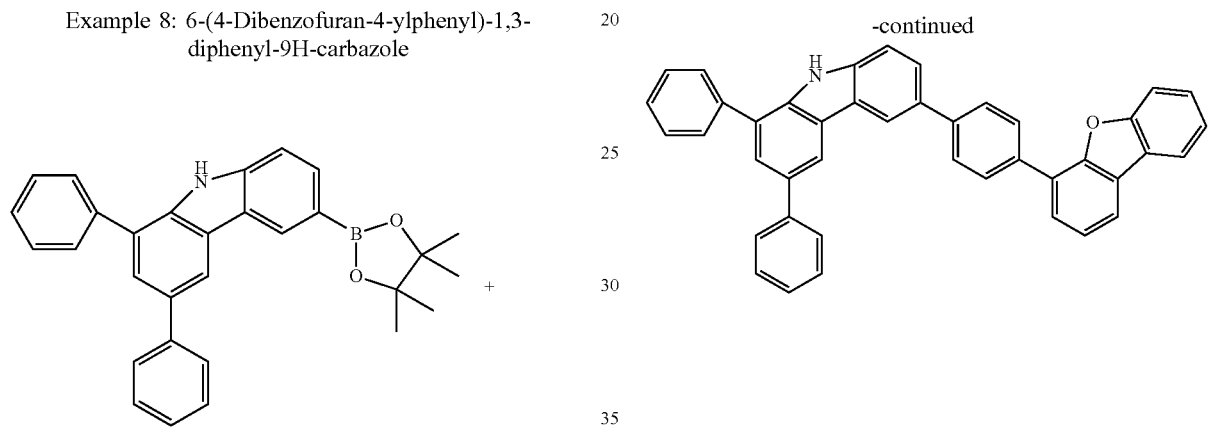 | | 82% |

Example 8: 6-(4-Dibenzofuran-4-ylphenyl)-1,3-diphenyl-9H-carbazole

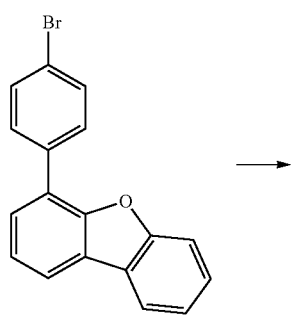

[955959-84-9]

-continued 30 g (68 mmol) of 1,3-diphenyl-6-(4,4,5,5-tetramethyl-[1,3,2]dioxaborolan-2-yl)-9H-carbazole, 26 g (81 mmol) of 4-(4-bromophenyl)dibenzofuran and 152 mg (0.67 mmol) of Pd(OAC)$_2$ and 178 mg (0.67 mmol) of P(o-Tol)$_3$ and 136 g (980 mmol) of potassium carbonate are suspended in 1000 mL of THF and 300 mL of water. The reaction mixture is heated under reflux at 130° C. for 16 h. The mixture is subsequently partitioned between ethyl acetate and water, and the organic phase is washed three times with water and dried over Na$_2$SO$_4$ and concentrated by rotary evaporation. The remaining residue is recrystallized from heptane/toluene. The yield is 34 g (60 mmol, 90%).

In an analogous manner, it is possible to obtain the following compounds:

| | Reactant 1 | Reactant 1 | Product | Yield |
|---|---|---|---|---|
| 8a | | | | 81% |
| 8b | | | | 80% |
| 8c | | [1257247-97-4] | | 86% |
| 8d | | [1153-85-1] | | 84% |
| 8e | | | | 88% |

-continued
| | Reactant 1 | Reactant 1 | Product | Yield |
|---|---|---|---|---|
| 8f | 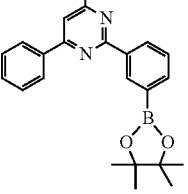 [1381862-91-4] | 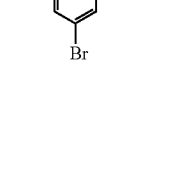 | 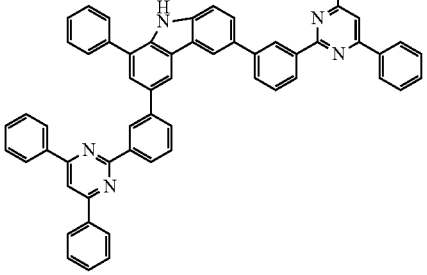 | 89% |
| 8g | 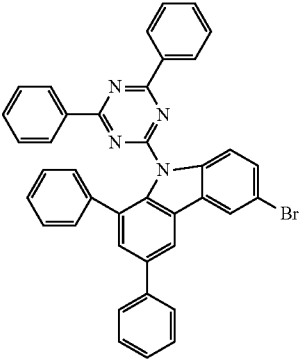 [SMILES: Brc1ccc2c(c1)c1cc(-c3ccccc3)cc(-c3ccccc3)c1n2-c1nc(-c2ccccc2)nc(-c2ccccc2)n1] | 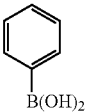 | 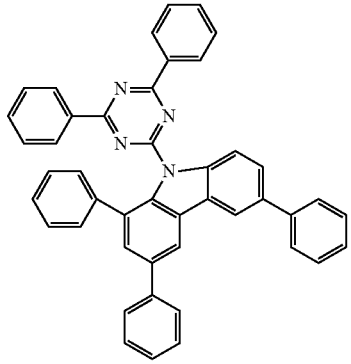 [SMILES: c1ccc(-c2ccc3c(c2)c2cc(-c4ccccc4)cc(-c4ccccc4)c2n3-c2nc(-c3ccccc3)nc(-c3ccccc3)n2)cc1] | 80% |
| 8h | 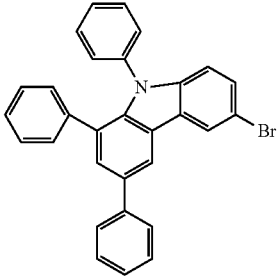 [SMILES: Brc1ccc2c(c1)c1cc(-c3ccccc3)cc(-c3ccccc3)c1n2-c1ccccc1] | 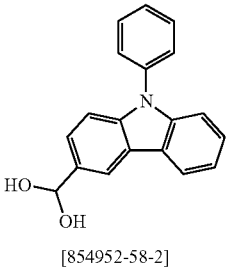 [SMILES: OC(O)c1ccc2c(c1)c1ccccc1n2-c1ccccc1] [854952-58-2] | 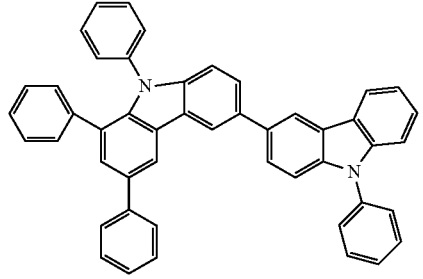 [SMILES: c1ccc(-c2cc(-c3ccccc3)c3c(c2)c2cc(-c4ccc5c(c4)c4ccccc4n5-c4ccccc4)ccc2n3-c2ccccc2)cc1] | 83% |
Example 9
Analogously to example 5, it is possible to use the corresponding carbazole derivatives to prepare the following compounds:
| | Reactant 1 | Reactant 1 | Product | Yield |
|---|---|---|---|---|
| 9a | | | | 83% |

-continued

| | Reactant 1 | Reactant 1 | Product | Yield |
|---|---|---|---|---|
| 9b | | | | 82% |
| 9c | | | | 80% |
| 9d | [103012-28-6] | | | 69% |
| 9e | | [1257220-44-2] | | 78% |

Analogously to example 5, it is possible to use 0.5 eq of the corresponding carbazole derivative to prepare the following compounds:

| | Reactant 1 | Reactant 1 | Product | Yield |
|---|---|---|---|---|
| 9f | | | | 77% |
| 9g | | | | 75% |
| 9h | | [103068-20-8] | | 74% |
| 9i | | | | 73% |
| 9j | | | | 77% |

Production of the OLEDs

In examples C1 to I20 which follow (see Tables 2 and 3), the data of various OLEDs are presented.

Pretreatment for Examples C1-I20:

Glass plaques coated with structured ITO (indium tin oxide) of thickness 50 nm, for improved processing, are coated with 20 nm of PEDOT:PSS (poly(3,4-ethylenedioxythiophene) poly(styrenesulfonate), purchased as CLEVIOS™ P VP AI 4083 from Heraeus Precious Metals GmbH, Germany, spun on from aqueous solution). These coated glass plaques form the substrates to which the OLEDs are applied.

The OLEDs basically have the following layer structure: substrate/hole transport layer (HTL)/optional interlayer (IL)/electron blocker layer (EBL)/emission layer (EML)/optional hole blocker layer (HBL)/electron transport layer (ETL)/optional electron injection layer (EIL) and finally a cathode. The cathode is formed by an aluminum layer of thickness 100 nm. The exact structure of the OLEDs can be found in Table 2. The materials required for production of the OLEDs are shown in Table 1.

All materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as ST2:L1:TEG1 (55%:35%:10%) mean here that the material ST2 is present in the layer in a proportion by volume of 55%, L1 in a proportion of 35% and TEG1 in a proportion of 10%. Analogously, the electron transport layer may also consist of a mixture of two materials.

The OLEDs are characterized in a standard manner. For this purpose, the electroluminescence spectra, the current efficiency (measured in cd/A), the power efficiency (measured in lm/W) and the external quantum efficiency (EQE, measured in percent) as a function of luminance, calculated from current-voltage-luminance characteristics (IUL characteristics) assuming Lambertian emission characteristics, and also the lifetime are determined. The electroluminescence spectra are determined at a luminance of 1000 cd/m², and the CIE 1931 x and y color coordinates are calculated therefrom. The parameter U1000 in Table 3 refers to the voltage which is required for a luminance of 1000 cd/m². CE1000 and PE1000 respectively refer to the current and power efficiencies which are achieved at 1000 cd/m². Finally, EQE1000 refers to the external quantum efficiency at an operating luminance of 1000 cd/m². The lifetime LT is defined as the time after which the luminance drops from the starting luminance to a certain proportion $L_1$ in the course of operation with constant current. A figure of $L_0$; $j_0$=4000 cd/m² and $L_1$=70% in Table 3 means that the lifetime reported in the LT column corresponds to the time after which the starting luminance falls from 4000 cd/m² to 2800 cd/m². Analogously, $L_0$; $j_0$=20 mA/cm², $L_1$=80% means that the luminance in the course of operation at 20 mA/cm² falls to 80% of its starting value after the time LT.

The data for the various OLEDs are collated in Table 3. Examples C1 and C2 are comparative examples according to the prior art; examples I1 to I20 show data of OLEDs of the invention.

Some of the examples are elucidated in detail hereinafter, in order to illustrate the advantages of the OLEDs of the invention.

Use of Mixtures of the Invention in the Hole Transport Layer of Phosphorescent OLEDs The materials of the invention, when used as electron blocker layer (EBL) in phosphorescent OLEDs, give significant improvements over the prior art in all parameters, particularly with regard to voltage, external quantum efficiency and power efficiency. By use of the inventive compounds e4 and f4, it is possible to observe an improvement in the voltage by about 20%-40% and an improvement in the external power efficiency by about 25% compared to the prior art PA1 and PA2. The power efficiency is improved over the prior art by about 40% (examples C1, I1 and C2, I2).

TABLE 1

Structural formulae of the materials for the OLEDs

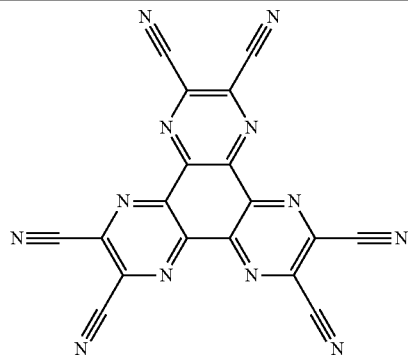

HATCN

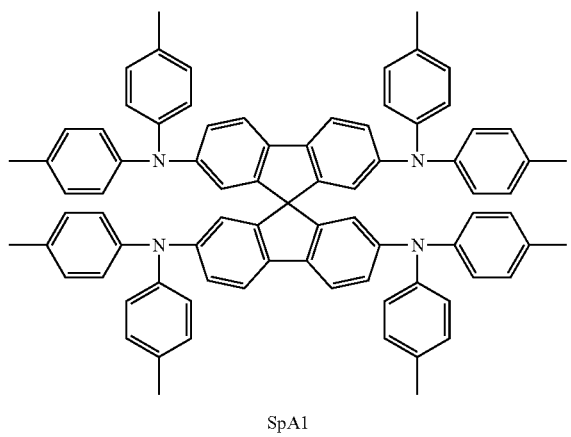

SpA1

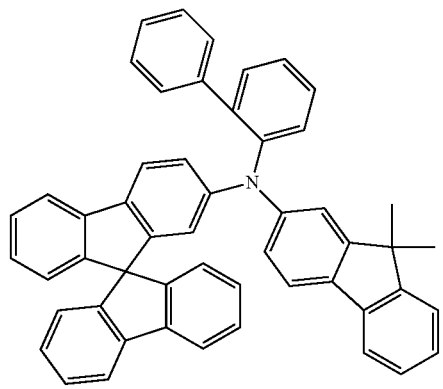

SpMA1

TABLE 1-continued
Structural formulae of the materials for the OLEDs
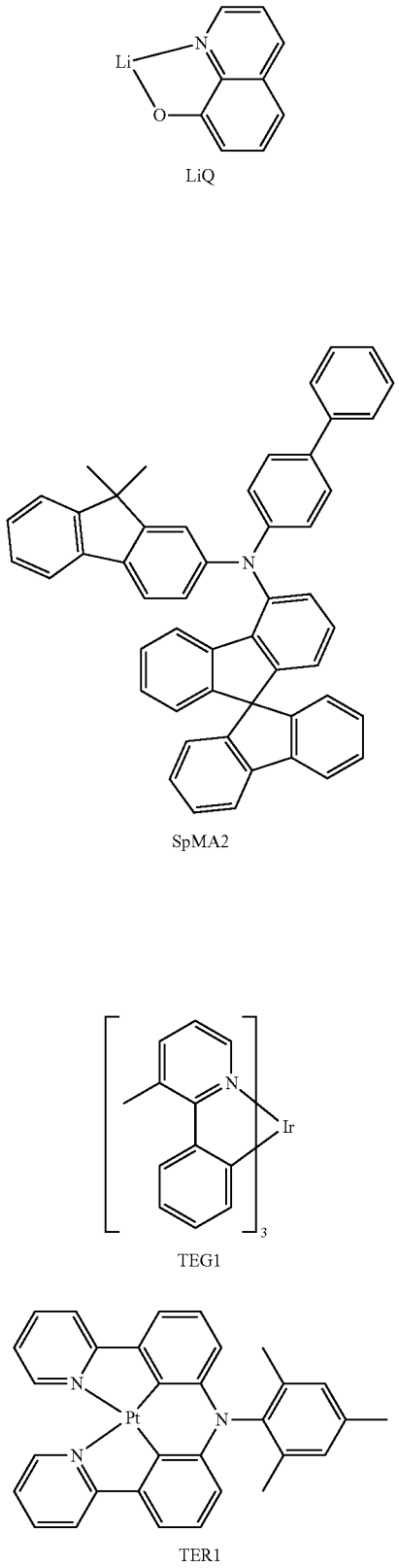
LiQ
SpMA2
TEG1
TER1
TABLE 1-continued
Structural formulae of the materials for the OLEDs
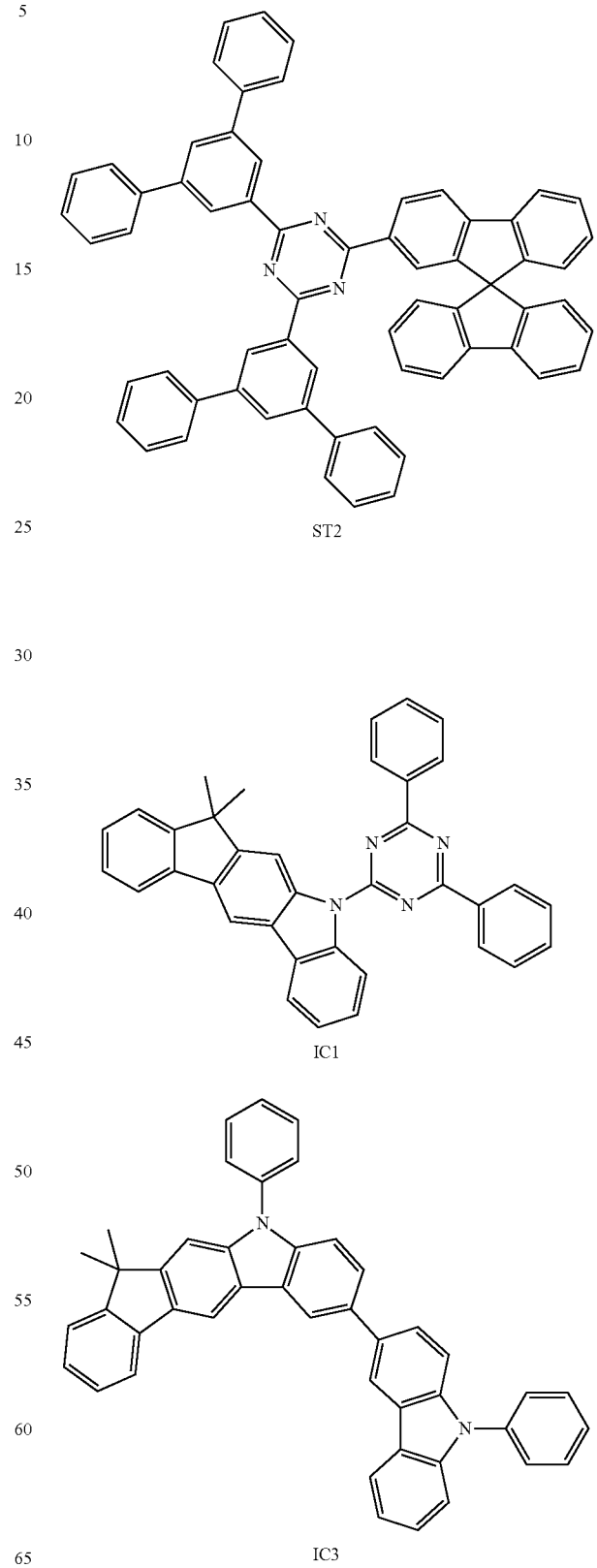
ST2
IC1
IC3

TABLE 1-continued
Structural formulae of the materials for the OLEDs
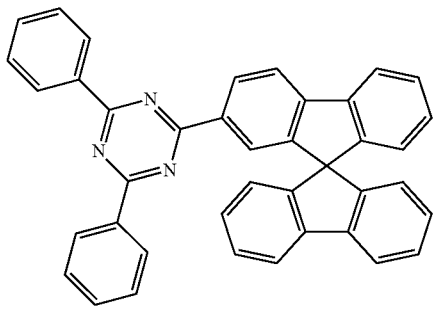
ST1
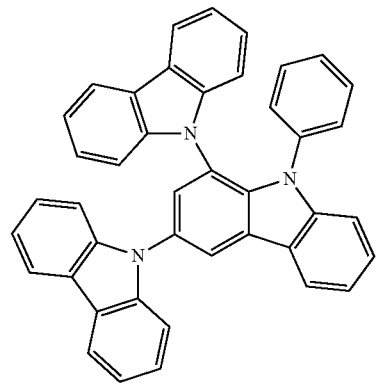
SdT1
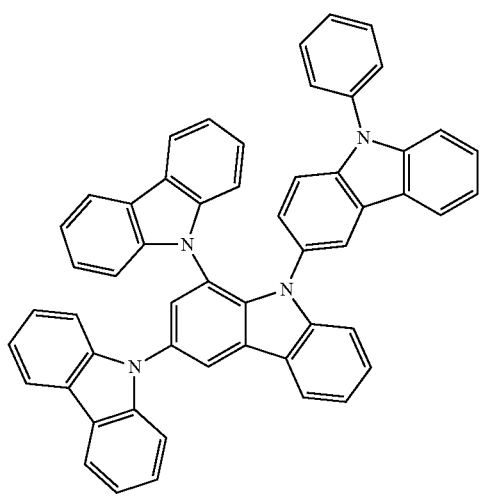
SdT2
TABLE 1-continued
Structural formulae of the materials for the OLEDs
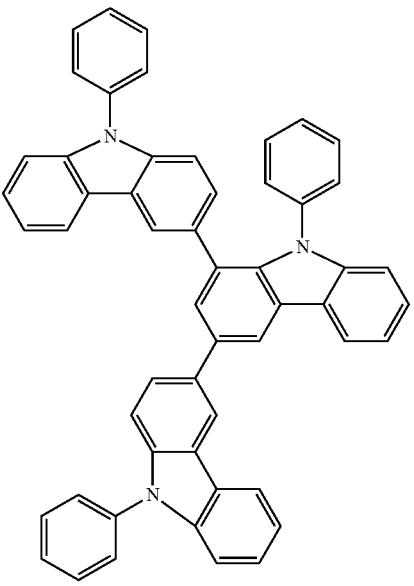
e4
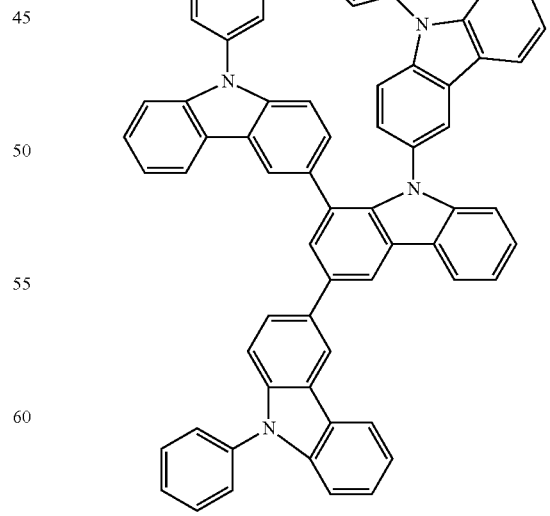
f4

TABLE 1-continued
Structural formulae of the materials for the OLEDs
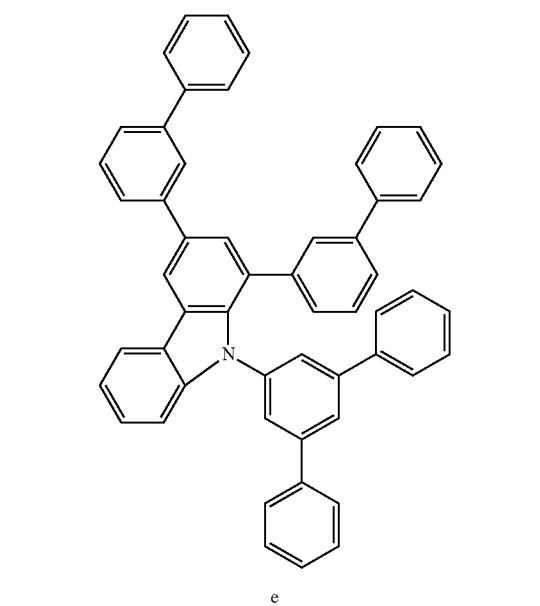 [SMILES: c1ccc(-c2cccc(-c3cc(-c4cccc(-c5ccccc5)c4)c4c(c3)c3ccccc3n4-c3cc(-c4ccccc4)cc(-c4ccccc4)c3)c2)cc1]
e
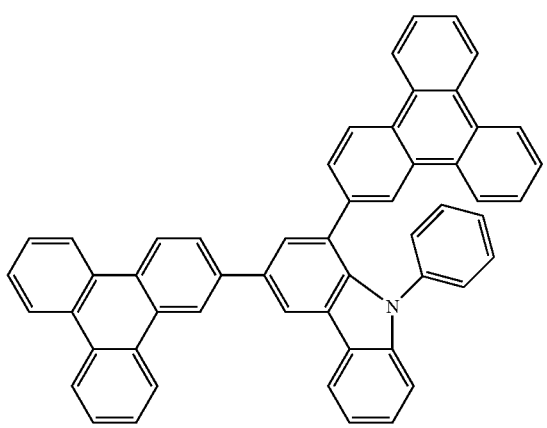
e3
TABLE 1-continued
Structural formulae of the materials for the OLEDs
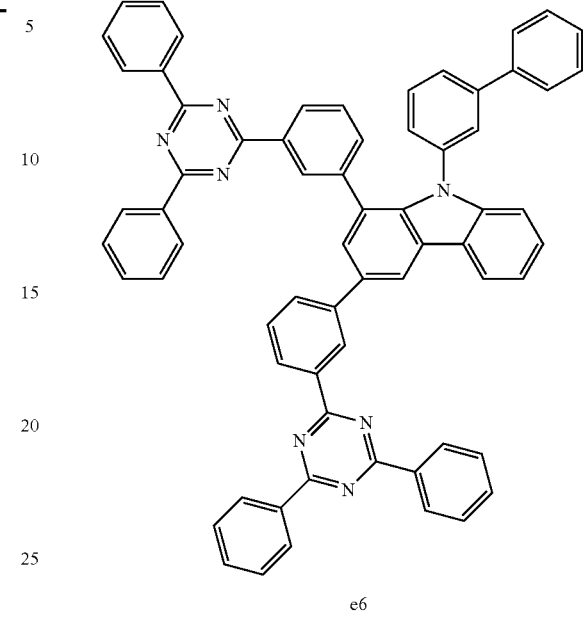
e6
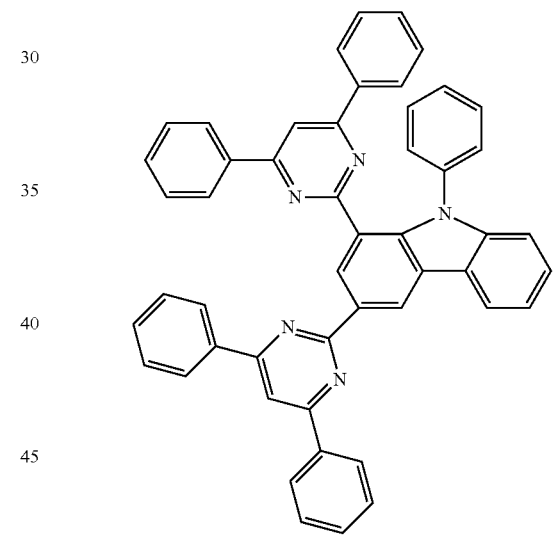
e7
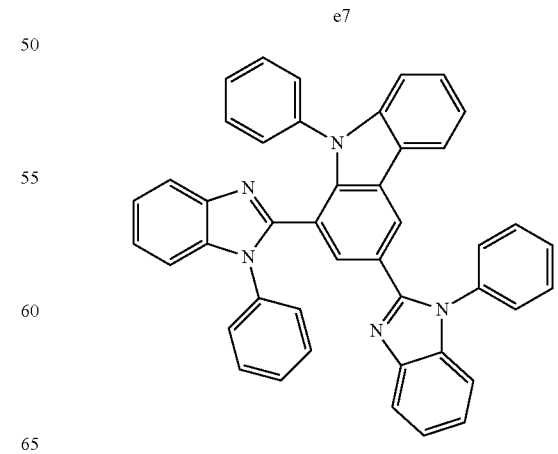
e8

TABLE 1-continued
Structural formulae of the materials for the OLEDs
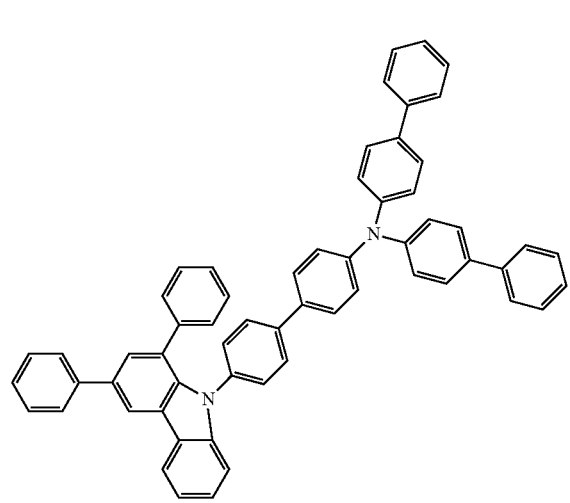
f3
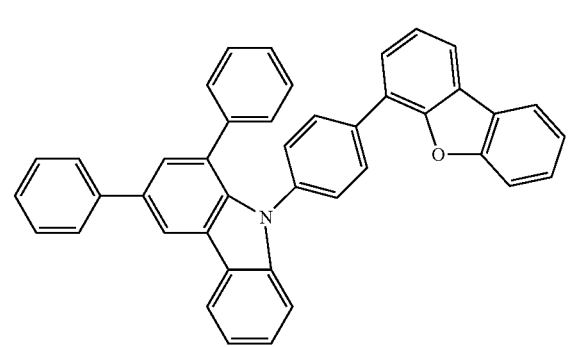
f7
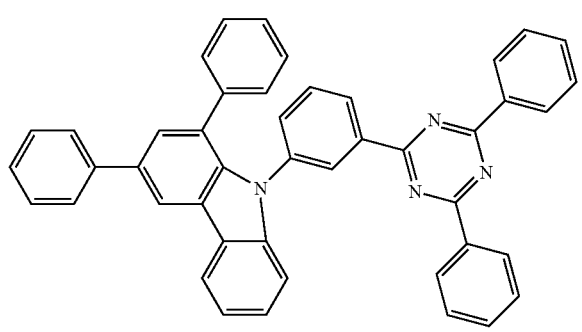
f8
TABLE 1-continued
Structural formulae of the materials for the OLEDs
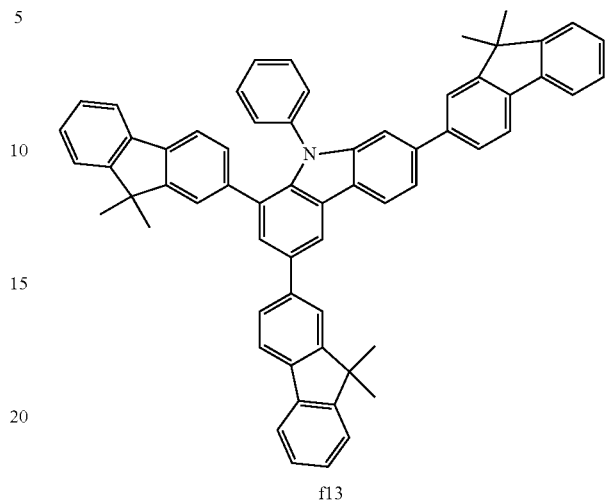
f13
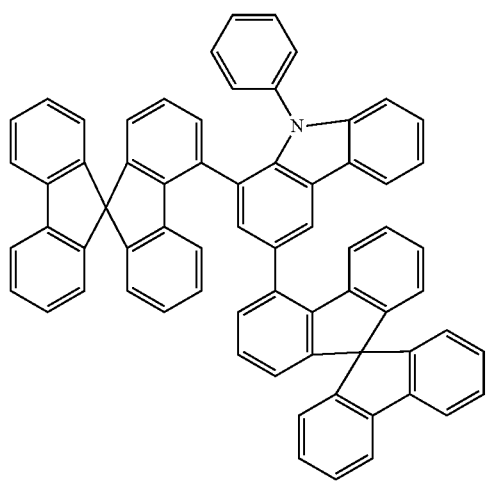
f16

TABLE 1-continued
Structural formulae of the materials for the OLEDs
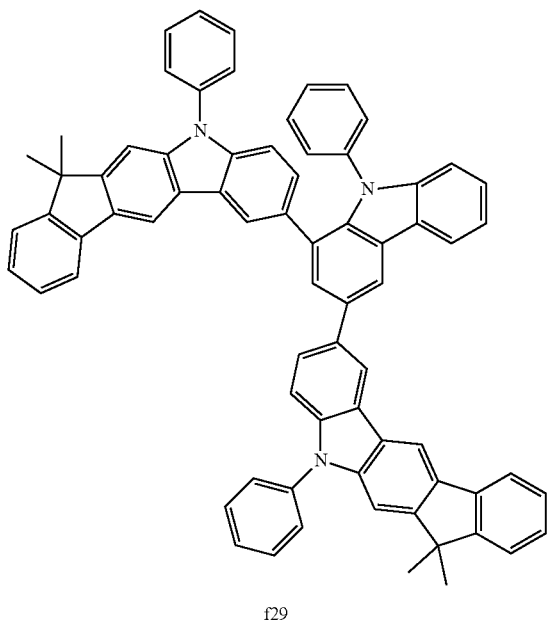 [SMILES: CC1(C)c2ccccc2-c2cc3c4cc(-c5cc(-c6ccc7c(c6)c6cc8c(cc6n7-c6ccccc6)C(C)(C)c6ccccc6-8)c6c(c5)c5ccccc5n6-c5ccccc5)ccc4n(-c4ccccc4)c3cc21]
f29
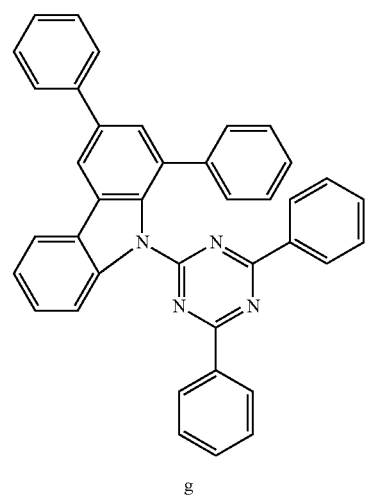 [SMILES: c1ccc(-c2cc(-c3ccccc3)c3c(c2)c2ccccc2n3-c2nc(-c3ccccc3)nc(-c3ccccc3)n2)cc1]
g
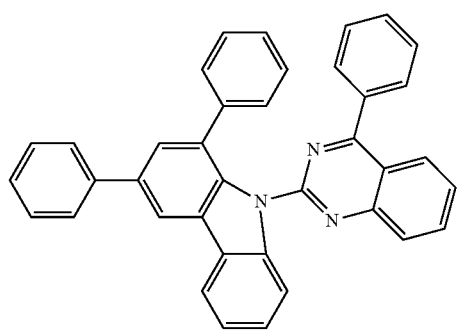
g3
TABLE 1-continued
Structural formulae of the materials for the OLEDs
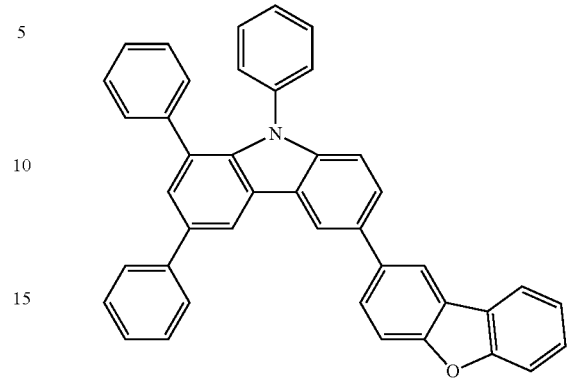
i1
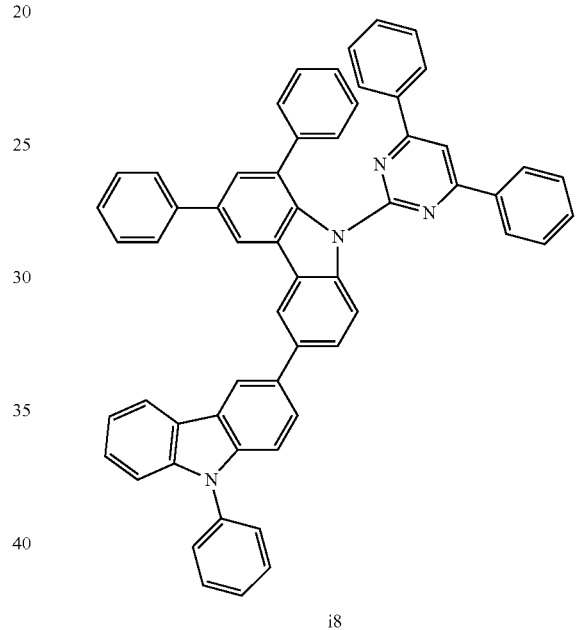
i8
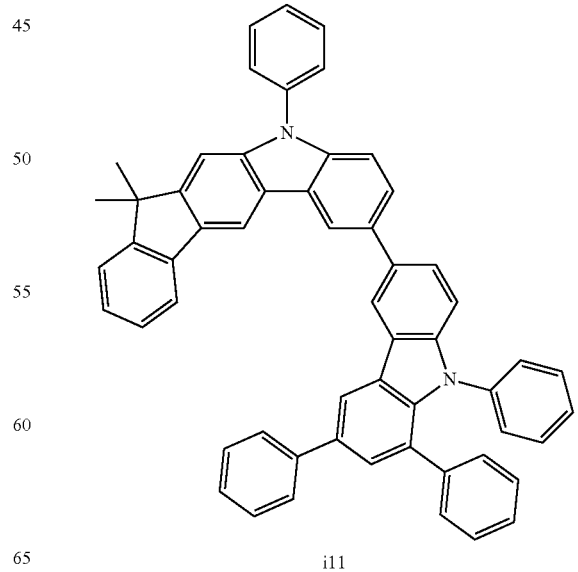
i11

TABLE 1-continued

Structural formulae of the materials for the OLEDs

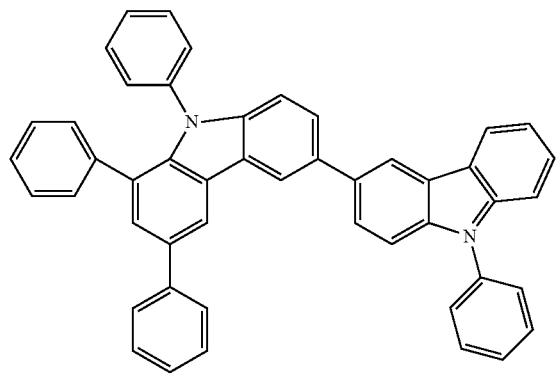

k8

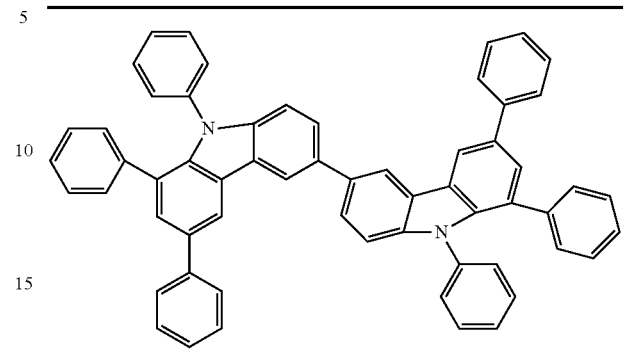

l7

TABLE 2

Structure of the OLEDs

| Ex. | HIL thickness | IL thickness | HTL thickness | EBL thickness | EML thickness | HBL thickness | ETL thickness | EIL thickness |
|---|---|---|---|---|---|---|---|---|
| C1 | SpA1 70 nm | HATCN 5 nm | SpMA1 70 nm | SdT1 20 nm | IC1:TEG1 (90%:10%) 30 nm | — | ST2:LiQ (50%:50%) 40 nm | — |
| C2 | SpA1 70 nm | HATCN 5 nm | SpMA1 70 nm | SdT2 20 nm | IC1:TEG1 (90%:10%) 30 nm | — | ST2:LiQ (50%:50%) 40 nm | — |
| I1 | SpA1 70 nm | HATCN 5 nm | SpMA1 70 nm | e4 20 nm | IC1:TEG1 (90%:10%) 30 nm | — | ST2:LiQ (50%:50%) 40 nm | — |
| I2 | SpA1 70 nm | HATCN 5 nm | SpMA1 70 nm | f4 20 nm | IC1:TEG1 (90%:10%) 30 nm | — | ST2:LiQ (50%:50%) 40 nm | — |
| I3 | SpA1 70 nm | HATCN 5 nm | SpMA1 90 nm | — | IC1:e:TEG1 (65%:30%:5%) 30 nm | IC1 10 nm | ST2:LiQ (50%:50%) 30 nm | — |
| I4 | SpA1 70 nm | HATCN 5 nm | SpMA1 90 nm | — | IC1:e3:TEG1 (65%:30%:5%) 30 nm | IC1 10 nm | ST2:LiQ (50%:50%) 30 nm | — |
| I5 | SpA1 70 nm | HATCN 5 nm | SpMA1 90 nm | — | IC1:TEG1 (90%:10%) 30 nm | IC1 10 nm | e6:LiQ (50%:50%) 30 nm | — |
| I6 | SpA1 70 nm | HATCN 5 nm | SpMA1 90 nm | — | IC1:TEG1 (90%:10%) 30 nm | — | e7:ST2 (50%:50%) 40 nm | LiQ 3 nm |
| I7 | SpA1 70 nm | HATCN 5 nm | SpMA1 90 nm | — | IC1:TEG1 (90%:10%) 30 nm | — | e8:ST2 (50%:50%) 40 nm | LiF 1 nm |
| I8 | SpA1 70 nm | HATCN 5 nm | SpMA1 70 nm | f3 20 nm | IC1:TEG1 (90%:10%) 30 nm | — | ST2:LiQ (50%:50%) 40 nm | — |
| I9 | SpA1 70 nm | HATCN 5 nm | SpMA1 90 nm | — | IC1:f7:TEG1 (60%:30%:10%) 30 nm | IC1 10 nm | ST2:LiQ (50%:50%) 30 nm | — |
| I10 | SpA1 70 nm | HATCN 5 nm | SpMA1 90 nm | — | f8:TEG1 (90%:10%) 30 nm | IC1 10 nm | ST2:LiQ (50%:50%) 30 nm | — |
| I11 | SpA1 70 nm | HATCN 5 nm | SpMA1 90 nm | — | IC1:f13:TEG1 (45%:45%:10%) 30 nm | IC1 10 nm | ST2:LiQ (50%:50%) 30 nm | — |
| I12 | SpA1 70 nm | HATCN 5 nm | SpMA1 90 nm | — | IC1:TEG1 (90%:10%) 30 nm | f16 10 nm | ST2:LiQ (50%:50%) 30 nm | — |
| I13 | SpA1 70 nm | HATCN 5 nm | SpMA1 90 nm | — | IC1:f29:TEG1 (45%:45%:10%) 30 nm | IC1 10 nm | ST2:LiQ (50%:50%) 30 nm | — |
| I14 | SpA1 70 nm | HATCN 5 nm | SpMA1 90 nm | — | g:TEG1 (90%:10%) 30 nm | IC1 10 nm | ST2:LiQ (50%:50%) 30 nm | — |

TABLE 2-continued

Structure of the OLEDs

| Ex. | HIL thickness | IL thickness | HTL thickness | EBL thickness | EML thickness | HBL thickness | ETL thickness | EIL thickness |
|---|---|---|---|---|---|---|---|---|
| I15 | SpA1 90 nm | HATCN 5 nm | SpMA1 130 nm | — | g3:TER1 (92%:8%) 40 nm | — | ST2:LiQ (50%:50%) 40 nm | — |
| I16 | SpA1 70 nm | HATCN 5 nm | SpMA1 90 nm | — | IC1:i1:TEG1 (60%:30%:10%) 30 nm | IC1 10 nm | ST2:LiQ (50%:50%) 30 nm | — |
| I17 | SpA1 70 nm | HATCN 5 nm | SpMA1 90 nm | — | i8:TEG1 (90%:10%) 30 nm | IC1 10 nm | ST2:LiQ (50%:50%) 30 nm | — |
| I18 | SpA1 70 nm | HATCN 5 nm | SpMA1 90 nm | — | IC1:i11:TEG1 (50%:40%:10%) 30 nm | IC1 10 nm | ST2:LiQ (50%:50%) 30 nm | — |
| I19 | SpA1 70 nm | HATCN 5 nm | SpMA1 90 nm | — | IC1:k8:TEG1 (30%:60%:10%) 30 nm | IC1 10 nm | ST1:LiQ (50%:50%) 30 nm | — |
| I20 | SpA1 70 nm | HATCN 5 nm | SpMA1 90 nm | — | IC1:l7:TEG1 (30%:60%:10%) 30 nm | IC1 10 nm | ST1:LiQ (50%:50%) 30 nm | — |

TABLE 3

Data of the OLEDs

| Ex. | U1000 (V) | SE1000 (cd/A) | LE1000 (lm/W) | EQE 1000 | CIE x/y at Efficiency at 1000 cd/m$^2$ | $L_0$:$j_0$ | L1 % | LT (h) |
|---|---|---|---|---|---|---|---|---|
| C1 | 4.4 | 52 | 37 | 14.4% | 0.35/0.61 | 20 mA/cm$^2$ | 80 | 100 |
| C2 | 4.1 | 54 | 41 | 14.7% | 0.34/0.63 | 20 mA/cm$^2$ | 80 | 110 |
| I1 | 3.3 | 67 | 64 | 18.0% | 0.33/0.63 | 20 mA/cm$^2$ | 80 | 140 |
| I2 | 3.2 | 70 | 69 | 18.1% | 0.34/0.63 | 20 mA/cm$^2$ | 80 | 150 |
| I3 | 3.4 | 59 | 55 | 16.6% | 0.33/0.62 | 20 mA/cm$^2$ | 80 | 140 |
| I4 | 3.5 | 64 | 57 | 17.2% | 0.32/0.64 | 20 mA/cm$^2$ | 80 | 160 |
| I5 | 4.2 | 66 | 49 | 17.6% | 0.33/0.63 | 20 mA/cm$^2$ | 80 | 340 |
| I6 | 3.3 | 69 | 66 | 18.4% | 0.33/0.62 | 20 mA/cm$^2$ | 80 | 170 |
| I7 | 3.4 | 66 | 60 | 17.8% | 0.33/0.64 | 20 mA/cm$^2$ | 80 | 140 |
| I8 | 3.1 | 70 | 71 | 18.1% | 0.34/0.63 | 20 mA/cm$^2$ | 80 | 160 |
| I9 | 3.2 | 62 | 61 | 16.9% | 0.33/0.63 | 20 mA/cm$^2$ | 80 | 180 |
| I10 | 3.1 | 67 | 68 | 18.2% | 0.34/0.63 | 20 mA/cm$^2$ | 80 | 150 |
| I11 | 3.6 | 63 | 55 | 17.1% | 0.34/0.63 | 20 mA/cm$^2$ | 80 | 160 |
| I12 | 3.4 | 63 | 58 | 17.3% | 0.32/0.63 | 20 mA/cm$^2$ | 80 | 190 |
| I13 | 3.3 | 59 | 56 | 16.4% | 0.33/0.62 | 20 mA/cm$^2$ | 80 | 200 |
| I14 | 3.2 | 61 | 60 | 16.5% | 0.32/0.64 | 20 mA/cm$^2$ | 80 | 140 |
| I15 | 4.6 | 11 | 8 | 11.4% | 0.67/0.33 | 4000 cd/m$^2$ | 80 | 310 |
| I16 | 3.3 | 62 | 59 | 16.8% | 0.34/0.62 | 20 mA/cm$^2$ | 80 | 190 |
| I17 | 3.2 | 60 | 59 | 16.2% | 0.33/0.63 | 20 mA/cm$^2$ | 80 | 155 |
| I18 | 3.2 | 62 | 61 | 16.8% | 0.35/0.62 | 20 mA/cm$^2$ | 80 | 210 |
| I19 | 3.4 | 59 | 55 | 15.9% | 0.33/0.64 | 10000 cd/m$^2$ | 70 | 220 |
| I20 | 3.5 | 60 | 54 | 16.3% | 0.32/0.63 | 10000 cd/m$^2$ | 70 | 180 |

The invention claimed is:

1. A compound of formula (1)

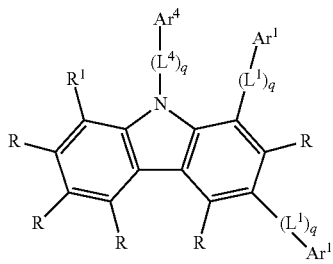

Formula (4)

where the symbols and indices used are as follows:

$L^1$ and $L^4$, are the same or different at each instance and are a bivalent aromatic or heteroaromatic ring system which has 5 to 40 aromatic ring atoms selected from the formulae (Ar2-1) to (Ar2-12):

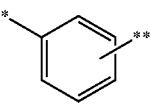

Formula (Ar2-1)

-continued

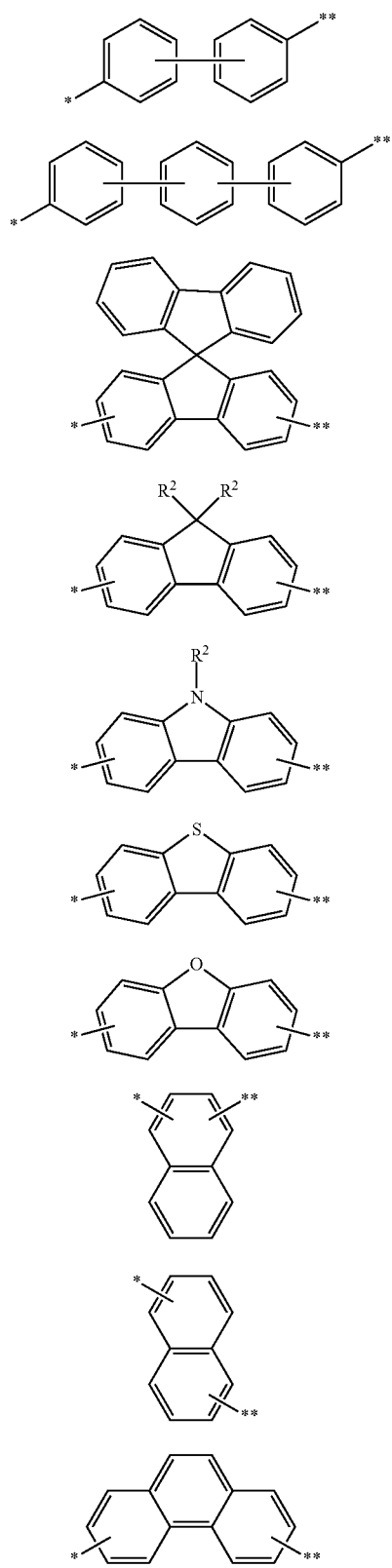

Formula (Ar2-2)

Formula (Ar2-3)

Formula (Ar2-4)

Formula (Ar2-5)

Formula (Ar2-6)

Formula (Ar2-7)

Formula (Ar2-8)

Formula (Ar2-10)

Formula (Ar2-11)

Formula (Ar2-12)

where the bond identified by * indicates the bond to the base skeleton, the bond identified by** the bond to the corresponding $Ar^1$, $Ar^2$, $Ar^3$ or $Ar^4$ radical and where the groups (Ar2-1) to (Ar2-8) and (Ar2-10) to (Ar2-12) may be substituted by $R^2$ at the free positions;

$Ar^4$ is an aromatic or heteroaromatic ring system which has 6 to 60 aromatic ring atoms and may in each case also be substituted by one or more $R^2$ radicals;

$Ar^1$ is selected from one of the formulae (Ar-5), (Ar-6) or (Ar-8),

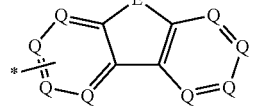

Formula (Ar-5)

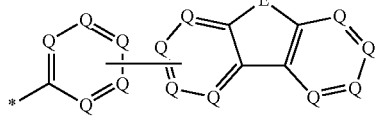

Formula (Ar-6)

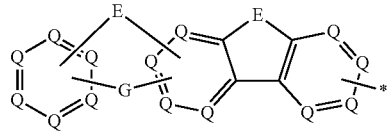

Formula (Ar-8)

Q is the same or different at each instance and is $CR^2$ or N, where not more than 3 Q symbols per cycle are N;

E is the same or different at each instance and is $NR^2$;

G at each instance is a single bond, $(CR^2)_2$, $NR^2$, O, S or C=O;

* represents the bond to $L^1$ or the base skeleton;

Ar is the same or different at each instance and is an aromatic or heteroaromatic ring system;

R is the same or different at each instance and is H, D, F or an aliphatic hydrocarbyl radical having 1 to 20 carbon atoms;

$R^2$ is the same or different at each instance and is H, D, F, Cl, Br, I, $N(R^3)_2$, $N(Ar)_2$, C(=O)Ar, P(=O)Ar$_2$, S(=O)Ar, S(=O)$_2$Ar, $CR^3$—$CR^3$Ar, CN, NO$_2$, Si(R$^3$)$_3$, B(OR$^3$)$_2$, OSO$_2$R$^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent CH$_2$ groups may be replaced by $R^3C$=$CR^3$, C≡C, Si(R$^3$)$_2$, C=O, C=NR$^3$, P(=O)(R$^3$), SO, SO$_2$, NR$^3$, O, S or CONR$^3$ and where one or more hydrogen atoms may be replaced by D, F, Cl, Br, I, CN or NO$_2$, or an aromatic or heteroaromatic ring system which has 5 to 60 aromatic ring atoms, each of which may be substituted by one or more $R^3$ radicals, or an aryloxy or heteroaryloxy group which has 5 to 40 aromatic ring atoms and may be substituted by one or more $R^3$ radicals, or an aralkyl or heteroaralkyl group which has 5 to 40 aromatic ring atoms and may be substituted by one or more $R^3$ radicals, or a combination of these systems; at the same time, two or more $R^2$ substituents together with the atoms to which they are bonded and also with one another, or two adjacent R substituents, may form a mono- or polycyclic, aliphatic or aromatic ring system;

$R^1$ is the same or different at each instance and is H, D, F or an aliphatic hydrocarbyl radical having 1 to 20 carbon atoms;

$R^3$ is the same or different at each instance and is H, D, F, Cl, Br, I, $N(R^4)_2$, $C(=O)Ar$, $P(=O)Ar_2$, $S(=O)Ar$, $S(=O)_2Ar$, $CR^3=CR^3Ar$, CN, $NO_2$, $Si(R^4)_3$, $B(OR^4)_2$, $OSO_2R^4$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent $CH_2$ groups may be replaced by $R^4C=CR^4$, $C\equiv C$, $Si(R^4)_2$, C=O, $C=NR^4$, $P(=O)(R^4)$, SO, $SO_2$, $NR^4$, O, S or $CONR^4$ and where one or more hydrogen atoms may be replaced by D, F, Cl, Br, I, CN or $NO_2$, or an aromatic or heteroaromatic ring system which has 5 to 60 aromatic ring atoms, each of which may be substituted by one or more $R^4$ radicals, or an aryloxy or heteroaryloxy group which has 5 to 40 aromatic ring atoms and may be substituted by one or more $R^3$ radicals, or an aralkyl or heteroaralkyl group which has 5 to 40 aromatic ring atoms and may be substituted by one or more $R^4$ radicals, or a combination of these systems;

$R^4$ is the same or different at each instance and is H, D, F or an aliphatic hydrocarbyl radical having 1 to 20 carbon atoms or an aryl or heteroaryl group which has 5 to 40 ring atoms and may be substituted by one or more $R^5$ radicals, or a combination of these groups;

$R^5$ is the same or different at each instance and is H, D, F or an aliphatic hydrocarbyl radical having 1 to 20 carbon atoms;

q is the same or different at each instance and is 0 or 1; and the two groups $(L^1)_q Ar^1$, are the same.

2. A process for preparing The compound as claimed in claim 1, wherein the compound of the formula (4) is formed by one or more coupling reactions and/or cyclizations.

3. A mixture comprising at least one compound as claimed in claim 1 and at least one fluorescent or phosphorescent dopant.

4. A formulation comprising at least one compound as claimed in claim 1 and one or more solvents.

5. A formulation comprising the mixture as claimed in claim 3 and one or more solvents.

6. A solution, a suspension or a miniemulsion comprising at least one compound as claimed in claim 1 one or more solvents.

7. A solution, a suspension or a miniemulsion comprising the mixture as claimed in claim 3 and one or more solvents.

8. An electronic device which comprises the compound as claimed in claim 1.

9. An electronic device which comprises the mixture as claimed in claim 3.

10. The electronic device as claimed in claim 8, wherein the device is selected from the group consisting of organic electroluminescent device, organic integrated circuit, organic field-effect transistor, organic thin-film transistor, organic light-emitting transistor, organic solar cell, organic dye-sensitized solar cell, organic optical detector, organic photoreceptor, organic field-quench device, light-emitting electrochemical cell, organic laser diode and organic plasmon emitting device.

11. An organic electroluminescent device comprising the compound as claimed in claim 1 is used as matrix material for a fluorescent or phosphorescent compound in an emitting layer and/or in a hole transport layer and/or in an electron blocker layer.

* * * * *